(12) United States Patent
Bahrenberg et al.

(10) Patent No.: US 9,108,936 B2
(45) Date of Patent: Aug. 18, 2015

(54) SUBSTITUTED 4-AMINOBENZAMIDES AS KCNQ2/3 MODULATORS

(71) Applicant: GRUENENTHAL GMBH, Aachen (DE)

(72) Inventors: Gregor Bahrenberg, Monschau-Konzen (DE); Sven Kuehnert, Dueren (DE); Simon Lucas, Vienna (AT); Wolfgang Schroeder, Aachen (DE)

(73) Assignee: GRUENENTHAL GMBH, Aachen (DE)

( * ) Notice: Subject to any disclaimer, the term of this patent is extended or adjusted under 35 U.S.C. 154(b) by 0 days.

(21) Appl. No.: 13/865,343

(22) Filed: Apr. 18, 2013

(65) Prior Publication Data

US 2013/0281452 A1 Oct. 24, 2013

Related U.S. Application Data

(60) Provisional application No. 61/625,711, filed on Apr. 18, 2012.

(30) Foreign Application Priority Data

Apr. 18, 2012 (EP) .................................... 12002688

(51) Int. Cl.
| | |
|---|---|
| *C07D 265/30* | (2006.01) |
| *C07D 413/10* | (2006.01) |
| *C07D 207/06* | (2006.01) |
| *C07D 295/155* | (2006.01) |
| *C07D 413/12* | (2006.01) |

(52) U.S. Cl.
CPC ............ *C07D 265/30* (2013.01); *C07D 207/06* (2013.01); *C07D 295/155* (2013.01); *C07D 413/10* (2013.01); *C07D 413/12* (2013.01)

(58) Field of Classification Search
CPC ................................................... C07D 265/30
USPC ....................................................... 544/162
See application file for complete search history.

(56) References Cited

U.S. PATENT DOCUMENTS

| | | | |
|---|---|---|---|
| 7,625,900 | B2 | 12/2009 | Merla et al. |
| 7,812,020 | B2 | 10/2010 | Tornoe et al. |
| 7,879,858 | B2 | 2/2011 | Merla et al. |
| 8,017,772 | B2 | 9/2011 | Merla et al. |
| 8,178,684 | B2 | 5/2012 | Kuhnert et al. |
| 2002/0128277 | A1 | 9/2002 | Dworetzky et al. |
| 2008/0167315 | A1 | 7/2008 | Merla et al. |
| 2009/0258880 | A1 | 10/2009 | Merla et al. |
| 2010/0004252 | A1 | 1/2010 | Merla et al. |
| 2010/0105722 | A1 | 4/2010 | Kuehnert et al. |

FOREIGN PATENT DOCUMENTS

| | | |
|---|---|---|
| DE | 2513949 A1 | 10/1976 |
| GB | 791599 A | 3/1958 |
| GB | 896720 A | 5/1962 |
| GB | 1420987 | 1/1976 |
| GB | 1495124 | 12/1977 |
| WO | 02 066036 | 8/2002 |
| WO | 2008/046582 | 4/2008 |
| WO | 2010/046108 | 4/2010 |
| WO | WO 2010/102809 A1 | 9/2010 |
| WO | WO 2012/052167 | 4/2012 |

OTHER PUBLICATIONS

Jia, et al. Pharmacology 2011, 87, 297-310.*
Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet, URL; http:llwww.cnn.com120031HEALTHlconditionslO91241alzheimers.drug.aplindexhtml>.*
Dementia [online], [retrieved on Dec. 28, 2014]. Retrieved from the Internet, URL; http://en.wikipedia.org/wiki/Dementia.*
Avis, Kenneth. Parenteral Preparations. Chapter 85. In Remington's Pharmaceutical Sciences, 17th Ed, 1985.
Block, Lawrence. Medicated Applications. Chapter 88. In Remington's Pharmaceutical Sciences, 17th Ed, 1985.
Disanto, Anthony. Bioavailability and Bioequivalency Testing. Chapter 77. In Remington's Pharmaceutical Sciences, 17th Ed, 1985.
Erskine, Jr., Clyde. Quality Assurance and Control. Chapter 83. In Remington's Pharmaceutical Sciences, 17th Ed, 1985.
Giles et al. Plastic Packaging Materials. Chapter 81. In Remington's Pharmaceutical Sciences, 17th Ed, 1985.
King et al. Oral Solid Dosage Forms. Chapter 90. In Remington's Pharmaceutical Sciences, 17th Ed, 1985.
Knevel, Adelbert. Separation. Chapter 78. In Remington's Pharmaceutical Sciences, 17th Ed, 1985.
Lintner, Carl. Stability of Pharmaceutical Products. Chapter 82. In Remington's Pharmaceutical Sciences, 17th Ed, 1985.
Longer et al. Sustained-Release Drug Delivery Systems. Chapter 92. In Remington's Pharmaceutical Sciences, 17th Ed, 1985.
Mullins, John. Ophthalmic Preparations. Chapter 87. In Remington's Pharmaceutical Sciences, 17th Ed, 1985.
Nairn, J.G., Solutions, Emulsion, Suspensions and Extractives. Chapter 84. In Remington's Pharmaceutical Sciences, 17th Ed, 1985.
Phillips, G. Briggs. Sterilization. Chapter 79. In Remington's Pharmaceutical Sciences, 17th Ed, 1985.
Porter, Stuart. Coating of Pharmaceutical Dosage Forms. Chapter 91. In Remington's Pharmaceutical Sciences, 17th Ed, 1985.
Ravin, Louis. Preformulation. Chapter 76. In Remington's Pharmaceutical Sciences, 17th Ed, 1985.

(Continued)

*Primary Examiner* — Shawquia Jackson
(74) *Attorney, Agent, or Firm* — Norris McLaughlin & Marcus, P.A.

(57) ABSTRACT

Substituted 4-aminobenzamides, pharmaceutical compositions containing these compounds and also methods of using these compounds in the treatment and/or prophylaxis of pain and further diseases and/or disorders.

14 Claims, No Drawings

(56) References Cited

OTHER PUBLICATIONS

Rippie, Edward. Powders. Chapter 89. In Remington's Pharmaceutical Sciences, 17th Ed, 1985.
Siegel, Frederick. Tonicity, Osmoticity, Osmolality, and Osmolarity. Chapter 80. In Remington's Pharmaceutical Sciences, 17th Ed, 1985.
Sciarra et al. Aerosols. Chapter 93. In Remington's Pharmaceutical Sciences, 17th Ed, 1985.
Turco et al. Intravenous Admixtures. Chapter 86. In Remington's Pharmaceutical Sciences, 17th Ed, 1985.
Miceli et al., "Molecular Pharmacology and Therapeutic Potential of Neuronal Kv7-Modulating Drugs," Current Opinion in Pharmacology, 8(1), pp. 65-74, 2008.
Patani et al., "Bioisosterism: A Rational Approach in Drug Design," Chem. Rev., pp. 3147-3176, 1996.
Richter et al., "Antidystonic Effects of Kv7 (KCNQ) Channel Openers in the dtsz Mutant, An Animal Model of Primary Paroxysmal Dystonia," Br. J. Pharmacol., 149(6), pp. 747-753, 2006.
Honkanen, "Preparation of Various Sterically Hindered Compounds with Local Anesthetic Activity;" Ann Acad Sci Fen A2 Chem; pp. 5-80, 99; 1960 (English abstract attached).
International Search Report for related PCT/EP2013/001135 mailed Sep. 5, 2013.
Passmore et al., "KCNQ/M currents in sensory neurons: significance for pain therapy"; J. Neurosci. 2003; 23(18): 7227-36.
Blackburn-Munro and Jensen, "The anticonvulsant retigabine attenuates nociceptive behaviours in rat models of persistent and neuropathic pain"; Eur J Pharmacol. 2003; 460(2-3); 109-116.
Dost et al., "The anit-hyperalgesic activity of retigabine is mediated by KCNQ potassium channel activation" Naunyn Schmiedebergs Arch Pharmacol 2004; 369(4): 382-390.
Nielsen et al., "Pharmacological characterisation of acid-induced muscle allodynia in rats" Eur J Pharmacol. 2004; 487(1-3): 93-103.
Gribkoff, "The therapeutic potential of neuronal KCNQ channel modulators" Expert Opin Ther Targets 2003; 7(6): 737-748.
Korsgaard et al., "Anxiolytic effects of maxipost (BMS-204352) and retigabine via activation of neuronal Kv7 channels"; J Pharmacol Exp Ther. 2005, 14(1): 282-92.
Wickenden et al., "KCNQ potassium channels: drug targets for the treatment of epilepsy and pain"; Expert Opin Ther Pat 2004; 14(4): 457-469.
Gribkoff, "The therapeutic potential of neuronal Kv7 (KCNQ) channel modulators: an update", Expert Opin Ther Targets 2008, 12(5): 565-81.
Miceli et al., "Molecular pharmacology and therapeutic potential of neuronal Kv7-modulating drugs"; Curr Opin Pharmacol 2008, 8(1): 65-74.
Streng et al., "Urodynamic effects of the K+ channel (KCNQ) opener retigabine in freely moving, conscious rats"; J Urol 2004; 172: 2054-2058.
Hansen et al., "The neuronal KCNQ channel opener retigabine inhibits locomotor activity and reduces forebrain excitatory responses to the psychostimulants cocaine, methylphenidate and phencyclidine"; Eur J Pharmacol 2007, 570(1-3): 77-88.
Dencker et al., "Effect of the new antiepileptic drug retigabine in a rodent model of mania"; Epilepsy Behav 2008, 12(1): 49-53.
Richter et al., "Antidystonic effects of Kv7 (KCNQ) channel openers in the dtsz mutant, an animal model of primary paroxysmal dystonia"; Br J Pharmacol 2006, 149(6): 747-53.
Remington's Pharmaceutical Sciences, A.R. Gennaro (Editor), 17th edition, Mack Publishing Company, Easton, Pa, 1985, Part 8, Chapters 76 to 93.
Bennett, G.J. and Xie, Y.K., A peripheral mononeuropathy in rat that produces disorders of pain sensation like those seen in man, Pain 1988, 33(1), 87-107.
Kim, S.H. and Chung, J.M., An experimental model for peripheral neuropathy produced by segmental spinal nerve ligation in the rat, Pain 1992, 50(3), 355-363.
D'Amour and Smith, "A method for determining loss of pain sensation"; J. Pharm. Exp. Ther. 72, 74 79 (1941).
D. Dubuisson et al., "The formalin test: a quantitative study of the analgesic effects of morphine, meperidine, and brain stem stimulation in rats and cats"; Pain 1977, 4, 161-174.
De Sarro et al., "Influence of retigabine on the anticonvulsant activity of some antiepileptic drugs against audiogenic seizures in DBA/2 mice"; Naunyn-Schmiedeberg's Arch. Pharmacol. 2001, 363, 330-336.

* cited by examiner

SUBSTITUTED 4-AMINOBENZAMIDES AS KCNQ2/3 MODULATORS

This application claims priority of European Patent Application No. 12002688.5, filed Apr. 18, 2012, and of U.S. Provisional Patent Application No. 61/625,711, filed Apr. 18, 2012, the entire contents of which patent applications are fully incorporated herein by reference.

The invention relates to substituted 4-aminobenzamides, to pharmaceutical compositions containing these compounds and also to these compounds for use in the treatment and/or prophylaxis of pain and further diseases and/or disorders.

The treatment of pain, in particular of neuropathic pain, is of great importance in medicine. There is a worldwide need for effective pain therapies. The urgent need for action for a target-orientated treatment of chronic and non-chronic states of pain appropriate for the patient, by which is to be understood the successful and satisfactory treatment of pain for the patient, is also documented in the large number of scientific works which have recently been published in the field of applied analgesics and of fundamental research into nociception.

A pathophysiological feature of chronic pain is the over-excitability of neurons. Neuronal excitability is influenced decisively by the activity of $K^+$ channels, since these determine decisively the resting membrane potential of the cell and therefore the excitability threshold. Heteromeric $K^+$ channels of the molecular subtype KCNQ2/3 (Kv7.2/7.3) are expressed in neurons of various regions of the central (hippocampus, amygdala) and peripheral (dorsal root ganglia) nervous system and regulate the excitability thereof. Activation of KCNQ2/3 $K^+$ channels leads to a hyperpolarization of the cell membrane and, accompanying this, to a decrease in the electrical excitability of these neurons. KCNQ2/3-expressing neurons of the dorsal root ganglia are involved in the transmission of nociceptive stimuli from the periphery into the spinal marrow (Passmore et al., J. Neurosci. 2003; 23(18): 7227-36).

It has accordingly been possible to detect an analgesic activity in preclinical neuropathy and inflammatory pain models for the KCNQ2/3 agonist retigabine (Blackburn-Munro and Jensen, Eur J Pharmacol. 2003; 460(2-3); 109-16; Dost et al., Naunyn Schmiedebergs Arch Pharmacol 2004; 369(4): 382-390).

The KCNQ2/3 $K^+$ channel thus represents a suitable starting point for the treatment of pain; in particular of pain selected from the group consisting of chronic pain, acute pain, neuropathic pain, inflammatory pain, visceral pain and muscular pain (Nielsen et al., Eur J Pharmacol. 2004; 487(1-3): 93-103), in particular of neuropathic and inflammatory pain. Moreover, the KCNQ2/3 $K^+$ channel is a suitable target for therapy of a large number of further diseases, such as, for example, migraine (US2002/0128277), cognitive diseases (Gribkoff, Expert Opin Ther Targets 2003; 7(6): 737-748), anxiety (Korsgaard et al., J Pharmacol Exp Ther. 2005, 14(1): 282-92), epilepsy (Wickenden et al., Expert Opin Ther Pat 2004; 14(4): 457-469; Gribkoff, Expert Opin Ther Targets 2008, 12(5): 565-81; Miceli et al., Curr Opin Pharmacol 2008, 8(1): 65-74), urinary incontinence (Streng et al., J Urol 2004; 172: 2054-2058), dependency (Hansen et al., Eur J Pharmacol 2007, 570(1-3): 77-88), mania/bipolar disorders (Dencker et al., Epilepsy Behav 2008, 12(1): 49-53) and dystonia-associated dyskinesias (Richter et al., Br J Pharmacol 2006, 149(6): 747-53).

Substituted compounds that have an affinity for the KCNQ2/3 $K^+$ channel are e.g. known from the prior art (WO 2008/046582, WO 2010/046108, WO 2002/066036).

There is a demand for further compounds having comparable or better properties, not only with regard to affinity to KCNQ2/3 $K^+$ channels per se (potency, efficacy).

Thus, it may be advantageous to improve the metabolic stability, the solubility in aqueous media or the permeability of the compounds. These factors can have a beneficial effect on oral bioavailability or can alter the PK/PD (pharmacokinetic/pharmacodynamic) profile; this can lead to a more beneficial period of effectiveness, for example. A weak or non-existent interaction with transporter molecules, which are involved in the ingestion and the excretion of pharmaceutical compositions, is also to be regarded as an indication of improved bioavailability and at most low interactions of pharmaceutical compositions. Furthermore, the interactions with the enzymes involved in the decomposition and the excretion of pharmaceutical compositions should also be as low as possible, as such test results also suggest that at most low interactions, or no interactions at all, of pharmaceutical compositions are to be expected.

In addition, it may be advantageous if the compounds show a high selectivity towards other receptors of the KCNQ family (specificity), e.g. towards KCNQ1, KCNQ3/5 or KCNQ4. A high selectivity may have a positive effect on the side effects profile: for example it is known that compounds which (also) have an affinity to KCNQ1 are likely to have a potential for cardial side effects. Therefore, a high selectivity towards KCNQ1 may be desirable. However, it may also be advantageous for the compounds to show a high selectivity towards other receptors. For instance, it may be advantageous for the compounds to show a low affinity for the hERG ion channel or the L-type calcium ion channel (phenylalkylamine-, benzothiazepin-, dihydropyridine-binding site) since these receptors are known to possibly have a potential for cardial side effects. Further, an improved selectivity towards binding to other endogenic proteins (i.e. receptors or enzymes) may result in a better side effects profile and, consequently to an improved tolerance.

It was therefore an object of the invention to provide new compounds having advantages over the compounds of the prior art. These compounds should be suitable in particular as pharmacological active ingredients in pharmaceutical compositions, preferably in pharmaceutical compositions for the treatment and/or prophylaxis of disorders and/or diseases which are mediated, at least in part, by KCNQ2/3 $K^+$ channels.

That object is achieved by the subject-matter described herein.

It has been found, surprisingly, that substituted compounds of the general formula (I) given below are suitable for the treatment of pain. It has also been found, surprisingly, that substituted compounds of the general formula (I) given below also have an excellent affinity for the KCNQ2/3 $K^+$ channel and are therefore suitable for the prophylaxis and/or treatment of disorders and/or diseases that are mediated at least in part by KCNQ2/3 $K^+$ channels. The substituted compounds thereby act as modulators, i.e. agonists or antagonists, of the KCNQ2/3 $K^+$ channel.

The present invention therefore relates to a substituted compound of general formula (I),

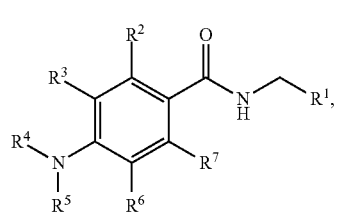

wherein
$R^1$ represents a $C_{1-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted; aryl or heteroaryl, in each case unsubstituted or mono- or polysubstituted and in each case optionally bridged via a $C_{1-8}$ aliphatic group, which in turn may be unsubstituted or mono- or polysubstituted;

$R^2$ represents F; Cl; Br; I; CN; $CH_2F$; $CHF_2$; $CF_3$; C(=O)H; $NO_2$; $OCH_2F$; $OCHF_2$; $OCF_3$; $SCF_3$; a $C_{1-4}$-aliphatic residue, a C(=O)—$C_{1-4}$ aliphatic residue, a C(=O)—O—$C_{1-4}$ aliphatic residue, a C(=O)—NH—$C_{1-4}$ aliphatic residue, a C(=O)—N($C_{1-4}$ aliphatic residue)$_2$, wherein the $C_{1-4}$ aliphatic residue may in each case be unsubstituted or mono- or polysubstituted; a O—$C_{1-4}$-aliphatic residue, a O—C(=O)—$C_{1-4}$-aliphatic residue, a S—$C_{1-4}$-aliphatic residue, a S(=O)—$C_{1-4}$-aliphatic residue, a S(=O)$_2$—$C_{1-4}$-aliphatic residue, a S(=O)$_2$—O—$C_{1-4}$-aliphatic residue, a S(=O)$_2$—NH($C_{1-4}$-aliphatic residue) or a S(=O)$_2$—N($C_{1-4}$-aliphatic residue)$_2$, wherein the $C_{1-4}$ aliphatic residue may in each case be unsubstituted or mono- or polysubstituted; a $C_{3-6}$-cycloaliphatic residue or a 3 to 6 membered heterocycloaliphatic residue, in each case unsubstituted or mono- or polysubstituted and in each case optionally bridged via a $C_{1-4}$ aliphatic group, which in turn may be unsubstituted or mono- or polysubstituted;

$R^3$ represents H; F; Cl; Br; I; CN; $CH_2F$; $CHF_2$; $CF_3$; $SCF_3$; $NO_2$; $OCH_2F$; $OCHF_2$; $OCF_3$; a $C_{1-4}$-aliphatic residue, a O—$C_{1-4}$-aliphatic residue, a S—$C_{1-4}$-aliphatic residue, a S(=O)—$C_{1-4}$-aliphatic residue, or a S(=O)$_2$—$C_{1-4}$-aliphatic residue, wherein the $C_{1-4}$ aliphatic residue may in each case be unsubstituted or mono- or polysubstituted; a $C_{3-6}$-cycloaliphatic residue or a 3 to 6 membered heterocycloaliphatic residue, in each case unsubstituted or mono- or polysubstituted and in each case optionally bridged via a $C_{1-4}$ aliphatic group, which in turn may be unsubstituted or mono- or polysubstituted;

$R^4$ represents a $C_{1-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted; aryl or heteroaryl, in each case unsubstituted or mono- or polysubstituted and in each case optionally bridged via a $C_{1-8}$ aliphatic group, which in turn may be unsubstituted or mono- or polysubstituted;

on the condition that if $R^4$ denotes a 3 to 10 membered heterocycloaliphatic residue or a heteroaryl, the 3 to 10 membered heterocycloaliphatic residue or the heteroaryl is linked via a carbon atom;

$R^5$ denotes H or a $C_{1-10}$-aliphatic residue, unsubstituted or mono- or polysubstituted;

or $R^4$ and $R^5$ form together with the nitrogen atom connecting them a 3 to 10 membered heterocycloaliphatic residue, unsubstituted or mono- or polysubstituted;

$R^6$ represents H; F; Cl; Br; I; CN; $CH_2F$; $CHF_2$; $CF_3$; $SCF_3$; $NO_2$; $OCH_2F$; $OCHF_2$; $OCF_3$; a $C_{1-4}$-aliphatic residue, a O—$C_{1-4}$-aliphatic residue, a S—$C_{1-4}$-aliphatic residue, a S(=O)—$C_{1-4}$-aliphatic residue, or a S(=O)$_2$—$C_{1-4}$-aliphatic residue, wherein the $C_{1-4}$ aliphatic residue may be in each case be unsubstituted or mono- or polysubstituted; a $C_{3-6}$-cycloaliphatic residue or a 3 to 6 membered heterocycloaliphatic residue, in each case unsubstituted or mono- or polysubstituted and in each case optionally bridged via a $C_{1-4}$ aliphatic group, which in turn may be unsubstituted or mono- or polysubstituted;

$R^7$ represents a $C_1$-aliphatic residue, mono- or polysubstituted; a $C_{2-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted;

on the condition that if $R^7$ denotes a 3 to 10 membered heterocycloaliphatic residue, the 3 to 10 membered heterocycloaliphatic residue is linked via a carbon atom, or denotes S—$R^{8a}$, S(=O)—$R^{8b}$, S(=O)$_2$—$R^{8c}$, O—$R^9$ or N($R^{10}R^{11}$), wherein $R^{8a}$, $R^{8b}$, $R^{8c}$ and $R^9$ in each case represent a $C_{1-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted;

on the condition that if $R^{8a}$, $R^{8b}$, $R^{8c}$ or $R^9$ denotes a 3 to 10 membered heterocycloaliphatic residue, the 3 to 10 membered heterocycloaliphatic residue is linked via a carbon atom, $R^{10}$ represents a $C_{1-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted;

on the condition that if $R^{10}$ denotes a 3 to 10 membered heterocycloaliphatic residue, the 3 to 10 membered heterocycloaliphatic residue is linked via a carbon atom;

$R^{11}$ denotes H or a $C_{1-10}$-aliphatic residue, unsubstituted or mono- or polysubstituted;

or $R^{10}$ and $R^{11}$ form together with the nitrogen atom connecting them a 3 to 10 membered heterocycloaliphatic residue, unsubstituted or mono- or polysubstituted; which may optionally be condensed with aryl or heteroaryl, wherein the aryl or heteroaryl residues condensed in this way can for their part be respectively unsubstituted or mono- or polysubstituted;

in which an "aliphatic group" and an "aliphatic residue" can in each case be branched or unbranched, saturated or unsaturated, in which a "cycloaliphatic residue" and a "heterocycloaliphatic residue" can in each case be saturated or unsaturated, in which "mono- or polysubstituted" with respect to an "aliphatic group" and an "aliphatic residue" relates, with respect to the corresponding residues or groups, to the substitution of one or more hydrogen atoms each independently of one another by at least one substituent selected from the group consisting of F, Cl, Br, I, $NO_2$, $NH_2$, an NH($C_{1-4}$ aliphatic residue), an N($C_{1-4}$ aliphatic residue)$_2$, a NH—C(=O)—$C_{1-4}$ aliphatic residue, a N($C_{1-4}$-aliphatic residue)-C(=O)—$C_{1-4}$ aliphatic residue, a NH—S(=O)$_2$—$C_{1-4}$ aliphatic residue, a N($C_{1-4}$-aliphatic residue)-S(=O)$_2$—$C_{1-4}$ aliphatic residue, =O, OH, $OCH_2F$, $OCHF_2$, $OCF_3$, a O—$C_{1-4}$-aliphatic residue, a O—C(=O)—$C_{1-4}$-aliphatic residue, SH, $SCF_3$, a S—$C_{1-4}$-aliphatic residue, S(=O)$_2$OH, a S(=O)—$C_{1-4}$-aliphatic residue, a S(=O)$_2$—$C_{1-4}$-aliphatic residue, a S(=O)$_2$—O—

$C_{1-4}$-aliphatic residue, a S(=O)$_2$—NH—$C_{1-4}$-aliphatic residue, a S(=O)$_2$—N($C_{1-4}$-aliphatic residue)$_2$, CN, CH$_2$F, CHF$_2$, CF$_3$, CHO, COOH, a $C_{1-4}$-aliphatic residue, CH$_2$OH, CH$_2$—OCH$_3$, C$_2$H$_4$—OH, C$_2$H$_4$—OCH$_3$CH$_2$—CF$_3$, a C(=O)—$C_{1-4}$-aliphatic residue, a C(=O)—O—$C_{1-4}$-aliphatic residue, a $C_{3-6}$-cycloaliphatic residue, a 3 to 6 membered heterocycloaliphatic residue, C(=O)—NH$_2$, a C(=O)—NH($C_{1-4}$ aliphatic residue), and a C(=O)—N ($C_{1-4}$ aliphatic residue)$_2$.

in which "mono- or polysubstituted" with respect to a "cycloaliphatic residue" and a "heterocycloaliphatic residue" relates, with respect to the corresponding residues, to the substitution of one or more hydrogen atoms each independently of one another by at least one substituent selected from the group consisting of F, Cl, Br, I, NO$_2$, NH$_2$, an NH($C_{1-4}$ aliphatic residue), an N($C_{1-4}$ aliphatic residue)$_2$, a NH—C(=O)—$C_{1-4}$ aliphatic residue, a N($C_{1-4}$-aliphatic residue)-C(=O)—$C_{1-4}$ aliphatic residue, a NH—S(=O)$_2$—$C_{1-4}$ aliphatic residue, a N($C_{1-4}$-aliphatic residue)-S(=O)$_2$—$C_{1-4}$ aliphatic residue, =O, OH, OCH$_2$F, OCHF$_2$, OCF$_3$, a O—$C_{1-4}$-aliphatic residue, a O—C(=O)—$C_{1-4}$-aliphatic residue, SH, SCF$_3$, a S—$C_{1-4}$-aliphatic residue, S(=O)$_2$OH, a S(=O)—$C_{1-4}$-aliphatic residue, a S(=O)$_2$—$C_{1-4}$-aliphatic residue, a S(=O)$_2$—O—$C_{1-4}$-aliphatic residue, a S(=O)$_2$—NH—$C_{1-4}$-aliphatic residue, a S(=O)$_2$—N($C_{1-4}$-aliphatic residue)$_2$, CN, CH$_2$F, CHF$_2$, CF$_3$, CHO, COOH, a $C_{1-4}$-aliphatic residue, CH$_2$OH, CH$_2$—OCH$_3$, C$_2$H$_4$—OH, C$_2$H$_4$—OCH$_3$CH$_2$—CF$_3$, a C(=O)—$C_{1-4}$-aliphatic residue, a C(=O)—O—$C_{1-4}$-aliphatic residue, a $C_{3-6}$-cycloaliphatic residue, a 3 to 6 membered heterocycloaliphatic residue, C(=O)—NH$_2$, a C(=O)—NH($C_{1-4}$ aliphatic residue), and a C(=O)—N($C_{1-4}$ aliphatic residue)$_2$;

in which "mono- or polysubstituted" with respect to "aryl" and a "heteroaryl" relates, with respect to the corresponding residues, to the substitution of one or more hydrogen atoms each independently of one another by at least one substituent selected from the group consisting of F, Cl, Br, I, NO$_2$, NH$_2$,

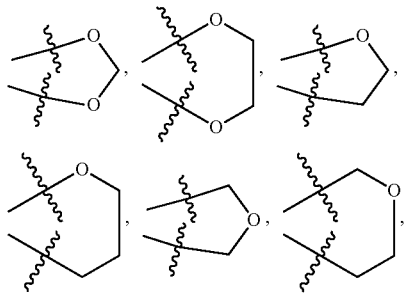

an NH($C_{1-4}$ aliphatic residue), an N($C_{1-4}$ aliphatic residue)$_2$, an NH—C(=O)—$C_{1-4}$ aliphatic residue, a N($C_{1-4}$-aliphatic residue)-C(=O)—$C_{1-4}$ aliphatic residue, an NH—S(=O)$_2$—$C_{1-4}$ aliphatic residue, a N($C_{1-4}$-aliphatic residue)-S(=O)$_2$—$C_{1-4}$ aliphatic residue, OH, OCH$_2$F, OCHF$_2$, OCF$_3$, OCFH$_2$, OCF$_2$H, a O—$C_{1-4}$-aliphatic residue, a O—C(=O)—$C_{1-4}$-aliphatic residue, SH, SCF$_3$, a S—$C_{1-4}$-aliphatic residue, S(=O)$_2$OH, a S(=O)—$C_{1-4}$-aliphatic residue, a S(=O)$_2$—$C_{1-4}$-aliphatic residue, a S(=O)$_2$—O—$C_{1-4}$-aliphatic residue, a S(=O)$_2$—NH—$C_{1-4}$-aliphatic residue, a S(=O)$_2$—N($C_{1-4}$-aliphatic residue)$_2$, CN, CF$_3$, CF$_2$H, CHF$_2$, C(=O)H, C(=O)OH, a $C_{1-4}$-aliphatic residue, CH$_2$OH, CH$_2$—OCH$_3$, C$_2$H$_4$—OH, C$_2$H$_4$—OCH$_3$, a C(=O)—$C_{1-4}$-aliphatic residue, a C(=O)—O—$C_{1-4}$-aliphatic residue, a $C_{3-6}$-cycloaliphatic residue, a 3 to 6 membered heterocycloaliphatic residue, benzyl, aryl, heteroaryl, C(=O)—NH$_2$, a C(=O)—NH($C_{1-4}$ aliphatic residue), and a C(=O)—N($C_{1-4}$ aliphatic residue)$_2$;

optionally in the form of a single stereoisomer or a mixture of stereoisomers, in the form of the free compound and/or a physiologically acceptable salt thereof and/or a physiologically acceptable solvate, in particular hydrate, thereof.

The term "single stereoisomer" preferably means in the sense of the present invention an individual enantiomer or diastereomer. The term "mixture of stereoisomers" preferably means in the sense of this invention the racemate and mixtures of enantiomers and/or diastereomers in any mixing ratio.

The term "physiologically acceptable salt" preferably comprises in the sense of this invention a salt of at least one compound according to the present invention and at least one physiologically acceptable acid or base.

A physiologically acceptable salt of at least one compound according to the present invention and at least one physiologically acceptable acid preferably refers in the sense of this invention to a salt of at least one compound according to the present invention with at least one inorganic or organic acid which is physiologically acceptable—in particular when used in human beings and/or other mammals. Examples of physiologically acceptable acids are: hydrochloric acid, hydrobromic acid, sulphuric acid, methanesulphonic acid, p-toluenesulphonic acid, carbonic acid, formic acid, acetic acid, oxalic acid, succinic acid, tartaric acid, mandelic acid, fumaric acid, maleic acid, lactic acid, citric acid, glutamic acid, saccharic acid, monomethylsebacic acid, 5-oxoproline, hexane-1-sulphonic acid, nicotinic acid, 2, 3 or 4-aminobenzoic acid, 2,4,6-trimethylbenzoic acid, α-lipoic acid, acetyl glycine, hippuric acid, phosphoric acid, aspartic acid. Citric acid and hydrochloric acid are particularly preferred. Hydrochloride salts and citrate salts are therefore particularly preferred salts.

A physiologically acceptable salt of at least one compound according to the present invention and at least one physiologically acceptable base preferably refers in the sense of this invention to a salt of at least one compound according to the present invention as an anion with at least one preferably inorganic cation, which is physiologically acceptable—in particular when used in human beings and/or other mammals. Particularly preferred are the salts of the alkali and alkaline earth metals but also ammonium salts [NH$_x$R$_{4-x}$]$^+$, in which x=0, 1, 2, 3 or 4 and R represents a branched or unbranched $C_{1-4}$ aliphatic residue residue, in particular (mono-) or (di) sodium, (mono-) or (di)potassium, magnesium or calcium salts.

The terms "$C_{1-10}$-aliphatic residue", "$C_{2-10}$-aliphatic residue", "$C_{1-8}$-aliphatic residue", "$C_{2-8}$-aliphatic residue", "$C_{1-6}$-aliphatic residue", "$C_{2-6}$-aliphatic residue", and "$C_{1-4}$-aliphatic residue" and "$C_{1-2}$-aliphatic residue" as well as "$C_1$-aliphatic residue", preferably comprise in the sense of this invention acyclic saturated or unsaturated aliphatic hydrocarbon residues, which can be branched or unbranched and also unsubstituted or mono- or polysubstituted, containing 1 to 10, or 2 to 10, or 1 to 8, or 2 to 8, or 1 to 6, or 2 to 6, or 1 to 4 or 1 to 2 or 1 carbon atom(s), respectively, i.e. $C_{1-10}$ alkanyls, $C_{2-10}$ alkenyls and $C_{2-10}$ alkynyls as well as $C_{2-10}$ alkanyls as well as $C_{1-8}$ alkanyls, $C_{2-8}$ alkenyls, $C_{2-8}$ alkynyls and $C_{2-8}$ alkynyls as well as $C_{1-6}$ alkanyls, $C_{2-6}$ alkanyls, $C_{2-6}$ alkenyls and $C_{2-6}$ alkynyls as well as $C_{1-4}$ alkanyls, $C_{2-4}$ alkenyls and $C_{2-4}$ alkynyls, as well as $C_{1-2}$ alkanyls, $C_2$-alkenyls and $C_2$-alkynyls, and $C_1$-alkanyls, respectively. In this case, alkenyls comprise at least one C—C double bond (a C=C-bond) and alkynyls comprise at least one C—C triple bond (a C≡C-bond). Preferably, aliphatic residues are selected from the group consisting of alkanyl (alkyl) and alkenyl residues, more preferably are alkanyl residues. Preferred $C_{1-10}$ alkanyl residues are selected from the group consisting of methyl, ethyl, n-propyl, 2-propyl, n-butyl, isobutyl, sec.-butyl, tert.-butyl, n-pentyl, isopentyl, neopentyl, n-hexyl, n-heptyl, n-octyl, n-nonyl and n-decyl. Preferred $C_{2-10}$ alkanyl residues are selected from the group consisting of ethyl, n-propyl, 2-propyl, n-butyl, isobutyl, sec.-butyl, tert.-butyl, n-pentyl, isopentyl, neopentyl, n-hexyl, n-heptyl, n-octyl, n-nonyl and n-decyl. Preferred $C_{1-8}$ alkanyl residues are selected from the group consisting of methyl, ethyl, n-propyl, 2-propyl, n-butyl, isobutyl, sec.-butyl, tert.-butyl, n-pentyl, isopentyl, neopentyl, n-hexyl, n-heptyl and n-octyl. Preferred $C_{1-6}$ alkanyl residues are selected from the group consisting of methyl, ethyl, n-propyl, 2-propyl, n-butyl, isobutyl, sec.-butyl, tert.-butyl, n-pentyl, isopentyl, neopentyl and n-hexyl. Preferred $C_{1-4}$ alkanyl residues are selected from the group consisting of methyl, ethyl, n-propyl, 2-propyl, n-butyl, isobutyl, sec.-butyl and tert.-butyl. Preferred $C_{2-10}$ alkenyl residues are selected from the group consisting of ethenyl (vinyl), propenyl (—CH$_2$CH=CH$_2$, —CH=CH—CH$_3$, —C(=CH$_2$)—CH$_3$), butenyl, pentenyl, hexenyl heptenyl, octenyl, nonenyl and decenyl. Preferred $C_{2-8}$ alkenyl residues are selected from the group consisting of ethenyl (vinyl), propenyl (—CH$_2$CH=CH$_2$, —CH=CH—CH$_3$, —C(=CH$_2$)—CH$_3$), butenyl, pentenyl, hexenyl heptenyl and octenyl. Preferred $C_{2-6}$ alkenyl residues are selected from the group consisting of ethenyl (vinyl), propenyl (—CH$_2$CH=CH$_2$, —CH=CH—CH$_3$, —C(=CH$_2$)—CH$_3$), butenyl, pentenyl and hexenyl. Preferred $C_{2-4}$ alkenyl residues are selected from the group consisting of ethenyl (vinyl), propenyl (—CH$_2$CH=CH$_2$, —CH=CH—CH$_3$, —C(=CH$_2$)—CH$_3$) and butenyl. Preferred $C_{2-10}$ alkynyl residues are selected from the group consisting of ethynyl, propynyl (—CH$_2$—C≡CH, —C≡C—CH$_3$), butynyl, pentynyl, hexynyl, heptynyl, octynyl, nonynyl and decynyl. Preferred $C_{2-8}$ alkynyl residues are selected from the group consisting of ethynyl, propynyl (—CH$_2$—C≡CH, —C≡C—CH$_3$), butynyl, pentynyl, hexynyl, heptynyl and octynyl. Preferred $C_{2-6}$ alkynyl residues are selected from the group consisting of ethynyl, propynyl (—CH$_2$—C≡CH, —C≡C—CH$_3$), butynyl, pentynyl and hexynyl Preferred $C_{2-4}$ alkynyl residues are selected from the group consisting of ethynyl, propynyl (—CH$_2$—C≡CH, —C≡C—CH$_3$) and butynyl.

The terms "$C_{3-6}$-cycloaliphatic residue" and "$C_{3-10}$-cycloaliphatic residue" preferably mean for the purposes of this invention cyclic aliphatic hydrocarbons containing 3, 4, 5 or 6 carbon atoms and 3, 4, 5, 6, 7, 8, 9 or 10 carbon atoms, respectively, wherein the hydrocarbons in each case can be saturated or unsaturated (but not aromatic), unsubstituted or mono- or polysubstituted. The cycloaliphatic residues can be bound to the respective superordinate general structure via any desired and possible ring member of the cycloaliphatic residue. The cycloaliphatic residues can also be condensed with further saturated, (partially) unsaturated, (hetero)cyclic, aromatic or heteroaromatic ring systems, i.e. with cycloaliphatic, heterocycloaliphatic, aryl or heteroaryl residues which can in turn be unsubstituted or mono- or polysubstituted. $C_{3-10}$ cycloaliphatic residue can furthermore be singly or multiply bridged such as, for example, in the case of adamantyl, bicyclo[1.1.1]pentyl, bicyclo[2.2.1]heptyl or bicyclo[2.2.2]octyl. Preferred $C_{3-10}$ cycloaliphatic residues are selected from the group consisting of cyclopropyl, cyclobutyl, cyclopentyl, cyclohexyl, cycloheptyl, cyclooctyl, cyclononyl, cyclodecyl, adamantyl,

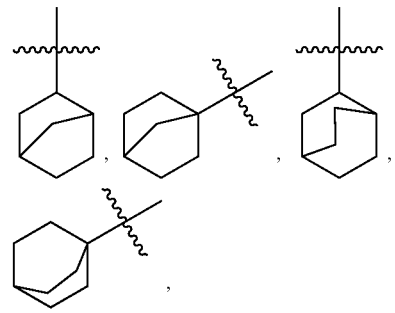

cyclopentenyl, cyclohexenyl, cycloheptenyl and cyclooctenyl. Preferred $C_{3-6}$ cycloaliphatic residues are selected from the group consisting of cyclopropyl, cyclobutyl, cyclopentyl, cyclohexyl, cyclopentenyl and cyclohexenyl.

The terms "3-6-membered heterocycloaliphatic residue", "4-7-membered heterocycloaliphatic residue" and "3-10-membered heterocycloaliphatic residue" preferably mean for the purposes of this invention heterocycloaliphatic saturated or unsaturated (but not aromatic) residues having 3-6, i.e. 3, 4, 5 or 6 ring members, and 4-7, i.e. 4, 5, 6 or 7 ring members, and 3-10, i.e. 3, 4, 5, 6, 7, 8, 9 or 10 ring members, respectively, in which in each case at least one, if appropriate also two or three carbon atoms are replaced by a heteroatom or a heteroatom group each selected independently of one another from the group consisting of O, S, S(=O)$_2$, N, NH and N($C_{1-8}$ alkyl), preferably N(CH$_3$), wherein the ring members can be unsubstituted or mono- or polysubstituted. The heterocycloaliphatic residue can be bound to the superordinate general structure via any desired and possible ring member of the heterocycloaliphatic residue if not indicated otherwise. The heterocycloaliphatic residues can also be condensed with further saturated, (partially) unsaturated (hetero)cycloaliphatic or aromatic or heteroaromatic ring systems, i.e. with cycloaliphatic, heterocycloaliphatic, aryl or heteroaryl residues, which can in turn be unsubstituted or mono- or polysubstituted. The term "condensed" also optionally includes spirocycles, i.e. an at least bicyclic ring system, wherein the heterocycloaliphatic residue is connected through just one (spiro)atom with a further saturated, (partially) unsaturated (hetero)cycloaliphatic or aromatic or heteroaromatic ring system. Example of such spirocycles are e.g.

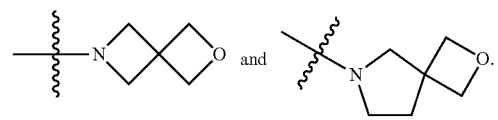 [SMILES: *N1CC2(COC2)C1 ; "and" ; *N1CCC2(COC2)C1]

The heterocycloaliphatic residues can furthermore optionally be singly or multiply bridged with a $C_1$- or $C_2$-aliphatic group such as, for example, in the case of

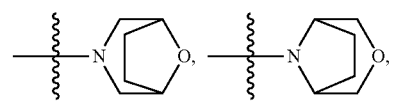

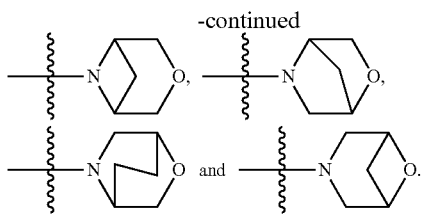

Preferred heterocycloaliphatic residues are selected from the group consisting of azetidinyl, aziridinyl, azepanyl, azocanyl, diazepanyl, dithiolanyl, dihydroquinolinyl, dihydropyrrolyl, dioxanyl, dioxolanyl, dioxepanyl, dihydroindenyl, dihydropyridinyl, dihydrofuranyl, dihydroisoquinolinyl, dihydroindolinyl, dihydroisoindolyl, imidazolidinyl, isoxazolidinyl, morpholinyl, oxiranyl, oxetanyl, oxazepanyl, pyrrolidinyl, piperazinyl, 4-methylpiperazinyl, piperidinyl, pyrazolidinyl, pyranyl, tetrahydropyrrolyl, tetrahydropyranyl, tetrahydroquinolinyl, tetrahydroisoquinolinyl, tetrahydroindolinyl, tetrahydrofuranyl, tetrahydropyridinyl, tetrahydrothiophenyl, tetrahydropyridoindolyl, tetrahydronaphthyl, tetrahydrocarbolinyl, tetrahydroisoxazolo-pyridinyl, thiazolidinyl, tetrahydroimidazo[1,2-a]pyrazinyl, octahydropyrrolo[1,2-a]pyrazinyl and thiomorpholinyl. More preferred heterocycloaliphatic residues are pyrrolidinyl, piperidinyl, oxazepanyl, azetidinyl, morpholinyl, piperazinyl, tetrahydroquinolinyl, tetrahydroisoquinolinyl, dihydroindolinyl, and dihydroisoindolyl. Most preferred heterocycloaliphatic residues are pyrrolidinyl, piperidinyl, oxazepanyl, azetidinyl, tetrahydroquinolinyl, tetrahydroisoquinolinyl, dihydroindolinyl, and dihydroisoindolyl.

The term "aryl" preferably means for the purpose of this invention aromatic hydrocarbons having 6 to 14 ring members, i.e. 6, 7, 8, 9, 10, 11, 12, 13 or 14 ring members, including phenyls and naphthyls. Each aryl residue can be unsubstituted or mono- or polysubstituted, wherein the aryl substituents can be the same or different and in any desired and possible position of the aryl. The aryl can be bound to the superordinate general structure via any desired and possible ring member of the aryl residue. The aryl residues can also be condensed with further saturated, (partially) unsaturated, (hetero)cycloaliphatic, aromatic or heteroaromatic ring systems, i.e. with a cycloaliphatic, heterocycloaliphatic, aryl or heteroaryl residue, which can in turn be unsubstituted or mono- or polysubstituted. Examples of condensed aryl residues are benzodioxolanyl and benzodioxanyl. Preferably, aryl is selected from the group consisting of phenyl, 1-naphthyl, 2-naphthyl, fluorenyl and anthracenyl, each of which can be respectively unsubstituted or mono- or polysubstituted. A particularly preferred aryl is phenyl, unsubstituted or mono- or polysubstituted.

The term "heteroaryl" for the purpose of this invention preferably represents a 5 or 6-membered cyclic aromatic residue containing at least 1, if appropriate also 2, 3, 4 or 5 heteroatoms, wherein the heteroatoms are each selected independently of one another from the group S, N and O and the heteroaryl residue can be unsubstituted or mono- or polysubstituted; in the case of substitution on the heteroaryl, the substituents can be the same or different and be in any desired and possible position of the heteroaryl. The binding to the superordinate general structure can be carried out via any desired and possible ring member of the heteroaryl residue. The heteroaryl can also be part of a bi- or polycyclic system having up to 14 ring members, wherein the ring system can be formed with further saturated, (partially) unsaturated, (hetero)cycloaliphatic or aromatic or heteroaromatic rings, i.e. with a cycloaliphatic, heterocycloaliphatic, aryl or heteroaryl residue, which can in turn be unsubstituted or mono- or polysubstituted. It is preferable for the heteroaryl residue to be selected from the group consisting of benzofuranyl, benzoimidazolyl, benzothienyl, benzothiadiazolyl, benzothiazolyl, benzotriazolyl, benzooxazolyl, benzooxadiazolyl, quinazolinyl, quinoxalinyl, carbazolyl, quinolinyl, dibenzofuranyl, dibenzothienyl, furyl (furanyl), imidazolyl, imidazothiazolyl, indazolyl, indolizinyl, indolyl, isoquinolinyl, isoxazoyl, isothiazolyl, indolyl, naphthyridinyl, oxazolyl, oxadiazolyl, phenazinyl, phenothiazinyl, phthalazinyl, pyrazolyl, pyridyl (2-pyridyl, 3-pyridyl, 4-pyridyl), pyrrolyl, pyridazinyl, pyrimidinyl, pyrazinyl, purinyl, phenazinyl, thienyl (thiophenyl), triazolyl, tetrazolyl, thiazolyl, thiadiazolyl and triazinyl. Furyl, pyridyl, oxazolyl, thiazolyl and thienyl are particularly preferred.

The terms "aryl, heteroaryl, a heterocycloaliphatic residue, or a cycloaliphatic residue bridged via a $C_{1-4}$-aliphatic group or via a $C_{1-8}$-aliphatic group" preferably mean for the purpose of the invention that the expressions "aryl, heteroaryl, heterocycloaliphatic residue and cycloaliphatic residue" have the above-defined meanings and are bound to the respective superordinate general structure via a $C_{1-4}$-aliphatic group or via a $C_{1-8}$-aliphatic group, respectively. The $C_{1-4}$ aliphatic group and the $C_{1-8}$-aliphatic group can in all cases be branched or unbranched, unsubstituted or mono- or polysubstituted. The $C_{1-4}$ aliphatic group can in all cases be furthermore saturated or unsaturated, i.e. can be a $C_{1-4}$ alkylene group, a $C_{2-4}$ alkenylene group or a $C_{2-4}$ alkynylene group. The same applies to a $C_{1-8}$-aliphatic group, i.e. a $C_{1-8}$-aliphatic group can in all cases be furthermore saturated or unsaturated, i.e. can be a $C_{1-8}$ alkylene group, a $C_{2-8}$ alkenylene group or a $C_{2-8}$ alkynylene group. Preferably, the $C_{1-4}$-aliphatic group is a $C_{1-4}$ alkylene group or a $C_{2-4}$ alkenylene group, more preferably a $C_{1-4}$ alkylene group. Preferably, the $C_{1-8}$-aliphatic group is a $C_{1-8}$ alkylene group or a $C_{2-8}$ alkenylene group, more preferably a $C_{1-8}$ alkylene group. Preferred $C_{1-4}$ alkylene groups are selected from the group consisting of —CH$_2$—, —CH$_2$—CH$_2$—, —CH(CH$_3$)—, —CH$_2$—CH$_2$—CH$_2$—, —CH(CH$_3$)—CH$_2$—, —CH(CH$_2$CH$_3$)—, —CH$_2$—(CH$_2$)$_2$—CH$_2$—, —CH(CH$_3$)—CH$_2$—CH$_2$—, —CH$_2$—CH(CH$_3$)—CH$_2$—, —CH(CH$_3$)—CH(CH$_3$)—, —CH(CH$_2$CH$_3$)—CH$_2$—, —C(CH$_3$)$_2$—CH$_2$—, —CH(CH$_2$CH$_2$CH$_3$)— and —C(CH$_3$)(CH$_2$CH$_3$)—. Preferred $C_{2-4}$ alkenylene groups are selected from the group consisting of —CH=CH—, —CH=CH—CH$_2$—, —C(CH$_3$)=CH$_2$—, —CH=CH—CH$_2$—CH$_2$—, —CH$_2$—CH=CH—CH$_2$—, —CH=CH—CH=CH—, —C(CH$_3$)=CH—CH$_2$—, —CH=C(CH$_3$)—CH$_2$—, —C(CH$_3$)=C(CH$_3$)— and —C(CH$_2$CH$_3$)=CH—. Preferred $C_{2-4}$ alkynylene groups are selected from the group consisting of —C≡C—, —C≡C—CH$_2$—, —C≡C—CH$_2$—CH$_2$—, —C≡C—CH(CH$_3$)—, —CH$_2$—C≡C—CH$_2$— and —C≡C—C≡C—. Preferred $C_{1-8}$ alkylene groups are selected from the group consisting of —CH$_2$—, —CH$_2$—CH$_2$—, —CH(CH$_3$)—, —CH$_2$—CH$_2$—CH$_2$—, —CH(CH$_3$)—CH$_2$—, —CH(CH$_2$CH$_3$)—, —CH$_2$—(CH$_2$)$_2$—CH$_2$—, —CH(CH$_3$)—CH$_2$—CH$_2$—, —CH$_2$—CH(CH$_3$)—CH$_2$—, —CH(CH$_3$)—CH(CH$_3$)—, —CH(CH$_2$CH$_3$)—CH$_2$—, —C(CH$_3$)$_2$—CH$_2$—, —CH(CH$_2$CH$_2$CH$_3$)—, —C(CH$_3$)(CH$_2$CH$_3$)—, —CH$_2$—(CH$_2$)$_3$—CH$_2$—, —CH(CH$_3$)—CH$_2$—CH$_2$—CH$_2$—, —CH$_2$—CH(CH$_3$)—CH$_2$—CH$_2$—, —CH(CH$_3$)—CH$_2$—CH(CH$_3$)—, —CH(CH$_3$)—CH(CH$_3$)—CH$_2$—, —C(CH$_3$)$_2$—CH$_2$—CH$_2$—, —CH$_2$—C(CH$_3$)$_2$—CH$_2$—, —CH(CH$_2$CH$_3$)—CH$_2$—CH$_2$—, —CH$_2$—CH(CH$_2$CH$_3$)—CH$_2$—, —C(CH$_3$)$_2$—CH(CH$_3$)—, —CH(CH$_2$CH$_3$)—CH(CH$_3$)—, —C(CH$_3$)

—(CH₂CH₃)—CH₂—, —CH(CH₂CH₂CH₃)—CH₂—, —C(CH₂CH₂CH₃)—CH₂—, —CH(CH₂CH₂CH₂CH₃)—, —C(CH₃)(CH₂CH₂CH₃)—, —C(CH₂CH₃)₂— and —CH₂—(CH₂)₄—CH₂—. Preferred C₂₋₈ alkenylene groups are selected from the group consisting of —CH═CH—, —CH═CH—CH₂—, —C(CH₃)═CH₂—, —CH═CH—CH₂—CH₂—, —CH₂—CH═CH—CH₂—, —CH═CH—CH═CH—, —C(CH₃)═CH—CH₂—, —CH═C(CH₃)—CH₂—, —C(CH₃)═C(CH₃)—, —C(CH₂CH₃)═CH—, —CH═CH—CH₂—CH₂—CH₂—, —CH₂—CH═CH—CH₂—CH₂—, —CH═CH—CH═CH—CH₂— and —CH═CH₂—CH═CH—CH₂—. Preferred C₂₋₈ alkynylene groups are selected from the group consisting of —C≡C—, —C≡C—CH₂—, —C≡C—CH₂—CH₂—, —C≡C—CH(CH₃)—, —CH₂—C≡C—CH₂—, —C≡C—C≡C—, —C≡C—C(CH₃)₂—, —C≡C—CH₂—CH₂—CH₂—, —CH₂—C≡C—CH₂—CH₂—, —C≡C—C≡C—CH₂— and —C≡C—CH₂—C≡C.

In relation to "aliphatic residue" and "aliphatic group" the term "mono- or polysubstituted" preferably refers in the sense of this invention, with respect to the corresponding residues or groups, to the single substitution or multiple substitution, e.g. disubstitution, trisubstitution and tetrasubstitution, of one or more hydrogen atoms each independently of one another by at least one substituent selected from the group consisting of F, Cl, Br, I, NO₂, NH₂, an NH(C₁₋₄ aliphatic residue), an N(C₁₋₄ aliphatic residue)₂, a NH—C(═O)—C₁₋₄ aliphatic residue, a N(C₁₋₄ aliphatic residue)-C(═O)—C₁₋₄ aliphatic residue, a NH—S(═O)₂—C₁₋₄ aliphatic residue, N(C₁₋₄ aliphatic residue)-S(═O)₂—C₁₋₄ aliphatic residue, ═O, OH, OCH₂F, OCHF₂, OCF₃, a O—C₁₋₄-aliphatic residue, a O—C(═O)—C₁₋₄-aliphatic residue, SH, SCF₃, a S—C₁₋₄-aliphatic residue, S(═O)₂OH, a S(═O)—C₁₋₄-aliphatic residue, a S(═O)₂—C₁₋₄-aliphatic residue, a S(═O)₂—O—C₁₋₄-aliphatic residue, a S(═O)₂—NH—C₁₋₄-aliphatic residue, a S(═O)₂—N(C₁₋₄-aliphatic residue)₂, CN, CH₂F, CHF₂, CF₃, CHO, COOH, a C₁₋₄-aliphatic residue, CH₂OH, CH₂—OCH₃, C₂H₄—OH, C₂H₄—OCH₃CH₂—CF₃, a C(═O)—C₁₋₄-aliphatic residue, a C(═O)—O—C₁₋₄-aliphatic residue, a C₃₋₆-cycloaliphatic residue, a 3 to 6 membered heterocycloaliphatic residue, C(═O)—NH₂, a C(═O)—NH(C₁₋₄ aliphatic residue), and a C(═O)—N(C₁₋₄ aliphatic residue)₂. The term "polysubstituted" with respect to polysubstituted residues and groups includes the polysubstitution of these residues and groups either on different or on the same atoms, for example trisubstituted on the same carbon atom, as in the case of CF₃ or CH₂CF₃, or at various points, as in the case of CH(OH)—CH═CH—CHCl₂. A substituent can if appropriate for its part in turn be mono- or polysubstituted. The multiple substitution can be carried out using the same or using different substituents.

In relation to "cycloaliphatic residue" and "heterocycloaliphatic residue" the term "mono- or polysubstituted" preferably refers in the sense of this invention, with respect to the corresponding residues, to the single substitution or multiple substitution, e.g. disubstitution, trisubstitution and tetrasubstitution, of one or more hydrogen atoms each independently of one another by at least one substituent selected from the group consisting of F, Cl, Br, I, NO₂, NH₂, an NH(C₁₋₄ aliphatic residue), an N(C₁₋₄ aliphatic residue)₂, a NH—C(═O)—C₁₋₄ aliphatic residue, a N(C₁₋₄ aliphatic residue)-C(═O)—C₁₋₄ aliphatic residue, a NH—S(═O)₂—C₁₋₄ aliphatic residue, a N(C₁₋₄ aliphatic residue)-S(═O)₂—C₁₋₄ aliphatic residue, ═O, OH, OCH₂F, OCHF₂, OCF₃, a O—C₁₋₄-aliphatic residue, a O—C(═O)—C₁₋₄-aliphatic residue, SH, SCF₃, a S—C₁₋₄-aliphatic residue, S(═O)₂OH, a S(═O)—C₁₋₄-aliphatic residue, a S(═O)₂—C₁₋₄-aliphatic residue, a S(═O)₂—O—C₁₋₄-aliphatic residue, a S(═O)₂—NH—C₁₋₄-aliphatic residue, a S(═O)₂—N(C₁₋₄-aliphatic residue)₂, CN, CH₂F, CHF₂, CF₃, CHO, COOH, a C₁₋₄-aliphatic residue, CH₂OH, CH₂—OCH₃, C₂H₄—OH, C₂H₄—OCH₃CH₂—CF₃, a C(═O)—C₁₋₄-aliphatic residue, a C(═O)—O—C₁₋₄-aliphatic residue, a C₃₋₆-cycloaliphatic residue, a 3 to 6 membered heterocycloaliphatic residue, C(═O)—NH₂, a C(═O)—NH(C₁₋₄ aliphatic residue), and a C(═O)—N(C₁₋₄ aliphatic residue)₂. The term "polysubstituted" with respect to polysubstituted residues and groups includes the polysubstitution of these residues and groups either on different or on the same atoms, for example disubstituted on the same carbon atom, as in the case of 1,1-difluorocyclohexyl, or at various points, as in the case of 1-chloro-3-fluorocyclohexyl. A substituent can if appropriate for its part in turn be mono- or polysubstituted. The multiple substitution can be carried out using the same or using different substituents.

Preferred substituents of "aliphatic residue" and "aliphatic group" are selected from the group consisting of F, Cl, Br, I, NO₂, NH₂, an NH(C₁₋₄ aliphatic residue), an N(C₁₋₄ aliphatic residue)₂, ═O, OH, OCH₂F, OCHF₂, OCF₃, a O—C₁₋₄-aliphatic residue, SH, SCF₃, a S—C₁₋₄-aliphatic residue, a S(═O)—C₁₋₄-aliphatic residue, a S(═O)₂—C₁₋₄-aliphatic residue, a S(═O)₂—NH—C₁₋₄-aliphatic residue, a S(═O)₂—N(C₁₋₄-aliphatic residue)₂, CN, CH₂F, CHF₂, CF₃, a C₁₋₄-aliphatic residue, CH₂OH, CH₂—OCH₃, C₂H₄—OH, C₂H₄—OCH₃CH₂—CF₃, a C(═O)—C₁₋₄-aliphatic residue, a C(═O)—O—C₁₋₄-aliphatic residue, CONH₂, a C(═O)—NH(C₁₋₄ aliphatic residue), and a C(═O)—N(C₁₋₄ aliphatic residue)₂.

Preferred substituents of "cycloaliphatic residue" and "heterocycloaliphatic residue" are selected from the group consisting of F, Cl, Br, I, NO₂, NH₂, an NH(C₁₋₄ aliphatic residue), an N(C₁₋₄ aliphatic residue)₂, ═O, OH, OCH₂F, OCHF₂, OCF₃, a O—C₁₋₄-aliphatic residue, SH, SCF₃, a S—C₁₋₄-aliphatic residue, a S(═O)—C₁₋₄-aliphatic residue, a S(═O)₂—C₁₋₄-aliphatic residue, a S(═O)₂—NH—C₁₋₄-aliphatic residue, a S(═O)₂—N(C₁₋₄-aliphatic residue)₂, CN, CH₂F, CHF₂, CF₃, a C₁₋₄-aliphatic residue, CH₂OH, CH₂—OCH₃, C₂H₄—OH, C₂H₄—OCH₃CH₂—CF₃, a C(═O)—C₁₋₄-aliphatic residue, a C(═O)—O—C₁₋₄-aliphatic residue, CONH₂, a C(═O)—NH(C₁₋₄ aliphatic residue), and a C(═O)—N(C₁₋₄ aliphatic residue)₂.

In relation to "aryl" and "heteroaryl" the term "mono- or polysubstituted" preferably refers in the sense of this invention to the single substitution or multiple substitution, e.g. disubstitution, trisubstitution and tetrasubstitution, of one or more hydrogen atoms each independently of one another by at least one substituent selected from the group consisting of F, Cl, Br, I, NO₂, NH₂,

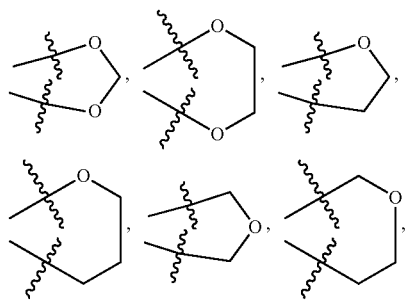

an NH(C$_{1-4}$ aliphatic residue), an N(C$_{1-4}$ aliphatic residue)$_2$, an NH—C(=O)—C$_{1-4}$ aliphatic residue, N(C$_{1-4}$ aliphatic residue)-C(=O)—C$_{1-4}$ aliphatic residue, an NH—S(=O)$_2$—C$_{1-4}$ aliphatic residue, a N(C$_{1-4}$ aliphatic residue)-S(=O)$_2$—C$_{1-4}$ aliphatic residue, OH, OCF$_3$, OCFH$_2$, OCF$_2$H, a O—C$_{1-4}$-aliphatic residue, a O—C(=O)—C$_{1-4}$-aliphatic residue, SH, SCF$_3$, a S—C$_{1-4}$-aliphatic residue, S(=O)$_2$OH, a S(=O)—C$_{1-4}$-aliphatic residue, a S(=O)$_2$—C$_{1-4}$-aliphatic residue, a S(=O)$_2$—O—C$_{1-4}$-aliphatic residue, a S(=O)$_2$—NH—C$_{1-4}$-aliphatic residue, a S(=O)$_2$—N(C$_{1-4}$-aliphatic residue)$_2$, CN, CF$_3$, CF$_2$H, CHF$_2$, C(=O)H, C(=O)OH, a C$_{1-4}$-aliphatic residue, CH$_2$OH, CH$_2$—OCH$_3$, C$_2$H$_4$—OH, C$_2$H$_4$—OCH$_3$, a C(=O)—C$_{1-4}$-aliphatic residue, a C(=O)—O—C$_{1-4}$-aliphatic residue, a C$_{3-6}$-cycloaliphatic residue, a 3 to 6 membered heterocycloaliphatic residue, benzyl, aryl, heteroaryl, C(=O)—NH$_2$, a C(=O)—NH(C$_{1-4}$ aliphatic residue), and a C(=O)—N(C$_{1-4}$ aliphatic residue)$_2$ on one or if appropriate different atoms, wherein a substituent can if appropriate for its part in turn be mono- or polysubstituted. The multiple substitution is carried out employing the same or using different substituents.

Preferred substituents of "aryl" and "heteroaryl" are selected from the group consisting of F, Cl, Br, I, NO$_2$, NH$_2$,

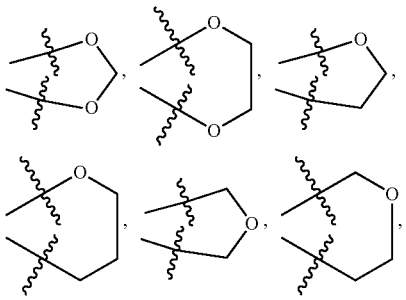

an NH(C$_{1-4}$ aliphatic residue), an N(C$_{1-4}$ aliphatic residue)$_2$, an NH—C(=O)—C$_{1-4}$ aliphatic residue, an NH—S(=O)$_2$—C$_{1-4}$ aliphatic residue, OH, OCF$_3$, OCFH$_2$, OCF$_2$H, a O—C$_{1-4}$-aliphatic residue, SH, SCF$_3$, a S—C$_{1-4}$-aliphatic residue, S(=O)$_2$OH, a S(=O)—C$_{1-4}$-aliphatic residue, a S(=O)$_2$—C$_{1-4}$-aliphatic residue, a S(=O)$_2$—NH—C$_{1-4}$-aliphatic residue, a S(=O)$_2$—N(C$_{1-4}$-aliphatic residue)$_2$, CN, CF$_3$, CF$_2$H, CHF$_2$, a C$_{1-4}$-aliphatic residue, CH$_2$OH, CH$_2$—OCH$_3$, C$_2$H$_4$—OH, C$_2$H$_4$—OCH$_3$, a C(=O)—C$_{1-4}$-aliphatic residue, a C(=O)—O—C$_{1-4}$-aliphatic residue, a C$_{3-6}$-cycloaliphatic residue, a 3 to 6 membered heterocycloaliphatic residue, CONH$_2$, a C(=O)—NH(C$_{1-4}$ aliphatic residue), a C(=O)—N(C$_{1-4}$ aliphatic residue)$_2$, aryl, preferably phenyl, or benzyl, in each case unsubstituted or mono- or polysubstituted with at least one substituent selected from the group consisting of F, Cl, Br, I, CN, CF$_3$, CH$_3$, C$_2$H$_5$, iso-propyl, tert.-butyl, C(=O)—OH, C(=O)—CH$_3$, C(=O)—C$_2$H$_5$, C(=O)—O—CH$_3$ and C(=O)—O—C$_2$H$_5$, O—CH$_3$, OCF$_3$, O—CH$_2$—OH, O—CH$_2$—O—CH$_3$, SH, S—CH$_3$, SCF$_3$, NO$_2$, NH$_2$, N(CH$_3$)$_2$, N(CH$_3$)(C$_2$H$_5$) and N(C$_2$H$_5$)$_2$, heteroaryl, preferably pyridyl, thienyl, furyl, thiazolyl or oxazolyl, in each case unsubstituted or mono- or polysubstituted with at least one substituent selected from the group consisting of F, Cl, Br, I, CN, CF$_3$, CH$_3$, C$_2$H$_5$, iso-propyl, tert.-butyl, C(=O)—OH, C(=O)—CH$_3$, C(=O)—C$_2$H$_5$, C(=O)—O—CH$_3$ and C(=O)—O—C$_2$H$_5$, O—CH$_3$, OCF$_3$, O—CH$_2$—OH, O—CH$_2$—O—CH$_3$, SH, S—CH$_3$, SCF$_3$, NO$_2$, NH$_2$, N(CH$_3$)$_2$, N(CH$_3$)(C$_2$H$_5$) and N(C$_2$H$_5$)$_2$.

The compounds according to the invention are defined by substituents, for example by R$^1$, R$^2$ and R$^3$ (1$^{st}$ generation substituents) which are for their part if appropriate substituted (2$^{nd}$ generation substituents). Depending on the definition, these substituents of the substituents can for their part be re-substituted (3$^{rd}$ generation substituents). If, for example, R$^1$ is = a C$_{1-10}$ aliphatic residue (1$^{st}$ generation substituent), then the C$_{1-10}$ aliphatic residue can for its part be substituted, for example with a NH—C$_{1-4}$ aliphatic residue (2$^{nd}$ generation substituent). This produces the functional group R$^1$= (C$_{1-10}$ aliphatic residue-NH—C$_{1-4}$ aliphatic residue). The NH—C$_{1-4}$ aliphatic residue can then for its part be resubstituted, for example with Cl (3$^{rd}$ generation substituent). Overall, this produces the functional group R$^1$=C$_{1-10}$ aliphatic residue-NH—C$_{1-4}$ aliphatic residue, wherein the C$_{1-4}$ aliphatic residue of the NH—C$_{1-4}$ aliphatic residue is substituted by Cl.

However, in a preferred embodiment, the 3$^{rd}$ generation substituents may not be resubstituted, i.e. there are then no 4$^{th}$ generation substituents.

In another preferred embodiment, the 2$^{nd}$ generation substituents may not be resubstituted, i.e. there are then not even any 3$^{rd}$ generation substituents. In other words, in this embodiment, in the case of general formula (I), for example, the functional groups for R$^1$ to R$^7$ can each if appropriate be substituted; however, the respective substituents may then for their part not be resubstituted.

In some cases, the compounds according to the invention are defined by substituents which are or carry an aryl or heteroaryl residue, respectively unsubstituted or mono- or polysubstituted, or which form together with the carbon atom(s) or heteroatom(s) connecting them, as the ring member or as the ring members, a ring, for example an aryl or heteroaryl, in each case unsubstituted or mono- or polysubstituted. Both these aryl or heteroaryl residues and the (hetero)aromatic ring systems formed in this way can if appropriate be condensed with a cycloaliphatic, preferably a C$_{3-6}$ cycloaliphatic residue, or heterocycloaliphatic residue, preferably a 3 to 6 membered heterocycloaliphatic residue, or with aryl or heteroaryl, e.g. with a C$_{3-6}$ cycloaliphatic residue such as cyclopentyl, or a 3 to 6 membered heterocycloaliphatic residue such as morpholinyl, or an aryl such as phenyl, or a heteroaryl such as pyridyl, wherein the cycloaliphatic or heterocycloaliphatic residues, aryl or heteroaryl residues condensed in this way can for their part be respectively unsubstituted or mono- or polysubstituted.

In some cases, the compounds according to the invention are defined by substituents which are or carry a cycloaliphatic residue or a heterocycloaliphatic residue, respectively, in each case unsubstituted or mono- or polysubstituted, or which form together with the carbon atom(s) or heteroatom(s) connecting them, as the ring member or as the ring members, a ring, for example a cycloaliphatic or a heterocycloaliphatic ring system. Both these cycloaliphatic or heterocycloaliphatic ring systems and the (hetero)cycloaliphatic ring systems formed in this manner can if appropriate be condensed with aryl or heteroaryl, preferably selected from the group consisting of phenyl, pyridyl and thienyl, or with a cycloaliphatic residue, preferably a C$_{3-6}$ cycloaliphatic residue, or a heterocycloaliphatic residue, preferably a 3 to 6 membered heterocycloaliphatic residue, e.g. with an aryl such as phenyl, or a heteroaryl such as pyridyl, or a cycloaliphatic residue such as cyclohexyl, or a heterocycloaliphatic residue such as morpholinyl, wherein the aryl or heteroaryl residues or cycloaliphatic or heterocycloaliphatic residues condensed in this way can for their part be respectively unsubstituted or mono- or polysubstituted.

Within the scope of the present invention, the symbol

used in the formulae denotes a link of a corresponding residue to the respective superordinate general structure.

If a residue occurs multiply within a molecule, then this residue can have respectively different meanings for various substituents: if, for example, both $R^2$ and $R^3$ denote a 3 to 6 membered heterocycloaliphatic residue, then the 3 to 6 membered heterocycloaliphatic residue can e.g. represent morpholinyl for $R^2$ and can represent piperazinyl for $R^3$.

In a preferred embodiment of the compound according to general formula (I) the particular radicals $R^1$-$R^6$ have the meanings described herein in connection with the compounds according to the invention and preferred embodiments thereof and $R^7$ represents a $C_{2-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted;

on the condition that if $R^7$ denotes a 3 to 10 membered heterocycloaliphatic residue, the 3 to 10 membered heterocycloaliphatic residue is linked via a carbon atom, or denotes S—$R^{8a}$, S(=O)—$R^{8b}$, S(=O)$_2$—$R^{8c}$, O—$R^9$ or N($R^{10}R^{11}$), preferably denotes S—$R^{8a}$, S(=O)—$R^{8b}$, S(=O)$_2$—$R^{8c}$ or O—$R^9$, wherein $R^{8a}$, $R^{8b}$, $R^{8c}$ and $R^9$ in each case represent a $C_{1-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted;

on the condition that if $R^{8a}$, $R^{8b}$, $R^{8c}$ and $R^9$ denotes a 3 to 10 membered heterocycloaliphatic residue, the 3 to 10 membered heterocycloaliphatic residue is linked via a carbon atom, $R^{10}$ represents a $C_{1-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted;

on the condition that if $R^{10}$ denotes a 3 to 10 membered heterocycloaliphatic residue, the 3 to 10 membered heterocycloaliphatic residue is linked via a carbon atom;

$R^{11}$ denotes H or a $C_{1-10}$-aliphatic residue, unsubstituted or mono- or polysubstituted;

or $R^{10}$ and $R^{11}$ form together with the nitrogen atom connecting them a 3 to 10 membered heterocycloaliphatic residue, unsubstituted or mono- or polysubstituted; which may optionally be condensed with aryl or heteroaryl, wherein the aryl or heteroaryl residues condensed in this way can for their part be respectively unsubstituted or mono- or polysubstituted.

In another preferred embodiment of the compound according to general formula (I) the particular radicals $R^1$-$R^6$ have the meanings described herein in connection with the compounds according to the invention and preferred embodiments thereof and $R^7$ represents a $C_1$-aliphatic residue, mono- or polysubstituted; a $C_{2-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted; preferably represents a $C_{2-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted, on the condition that if $R^7$ denotes a 3 to 10 membered heterocycloaliphatic residue, the 3 to 10 membered heterocycloaliphatic residue is linked via a carbon atom.

Further preferred embodiments of the compound according to general formula (I) have the general formulae (I-a), (I-b) and/or (I-c),

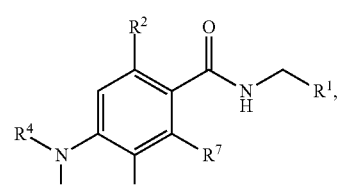

(I-a)

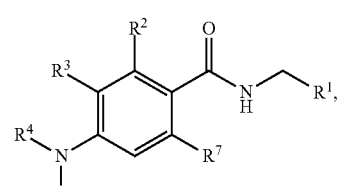

(I-b)

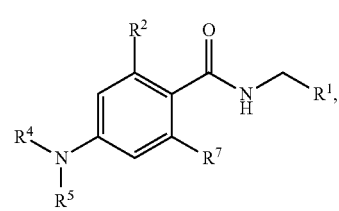

(I-c)

wherein the particular radicals $R^1$, $R^2$, $R^3$, $R^4$, $R^5$, $R^6$ and $R^7$ have the meanings described herein in connection with the compounds according to the invention and preferred embodiments thereof.

Another preferred embodiment of the compound according to general formula (I) has the general formula (I-d),

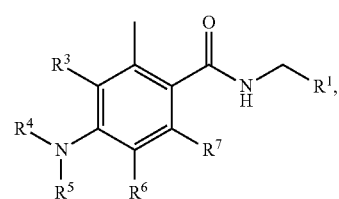

(I-d)

wherein the particular radicals $R^1$, $R^3$, $R^4$, $R^5$, $R^6$ and $R^7$ have the meanings described herein in connection with the compounds according to the invention and preferred embodiments thereof.

In yet another preferred embodiment of the compound according to general formula (I) radicals $R^2$, $R^3$, $R^4$, $R^5$, $R^6$ and $R^7$ have the meanings described herein in connection with the compounds according to the invention and preferred embodiments thereof, and $R^1$ represents aryl or heteroaryl, preferably aryl, in each case unsubstituted or mono- or polysubstituted.

In case $R^4$ and $R^5$ of the compound of general formula (I) form together with the nitrogen atom connecting them a 3 to 10 membered heterocycloaliphatic residue, preferably a 3 to 6 membered heterocycloaliphatic residue, unsubstituted or mono- or polysubstituted, said heterocycloaliphatic residue may optionally be condensed with aryl or heteroaryl or with a $C_{3-10}$ cycloaliphatic residue or with a 3 to 10 membered heterocycloaliphatic residue, wherein the aryl, heteroaryl, $C_{3-10}$ cycloaliphatic or 3 to 10 membered heterocycloaliphatic residues condensed in this way can for their part be respectively unsubstituted or mono- or polysubstituted.

In another particularly preferred embodiment of the compound according to general formula (I) radicals $R^1$, $R^2$, $R^3$, $R^6$ and $R^7$ have the meanings described herein in connection with the compounds according to the invention and preferred embodiments thereof, and $R^4$ and $R^5$ together with the nitrogen atom connecting them form a 3 to 10 membered heterocycloaliphatic residue, preferably a 3 to 10 membered heterocycloaliphatic residue, selected from the group consisting of morpholinyl, piperazinyl and piperidinyl, unsubstituted or mono- or polysubstituted, more preferably together with the nitrogen atom connecting them form a morpholinyl, unsubstituted or mono- or polysubstituted.

In another particularly preferred embodiment of the compound according to general formula (I) radicals $R^1$, $R^2$, $R^4$, $R^5$ and $R^7$ have the meanings described herein in connection with the compounds according to the invention and preferred embodiments thereof, and at least one of residues $R^3$ and $R^6$ denotes H, preferably both $R^3$ and $R^6$ denote H.

In case $R^{10}$ and $R^{11}$ of the compound of general formula (I) form together with the nitrogen atom connecting them a 3 to 10 membered heterocycloaliphatic residue, preferably a 3 to 6 membered heterocycloaliphatic residue, unsubstituted or mono- or polysubstituted, said heterocycloaliphatic residue may optionally be condensed with aryl or heteroaryl or with a $C_{3-10}$ cycloaliphatic residue or with a 3 to 10 membered heterocycloaliphatic residue, wherein the aryl, heteroaryl, $C_{3-10}$ cycloaliphatic or 3 to 10 membered heterocycloaliphatic residues condensed in this way can for their part be respectively unsubstituted or mono- or polysubstituted.

Yet another preferred embodiment of present invention is a compound according to general formula (I), wherein $R^1$ denotes a $C_{1-10}$-aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$-aliphatic residue, $OCH_2F$, $OCHF_2$, $OCF_3$, SH, $SCF_3$, a S—$C_{1-4}$-aliphatic residue, a S(=O)—$C_{1-4}$-aliphatic residue, a S(=O)$_2$—$C_{1-4}$-aliphatic residue, $CH_2F$, $CHF_2$, $CF_3$, CN, a $C_{1-4}$-aliphatic residue and C(=O)—OH,
wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a S(=O)$_2$—$C_{1-4}$-aliphatic residue, $CH_2F$, $CHF_2$, $CF_3$, CN, a $C_{1-4}$-aliphatic residue, C(=O)—OH, a $C_{3-6}$-cycloaliphatic residue, and a 3 to 6 membered heterocycloaliphatic residue,
wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue, and
wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a S(=O)$_2$—$C_{1-4}$-aliphatic residue, $CH_2F$, $CHF_2$, $CF_3$, CN, a $C_{1-4}$-aliphatic residue and C(=O)—OH, and wherein the $C_{3-10}$-cycloaliphatic residue or the 3 to 10 membered heterocycloaliphatic residue may in each case optionally bridged via a $C_{1-8}$ aliphatic group, which in turn may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a S(=O)$_2$—$C_{1-4}$-aliphatic residue, $CH_2F$, $CHF_2$, $CF_3$, CN, a $C_{1-4}$-aliphatic residue and C(=O)—OH, or denotes an aryl or heteroaryl, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a S(=O)$_2$—$C_{1-4}$-aliphatic residue, $CH_2F$, $CHF_2$, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, a $C_{3-6}$ cycloaliphatic residue, a 3 to 6 membered heterocycloaliphatic residue,

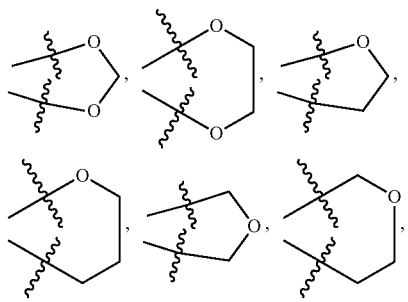

benzyl, phenyl, thienyl, pyridyl, furyl, thiazolyl and oxazolyl, wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted $O—C_{1-4}$-aliphatic residue, and wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, an $O—C_{1-4}$ aliphatic residue, $OCH_2F$, $OCHF_2$, $OCF_3$, $O—CH_2—OH$, $O—CH_2—O—CH_3$, SH, $SCF_3$, a $S—C_{1-4}$ aliphatic residue, a $S(=O)—C_{1-4}$-aliphatic residue, a $S(=O)_2—C_{1-4}$-aliphatic residue, $CH_2F$, $CHF_2$, $CF_3$, CN, a $C_{1-4}$-aliphatic residue, $C(=O)—OH$, $C(=O)—CH_3$, $C(=O)—C_2H_5$, $C(=O)—O—CH_3$ and $C(=O)—O—C_2H_5$, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an $O—C_{1-4}$ aliphatic residue, $OCH_2F$, $OCHF_2$, $OCF_3$, SH, $SCF_3$, a $S—C_{1-4}$ aliphatic residue, a $S(=O)—C_{1-4}$-aliphatic residue, a $S(=O)_2—C_{1-4}$-aliphatic residue, $CH_2F$, $CHF_2$, $CF_3$, CN, a $C_{1-4}$-aliphatic residue and $C(=O)—OH$, and wherein the aryl or the heteroaryl residue may in each case be optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an $O—C_{1-4}$ aliphatic residue, $OCH_2F$, $OCHF_2$, $OCF_3$, SH, $SCF_3$, a $S—C_{1-4}$ aliphatic residue, a $S(=O)—C_{1-4}$-aliphatic residue, a $S(=O)_2—C_{1-4}$-aliphatic residue, $CH_2F$, $CHF_2$, $CF_3$, CN and $C(=O)—OH$, $R^2$ represents F; Cl; Br; I; CN; $CH_2F$, $CHF_2$, $CF_3$; $NO_2$; $OCH_2F$, $OCHF_2$, $OCF_3$; $SCF_3$; a $C_{1-4}$-aliphatic residue, a $S—C_{1-4}$-aliphatic residue, a $S(=O)—C_{1-4}$-aliphatic residue, a $S(=O)_2—C_{1-4}$-aliphatic residue, or a $O—C_{1-4}$-aliphatic residue, wherein the $C_{1-4}$-aliphatic residue in each case may be unsubstituted or mono- or polysubstituted with at least one substituent selected from the group consisting of F, Cl, Br, I, =O, OH, and an unsubstituted $O—C_{1-4}$-aliphatic residue;

a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a $C_{1-4}$-aliphatic residue and an $O—C_{1-4}$-aliphatic residue, wherein the $C_{1-4}$-aliphatic residue in each case may be unsubstituted or mono- or polysubstituted with at least one substituent selected from the group consisting of F, Cl, Br, I, =O, OH, and an unsubstituted $O—C_{1-4}$-aliphatic residue, and wherein the $C_{3-6}$-cycloaliphatic residue or the 3 to 6 membered heterocycloaliphatic residue may in each case be optionally bridged via a $C_{1-4}$ aliphatic group, which in turn may be unsubstituted or mono- or polysubstituted with at least one substituent selected from the group consisting of F, Cl, Br, I, =O, OH, an unsubstituted $C_{1-4}$-aliphatic residue and an unsubstituted $O—C_{1-4}$-aliphatic residue, $R^3$ represents H; F; Cl; Br; I; CN; $CH_2F$, $CHF_2$, $CF_3$; $SCF_3$; $NO_2$; $OCH_2F$, $OCHF_2$, $OCF_3$; a $C_{1-4}$-aliphatic residue, a $O—C_{1-4}$-aliphatic residue, a $S—C_{1-4}$-aliphatic residue, a $S(=O)—C_{1-4}$-aliphatic residue, a $S(=O)_2—C_{1-4}$-aliphatic residue, wherein the $C_{1-4}$ aliphatic residue may in each case be unsubstituted or mono- or polysubstituted with at least one substituent selected from the group consisting of F, Cl, Br, I, =O, OH, and an unsubstituted $O—C_{1-4}$-aliphatic residue;

a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a $C_{1-4}$-aliphatic residue and a $O—C_{1-4}$-aliphatic residue, wherein the $C_{1-4}$-aliphatic residue in each case may be unsubstituted or mono- or polysubstituted with at least one substituent selected from the group consisting of F, Cl, Br, I, =O, OH, and an unsubstituted $O—C_{1-4}$-aliphatic residue, and wherein the $C_{3-6}$-cycloaliphatic residue or the 3 to 6 membered heterocycloaliphatic residue may in each case be optionally bridged via a $C_{1-4}$ aliphatic group, which in turn may be unsubstituted or mono- or polysubstituted with at least one substituent selected from the group consisting of F, Cl, Br, I, =O, OH, an unsubstituted $C_{1-4}$-aliphatic residue and an unsubstituted $O—C_{1-4}$-aliphatic residue, $R^4$ denotes a $C_{1-10}$-aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an $O—C_{1-4}$-aliphatic residue, $OCH_2F$, $OCHF_2$, $OCF_3$, SH, $SCF_3$, a $S—C_{1-4}$-aliphatic residue, a $S(=O)—C_{1-4}$-aliphatic residue, a $S(=O)_2—C_{1-4}$-aliphatic residue, $CH_2F$, $CHF_2$, $CF_3$, CN, a $C_{1-4}$-aliphatic residue, a $C(=O)—O—C_{1-4}$-aliphatic residue, and $C(=O)—OH$, wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted $O—C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an $O—C_{1-4}$ aliphatic residue, $OCH_2F$, $OCHF_2$, $OCF_3$, SH, $SCF_3$, a $S—C_{1-4}$ aliphatic residue, a $S(=O)—C_{1-4}$-aliphatic residue, a $S(=O)_2—C_{1-4}$-aliphatic residue, $CH_2F$, $CHF_2$, $CF_3$, CN, a $C_{1-4}$-aliphatic residue, $C(=O)—OH$, a $C(=O)—O—C_{1-4}$-aliphatic residue a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted $O—C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an $O—C_{1-4}$ aliphatic residue, $OCH_2F$, $OCHF_2$, $OCF_3$, SH, $SCF_3$, a $S—C_{1-4}$ aliphatic residue, a $S(=O)—C_{1-4}$- aliphatic residue, a S(=O)$_2$—C$_{1-4}$-aliphatic residue, CH$_2$F, CHF$_2$, CF$_3$, CN, a C$_{1-4}$-aliphatic residue and C(=O)—OH, and wherein the C$_{3-10}$-cycloaliphatic residue or the 3 to 10 membered heterocycloaliphatic residue may in each case optionally bridged via a C$_{1-8}$ aliphatic group, which in turn may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, a C(=O)—O—C$_{1-4}$-aliphatic residue, OCH$_2$F, OCHF$_2$, OCF$_3$, SH, SCF$_3$, a S—C$_{1-4}$ aliphatic residue, a S(=O)—C$_{1-4}$-aliphatic residue, a S(=O)$_2$—C$_{1-4}$-aliphatic residue, CH$_2$F, CHF$_2$, CF$_3$, CN, a C$_{1-4}$-aliphatic residue and C(=O)—OH, on the condition that if R$^4$ denotes a 3 to 10 membered heterocycloaliphatic residue, the 3 to 10 membered heterocycloaliphatic residue is linked via a carbon atom, or denotes an aryl or heteroaryl, in each case unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, an O—C$_{1-4}$ aliphatic residue, OCH$_2$F, OCHF$_2$, OCF$_3$, SH, SCF$_3$, a S—C$_{1-4}$ aliphatic residue, a S(=O)—C$_{1-4}$-aliphatic residue, a S(=O)$_2$—C$_{1-4}$-aliphatic residue, CH$_2$F, CHF$_2$, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, a C$_{3-6}$ cycloaliphatic residue, a 3 to 6 membered heterocycloaliphatic residue,

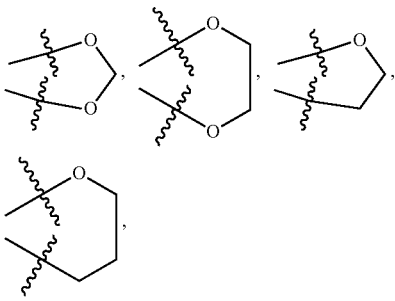

benzyl, phenyl, thienyl, pyridyl, furyl, thiazolyl and oxazolyl, wherein the C$_{1-4}$-aliphatic residue in each case may be unsubstituted or mono- or polysubstituted with at least one substituent selected from the group consisting of F, Cl, Br, I, OH, OCH$_2$F, OCHF$_2$, OCF$_3$, CH$_2$F, CHF$_2$, CF$_3$ and an unsubstituted O—C$_{1-4}$-aliphatic residue, and wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, an O—C$_{1-4}$ aliphatic residue, OCH$_2$F, OCHF$_2$, OCF$_3$, O—CH$_2$—OH, O—CH$_2$—O—CH$_3$, SH, SCF$_3$, a S—C$_{1-4}$ aliphatic residue, a S(=O)—C$_{1-4}$- aliphatic residue, a S(=O)$_2$—C$_{1-4}$-aliphatic residue, CH$_2$F, CHF$_2$, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, and wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCH$_2$F, OCHF$_2$, OCF$_3$, SH, SCF$_3$, a S—C$_{1-4}$ aliphatic residue, a S(=O)—C$_{1-4}$- aliphatic residue, a S(=O)$_2$—C$_{1-4}$-aliphatic residue, CH$_2$F, CHF$_2$, CF$_3$, CN, a C$_{1-4}$-aliphatic residue and C(=O)—OH, and wherein the aryl or the heteroaryl residue may in each case be optionally bridged via a C$_{1-8}$ aliphatic group, which in turn may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCH$_2$F, OCHF$_2$, OCF$_3$, SH, SCF$_3$, a S—C$_{1-4}$ aliphatic residue, a S(=O)—C$_{1-4}$-aliphatic residue, a S(=O)$_2$—C$_{1-4}$-aliphatic residue, CH$_2$F, CHF$_2$, CF$_3$, CN and C(=O)—OH, R$^5$ denotes H or a C$_{1-10}$-aliphatic residue, unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCH$_2$F, OCHF$_2$, OCF$_3$, SH, SCF$_3$, a S—C$_{1-4}$ aliphatic residue, a S(=O)—C$_{1-4}$-aliphatic residue, a S(=O)$_2$—C$_{1-4}$-aliphatic residue, CH$_2$F, CHF$_2$, CF$_3$, CN, a C$_{1-4}$-aliphatic residue and C(=O)—OH, wherein the C$_{1-4}$-aliphatic residue in each case may be unsubstituted or mono- or polysubstituted with at least one substituent selected from the group consisting of F, Cl, Br, I, OH, OCH$_2$F, OCHF$_2$, OCF$_3$, CH$_2$F, CHF$_2$, CF$_3$ and an unsubstituted O—C$_{1-4}$-aliphatic residue, or R$^4$ and R$^5$ form together with the nitrogen atom connecting them a 3 to 10 membered heterocycloaliphatic residue, unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCH$_2$F, OCHF$_2$, OCF$_3$, SH, SCF$_3$, a S—C$_{1-4}$ aliphatic residue, a S(=O)—C$_{1-4}$-aliphatic residue, a S(=O)$_2$—C$_{1-4}$-aliphatic residue, CH$_2$F, CHF$_2$, CF$_3$, CN, a C$_{1-4}$-aliphatic residue, C(=O)—OH, a C$_{3-6}$ cycloaliphatic residue, and a 3 to 6 membered heterocycloaliphatic residue, wherein the C$_{1-4}$-aliphatic residue in each case may be unsubstituted or mono- or polysubstituted with at least one substituent selected from the group consisting of F, Cl, Br, I, =O, OH, OCH$_2$F, OCHF$_2$, OCF$_3$, CH$_2$F, CHF$_2$, CF$_3$ and an unsubstituted O—C$_{1-4}$-aliphatic residue, and wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCH$_2$F, OCHF$_2$, OCF$_3$, SH, SCF$_3$, a S—C$_{1-4}$ aliphatic residue, a S(=O)—C$_{1-4}$- aliphatic residue, a S(=O)$_2$—C$_{1-4}$-aliphatic residue, CH$_2$F, CHF$_2$, CF$_3$, CN, a C$_{1-4}$-aliphatic residue and C(=O)—OH, and wherein the 3 to 10 membered heterocycloaliphatic residue formed by R$^4$ and R$^5$ together with the nitrogen atom connecting them may optionally be condensed with aryl or heteroaryl, wherein the aryl or heteroaryl residues condensed in this way can for their part be respectively unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, an O—C$_{1-4}$ aliphatic residue, OCH$_2$F, OCHF$_2$, OCF$_3$, SH, SCF$_3$, a S—C$_{1-4}$ aliphatic residue, a S(=O)—C$_{1-4}$-aliphatic residue, a S(=O)$_2$—C$_{1-4}$-aliphatic residue, CH$_2$F, CHF$_2$, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, a C$_{3-6}$ cycloaliphatic residue, a 3 to 6 membered heterocycloaliphatic residue,

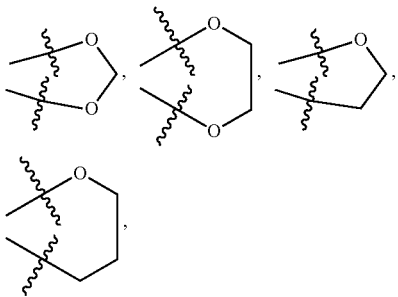

benzyl, phenyl, thienyl, pyridyl, furyl, thiazolyl and oxazolyl, and wherein the 3 to 10 membered heterocycloaliphatic residue formed by R$^4$ and R$^5$ together with the nitrogen atom connecting them may optionally be condensed with a C$_{3-10}$ cycloaliphatic residue or a 3 to 10 membered heterocycloaliphatic residue, wherein the C$_{3-10}$ cycloaliphatic residue or a 3 to 10 membered heterocycloaliphatic residue condensed in this way can for their part be respectively unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, =O, OH, an O—C$_{1-4}$ aliphatic residue, OCH$_2$F, OCHF$_2$, OCF$_3$, SH, SCF$_3$, a S—C$_{1-4}$ aliphatic residue, a S(=O)—C$_{1-4}$-aliphatic residue, a S(=O)$_2$—C$_{1-4}$-aliphatic residue, CH$_2$F, CHF$_2$, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, a C$_{3-6}$ cycloaliphatic residue, a 3 to 6 membered heterocycloaliphatic residue, benzyl, phenyl, thienyl, pyridyl, furyl, thiazolyl and oxazolyl, wherein the C$_{1-4}$-aliphatic residue in each case may be unsubstituted or mono- or polysubstituted with at least one substituent selected from the group consisting of F, Cl, Br, I, OH, OCH$_2$F, OCHF$_2$, OCF$_3$, CH$_2$F, CHF$_2$, CF$_3$ and an unsubstituted O—C$_{1-4}$-aliphatic residue, and wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, an O—C$_{1-4}$ aliphatic residue, OCH$_2$F, OCHF$_2$, OCF$_3$, O—CH$_2$—OH, O—CH$_2$—O—CH$_3$, SH, SCF$_3$, a S—C$_{1-4}$ aliphatic residue, a S(=O)—C$_{1-4}$-aliphatic residue, a S(=O)$_2$—C$_{1-4}$-aliphatic residue, CH$_2$F, CHF$_2$, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, and wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCH$_2$F, OCHF$_2$, OCF$_3$, SH, SCF$_3$, a S—C$_{1-4}$ aliphatic residue, a S(=O)—C$_{1-4}$-aliphatic residue, a S(=O)$_2$—C$_{1-4}$-aliphatic residue, CH$_2$F, CHF$_2$, CF$_3$, CN, a C$_{1-4}$-aliphatic residue and C(=O)—OH, R$^6$ represents H; F; Cl; Br; I; CN; CH$_2$F, CHF$_2$, CF$_3$; SCF$_3$; NO$_2$; OCH$_2$F, OCHF$_2$, OCF$_3$; a C$_{1-4}$-aliphatic residue, a O—C$_{1-4}$-aliphatic residue, a S—C$_{1-4}$-aliphatic residue, a S(=O)—C$_{1-4}$-aliphatic residue, a S(=O)$_2$—C$_{1-4}$-aliphatic residue, wherein the C$_{1-4}$ aliphatic residue may in each case be unsubstituted or mono- or polysubstituted with at least one substituent selected from the group consisting of F, Cl, Br, I, =O, OH, and an unsubstituted O—C$_{1-4}$-aliphatic residue;

a C$_{3-6}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a C$_{1-4}$-aliphatic residue and a O—C$_{1-4}$-aliphatic residue, wherein the C$_{1-4}$-aliphatic residue in each case may be unsubstituted or mono- or polysubstituted with at least one substituent selected from the group consisting of F, Cl, Br, I, =O, OH, and an unsubstituted O—C$_{1-4}$-aliphatic residue, and wherein the C$_{3-6}$-cycloaliphatic residue or the 3 to 6 membered heterocycloaliphatic residue may in each case be optionally bridged via a C$_{1-4}$ aliphatic group, which in turn may be unsubstituted or mono- or polysubstituted with at least one substituent selected from the group consisting of F, Cl, Br, I, =O, OH, an unsubstituted C$_{1-4}$-aliphatic residue and an unsubstituted O—C$_{1-4}$-aliphatic residue, R$^7$ denotes CF$_3$, CHF$_2$, CH$_2$F, CF$_2$Cl, CFCl$_2$, CH$_2$OH, CH$_2$OCH$_3$, a C$_{2-10}$-aliphatic residue, unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$-aliphatic residue, OCH$_2$F, OCHF$_2$, OCF$_3$, SH, SCF$_3$, a S—C$_{1-4}$-aliphatic residue, a S(=O)—C$_{1-4}$-aliphatic residue, a S(=O)$_2$—C$_{1-4}$-aliphatic residue, CN, a C$_{1-4}$-aliphatic residue and C(=O)—OH, wherein the C$_{1-4}$-aliphatic residue in each case may be unsubstituted or mono- or polysubstituted with at least one substituent selected from the group consisting of F, Cl, Br, I, OH, OCH$_2$F, OCHF$_2$, OCF$_3$, CH$_2$F, CHF$_2$, CF$_3$ and an unsubstituted O—C$_{1-4}$-aliphatic residue, or denotes a C$_{3-10}$-cycloaliphatic residue or a 3 to 10 membered heterocycloaliphatic residue, in each case unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCH$_2$F, OCHF$_2$, OCF$_3$, SH, SCF$_3$, a S—C$_{1-4}$ aliphatic residue, a S(=O)—C$_{1-4}$-aliphatic residue, a S(=O)$_2$—C$_{1-4}$-aliphatic residue, CH$_2$F, CHF$_2$, CF$_3$, CN, a C$_{1-4}$-aliphatic residue, and C(=O)—OH, wherein the C$_{1-4}$-aliphatic residue in each case may be unsubstituted or mono- or polysubstituted with at least one substituent selected from the group consisting of F, Cl, Br, I, OH, OCH$_2$F, OCHF$_2$, OCF$_3$, CH$_2$F, CHF$_2$, CF$_3$ and an unsubstituted O—C$_{1-4}$-aliphatic residue, and and wherein the C$_{3-10}$-cycloaliphatic residue or the 3 to 10 membered heterocycloaliphatic residue may in each case optionally bridged via a C$_{1-8}$ aliphatic group, which in turn may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a $S(=O)_2$—$C_{1-4}$-aliphatic residue, $CH_2F$, $CHF_2$, $CF_3$, CN, a $C_{1-4}$-aliphatic residue and C(=O)—OH, on the condition that if $R^7$ denotes a 3 to 10 membered heterocycloaliphatic residue, the binding is carried out via a carbon atom of the 3 to 10 membered heterocycloaliphatic residue, or $R^7$ denotes S—$R^{8a}$, S(=O)—$R^{8b}$, $S(=O)_2$—$R^{8c}$, O—$R^9$ or $N(R^{10}R^{11})$, wherein $R^{8a}$, $R^{8b}$, $R^{8c}$ and $R^9$ in each case represent a $C_{1-10}$-aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$-aliphatic residue, $OCH_2F$, $OCHF_2$, $OCF_3$, SH, $SCF_3$, a S—$C_{1-4}$-aliphatic residue, a S(=O)—$C_{1-4}$-aliphatic residue, a $S(=O)_2$—$C_{1-4}$-aliphatic residue, $CH_2F$, $CHF_2$, $CF_3$, CN, a $C_{1-4}$-aliphatic residue and C(=O)—OH, wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue, or in each case represent a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a $S(=O)_2$—$C_{1-4}$-aliphatic residue, $CH_2F$, $CHF_2$, $CF_3$, CN, a $C_{1-4}$-aliphatic residue, C(=O)—OH, a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a $S(=O)_2$—$C_{1-4}$-aliphatic residue, $CH_2F$, $CHF_2$, $CF_3$, CN, a $C_{1-4}$-aliphatic residue and C(=O)—OH, and wherein the $C_{3-10}$-cycloaliphatic residue or the 3 to 10 membered heterocycloaliphatic residue may in each case optionally bridged via a $C_{1-8}$ aliphatic group, which in turn may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a $S(=O)_2$—$C_{1-4}$-aliphatic residue, $CH_2F$, $CHF_2$, $CF_3$, CN, a $C_{1-4}$-aliphatic residue and C(=O)—OH, on the condition that if $R^{8a}$, $R^{8b}$, $R^{8c}$ or $R^9$ denotes a 3 to 10 membered heterocycloaliphatic residue, the binding is carried out via a carbon atom of the 3 to 10 membered heterocycloaliphatic residue, $R^{10}$ denotes a $C_{1-10}$-aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$-aliphatic residue, $OCH_2F$, $OCHF_2$, $OCF_3$, SH, $SCF_3$, a S—$C_{1-4}$-aliphatic residue, a S(=O)—$C_{1-4}$-aliphatic residue, a $S(=O)_2$—$C_{1-4}$-aliphatic residue, $CH_2F$, $CHF_2$, $CF_3$, CN, a $C_{1-4}$-aliphatic residue, a C(=O)—O—$C_{1-4}$-aliphatic residue, and C(=O)—OH, wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a $S(=O)_2$—$C_{1-4}$-aliphatic residue, $CH_2F$, $CHF_2$, $CF_3$, CN, a $C_{1-4}$-aliphatic residue, C(=O)—OH, a C(=O)—O—$C_{1-4}$-aliphatic residue a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a $S(=O)_2$—$C_{1-4}$-aliphatic residue, $CH_2F$, $CHF_2$, $CF_3$, CN, a $C_{1-4}$-aliphatic residue and C(=O)—OH, and wherein the $C_{3-10}$-cycloaliphatic residue or the 3 to 10 membered heterocycloaliphatic residue may in each case optionally bridged via a $C_{1-8}$ aliphatic group, which in turn may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$ aliphatic residue, a C(=O)—O—$C_{1-4}$-aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a $S(=O)_2$—$C_{1-4}$-aliphatic residue, $CH_2F$, $CHF_2$, $CF_3$, CN, a $C_{1-4}$-aliphatic residue and C(=O)—OH, on the condition that if $R^{10}$ denotes a 3 to 10 membered heterocycloaliphatic residue, the binding is carried out via a carbon atom of the 3 to 10 membered heterocycloaliphatic residue, $R^{11}$ denotes H or a $C_{1-10}$-aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$ aliphatic residue, $OCH_2F$, OCHF$_2$, OCF$_3$, SH, SCF$_3$, a S—C$_{1-4}$ aliphatic residue, a S(=O)—C$_{1-4}$-aliphatic residue, a S(=O)$_2$—C$_{1-4}$-aliphatic residue, CH$_2$F, CHF$_2$, CF$_3$, CN, a C$_{1-4}$-aliphatic residue and C(=O)—OH, wherein the C$_{1-4}$-aliphatic residue in each case may be unsubstituted or mono- or polysubstituted with at least one substituent selected from the group consisting of F, Cl, Br, I, OH, OCH$_2$F, OCHF$_2$, OCF$_3$, CH$_2$F, CHF$_2$, CF$_3$ and an unsubstituted O—C$_{1-4}$-aliphatic residue, or R$^{10}$ and R$^{11}$ form together with the nitrogen atom connecting them a 3 to 10 membered heterocycloaliphatic residue, unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCH$_2$F, OCHF$_2$, OCF$_3$, SH, SCF$_3$, a S—C$_{1-4}$ aliphatic residue, a S(=O)—C$_{1-4}$-aliphatic residue, a S(=O)$_2$—C$_{1-4}$-aliphatic residue, CH$_2$F, CHF$_2$, CF$_3$, CN, a C$_{1-4}$-aliphatic residue, C(=O)—OH, a C$_{3-6}$ cycloaliphatic residue, and a 3 to 6 membered heterocycloaliphatic residue, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and wherein the C$_{3-6}$ cycloaliphatic residue and the 3 to 6 membered heterocycloaliphatic residue may in each case be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCH$_2$F, OCHF$_2$, OCF$_3$, SH, SCF$_3$, a S—C$_{1-4}$ aliphatic residue, a S(=O)—C$_{1-4}$-aliphatic residue, a S(=O)$_2$—C$_{1-4}$-aliphatic residue, CH$_2$F, CHF$_2$, CF$_3$, CN, a C$_{1-4}$-aliphatic residue and C(=O)—OH, and wherein the 3 to 10 membered heterocycloaliphatic residue formed by R$^{10}$ and R$^{11}$ together with the nitrogen atom connecting them may optionally be condensed with aryl or heteroaryl, wherein the aryl or heteroaryl residues condensed in this way can for their part be respectively unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, an O—C$_{1-4}$ aliphatic residue, OCH$_2$F, OCHF$_2$, OCF$_3$, SH, SCF$_3$, a S—C$_{1-4}$ aliphatic residue, a S(=O)—C$_{1-4}$-aliphatic residue, a S(=O)$_2$—C$_{1-4}$-aliphatic residue, CH$_2$F, CHF$_2$, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, a C$_{3-6}$ cycloaliphatic residue, a 3 to 6 membered heterocycloaliphatic residue,

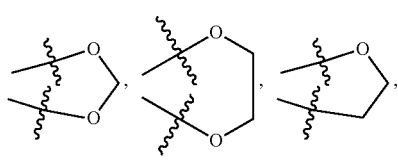

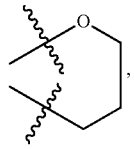

benzyl, phenyl, thienyl, pyridyl, furyl, thiazolyl and oxazolyl, wherein the C$_{1-4}$-aliphatic residue in each case may be unsubstituted or mono- or polysubstituted with at least one substituent selected from the group consisting of F, Cl, Br, I, OH, OCH$_2$F, OCHF$_2$, OCF$_3$, CH$_2$F, CHF$_2$, CF$_3$ and an unsubstituted O—C$_{1-4}$-aliphatic residue, and wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, an O—C$_{1-4}$ aliphatic residue, OCH$_2$F, OCHF$_2$, OCF$_3$, O—CH$_2$—OH, O—CH$_2$—O—CH$_3$, SH, SCF$_3$, a S—C$_{1-4}$ aliphatic residue, a S(=O)—C$_{1-4}$-aliphatic residue, a S(=O)$_2$—C$_{1-4}$-aliphatic residue, CH$_2$F, CHF$_2$, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, and wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCH$_2$F, OCHF$_2$, OCF$_3$, SH, SCF$_3$, a S—C$_{1-4}$ aliphatic residue, a S(=O)—C$_{1-4}$-aliphatic residue, a S(=O)$_2$—C$_{1-4}$-aliphatic residue, CH$_2$F, CHF$_2$, CF$_3$, CN, a C$_{1-4}$-aliphatic residue and C(=O)—OH.

In a preferred embodiment of the compound according to general formula (I), the residue R$^1$ denotes a C$_{1-10}$-aliphatic residue, unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$-aliphatic residue, OCH$_2$F, OCHF$_2$, OCF$_3$, SH, SCF$_3$, a S—C$_{1-4}$-aliphatic residue, a S(=O)—C$_{1-4}$-aliphatic residue, a S(=O)$_2$—C$_{1-4}$-aliphatic residue, CH$_2$F, CHF$_2$, CF$_3$, CN, a C$_{1-4}$-aliphatic residue and C(=O)—OH, wherein the C$_{1-4}$-aliphatic residue in each case may be unsubstituted or mono- or polysubstituted with at least one substituent selected from the group consisting of F, Cl, Br, I, OH, OCH$_2$F, OCHF$_2$, OCF$_3$, CH$_2$F, CHF$_2$, CF$_3$ and an unsubstituted O—C$_{1-4}$-aliphatic residue, or denotes a C$_{3-10}$-cycloaliphatic residue or a 3 to 10 membered heterocycloaliphatic residue, in each case unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCH$_2$F, OCHF$_2$, OCF$_3$, SH, SCF$_3$, a S—C$_{1-4}$ aliphatic residue, a S(=O)—C$_{1-4}$-aliphatic residue, a S(=O)$_2$—C$_{1-4}$-aliphatic residue, CH$_2$F, CHF$_2$, CF$_3$, CN, a C$_{1-4}$-aliphatic residue, C(=O)—OH, a C$_{3-6}$-cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a S(=O)$_2$—$C_{1-4}$-aliphatic residue, $CH_2F$, $CHF_2$, $CF_3$, CN, a $C_{1-4}$-aliphatic residue and C(=O)—OH, and wherein the $C_{3-10}$-cycloaliphatic residue or the 3 to 10 membered heterocycloaliphatic residue may in each case optionally bridged via a $C_{1-8}$ aliphatic group, which in turn may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a S(=O)$_2$—$C_{1-4}$-aliphatic residue, $CH_2F$, $CHF_2$, $CF_3$, CN, a $C_{1-4}$-aliphatic residue and C(=O)—OH, or denotes an aryl or heteroaryl, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a S(=O)$_2$—$C_{1-4}$-aliphatic residue, $CH_2F$, $CHF_2$, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, a $C_{3-6}$ cycloaliphatic residue, a 3 to 6 membered heterocycloaliphatic residue,

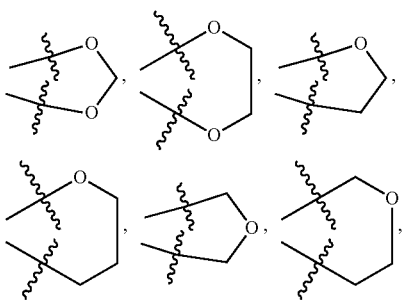

benzyl, phenyl, thienyl, pyridyl, furyl, thiazolyl and oxazolyl, wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue, and wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, an O—$C_{1-4}$ aliphatic residue, $OCH_2F$, $OCHF_2$, $OCF_3$, O—$CH_2$—OH, O—$CH_2$—O—$CH_3$, SH, $SCF_3$, a S—$C_{1-4}$ aliphatic residue, a S(=O)—$C_{1-4}$-aliphatic residue, a S(=O)$_2$—$C_{1-4}$-aliphatic residue, $CH_2F$, $CHF_2$, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a S(=O)$_2$—$C_{1-4}$-aliphatic residue, $CH_2F$, $CHF_2$, $CF_3$, CN, a $C_{1-4}$-aliphatic residue and C(=O)—OH, and wherein the aryl or the heteroaryl residue may in each case be optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a S(=O)$_2$—$C_{1-4}$-aliphatic residue, $CH_2F$, $CHF_2$, $CF_3$, CN and C(=O)—OH, In a further preferred embodiment of the compound according to general formula (I), the residue $R^1$ represents the partial structure (T1)

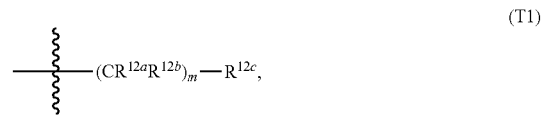

(T1)

wherein m denotes 0, 1, 2, 3 or 4, preferably denotes 0, 1, 2 or 3, more preferably denotes 0, 1, or 2, $R^{12a}$ and $R^{12b}$ each independently of one another represent H, F, Cl, Br, I, $NO_2$, $NH_2$, a $NH(C_{1-4}$ aliphatic residue), an $N(C_{1-4}$ aliphatic residue)$_2$, OH, an O—$C_{1-4}$ aliphatic residue, $OCF_3$, $OCH_2F$, $OCHF_2$, SH, $SCF_3$, a S—$C_{1-4}$ aliphatic residue, a S(=O)—$C_{1-4}$ aliphatic residue, a S(=O)$_2$—$C_{1-4}$ aliphatic residue, $CH_2F$, $CHF_2$, $CF_3$, CN, a $C_{1-4}$ aliphatic residue or C(=O)—OH, or together denote =O, preferably each independently of one another represent H, F, Cl, Br, I, $NH_2$, a $NH(C_{1-4}$ aliphatic residue), a $N(C_{1-4}$ aliphatic residue)$_2$, OH, O—$C_{1-4}$ aliphatic residue or a $C_{1-4}$ aliphatic residue, or together denote =O, more preferably each independently of one another represent H, F, Cl, Br, I, OH, an O—$C_{1-4}$ aliphatic residue or a $C_{1-4}$ aliphatic residue, or together denote =O, even more preferably each independently of one another represent H, F, OH, an O—$C_{1-4}$ aliphatic residue or a $C_{1-4}$ aliphatic residue, or together denote =O, and $R^{12c}$ denotes a $C_{1-4}$ aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$ aliphatic residue, a S(=O)$_2$—$C_{1-4}$ aliphatic residue, $CH_2F$, $CHF_2 CF_3$, CN, a $C_{1-4}$-aliphatic residue and C(=O)—OH, preferably denotes a C$_{1-4}$ aliphatic residue, unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCH$_2$F, OCHF$_2$, OCF$_3$, SH, SCF$_3$, a S—C$_{1-4}$ aliphatic residue, OCH$_2$F, OCHF$_2$, CF$_3$, CN, a C$_{1-4}$-aliphatic residue and C(=O)—OH, or denotes a C$_{3-10}$-cycloaliphatic residue or a 3 to 10 membered heterocycloaliphatic residue, in each case unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCH$_2$F, OCHF$_2$, OCF$_3$, SH, SCF$_3$, a S—C$_{1-4}$ aliphatic residue, a S(=O)—C$_{1-4}$ aliphatic residue, a S(=O)$_2$—C$_{1-4}$ aliphatic residue, CH$_2$F, CHF$_2$, CF$_3$, CN, a C$_{1-4}$-aliphatic residue, C(=O)—OH, a C$_{3-6}$ cycloaliphatic residue and a 3 to 6 membered heterocycloaliphatic residue, preferably when m is ≠0, wherein the C$_{1-4}$-aliphatic residue in each case may be unsubstituted or mono- or polysubstituted with at least one substituent selected from the group consisting of F, Cl, Br, I, OH, OCH$_2$F, OCHF$_2$, OCF$_3$, CH$_2$F, CHF$_2$, CF$_3$ and an unsubstituted O—C$_{1-4}$-aliphatic residue, and wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCH$_2$F, OCHF$_2$, OCF$_3$, SH, SCF$_3$, a S—C$_{1-4}$ aliphatic residue, a S(=O)—C$_{1-4}$ aliphatic residue, a S(=O)$_2$—C$_{1-4}$ aliphatic residue, CH$_2$F, CHF$_2$, CF$_3$, CN, a C$_{1-4}$-aliphatic residue and C(=O)—OH, or denotes—preferably when m is 0 or 2, more preferably when m is 0—an aryl or heteroaryl, in each case unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, an O—C$_{1-4}$ aliphatic residue, OCH$_2$F, OCHF$_2$, OCF$_3$, SH, SCF$_3$, a S—C$_{1-4}$ aliphatic residue, a S(=O)—C$_{1-4}$ aliphatic residue, a S(=O)$_2$—C$_{1-4}$ aliphatic residue, CH$_2$F, CHF$_2$, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, a C$_{3-6}$ cycloaliphatic residue, a 3 to 6 membered heterocycloaliphatic residue,

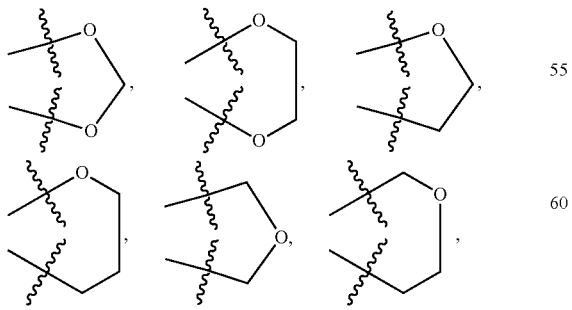

benzyl, phenyl, thienyl, pyridyl, furyl, thiazolyl and oxazolyl, preferably denotes an aryl or heteroaryl, in each case unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, an O—C$_{1-4}$ aliphatic residue, OCH$_2$F, OCHF$_2$, OCF$_3$, SH, SCF$_3$, a S—C$_{1-4}$ aliphatic residue, a S(=O)—C$_{1-4}$ aliphatic residue, a S(=O)$_2$—C$_{1-4}$ aliphatic residue, CH$_2$F, CHF$_2$, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, a C$_{3-6}$ cycloaliphatic residue, a 3 to 6 membered heterocycloaliphatic residue,

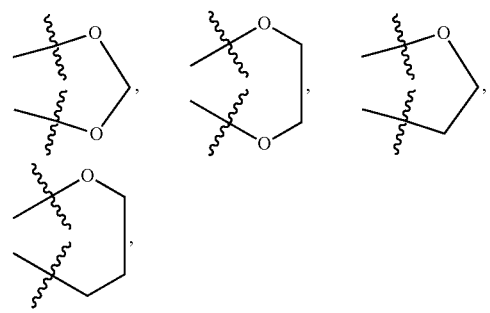

benzyl, phenyl, thienyl, pyridyl, furyl, thiazolyl and oxazolyl, preferably when m is =0, wherein the C$_{1-4}$-aliphatic residue in each case may be unsubstituted or mono- or polysubstituted with at least one substituent selected from the group consisting of F, Cl, Br, I, OH, OCH$_2$F, OCHF$_2$, OCF$_3$, CH$_2$F, CHF$_2$, CF$_3$ and an unsubstituted O—C$_{1-4}$-aliphatic residue, and wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, an O—C$_{1-4}$ aliphatic residue, OCH$_2$F, OCHF$_2$, OCF$_3$, SH, SCF$_3$, a S—C$_{1-4}$ aliphatic residue, a S(=O)—C$_{1-4}$ aliphatic residue, a S(=O)$_2$—C$_{1-4}$ aliphatic residue, CH$_2$F, CHF$_2$, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, and wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCH$_2$F, OCHF$_2$, OCF$_3$, SH, SCF$_3$, a S—C$_{1-4}$ aliphatic residue, a S(=O)—C$_{1-4}$ aliphatic residue, a S(=O)$_2$—C$_{1-4}$ aliphatic residue, CH$_2$F, CHF$_2$, CF$_3$, CN, a C$_{1-4}$-aliphatic residue and C(=O)—OH.

Preferably,

R$^1$ represents the partial structure (T1), wherein m denotes 0, 1, 2 or 3, preferably denotes 0, 1 or 2, R$^{12a}$ and R$^{12b}$ each independently of one another represent H, F, Cl, Br, I, OH, an O—C$_{1-4}$ aliphatic residue or a C$_{1-4}$ aliphatic residue, or together denote =O, preferably each independently of one another represent H, F, OH, a O—$C_{1-2}$ aliphatic residue or a $C_{1-2}$ aliphatic residue, or together denote =O, and $R^{12c}$ denotes a $C_{1-4}$ aliphatic residue, unsubstituted or mono- or polysubstituted with at least one substituent selected from the group consisting of F, Cl, Br, I, OH, =O, an O—$C_{1-4}$ aliphatic residue, $OCH_2F$, $OCHF_2$, $OCF_3$, $CH_2F$, $CHF_2$, $CF_3$, CN, a $C_{1-4}$-aliphatic residue, a S(=O)—$C_{1-4}$ aliphatic residue, a $S(=O)_2$—$C_{1-4}$ aliphatic residue, and C(=O)—OH, preferably denotes denotes a $C_{1-4}$ aliphatic residue, unsubstituted or mono- or polysubstituted with at least one substituent selected from the group consisting of F, Cl, Br, I, OH, =O, an O—$C_{1-4}$ aliphatic residue, $OCH_2F$, $OCHF_2$, $OCF_3$, $CH_2F$, $CHF_2$, $CF_3$, a $C_{1-4}$-aliphatic residue and C(=O)—OH, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, $OCH_2F$, $OCHF_2$, $OCF_3$, $CH_2F$, $CHF_2$, $CF_3$, a $C_{1-4}$-aliphatic residue, C(=O)—OH, a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, OH, =O, an O—$C_{1-4}$ aliphatic residue, $OCH_2F$, $OCHF_2$, $OCF_3$, $CH_2F$, $CHF_2$, $CF_3$, a $C_{1-4}$-aliphatic residue and C(=O)—OH, or denotes—preferably when m is 0 or 2, more preferably when m is 0—an aryl or heteroaryl, in each case unsubstituted or mono- or polysubstituted with at least one substituent selected from the group consisting of F, Cl, Br, I, OH, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$ aliphatic residue, a $S(=O)_2$—$C_{1-4}$ aliphatic residue, $NO_2$, N($C_{1-4}$ aliphatic residue)$_2$, $CH_2F$, $CHF_2$, $CF_3$, CN, a $C_{1-4}$-aliphatic residue, C(=O)—OH, C(=O)—$CH_3$, C(=O)—$C_2H_5$, C(=O)—O—$CH_3$, C(=O)—O—$C_2H_5$,

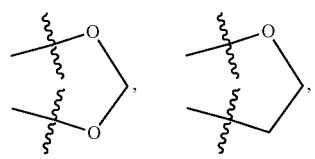 [SMILES: *OCO* ; *CCO*]

a $C_{3-6}$ cycloaliphatic residue, a 3 to 6 membered heterocycloaliphatic residue, benzyl, phenyl, thienyl, pyridyl, furyl, thiazolyl or oxazolyl, preferably denotes an aryl or heteroaryl, in each case unsubstituted or mono- or polysubstituted with at least one substituent selected from the group consisting of F, Cl, Br, I, OH, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$ aliphatic residue, a $S(=O)_2$—$C_{1-4}$ aliphatic residue, $CH_2F$, $CHF_2$, $CF_3$, CN, a $C_{1-4}$-aliphatic residue, C(=O)—OH, C(=O)—$CH_3$, C(=O)—$C_2H_5$, C(=O)—O—$CH_3$, C(=O)—O—$C_2H_5$, a $C_{3-6}$ cycloaliphatic residue, a 3 to 6 membered heterocycloaliphatic residue, benzyl, phenyl, thienyl, pyridyl, furyl, thiazolyl or oxazolyl, preferably when m is 0, wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue, and wherein benzyl, phenyl, thienyl, pyridyl, furyl, thiazolyl and oxazolyl may in each case may be unsubstituted or mono- or polysubstituted, preferably unsubstituted or mono- or disubstituted with at least one substituent selected from the group consisting of F, Cl, Br, I, OH, an O—$C_{1-4}$ aliphatic residue, $OCH_2F$, $OCHF_2$, $OCF_3$, $CH_2F$, $CHF_2$, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, preferably with at least one substituent selected from the group consisting of F, Cl, $CH_3$, O—$CH_3$, $CH_2F$, $CHF_2$, $CF_3$ and $OCF_3$ and $OCH_2F$, and $OCHF_2$, wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, OH, =O, an O—$C_{1-4}$ aliphatic residue, $OCF_3$, $OCH_2F$, $OCHF_2$, $CH_2F$, $CHF_2$, $CF_3$ a $C_{1-4}$-aliphatic residue and C(=O)—OH.

More preferably, $R^1$ represents the partial structure (T1), wherein m denotes 0, 1, or 2 or 3, preferably denotes 0, 1 or 2, $R^{12a}$ and $R^{12b}$ each independently of one another represent H, F, Cl, Br, I, OH, an O—$C_{1-4}$ aliphatic residue or a $C_{1-4}$ aliphatic residue, or together denote =O, preferably each independently of one another represent H, F, OH, a O—$C_{1-2}$ aliphatic residue or a $C_{1-2}$ aliphatic residue, or together denote =O, and $R^{12c}$ denotes a $C_{1-4}$ aliphatic residue, unsubstituted or mono- or polysubstituted with at least one substituent selected from the group consisting of F, Cl, Br, I, OH, an O—$C_{1-4}$ aliphatic residue, $CH_2F$, $CHF_2$, $CF_3$, CN, a S(=O)—$C_{1-4}$-aliphatic residue, a $S(=O)_2$—$C_{1-4}$-aliphatic residue and a $C_{1-4}$-aliphatic residue, preferably denotes a $C_{1-4}$ aliphatic residue, unsubstituted or mono- or polysubstituted with at least one substituent selected from the group consisting of F, Cl, Br, I, an O—$C_{1-4}$ aliphatic residue, $CH_2F$, $CHF_2$, $CF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, $CH_2F$, $CHF_2$, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, an O—$C_{1-4}$ aliphatic residue, $CH_2F$, $CHF_2$, $CF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, $CH_2F$, $CHF_2$, $CF_3$ and an unsubstituted $O-C_{1-4}$-aliphatic residue, or denotes—preferably when m is 0 or 2, more preferably when m is 0—an aryl or heteroaryl, in each case unsubstituted or mono- or polysubstituted with at least one substituent selected from the group consisting of F, Cl, Br, I, OH, an $O-C_{1-4}$ aliphatic residue, $OCH_2F$, $OCHF_2$, $OCF_3$, $CF_3$, $CH_2F$, $CHF_2$, CN, a $C_{1-4}$-aliphatic residue, $C(=O)-CH_3$, $C(=O)-C_2H_5$, $CH_2-OH$, $CH_2-OCH_3$, $S(=O)_2-CH_3$, $SCF_3$, $NO_2$, $N(C_{1-4}$ aliphatic residue$)_2$,

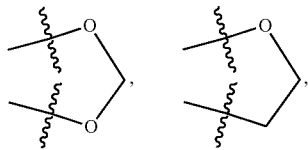 [SMILES: *OCO* ; *CCO*]

$C(=O)-O-CH_3$ and $C(=O)-O-C_2H_5$, a $C_{3-6}$ cycloaliphatic residue, a 3 to 6 membered heterocycloaliphatic residue, benzyl, phenyl, thienyl or pyridyl, preferably denotes—preferably when m is 0 or 2, more preferably when m is 0—an aryl or heteroaryl, in each case unsubstituted or mono- or polysubstituted with at least one substituent selected from the group consisting of F, Cl, Br, I, OH, an $O-C_{1-4}$ aliphatic residue, $OCH_2F$, $OCHF_2$, $OCF_3$, $CH_2F$, $CHF_2$, $CF_3$, CN, a $C_{1-4}$-aliphatic residue, $C(=O)-CH_3$, $C(=O)-C_2H_5$, $C(=O)-O-CH_3$ and $C(=O)-O-C_2H_5$, a $C_{3-6}$ cycloaliphatic residue, a 3 to 6 membered heterocycloaliphatic residue, benzyl, phenyl, thienyl or pyridyl, wherein benzyl, phenyl, thienyl and pyridyl, may in each case may be unsubstituted or mono- or polysubstituted, preferably unsubstituted or mono- or disubstituted with at least one substituent selected from the group consisting of F, Cl, Br, I, OH, an $O-C_{1-4}$ aliphatic residue, $OCH_2F$, $OCHF_2$, $OCF_3$, $CH_2F$, $CHF_2$, $CF_3$, CN, a $C_{1-4}$-aliphatic residue, $C(=O)-CH_3$, $C(=O)-C_2H_5$, $C(=O)-O-CH_3$ and $C(=O)-O-C_2H_5$, preferably with at least one substituent selected from the group consisting of F, Cl, $CH_3$, $O-CH_3$, $CH_2F$, $CHF_2$, $CF_3$ and $OCF_3$, and $OCH_2F$, and $OCHF_2$, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, OH, =O, an $O-C_{1-4}$ aliphatic residue, $OCH_2F$, $OCHF_2$, $OCF_3$, $CH_2F$, $CHF_2$, $CF_3$ a $C_{1-4}$-aliphatic residue and $C(=O)-OH$.

In a further preferred embodiment of the compound according to general formula (I), the residue $R^1$ represents the partial structure (T1), wherein m is 0, 1 or 2, preferably 0 or 2, more preferably 2, and $R^{12a}$ and $R^{12b}$ each independently of one another represent H, F, OH, a $O-C_{1-4}$ aliphatic residue or a $C_{1-4}$ aliphatic residue or together denote =O; preferably H, F, OH, $CH_3$ or $OCH_3$ or together denote =O;

$R^{12c}$ denotes a $C_{1-4}$ aliphatic residue, unsubstituted or mono- or polysubstituted with at least one substituent selected from the group consisting of F, Cl, Br, I, CN, OH, an unsubstituted $O-C_{1-4}$ aliphatic residue, an unsubstituted $S(=O)_2-C_{1-4}$ aliphatic residue, $CH_2F$, $CHF_2$, $CF_3$, and an unsubstituted $C_{1-4}$-aliphatic residue, preferably denotes a $C_{1-4}$ aliphatic residue, unsubstituted or mono- or polysubstituted with at least one substituent selected from the group consisting of F, Cl, Br, I, an unsubstituted $O-C_{1-4}$ aliphatic residue, $CH_2F$, $CHF_2$, $CF_3$, and an unsubstituted $C_{1-4}$-aliphatic residue or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, an unsubstituted $O-C_{1-4}$ aliphatic residue, $CH_2F$, $CHF_2$, $CF_3$, and an unsubstituted $C_{1-4}$-aliphatic residue, or
wherein
is 0 or 2, more preferably 0, and $R^{12a}$ and $R^{12b}$ each independently of one another represent H, F, OH, a $O-C_{1-4}$ aliphatic residue or a $C_{1-4}$ aliphatic residue; preferably H, F, OH, $CH_3$ or $OCH_3$; and $R^{12c}$ denotes an aryl or heteroaryl, in each case unsubstituted or mono- or polysubstituted with at least one substituent selected from the group consisting of F, Cl, Br, I, OH, an $O-C_{1-4}$ aliphatic residue, $OCF_3$, $OCH_2F$, $OCHF_2$, $CH_2-OH$, $CH_2-OCH_3$, $S(=O)_2-CH_3$, $SCF_3$, $NO_2$, $N(C_{1-4}$ aliphatic residue$)_2$,

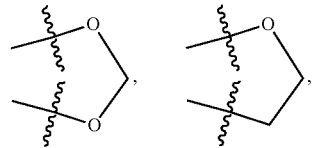 [SMILES: *OCO* ; *CCO*]

$CF_3$, $CH_2F$, $CHF_2$, CN, a $C_{1-4}$-aliphatic residue, $C(=O)-CH_3$, $C(=O)-C_2H_5$, $C(=O)-O-CH_3$, $C(=O)-O-C_2H_5$ and phenyl, preferably denotes an aryl or heteroaryl, in each case unsubstituted or mono- or polysubstituted with at least one substituent selected from the group consisting of F, Cl, Br, I, OH, an $O-C_{1-4}$ aliphatic residue, $OCF_3$, $OCH_2F$, $OCHF_2$, $CH_2F$, $CHF_2$, $CF_3$, CN, a $C_{1-4}$-aliphatic residue, $C(=O)-CH_3$, $C(=O)-C_2H_5$, $C(=O)-O-CH_3$, $C(=O)-O-C_2H_5$ and phenyl, wherein phenyl may be unsubstituted or mono- or polysubstituted, preferably unsubstituted or mono- or disubstituted with at least one substituent selected from the group consisting of F, Cl, Br, I, OH, an $O-C_{1-4}$ aliphatic residue, $OCH_2F$, $OCHF_2$, $OCF_3$, $CH_2F$, $CHF_2$, $CF_3$, CN, a $C_{1-4}$-aliphatic residue, $C(=O)-CH_3$, $C(=O)-C_2H_5$, $C(=O)-O-CH_3$ and $C(=O)-O-C_2H_5$, preferably with at least one substituent selected from the group consisting of F, Cl, $CH_3$, $O-CH_3$, $CH_2F$, $CHF_2$, $CF_3$ and $OCH_2F$, $OCHF_2$, and $OCF_3$.

Preferably,
$R^1$ represents the partial structure (T1),
wherein
m is 0, 1 or 2, preferably 0 or 2, more preferably 2, and $R^{12a}$ and $R^{12b}$ each independently of one another represent H, F, OH, $CH_3$ or $OCH_3$ or together denote =O, more preferably H, F, OH or $CH_3$, even more preferably H, $R^{12c}$ denotes a $C_{1-4}$ aliphatic residue, preferably methyl, ethyl, n-propyl, 2-propyl, n-butyl, isobutyl, sec.-butyl, or tert.-butyl, unsubstituted or mono- or polysubstituted with at least one substituent selected from the group consisting of F, Cl, Br, I, CN, OH, $S(=O)_2$—$CH_3$, an unsubstituted O—$C_{1-4}$ aliphatic residue, preferably O-methyl and O-tert.-butyl, and $CH_2F$, $CHF_2$, $CF_3$, preferably denotes a $C_{1-4}$ aliphatic residue, preferably methyl, ethyl, n-propyl, 2-propyl, n-butyl, isobutyl, sec.-butyl, or tert.-butyl, unsubstituted or mono- or polysubstituted with at least one substituent selected from the group consisting of F, Cl, Br, I, an unsubstituted O—$C_{1-4}$ aliphatic residue, preferably O-methyl and O-tert.-butyl, and $CF_3$ or denotes a $C_{3-10}$-cycloaliphatic residue or a 3 to 10 membered heterocycloaliphatic residue, preferably cyclopropyl, cyclopentyl, cyclohexyl, morpholinyl, oxetanyl, or tetrahydropyranyl, in each case unsubstituted or mono- or polysubstituted with at least one substituent selected from the group consisting of F, Cl, Br, I, an unsubstituted O—$C_{1-4}$ aliphatic residue, preferably O-methyl and O-ethyl, $CH_2F$, $CHF_2$, $CF_3$, and an unsubstituted $C_{1-4}$-aliphatic residue, preferably methyl or ethyl, or wherein m is 0 or 2, more preferably 0, and $R^{12a}$ and $R^{12b}$ each independently of one another represent H, F, OH, $CH_3$ or $OCH_3$; preferably H, OH or $CH_3$, and $R^{12c}$ denotes an aryl or heteroaryl, preferably phenyl or pyridyl, in each case unsubstituted or mono- or polysubstituted with at least one substituent selected from the group consisting of F, Cl, Br, I, OH, an O—$C_{1-4}$ aliphatic residue, preferably $OCH_3$, $OCF_3$, $OCH_2F$, $OCHF_2$, $CH_2$—OH, $CH_2$—$OCH_3$, $S(=O)_2$—$CH_3$, $SCF_3$, $NO_2$, $N(CH_3)_2$,

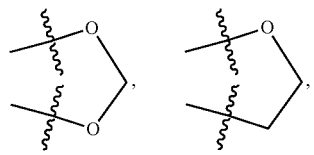

$CH_2F$, $CHF_2$, $CF_3$, CN, a $C_{1-4}$-aliphatic residue, $C(=O)$—$CH_3$, $C(=O)$—$C_2H_5$, $C(=O)$—O—$CH_3$, $C(=O)$—O—$C_2H_5$ and phenyl, preferably denotes an aryl or heteroaryl, preferably phenyl or pyridyl, in each case unsubstituted or mono- or polysubstituted with at least one substituent selected from the group consisting of F, Cl, Br, I, OH, an O—$C_{1-4}$ aliphatic residue, $OCF_3$, $OCH_2F$, $OCHF_2$, $CH_2F$, $CHF_2$, $CF_3$, CN, a $C_{1-4}$-aliphatic residue, $C(=O)$—$CH_3$, $C(=O)$—$C_2H_5$, $C(=O)$—O—$CH_3$, $C(=O)$—O—$C_2H_5$ and phenyl, wherein phenyl may be unsubstituted or mono- or polysubstituted, preferably unsubstituted or mono- or disubstituted with at least one substituent selected from the group consisting of F, Cl, Br, I, OH, an O—$C_{1-4}$ aliphatic residue, $OCH_2F$, $OCHF_2$, $OCF_3$, $CH_2F$, $CHF_2$, $CF_3$, CN, a $C_{1-4}$-aliphatic residue, $C(=O)$—$CH_3$, $C(=O)$—$C_2H_5$, $C(=O)$—O—$CH_3$ and $C(=O)$—O—$C_2H_5$, preferably with at least one substituent selected from the group consisting of F, Cl, $CH_3$, O—$CH_3$, $OCH_2F$, $OCHF_2$, $CH_2F$, $CHF_2$, $CF_3$ and $OCF_3$.

Particularly preferred is a compound according to general formula (I) which has the following general formula (I-e):

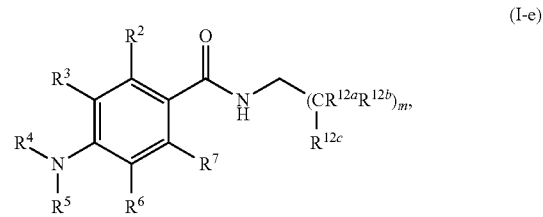

(I-e)

wherein the particular radicals and parameters have the meanings described herein in connection with the compounds according to the invention and preferred embodiments thereof.

In a preferred embodiment of the compound according to general formula (I), the residue $R^2$ represents F; Cl; Br; I; CN; $CH_2F$, $CHF_2$, $CF_3$; $NO_2$; $OCH_2F$, $OCHF_2$, $OCF_3$; $SCF_3$; a $C_{1-4}$-aliphatic residue, a S—$C_{1-4}$-aliphatic residue, a $S(=O)$—$C_{1-4}$-aliphatic residue, a $S(=O)_2$—$C_{1-4}$-aliphatic residue, a O—$C_{1-4}$-aliphatic residue, wherein the $C_{1-4}$ aliphatic residue may be in each case be unsubstituted or mono- or polysubstituted; a $C_{3-6}$-cycloaliphatic residue or a 3 to 6 membered heterocycloaliphatic residue, in each case unsubstituted or mono- or polysubstituted and in each case optionally bridged via a $C_{1-4}$ aliphatic group, which in turn may be unsubstituted or mono- or polysubstituted.

Preferably, $R^2$ represents F; Cl; Br; I; CN; $CH_2F$, $CHF_2$, $CF_3$; $NO_2$; $OCH_2F$, $OCHF_2$, $OCF_3$; $SCF_3$; a $C_{1-4}$-aliphatic residue, a S—$C_{1-4}$-aliphatic residue, a $S(=O)$—$C_{1-4}$-aliphatic residue, a $S(=O)_2$—$C_{1-4}$-aliphatic residue, a O—$C_{1-4}$-aliphatic residue, wherein the $C_{1-4}$-aliphatic residue in each case may be unsubstituted or mono- or polysubstituted with at least one substituent selected from the group consisting of F, Cl, Br, I, =O, OH, and an unsubstituted O—$C_{1-4}$-aliphatic residue, a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a $C_{1-4}$-aliphatic residue and a O—$C_{1-4}$-aliphatic residue, wherein the $C_{1-4}$-aliphatic residue in each case may be unsubstituted or mono- or polysubstituted with at least one substituent selected from the group consisting of F, Cl, Br, I, =O, OH, and an unsubstituted O—$C_{1-4}$-aliphatic residue, and wherein the $C_{3-6}$-cycloaliphatic residue or the 3 to 6 membered heterocycloaliphatic residue may in each case be optionally bridged via a $C_{1-4}$ aliphatic group, which in turn may be unsubstituted or mono- or polysubstituted with at least one substituent selected from the group consisting of F, Cl, Br, I, =O, OH, an unsubstituted $C_{1-4}$-aliphatic residue and an unsubstituted O—$C_{1-4}$-aliphatic residue.

More preferably, $R^2$ represents F; Cl; Br; I; CN; $CH_2F$, $CHF_2$, $CF_3$; $NO_2$; $OCH_2F$, $OCHF_2$, $OCF_3$; $SCF_3$; a $C_{1-4}$-aliphatic residue, a S—$C_{1-4}$-aliphatic residue, a $S(=O)$—$C_{1-4}$-aliphatic residue, a $S(=O)_2$—$C_{1-4}$-aliphatic residue, a O—$C_{1-4}$-aliphatic residue, wherein the $C_{1-4}$-aliphatic residue in each case may be unsubstituted or mono- or polysubstituted with at least one substituent selected from the group consisting of F, Cl, Br, I, =O, OH, and an unsubstituted O—$C_{1-4}$-aliphatic residue, cyclopropyl, cyclobutyl, cyclopentyl, cyclohexyl, pyrrolidinyl, piperazinyl, 4-methylpiperazinyl, morpholinyl, or piperidinyl, preferably cyclopropyl, cyclobutyl, cyclopentyl or cyclohexyl, in each case unsubstituted or mono- or polysubstituted with at least one substituent selected from the group consisting of F, Cl, Br, I, =O, OH, an unsubstituted $C_{1-4}$-aliphatic residue and an unsubstituted O—$C_{1-4}$-aliphatic residue, and wherein cyclopropyl, cyclobutyl, cyclopentyl, cyclohexyl, pyrrolidinyl, piperazinyl, 4-methylpiperazinyl, morpholinyl or piperidinyl may in each case be optionally bridged via an $C_{1-4}$ aliphatic group, which in turn may be unsubstituted or mono- or polysubstituted with at least one substituent selected from the group consisting of F, Cl, OH, an unsubstituted $C_{1-4}$-aliphatic residue and an unsubstituted O—$C_{1-4}$-aliphatic residue.

Even more preferably, $R^2$ represents F; Cl; Br; I; CN; $CH_2F$, $CHF_2$, $CF_3$; $NO_2$; $OCH_2F$, $OCHF_2$, $OCF_3$; $SCF_3$; methyl; ethyl; n-propyl; iso-propyl; n-butyl; sec.-butyl; tert.-butyl; $CH_2$—OH; $CH_2$—O—$CH_3$; $CH_2$—$CH_2$—OH; $CH_2$—$CH_2$—$OCH_3$; O-methyl; O-ethyl; O—$(CH_2)_2$—O—$CH_3$; O—$(CH_2)_2$—OH; S-Methyl; S-ethyl; cyclopropyl, cyclobutyl, cyclopentyl, and cyclohexyl; preferably represents F; Cl; Br; I; CN; $CF_3$; $NO_2$; $OCF_3$; $SCF_3$; methyl; ethyl; n-propyl; iso-propyl; n-butyl; sec.-butyl; tert.-butyl; O-methyl; O-ethyl; O—$(CH_2)_2$—O—$CH_3$; O—$(CH_2)_2$—OH; S-Methyl; S-ethyl; cyclopropyl, cyclobutyl, cyclopentyl, and cyclohexyl Still more preferably, $R^2$ is selected from the group consisting of F; Cl; $CH_2F$, $CHF_2$, $CF_3$; CN; $SCF_3$; $OCH_2F$, $OCHF_2$, $OCF_3$; $CH_3$; $C_2H_5$; n-propyl; iso-propyl; t-butyl; $CH_2$—OH; $CH_2$—O—$CH_3$; cyclopropyl; O—$CH_3$ and O—$C_2H_5$; preferably is selected from the group consisting of F; Cl; $CF_3$; CN; $SCF_3$; $OCF_3$; $CH_3$; $C_2H_5$; n-propyl; iso-propyl; t-butyl; cyclopropyl; O—$CH_3$ and O—$C_2H_5$;

In particular, $R^2$ is selected from the group consisting of F; Cl; $CH_2F$, $CHF_2$, $CF_3$; $CH_3$; $C_2H_5$, iso-propyl; $CH_2$—O—$CH_3$; cyclopropyl; and O—$CH_3$; preferably is selected from the group consisting of F; Cl; $CH_2F$, $CHF_2$, $CF_3$; $CH_3$; $C_2H_5$, iso-propyl; cyclopropyl; and O—$CH_3$;

More particular, $R^2$ is selected from the group consisting of $CH_2F$, $CHF_2$, $CF_3$; $CH_3$; $C_2H_5$, iso-propyl; $CH_2$—O—$CH_3$; and O—$CH_3$; preferably is selected from the group consisting of $CH_3$; $C_2H_5$, iso-propyl; $CH_2$—O—$CH_3$; and O—$CH_3$;

In a particular preferred embodiment of the compound according to general formula (I), the residue $R^2$ denotes $CH_3$ or $CF_3$, most preferably $R^2$ denotes $CH_3$.

In a further preferred embodiment of the compound according to general formula (I), the residue $R^3$ represents H; F; Cl; Br; I; CN; $CH_2F$, $CHF_2$, $CF_3$; $SCF_3$; $NO_2$; $OCH_2F$, $OCHF_2$, $OCF_3$; a $C_{1-4}$-aliphatic residue, a O—$C_{1-4}$-aliphatic residue, a S(=O)—$C_{1-4}$-aliphatic residue, a S(=O)$_2$—$C_{1-4}$-aliphatic residue, a S—$C_{1-4}$-aliphatic residue, wherein the $C_{1-4}$ aliphatic residue may be in each case be unsubstituted or mono- or polysubstituted with at least one substituent selected from the group consisting of F, Cl, Br, I, =O, OH, and an unsubstituted O—$C_{1-4}$-aliphatic residue;

a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a $C_{1-4}$-aliphatic residue and a O—$C_{1-4}$-aliphatic residue, wherein the $C_{1-4}$-aliphatic residue in each case may be unsubstituted or mono- or polysubstituted with at least one substituent selected from the group consisting of F, Cl, Br, I, =O, OH, and an unsubstituted O—$C_{1-4}$-aliphatic residue, and wherein the $C_{3-6}$-cycloaliphatic residue or the 3 to 6 membered heterocycloaliphatic residue may in each case be optionally bridged via a $C_{1-4}$ aliphatic group, which in turn may be unsubstituted or mono- or polysubstituted with at least one substituent selected from the group consisting of F, Cl, Br, I, =O, OH, an unsubstituted $C_{1-4}$-aliphatic residue and an unsubstituted O—$C_{1-4}$-aliphatic residue.

Preferably, $R^3$ represents H; F; Cl; Br; I; CN; $CH_2F$, $CHF_2$, $CF_3$; $SCF_3$; $NO_2$; $OCH_2F$, $OCHF_2$, $OCF_3$; a $C_{1-4}$-aliphatic residue, a O—$C_{1-4}$-aliphatic residue, a S—$C_{1-4}$-aliphatic residue, a S(=O)—$C_{1-4}$-aliphatic residue, a S(=O)$_2$—$C_{1-4}$-aliphatic residue, wherein the $C_{1-4}$ aliphatic residue may be in each case be unsubstituted or mono- or polysubstituted with at least one substituent selected from the group consisting of F, Cl, Br, I, =O, OH, and an unsubstituted O—$C_{1-4}$-aliphatic residue.

More preferably, $R^3$ represents H; F; Cl; Br; I; CN; $CH_2F$, $CHF_2$, $CF_3$; $SCF_3$; $NO_2$; $OCH_2F$, $OCHF_2$, $OCF_3$; methyl; ethyl; n-propyl; iso-propyl; n-butyl; sec.-butyl; tert.-butyl; O-methyl; O-ethyl; O—$(CH_2)_2$—O—$CH_3$; O—$(CH_2)_2$—OH; S-Methyl; or S-Ethyl.

Even more preferably $R^3$ represents H; F; Cl; Br; I; CN; $CH_2F$, $CHF_2$, $CF_3$; $SCF_3$; $OCH_2F$, $OCHF_2$, $OCF_3$; methyl; ethyl; O-methyl; or O-ethyl, preferably represents H; F; Cl; Br; I; $CH_2F$, $CHF_2$, $CF_3$; $SCF_3$; $OCH_2F$, $OCHF_2$, $OCF_3$; methyl; ethyl; O-methyl; or O-ethyl, Still more preferably $R^3$ represents H; F; Cl; Br; CN; $CH_2F$, $CHF_2$, $CF_3$; $SCF_3$; $OCH_2F$, $OCHF_2$, $OCF_3$; O-methyl or methyl, preferably represents H; F; Cl; $CH_2F$, $CHF_2$, $CF_3$; $SCF_3$; $OCH_2F$, $OCHF_2$, $OCF_3$; O-methyl or methyl.

In particular $R^3$ represents H; F; Cl; Br; CN; or methyl, preferably H, F, Cl, Br or CN, more preferably H, Cl or Br, most preferably H.

In a further preferred embodiment of the compound according to general formula (I), the residue $R^4$ denotes a $C_{1-10}$-aliphatic residue, unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$-aliphatic residue, $OCH_2F$, $OCHF_2$, $OCF_3$, SH, $SCF_3$, a S—$C_{1-4}$-aliphatic residue, a S(=O)—$C_{1-4}$-aliphatic residue, a S(=O)$_2$—$C_{1-4}$-aliphatic residue, $CH_2F$, $CHF_2$, $CF_3$, CN, a $C_{1-4}$-aliphatic residue, a C(=O)—O—$C_{1-4}$-aliphatic residue, and C(=O)—OH, wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a S(=O)$_2$—$C_{1-4}$-aliphatic residue, $CH_2F$, $CHF_2$, $CF_3$, CN, a $C_{1-4}$-aliphatic residue, C(=O)—OH, a C(=O)—O—$C_{1-4}$-aliphatic residue a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a S(=O)$_2$—$C_{1-4}$-aliphatic residue, $CH_2F$, $CHF_2$, $CF_3$, CN, a $C_{1-4}$-aliphatic residue and C(=O)—OH, and wherein the $C_{3-10}$-cycloaliphatic residue or the 3 to 10 membered heterocycloaliphatic residue may in each case optionally bridged via a $C_{1-8}$ aliphatic group, which in turn may be unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, a C(=O)—O—$C_{1-4}$-aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a S(=O)$_2$—$C_{1-4}$-aliphatic residue, $CH_2F$, $CHF_2$, $CF_3$, CN, a $C_{1-4}$-aliphatic residue and C(=O)—OH, on the condition that if $R^4$ denotes a 3 to 10 membered heterocycloaliphatic residue, the 3 to 10 membered heterocycloaliphatic residue is linked via a carbon atom, or denotes an aryl or heteroaryl, in each case unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a S(=O)$_2$—$C_{1-4}$-aliphatic residue, $CH_2F$, $CHF_2$, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, a $C_{3-6}$ cycloaliphatic residue, a 3 to 6 membered heterocycloaliphatic residue,

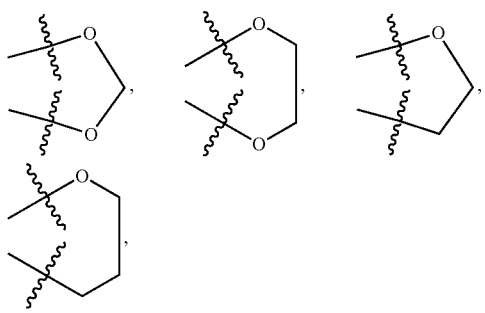

benzyl, phenyl, thienyl, pyridyl, furyl, thiazolyl and oxazolyl, wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue, and wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, an O—$C_{1-4}$ aliphatic residue, $OCH_2F$, $OCHF_2$, $OCF_3$, O—$CH_2$—OH, O—$CH_2$—O—$CH_3$, SH, $SCF_3$, a S—$C_{1-4}$ aliphatic residue, a S(=O)—$C_{1-4}$-aliphatic residue, a S(=O)$_2$—$C_{1-4}$-aliphatic residue, $CH_2F$, $CHF_2$, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a S(=O)$_2$—$C_{1-4}$-aliphatic residue, $CH_2F$, $CHF_2$, $CF_3$, CN, a $C_{1-4}$-aliphatic residue and C(=O)—OH, and wherein the aryl or the heteroaryl residue may in each case be optionally bridged via a $C_{1-8}$ aliphatic group, which in turn may be unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a S(=O)$_2$—$C_{1-4}$-aliphatic residue, $CH_2F$, $CHF_2$, $CF_3$, CN and C(=O)—OH, $R^5$ denotes H or a $C_{1-10}$-aliphatic residue, unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a S(=O)$_2$—$C_{1-4}$-aliphatic residue, $CH_2F$, $CHF_2$, $CF_3$, CN, a $C_{1-4}$-aliphatic residue and C(=O)—OH, wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue, or $R^4$ and $R^5$ form together with the nitrogen atom connecting them a 3 to 10 membered heterocycloaliphatic residue, unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a S(=O)$_2$—$C_{1-4}$-aliphatic residue, $CH_2F$, $CHF_2$, $CF_3$, CN, a $C_{1-4}$-aliphatic residue, C(=O)—OH, a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, =O, OH, $OCH_2F$, $OCHF_2$, $OCF_3$, $CH_2F$, $CHF_2$, $CF_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a S(=O)$_2$—$C_{1-4}$-aliphatic residue, $CH_2F$, $CHF_2$, $CF_3$, CN, a $C_{1-4}$-aliphatic residue and C(=O)—OH, and wherein the 3 to 10 membered heterocycloaliphatic residue formed by $R^4$ and $R^5$ together with the nitrogen atom connecting them may optionally be condensed with aryl or heteroaryl, wherein the aryl or heteroaryl residues condensed in this way can for their part be respectively unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a S(=O)$_2$—$C_{1-4}$-aliphatic residue, $CH_2F$, $CHF_2$, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, a $C_{3-6}$ cycloaliphatic residue, a 3 to 6 membered heterocycloaliphatic residue,

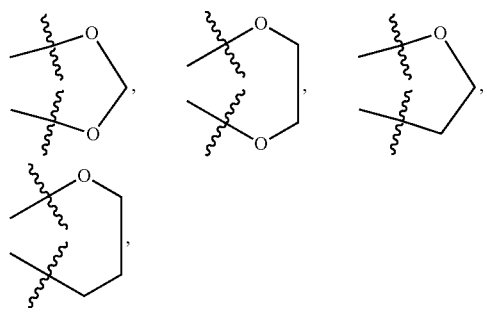

benzyl, phenyl, thienyl, pyridyl, furyl, thiazolyl and oxazolyl, and wherein the 3 to 10 membered heterocycloaliphatic residue formed by $R^4$ and $R^5$ together with the nitrogen atom connecting them may optionally be condensed with a $C_{3-10}$ cycloaliphatic residue or a 3 to 10 membered heterocycloaliphatic residue, wherein the $C_{3-10}$ cycloaliphatic residue or a 3 to 10 membered heterocycloaliphatic residue condensed in this way can for their part be respectively unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, =O, OH, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a S(=O)$_2$—$C_{1-4}$-aliphatic residue, $CH_2F$, $CHF_2$, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, a $C_{3-6}$ cycloaliphatic residue, a 3 to 6 membered heterocycloaliphatic residue, benzyl, phenyl, thienyl, pyridyl, furyl, thiazolyl and oxazolyl, wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue, and wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, an O—$C_{1-4}$ aliphatic residue, $OCH_2F$, $OCHF_2$, $OCF_3$, O—$CH_2$—OH, O—$CH_2$—O—$CH_3$, SH, $SCF_3$, a S—$C_{1-4}$ aliphatic residue, a S(=O)—$C_{1-4}$-aliphatic residue, a S(=O)$_2$—$C_{1-4}$-aliphatic residue, $CH_2F$, $CHF_2$, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a S(=O)$_2$—$C_{1-4}$-aliphatic residue, $CH_2F$, $CHF_2$, $CF_3$, CN, a $C_{1-4}$-aliphatic residue and C(=O)—OH.

In a further preferred embodiment of the compound according to general formula (I), the residue $R^4$ represents the partial structure (T2)

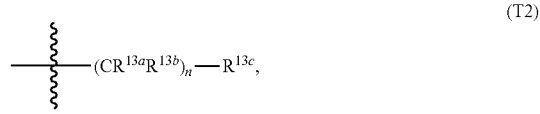

(T2)

wherein n denotes 0, 1, 2, or 3, preferably denotes 1, 2 or 3, more preferably denotes 1 or 2, even more preferably denotes 1, $R^{13a}$ and $R^{13b}$ each independently of one another represent H, F, Cl, Br, I, $NO_2$, $NH_2$, a $NH(C_{1-4}$ aliphatic residue), an $N(C_{1-4}$ aliphatic residue)$_2$, OH, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a S(=O)$_2$—$C_{1-4}$-aliphatic residue, $OCH_2F$, $OCHF_2$, $CF_3$, CN, a $C_{1-4}$ aliphatic residue or C(=O)—OH, or together denote =O, preferably each independently of one another represent H, F, Cl, Br, I, $NH_2$, a $NH(C_{1-4}$ aliphatic residue), a $N(C_{1-4}$ aliphatic residue)$_2$, OH, O—$C_{1-4}$ aliphatic residue or a $C_{1-4}$ aliphatic residue or together denote =O, more preferably each independently of one another represent H, F, Cl, Br, I, an O—$C_{1-4}$ aliphatic residue or a $C_{1-4}$ aliphatic residue or together denote =O, even more preferably each independently of one another represent H, F, an O—$C_{1-4}$ aliphatic residue or a $C_{1-4}$ aliphatic residue or together denote =O, and $R^{13c}$ denotes a $C_{1-4}$ aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a S(=O)$_2$—$C_{1-4}$-aliphatic residue, $CH_2F$, $CHF_2$, $CF_3$, CN, a $C_{1-4}$-aliphatic residue and C(=O)—OH, or denotes—preferably when n is ≠0, more preferably when n is 1—a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a $S(=O)_2$—$C_{1-4}$-aliphatic residue, $CH_2F$, $CHF_2$, $CF_3$, CN, a $C_{1-4}$-aliphatic residue, C(=O)—OH, a $C_{3-6}$ cycloaliphatic residue and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a $S(=O)_2$—$C_{1-4}$-aliphatic residue, $CH_2F$, $CHF_2$, $CF_3$, CN, a $C_{1-4}$-aliphatic residue and C(=O)—OH, or denotes—preferably when n is ≠0, more preferably when n is 1,—an aryl or heteroaryl, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a $S(=O)_2$—$C_{1-4}$-aliphatic residue, $CH_2F$, $CHF_2$, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, a $C_{3-6}$ cycloaliphatic residue, a 3 to 6 membered heterocycloaliphatic residue,

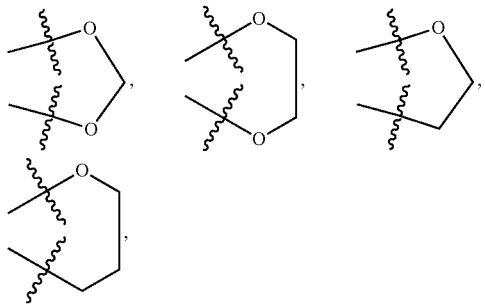

benzyl, phenyl, thienyl, pyridyl, furyl, thiazolyl and oxazolyl, wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue, and wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a $S(=O)_2$—$C_{1-4}$-aliphatic residue, $CH_2F$, $CHF_2$, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a $S(=O)_2$—$C_{1-4}$-aliphatic residue, $CH_2F$, $CHF_2$, $CF_3$, CN, a $C_{1-4}$-aliphatic residue and C(=O)—OH, $R^5$ denotes H or a $C_{1-10}$-aliphatic residue, preferably a $C_{1-6}$-aliphatic residue, unsubstituted or mono- or polysubstituted with at least one substituent selected from the group consisting of F, Cl, Br, I, $NO_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a $S(=O)_2$—$C_{1-4}$-aliphatic residue, $CH_2F$, $CHF_2$, $CF_3$, CN, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $CH_2F$, $CHF_2$, $CF_3$ and an unsubstituted O—$C_{1-4}$-aliphatic residue, or $R^4$ and $R^5$ form together with the nitrogen atom connecting them a 3 to 10 membered heterocycloaliphatic residue, preferably a 3 to 6 membered heterocycloaliphatic residue, or preferably selected from the group consisting of morpholinyl, piperidinyl, pyrrolidinyl, azetidinyl, piperazinyl, 4-methylpiperazinyl, oxazepanyl, thiomorpholinyl, azepanyl,

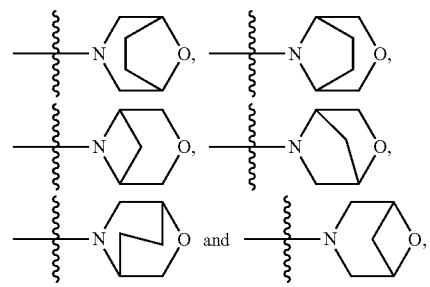

more preferably selected from the group consisting of morpholinyl, piperidinyl, pyrrolidinyl, azetidinyl, piperazinyl, 4-methylpiperazinyl, oxazepanyl, in each case unsubstituted or mono- or polysubstituted with at least one substituent selected from the group consisting of F, Cl, Br, I, $NO_2$, OH, =O, C(=O)—OH, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a $S(=O)_2$—$C_{1-4}$-aliphatic residue, $CH_2F$, $CHF_2$, $CF_3$, CN, and a $C_{1-4}$-aliphatic residue, a $C_{3-6}$ cycloaliphatic residue, preferably cyclopropyl, cyclobutyl or cyclopentyl, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, =O, OH, $CH_2F$, $CHF_2$, $CF_3$ and an unsubstituted O—$C_{1-4}$-aliphatic residue, preferably selected from the group consisting of F, Cl, Br, I, OH, $CH_2F$, $CHF_2$, $CF_3$ and an unsubstituted O—$C_{1-4}$-aliphatic residue, wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a S(=O)$_2$—$C_{1-4}$-aliphatic residue $CH_2F$, $CHF_2$, $CF_3$, CN, a $C_{1-4}$-aliphatic residue and C(=O)—OH, and wherein the 3 to 10 membered heterocycloaliphatic residue formed by $R^4$ and $R^5$ together with the nitrogen atom connecting them may optionally be condensed with aryl or heteroaryl, preferably with phenyl, pyridyl or thienyl, wherein the aryl or heteroaryl residues condensed in this way can for their part be respectively unsubstituted or mono- or polysubstituted with at least one substituent selected from the group consisting of F, Cl, Br, I, $NO_2$, OH, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a S(=O)$_2$—$C_{1-4}$-aliphatic residue, $CH_2F$, $CHF_2$, $CF_3$, CN, a $C_{1-4}$-aliphatic residue, C(=O)—OH, a $C_{3-6}$ cycloaliphatic residue, a 3 to 6 membered heterocycloaliphatic residue,

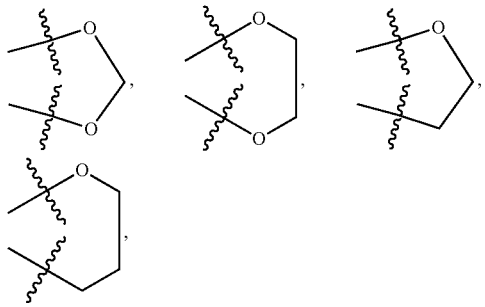

benzyl, phenyl, thienyl, and pyridyl, and wherein the 3 to 10 membered heterocycloaliphatic residue formed by $R^4$ and $R^5$ together with the nitrogen atom connecting them may optionally be condensed with a $C_{3-10}$ cycloaliphatic residue, preferably cyclopropyl, cyclobutyl or cyclopentyl, or a 3 to 10 membered heterocycloaliphatic residue, preferably oxetanyl or oxiranyl, wherein the $C_{3-10}$ cycloaliphatic residue or the 3 to 10 membered heterocycloaliphatic residue condensed in this way can for their part be respectively unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, =O, OH, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$ aliphatic residue, a S(=O)$_2$—$C_{1-4}$-aliphatic residue, $CH_2F$, $CHF_2$, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue, and wherein benzyl, phenyl, thienyl, and pyridyl, may in each case may be unsubstituted or mono- or polysubstituted with at least one substituent selected from the group consisting of F, Cl, Br, I, $NO_2$, OH, an O—$C_{1-4}$ aliphatic residue, $OCH_2F$, $OCHF_2$, $OCF_3$, O—$CH_2$—OH, O—$CH_2$—O—$CH_3$, SH, $SCF_3$, a S—$C_{1-4}$ aliphatic residue, a S(=O)—$C_{1-4}$-aliphatic residue, a S(=O)$_2$—$C_{1-4}$-aliphatic residue, $CH_2F$, $CHF_2$, $CF_3$, CN, a $C_{1-4}$-aliphatic residue, and C(=O)—OH, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a S(=O)$_2$—$C_{1-4}$-aliphatic residue, $CH_2F$, $CHF_2$, $CF_3$, CN, a $C_{1-4}$-aliphatic residue and C(=O)—OH.

Preferably, $R^4$ represents the partial structure (T2), wherein n denotes 0, 1, 2, or 3, preferably denotes 1, 2 or 3, more preferably denotes 1 or 2, even more preferably denotes 1, $R^{13a}$ and $R^{13b}$ each independently of one another represent H, F, Cl, Br, I, an O—$C_{1-4}$ aliphatic residue or a $C_{1-4}$ aliphatic residue or together denote =O, preferably each independently of one another represent H, F, a O—$C_{1-2}$ aliphatic residue or a $C_{1-2}$ aliphatic residue or together denote =O, and $R^{13c}$ denotes a $C_{1-4}$ aliphatic residue, unsubstituted or mono- or polysubstituted with at least one substituent selected from the group consisting of F, Cl, Br, I, OH, =O, an O—$C_{1-4}$ aliphatic residue, $OCH_2F$, $OCHF_2$, $OCF_3$, $CH_2F$, $CHF_2$, $CF_3$, a $C_{1-4}$-aliphatic residue and C(=O)—OH, or denotes—preferably when n is ≠0, more preferably when n is 1—a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, $OCH_2F$, $OCHF_2$, $OCF_3$, $CH_2F$, $CHF_2$, $CF_3$, a $C_{1-4}$-aliphatic residue, C(=O)—OH, a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, OH, =O, an O—$C_{1-4}$ aliphatic residue, $OCH_2F$, $OCHF_2$, $OCF_3$, $CH_2F$, $CHF_2$, $CF_3$, a $C_{1-4}$-aliphatic residue and C(=O)—OH, or denotes—preferably when n is ≠0, more preferably when n is 1—an aryl or heteroaryl, in each case unsubstituted or mono- or polysubstituted with at least one substituent selected from the group consisting of F, Cl, Br, I, OH, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$ aliphatic residue, a S(=O)$_2$—$C_{1-4}$ aliphatic residue, $CH_2F$, $CHF_2$, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, a $C_{3-6}$ cycloaliphatic residue, a 3 to 6 membered heterocycloaliphatic residue, benzyl, phenyl, thienyl, pyridyl, furyl, thiazolyl or oxazolyl, wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue, and wherein benzyl, phenyl, thienyl, pyridyl, furyl, thiazolyl and oxazolyl may in each case may be unsubstituted or mono- or polysubstituted, preferably unsubstituted or mono- or disubstituted with at least one substituent selected from the group consisting of F, Cl, Br, I, OH, an O—$C_{1-4}$ aliphatic residue, $OCH_2F$, $OCHF_2$, $OCF_3$, $CH_2F$, $CHF_2$, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, preferably with at least one substituent selected from the group consisting of F, Cl, $CH_3$, O—$CH_3$, $CH_2F$, $CHF_2$, $CF_3$ and $OCF_3$, $OCH_2F$, and $OCHF_2$, wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, OH, =O, an O—$C_{1-4}$ aliphatic residue, $OCH_2F$, $OCHF_2$, $OCF_3$, $CH_2F$, $CHF_2$, $CF_3$ a $C_{1-4}$-aliphatic residue and C(=O)—OH, $R^5$ denotes H or a $C_{1-6}$-aliphatic residue, preferably a $C_{1-4}$-aliphatic residue, unsubstituted or mono- or polysubstituted with at least one substituent selected from the group consisting of F, Cl, Br, I, $NO_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$ aliphatic residue, a S(=O)$_2$—$C_{1-4}$ aliphatic residue, $CH_2F$, $CHF_2$, $CF_3$, CN, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $CH_2F$, $CHF_2$, $CF_3$ and an unsubstituted O—$C_{1-4}$-aliphatic residue, or $R^4$ and $R^5$ form together with the nitrogen atom connecting them a 3 to 10 membered heterocycloaliphatic residue, preferably a 4 to 7 membered heterocycloaliphatic residue, or preferably selected from the group consisting of morpholinyl, piperidinyl, pyrrolidinyl, azetidinyl, piperazinyl, 4-methylpiperazinyl, oxazepanyl, thiomorpholinyl, azepanyl,

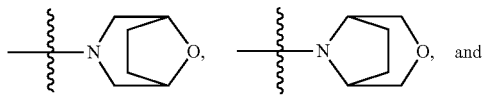

-continued

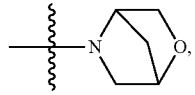

more preferably selected from the group consisting of morpholinyl, piperidinyl, pyrrolidinyl, azetidinyl, piperazinyl, 4-methylpiperazinyl, oxazepanyl, unsubstituted or mono- or polysubstituted with at least one substituent selected from the group consisting of F, Cl, Br, I, OH, =O, C(=O)—OH, an O—$C_{1-4}$ aliphatic residue, $OCH_2F$, $OCHF_2$, $OCF_3$, $SCF_3$, a S—$C_{1-4}$ aliphatic residue, a S(=O)—$C_{1-4}$ aliphatic residue, a S(=O)$_2$—$C_{1-4}$ aliphatic residue, $CH_2F$, $CHF_2$, $CF_3$, and a $C_{1-4}$-aliphatic residue, and a $C_{3-6}$ cycloaliphatic residue, preferably cyclopropyl, cyclobutyl or cyclopentyl, wherein the $C_{1-4}$-aliphatic residue in each case may be unsubstituted or mono- or polysubstituted with at least one substituent selected from the group consisting of F, Cl, Br, I, OH, =O, $CH_2F$, $CHF_2$, $CF_3$ and an unsubstituted O—$C_{1-4}$-aliphatic residue, preferably selected from the group consisting of F, Cl, Br, I, OH, $CH_2F$, $CHF_2$, $CF_3$ and an unsubstituted O—$C_{1-4}$-aliphatic residue, wherein the $C_{3-6}$ cycloaliphatic residue may in each case may be unsubstituted or mono- or polysubstituted with at least one substituent selected from the group consisting of F, Cl, Br, I, OH, =O, an O—$C_{1-4}$ aliphatic residue, $OCH_2F$, $OCHF_2$, $OCF_3$, $SCF_3$, a S—$C_{1-4}$ aliphatic residue, $CH_2F$, $CHF_2$, $CF_3$, CN, a $C_{1-4}$-aliphatic residue and C(=O)—OH, and wherein the 3 to 10 membered heterocycloaliphatic residue formed by $R^4$ and $R^5$ together with the nitrogen atom connecting them may optionally be condensed with aryl or heteroaryl, preferably with phenyl or pyridyl, wherein the aryl or heteroaryl residues condensed in this way can for their part be respectively unsubstituted or mono- or polysubstituted with at least one substituent selected from the group consisting of F, Cl, Br, I, OH, an O—$C_{1-4}$ aliphatic residue, $OCH_2F$, $OCHF_2$, $OCF_3$, $SCF_3$, a S—$C_{1-4}$ aliphatic residue, a S(=O)—$C_{1-4}$ aliphatic residue, a S(=O)$_2$—$C_{1-4}$ aliphatic residue, $CH_2F$, $CHF_2$, $CF_3$, a $C_{1-4}$-aliphatic residue, C(=O)—OH, a $C_{3-6}$ cycloaliphatic residue, benzyl, phenyl, thienyl, and pyridyl, and wherein the 3 to 10 membered heterocycloaliphatic residue formed by $R^4$ and $R^5$ together with the nitrogen atom connecting them may optionally be condensed with a $C_{3-10}$ cycloaliphatic residue, preferably cyclopropyl, cyclobutyl or cyclopentyl, or a 3 to 10 membered heterocycloaliphatic residue, preferably oxetanyl or oxiranyl, wherein the $C_{3-10}$ cycloaliphatic residue or the 3 to 10 membered heterocycloaliphatic residue condensed in this way can for their part be respectively unsubstituted or mono- or polysubstituted with at least one substituent selected from the group consisting of F, Cl, Br, I, =O, OH, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$ aliphatic residue, a S(=O)$_2$—$C_{1-4}$ aliphatic residue, $CH_2F$, $CHF_2$, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted $O$—$C_{1-4}$-aliphatic residue, and wherein benzyl, phenyl, thienyl, and pyridyl, may in each case may be unsubstituted or mono- or polysubstituted with at least one substituent selected from the group consisting of F, Cl, Br, I, OH, an $O$—$C_{1-4}$ aliphatic residue, $OCH_2F$, $OCHF_2$, $OCF_3$, $O$—$CH_2$—$OH$, $O$—$CH_2$—$O$—$CH_3$, $SCF_3$, a $S$—$C_{1-4}$ aliphatic residue, a $S(=O)$—$C_{1-4}$ aliphatic residue, a $S(=O)_2$—$C_{1-4}$ aliphatic residue, $CH_2F$, $CHF_2$, $CF_3$, CN, a $C_{1-4}$-aliphatic residue, and $C(=O)$—OH, and wherein the $C_{3-6}$ cycloaliphatic residue may in each case may be unsubstituted or mono- or polysubstituted with at least one substituent selected from the group consisting of F, Cl, Br, I, OH, =O, an $O$—$C_{1-4}$ aliphatic residue, $OCH_2F$, $OCHF_2$, $OCF_3$, $SCF_3$, a $S$—$C_{1-4}$ aliphatic residue, a $S(=O)$—$C_{1-4}$ aliphatic residue, a $S(=O)_2$—$C_{1-4}$ aliphatic residue, $CH_2F$, $CHF_2$, $CF_3$, a $C_{1-4}$-aliphatic residue and $C(=O)$—OH.

More preferably, $R^4$ represents the partial structure (T2), wherein n denotes 0, 1, 2 or 3, preferably denotes 1 or 2, more preferably denotes 1, $R^{13a}$ and $R^{13b}$ each independently of one another represent H, F, Cl, Br, I, an $O$—$C_{1-4}$ aliphatic residue or a $C_{1-4}$ aliphatic residue or together denote =O, preferably each independently of one another represent H, F, a $O$—$C_{1-2}$ aliphatic residue or a $C_{1-2}$ aliphatic residue or together denote =O, and $R^{13c}$ denotes a $C_{1-4}$ aliphatic residue, unsubstituted or mono- or polysubstituted with at least one substituent selected from the group consisting of F, Cl, Br, I, =O, an $O$—$C_{1-4}$ aliphatic residue, $CH_2F$, $CHF_2$, $CF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, $CH_2F$, $CHF_2$, $CF_3$ and an unsubstituted $O$—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, an $O$—$C_{1-4}$ aliphatic residue, $CH_2F$, $CHF_2$, $CF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, $CH_2F$, $CHF_2$, $CF_3$ and an unsubstituted $O$—$C_{1-4}$-aliphatic residue, or denotes an aryl or heteroaryl, in each case unsubstituted or mono- or polysubstituted with at least one substituent selected from the group consisting of F, Cl, Br, I, OH, an $O$—$C_{1-4}$ aliphatic residue, $OCH_2F$, $OCHF_2$, $OCF_3$, $CH_2F$, $CHF_2$, $CF_3$, CN, a $C_{1-4}$-aliphatic residue, $C(=O)$—$CH_3$, $C(=O)$—$C_2H_5$, $C(=O)$—$O$—$CH_3$ and $C(=O)$—$O$—$C_2H_5$, a $C_{3-6}$ cycloaliphatic residue, a 3 to 6 membered heterocycloaliphatic residue, benzyl, phenyl, thienyl or pyridyl, wherein benzyl, phenyl, thienyl and pyridyl, may in each case may be unsubstituted or mono- or polysubstituted, preferably unsubstituted or mono- or disubstituted with at least one substituent selected from the group consisting of F, Cl, Br, I, OH, an $O$—$C_{1-4}$ aliphatic residue, $OCH_2F$, $OCHF_2$, $OCF_3$, $CH_2F$, $CHF_2$, $CF_3$, CN, a $C_{1-4}$-aliphatic residue, $C(=O)$—$CH_3$, $C(=O)$—$C_2H_5$, $C(=O)$—$O$—$CH_3$ and $C(=O)$—$O$—$C_2H_5$, preferably with at least one substituent selected from the group consisting of F, Cl, $CH_3$, $O$—$CH_3$, $CH_2F$, $CHF_2$, $CF_3$ and $OCH_2F$, $OCHF_2$, $OCF_3$, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, OH, =O, an $O$—$C_{1-4}$ aliphatic residue, $OCH_2F$, $OCHF_2$, $OCF_3$, $CH_2F$, $CHF_2$, $CF_3$ a $C_{1-4}$-aliphatic residue and $C(=O)$—OH, $R^5$ denotes H or an unsubstituted $C_{1-4}$-aliphatic residue or a $C_{1-4}$-aliphatic residue monosubstituted with O-methyl, wherein the $C_{1-4}$-aliphatic residue is in each case preferably selected from the group consisting of methyl, ethyl, n-propyl, 2-propyl, n-butyl, isobutyl, sec.-butyl and tert.-butyl, more preferably selected from the group consisting of methyl and ethyl, or $R^4$ and $R^5$ form together with the nitrogen atom connecting them a 3 to 10 membered heterocycloaliphatic residue, more preferably selected from the group consisting of morpholinyl, piperidinyl, pyrrolidinyl, azetidinyl, piperazinyl, 4-methylpiperazinyl, oxazepanyl, thiomorpholinyl, azepanyl,

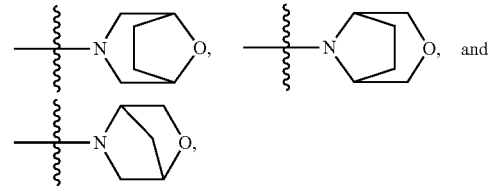

in each case unsubstituted or mono- or polysubstituted with at least one substituent selected from the group consisting of F, Cl, Br, I, OH, =O, $C(=O)$—OH, an $O$—$C_{1-4}$ aliphatic residue, $OCH_2F$, $OCHF_2$, $OCF_3$, $SCF_3$, a $S$—$C_{1-4}$ aliphatic residue, a $S(=O)$—$C_{1-4}$ aliphatic residue, a $S(=O)_2$—$C_{1-4}$ aliphatic residue, $CH_2F$, $CHF_2$, $CF_3$, and a $C_{1-4}$-aliphatic residue, cyclopropyl, cyclobutyl and cyclopentyl, wherein the $C_{1-4}$-aliphatic residue is in each case unsubstituted or mono- or polysubstituted with at least one substituent selected from the group consisting of F, Cl, OH, =O, $CH_2F$, $CHF_2$, $CF_3$ and an unsubstituted $O$—$C_{1-4}$-aliphatic residue, preferably is in each case unsubstituted, and wherein the 3 to 10 membered heterocycloaliphatic residue formed by $R^4$ and $R^5$ together with the nitrogen atom connecting them may optionally be condensed with phenyl or pyridyl, wherein the phenyl or pyridyl residues condensed in this way can for their part be respectively unsubstituted or mono- or polysubstituted with at least one substituent selected from the group consisting of F, Cl, Br, I, OH, an $O$—$C_{1-4}$ aliphatic residue, $OCH_2F$, $OCHF_2$, $OCF_3$, $SCF_3$, a $S$—$C_{1-4}$ aliphatic residue, a $S(=O)$—$C_{1-4}$ aliphatic residue, a $S(=O)_2$—$C_{1-4}$ aliphatic residue, $CH_2F$, $CHF_2$, $CF_3$, a $C_{1-4}$-aliphatic residue, $C(=O)$—OH, and a $C_{3-6}$ cycloaliphatic residue, wherein the $C_{1-4}$-aliphatic residue in each case may be unsubstituted or mono- or polysubstituted with at least one substituent selected from the group consisting of F, Cl, OH, OCH$_2$F, OCHF$_2$, OCF$_3$, CH$_2$F, CHF$_2$, CF$_3$ and an unsubstituted O—C$_{1-4}$-aliphatic residue, and wherein the C$_{3-6}$ cycloaliphatic residue may in each case may be unsubstituted or mono- or polysubstituted with at least one substituent selected from the group consisting of F, Cl, Br, I, OH, =O, an O—C$_{1-4}$ aliphatic residue, OCH$_2$F, OCHF$_2$, OCF$_3$, SCF$_3$, a S—C$_{1-4}$ aliphatic residue, a S(=O)—C$_{1-4}$ aliphatic residue, a S(=O)$_2$—C$_{1-4}$ aliphatic residue, CH$_2$F, CHF$_2$, CF$_3$, a C$_{1-4}$-aliphatic residue and C(=O)—OH, and wherein the 3 to 10 membered heterocycloaliphatic residue formed by R$^4$ and R$^5$ together with the nitrogen atom connecting them may optionally be condensed with a C$_{3-6}$ cycloaliphatic residue, preferably cyclopropyl, cyclobutyl or cyclopentyl, or a 4 to 7 membered heterocycloaliphatic residue, preferably oxetanyl or oxiranyl, wherein the C$_{3-6}$ cycloaliphatic residue or the 4 to 7 membered heterocycloaliphatic residue condensed in this way can for their part be respectively unsubstituted or mono- or polysubstituted with at least one substituent selected from the group consisting of F, Cl, Br, I, =O, OH, an O—C$_{1-4}$ aliphatic residue, OCH$_2$F, OCHF$_2$, OCF$_3$, SCF$_3$, CH$_2$F, CHF$_2$, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$.

Even more preferably,

R$^4$ represents the partial structure (T2), wherein n denotes 0, 1, 2 or 3, preferably denotes 1 or 2, more preferably denotes 1, R$^{13a}$ and R$^{13b}$ each independently of one another represent H, F, a O—C$_{1-4}$ aliphatic residue or a C$_{1-4}$ aliphatic residue or together denote =O; preferably each independently of one another represent H, F, CH$_3$ or OCH$_3$ or together denote =O;

R$^{13c}$ denotes a C$_{1-4}$ aliphatic residue, unsubstituted or mono- or polysubstituted with at least one substituent selected from the group consisting of F, Cl, Br, I, =O, an unsubstituted O—C$_{1-4}$ aliphatic residue, CH$_2$F, CHF$_2$, CF$_3$, and an unsubstituted C$_{1-4}$-aliphatic residue, or denotes a C$_{3-10}$-cycloaliphatic residue, preferably selected from the group consisting of cyclopropyl, cyclobutyl, cyclopentyl and cyclohexyl, or a 3 to 10 membered heterocycloaliphatic residue, preferably selected from the group consisting of pyrrolidinyl, morpholinyl, piperazinyl, piperidinyl and tetrahydropyranyl, more preferably tetrahydropyranyl, in each case unsubstituted or mono- or polysubstituted with at least one substituent selected from the group consisting of F, Cl, Br, I, an unsubstituted O—C$_{1-4}$ aliphatic residue, CH$_2$F, CHF$_2$, CF$_3$, and an unsubstituted C$_{1-4}$-aliphatic residue, or denotes an aryl or heteroaryl, preferably phenyl or pyridyl, in each case unsubstituted or mono- or polysubstituted with at least one substituent selected from the group consisting of F, Cl, Br, I, OH, an O—C$_{1-4}$ aliphatic residue, OCH$_2$F, OCHF$_2$, OCF$_3$, CH$_2$F, CHF$_2$, CF$_3$, CN, a C$_{1-4}$-aliphatic residue, C(=O)—CH$_3$, C(=O)—C$_2$H$_5$, C(=O)—O—CH$_3$, C(=O)—O—C$_2$H$_5$ and phenyl, wherein phenyl may be unsubstituted or mono- or polysubstituted, preferably unsubstituted or mono- or disubstituted with at least one substituent selected from the group consisting of F, Cl, Br, I, OH, an O—C$_{1-4}$ aliphatic residue, OCH$_2$F, OCHF$_2$, OCF$_3$, CH$_2$F, CHF$_2$, CF$_3$, CN, a C$_{1-4}$-aliphatic residue, C(=O)—CH$_3$, C(=O)—C$_2$H$_5$, C(=O)—O—CH$_3$ and C(=O)—O—C$_2$H$_5$, preferably with at least one substituent selected from the group consisting of F, Cl, CH$_3$, O—CH$_3$, CF$_3$ and OCF$_3$, R$^5$ denotes H or an unsubstituted C$_{1-4}$-aliphatic residue or a C$_{1-4}$-aliphatic residue, which is monosubstituted with OCH$_3$, preferably H, methyl, ethyl, n-propyl, 2-propyl, n-butyl, isobutyl, sec.-butyl or tert.-butyl or CH$_2$—OCH$_3$, C$_2$H$_4$—OCH$_3$ or C$_3$H$_6$—OCH$_3$, more preferably H, methyl or ethyl, preferably denotes H or an unsubstituted C$_{1-4}$-aliphatic residue, preferably H, methyl, ethyl, n-propyl, 2-propyl, n-butyl, isobutyl, sec.-butyl or tert.-butyl, more preferably H, methyl or ethyl, or R$^4$ and R$^5$ form together with the nitrogen atom connecting them a morpholinyl, piperidinyl, pyrrolidinyl, azetidinyl, piperazinyl, 4-methylpiperazinyl, oxazepanyl, thiomorpholinyl, azepanyl,

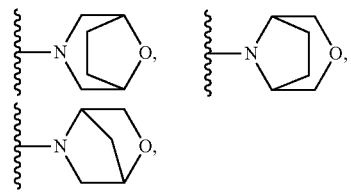

and tetrahydroquinolinyl, tetrahydroisoquinolinyl, tetrahydroimidazo[1,2-a]pyrazinyl, octahydropyrrolo[1,2-a]pyrazinyl,

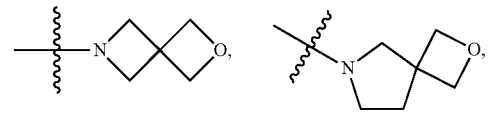 [SMILES: *N1CC2(COC2)C1 ; *N1CCC2(COC2)C1]

dihydroindolinyl, or dihydroisoindolyl, preferably a morpholinyl, piperidinyl, pyrrolidinyl, azetidinyl, piperazinyl, 4-methylpiperazinyl, oxazepanyl, tetrahydroquinolinyl, tetrahydroisoquinolinyl, dihydroindolinyl, or dihydroisoindolyl, in each case unsubstituted or mono- or polysubstituted with at least one substituent selected from the group consisting of F, Cl, Br, I, OH, =O, C(=O)—OH, an O—C$_{1-4}$ aliphatic residue, OCH$_2$F, OCHF$_2$, OCF$_3$, SCF$_3$, a S—C$_{1-4}$ aliphatic residue, a S(=O)—C$_{1-4}$ aliphatic residue, a S(=O)$_2$—C$_{1-4}$ aliphatic residue, CH$_2$F, CHF$_2$, CF$_3$, and a C$_{1-4}$-aliphatic residue, cyclopropyl, cyclobutyl and cyclopentyl, wherein the C$_{1-4}$-aliphatic residue is in each case unsubstituted or mono- or polysubstituted with at least one substituent selected from the group consisting of F, OH, =O, CH$_2$F, CHF$_2$, CF$_3$ and an unsubstituted O—C$_{1-4}$-aliphatic residue, preferably is in each case unsubstituted.

Still more preferably,

R$^4$ represents the partial structure (T2), wherein n denotes 0, 1, 2 or 3, preferably denotes 1 or 2, more preferably denotes 1, R$^{13a}$ and R$^{13b}$ each independently of one another represent H, F, CH$_3$ or OCH$_3$ or together denote =O, preferably each independently of one another represent H or CH$_3$, more preferably H, $R^{13c}$ denotes a $C_{1-4}$ aliphatic residue, preferably methyl, ethyl, n-propyl, 2-propyl, n-butyl, isobutyl, sec.-butyl, or tert.-butyl, unsubstituted or mono- or polysubstituted with at least one substituent selected from the group consisting of F, Cl, Br, I, =O, an unsubstituted O—$C_{1-4}$ aliphatic residue, and $CH_2F$, $CHF_2$, $CF_3$, or denotes cyclopropyl, cyclobutyl, cyclopentyl or cyclohexyl, pyrrolidinyl, morpholinyl, piperazinyl, piperidinyl and tetrahydropyranyl, more preferably tetrahydropyranyl or morpholinyl, in each case unsubstituted or mono- or polysubstituted with at least one substituent selected from the group consisting of F, Cl, Br, I, an unsubstituted O—$C_{1-4}$ aliphatic residue, $CH_2F$, $CHF_2$, $CF_3$, and an unsubstituted $C_{1-4}$-aliphatic residue, or denotes an aryl or heteroaryl, preferably phenyl or pyridyl, more preferably phenyl, in each case unsubstituted or mono- or polysubstituted with at least one substituent selected from the group consisting of F, Cl, Br, I, OH, an O—$C_{1-4}$ aliphatic residue, $OCH_2F$, $OCHF_2$, $OCF_3$, $CH_2F$, $CHF_2$, $CF_3$, CN, and a $C_{1-4}$-aliphatic residue, $R^5$ denotes H, methyl or ethyl or $C_2H_4OCH_3$ or $C_3H_6OCH_3$, more preferably H or methyl or ethyl, even more preferably methyl, or $R^4$ and $R^5$ form together with the nitrogen atom connecting them a morpholinyl, piperidinyl, pyrrolidinyl, azetidinyl, oxazepanyl, tetrahydroquinolinyl, tetrahydroisoquinolinyl, thiomorpholinyl, azepanyl,

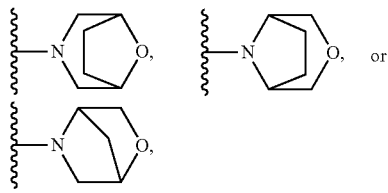

tetrahydroimidazo[1,2-a]pyrazinyl, octahydropyrrolo[1,2-a]pyrazinyl,

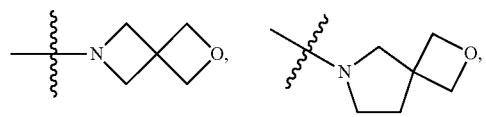 [SMILES: *N1CC2(COC2)C1 ; *N1CCC2(COC2)C1]

dihydroindolinyl, or dihydroisoindolyl, preferably a morpholinyl, piperidinyl, pyrrolidinyl, azetidinyl, oxazepanyl, tetrahydroquinolinyl, tetrahydroisoquinolinyl, dihydroindolinyl, or dihydroisoindolyl, more preferably a morpholinyl, piperidinyl, pyrrolidinyl, azetidinyl, oxazepanyl, tetrahydroquinolinyl, tetrahydroisoquinolinyl, more preferably a morpholinyl, oxazepanyl, tetrahydroquinolinyl, or tetrahydroisoquinolinyl, in each case unsubstituted or mono- or polysubstituted with at least one substituent selected from the group consisting of F, Cl, OH, =O, C(=O)—OH, C(=O)—$CH_3$, C(=O)—$OCH_3$, O-methyl, O-ethyl, $OCH_2F$, $OCHF_2$, $OCF_3$, $SCF_3$, $CH_2F$, $CHF_2$, $CF_3$, methyl, $CH_2CF_3$, $CH_2OH$, $CH_2$—$OCH_3$, $CH_2CH_2$—$OCH_3$, ethyl, n-propyl, 2-propyl, cyclopropyl, and cyclobutyl, preferably selected from the group consisting of F, Cl, OH, =O, C(=O)—OH, O-methyl, O-ethyl, $OCH_2F$, $OCHF_2$, $OCF_3$, $SCF_3$, $CH_2F$, $CHF_2$, $CF_3$, methyl, ethyl, n-propyl, 2-propyl, cyclopropyl, and cyclobutyl.

In particular, $R^4$ and $R^5$ form together with the nitrogen atom connecting them a morpholinyl, piperidinyl, pyrrolidinyl, azetidinyl, oxazepanyl, tetrahydroquinolinyl, tetrahydroisoquinolinyl, thiomorpholinyl, azepanyl, tetrahydroimidazo[1,2-a]pyrazinyl, octahydropyrrolo[1,2-a]pyrazinyl, dihydroindolinyl, or dihydroisoindolyl, preferably a morpholinyl, piperidinyl, pyrrolidinyl, azetidinyl, oxazepanyl, tetrahydroquinolinyl, tetrahydroisoquinolinyl, dihydroindolinyl, or dihydroisoindolyl, more preferably a morpholinyl, piperidinyl, pyrrolidinyl, azetidinyl, oxazepanyl, tetrahydroquinolinyl, tetrahydroisoquinolinyl, even more preferably a morpholinyl, oxazepanyl, tetrahydroquinolinyl, or tetrahydroisoquinolinyl, in particular a morpholinyl, in each case unsubstituted or mono- or polysubstituted with at least one substituent selected from the group consisting of F, Cl, OH, =O, C(=O)—OH, C(=O)—$CH_3$, C(=O)—$OCH_3$, O-methyl, O-ethyl, $OCH_2F$, $OCHF_2$, $OCF_3$, $SCF_3$, $CH_2F$, $CHF_2$, $CF_3$, methyl, $CH_2CF_3$, $CH_2OH$, $CH_2$—$OCH_3$, $CH_2CH_2$—$OCH_3$, ethyl, n-propyl, 2-propyl, cyclopropyl, and cyclobutyl, preferably selected from the group consisting of F, Cl, OH, =O, C(=O)—OH, O-methyl, O-ethyl, $OCF_3$, $OCH_2F$, $OCHF_2$, $SCF_3$, $CH_2F$, $CHF_2$, $CF_3$, methyl, ethyl, n-propyl, 2-propyl, cyclopropyl, and cyclobutyl.

In a further preferred embodiment of the compound according to general formula (I), the residue $R^6$ represents H; F; Cl; Br; I; CN; $CH_2F$, $CHF_2$, $CF_3$; $SCF_3$; $NO_2$; $OCH_2F$, $OCHF_2$, $OCF_3$; a $C_{1-4}$-aliphatic residue, a O—$C_{1-4}$-aliphatic residue, a S(=O)—$C_{1-4}$-aliphatic residue, a S(=O)$_2$—$C_{1-4}$-aliphatic residue, a S—$C_{1-4}$-aliphatic residue, wherein the $C_{1-4}$ aliphatic residue may be in each case be unsubstituted or mono- or polysubstituted with at least one substituent selected from the group consisting of F, Cl, Br, I, =O, OH, and an unsubstituted O—$C_{1-4}$-aliphatic residue;

a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a $C_{1-4}$-aliphatic residue and a O—$C_{1-4}$-aliphatic residue, wherein the $C_{1-4}$-aliphatic residue in each case may be unsubstituted or mono- or polysubstituted with at least one substituent selected from the group consisting of F, Cl, Br, I, =O, OH, and an unsubstituted O—$C_{1-4}$-aliphatic residue, and wherein the $C_{3-6}$-cycloaliphatic residue or the 3 to 6 membered heterocycloaliphatic residue may in each case be optionally bridged via a $C_{1-4}$ aliphatic group, which in turn may be unsubstituted or mono- or polysubstituted with at least one substituent selected from the group consisting of F, Cl, Br, I, =O, OH, an unsubstituted $C_{1-4}$-aliphatic residue and an unsubstituted O—$C_{1-4}$-aliphatic residue.

Preferably, $R^6$ represents H; F; Cl; Br; I; CN; $CH_2F$, $CHF_2$, $CF_3$; $SCF_3$; $NO_2$; $OCH_2F$, $OCHF_2$, $OCF_3$; a $C_{1-4}$-aliphatic residue, a O—$C_{1-4}$-aliphatic residue, a S—$C_{1-4}$-aliphatic residue, a S(=O)—$C_{1-4}$-aliphatic residue, a S(=O)$_2$—$C_{1-4}$-aliphatic residue, wherein the $C_{1-4}$ aliphatic residue may be in each case be unsubstituted or mono- or polysubstituted with at least one substituent selected from the group consisting of F, Cl, Br, I, =O, OH, and an unsubstituted O—$C_{1-4}$-aliphatic residue.

More preferably, $R^6$ represents H; F; Cl; Br; I; CN; $CH_2F$, $CHF_2$, $CF_3$; $SCF_3$; $NO_2$; $OCH_2F$, $OCHF_2$, $OCF_3$; methyl; ethyl; n-propyl; iso-propyl; n-butyl; sec.-butyl; tert.-butyl; O—methyl; O—ethyl; O—$(CH_2)_2$—O—$CH_3$; O—$(CH_2)_2$—OH; S—Methyl; or S—Ethyl.

Even more preferably $R^6$ represents H; F; Cl; Br; I; CN; $CH_2F$, $CHF_2$, $CF_3$; $SCF_3$; $OCH_2F$, $OCHF_2$, $OCF_3$; methyl; ethyl; O—methyl; or O—ethyl, preferably represents H; F; Cl; Br; I; $CH_2F$, $CHF_2$, $CF_3$; $SCF_3$; $OCH_2F$, $OCHF_2$, $OCF_3$; methyl; ethyl; O—methyl; or O—ethyl, Still more preferably $R^6$ represents H; F; Cl; Br; CN; $CH_2F$, $CHF_2$, $CF_3$; $SCF_3$; $OCH_2F$, $OCHF_2$, $OCF_3$; O—methyl or methyl, preferably represents H; F; Cl; $CH_2F$, $CHF_2$, $CF_3$; $SCF_3$; $OCH_2F$, $OCHF_2$, $OCF_3$; O—methyl or methyl.

In particular $R^6$ represents H; F; Cl; Br; CN; or methyl, preferably H, F, Cl, Br or CN, more preferably H, Cl or Br, most preferably H.

In a preferred embodiment of the compound according to general formula (I), the residue $R^7$ denotes a $CF_3$, $CHF_2$, $CH_2F$, $CF_2Cl$, $CFCl_2$, $CH_2OH$, $CH_2OCH_3$, a $C_{2-10}$-aliphatic residue, preferably a $C_{2-8}$-aliphatic residue, unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$-aliphatic residue, $OCH_2F$, $OCHF_2$, $OCF_3$, SH, $SCF_3$, a S—$C_{1-4}$-aliphatic residue, a S(=O)—$C_{1-4}$-aliphatic residue, a S(=O)$_2$—$C_{1-4}$-aliphatic residue, $CH_2F$, $CHF_2$, $CF_3$, CN, a $C_{1-4}$-aliphatic residue and C(=O)—OH, wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a S(=O)$_2$—$C_{1-4}$-aliphatic residue, $CH_2F$, $CHF_2$, $CF_3$, CN, a $C_{1-4}$-aliphatic residue, and C(=O)—OH, wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue, and and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a S(=O)$_2$—$C_{1-4}$-aliphatic residue, $CH_2F$, $CHF_2$, $CF_3$, CN, a $C_{1-4}$-aliphatic residue and C(=O)—OH, on the condition that if $R^7$ denotes a 3 to 10 membered heterocycloaliphatic residue, the binding is carried out via a carbon atom of the 3 to 10 membered heterocycloaliphatic residue, or $R^7$ denotes S—$R^{8a}$, S(=O)—$R^{8b}$, S(=O)$_2$—$R^{8c}$, O—$R^9$ or N($R^{10}R^{11}$), preferably S—$R^{8a}$, S(=O)—$R^{8b}$, S(=O)$_2$—$R^{8c}$ or O—$R^9$, wherein $R^{8a}$, $R^{8b}$, $R^{8c}$ and $R^9$ in each case represent a $C_{1-10}$-aliphatic residue, preferably a $C_{1-8}$-aliphatic residue, unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$-aliphatic residue, $OCH_2F$, $OCHF_2$, $OCF_3$, SH, $SCF_3$, a S—$C_{1-4}$-aliphatic residue, a S(=O)—$C_{1-4}$-aliphatic residue, a S(=O)$_2$—$C_{1-4}$-aliphatic residue, $CH_2F$, $CHF_2$, $CF_3$, CN, a $C_{1-4}$-aliphatic residue and C(=O)—OH, wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue, or in each case represent a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a S(=O)$_2$—$C_{1-4}$-aliphatic residue, $CH_2F$, $CHF_2$, $CF_3$, CN, a $C_{1-4}$-aliphatic residue, C(=O)—OH, a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a S(=O)$_2$—$C_{1-4}$-aliphatic residue, $CH_2F$, $CHF_2$, $CF_3$, CN, a $C_{1-4}$-aliphatic residue and C(=O)—OH, and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a S(=O)$_2$—C$_{1-4}$-aliphatic residue, CH$_2$F, CHF$_2$, CF$_3$, CN, a C$_{1-4}$-aliphatic residue and C(=O)—OH, on the condition that if R$^{8a}$, R$^{8b}$, R$^{8c}$ or R$^9$ denotes a 3 to 10 membered heterocycloaliphatic residue, the binding is carried out via a carbon atom of the 3 to 10 membered heterocycloaliphatic residue, R$^{10}$ denotes a C$_{1-10}$-aliphatic residue, preferably a C$_{1-8}$-aliphatic residue, unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$-aliphatic residue, OCH$_2$F, OCHF$_2$, OCF$_3$, SH, SCF$_3$, a S—C$_{1-4}$-aliphatic residue, a S(=O)—C$_{1-4}$-aliphatic residue, a S(=O)$_2$—C$_{1-4}$-aliphatic residue, CH$_2$F, CHF$_2$, CF$_3$, CN, a C$_{1-4}$-aliphatic residue, a C(=O)—O—C$_{1-4}$-aliphatic residue, and C(=O)—OH,
  wherein the C$_{1-4}$-aliphatic residue in each case may be unsubstituted or mono- or polysubstituted with at least one substituent selected from the group consisting of F, Cl, Br, I, OH, OCH$_2$F, OCHF$_2$, OCF$_3$, CH$_2$F, CHF$_2$, CF$_3$ and an unsubstituted O—C$_{1-4}$-aliphatic residue,
  or denotes a C$_{3-10}$-cycloaliphatic residue or a 3 to 10 membered heterocycloaliphatic residue, in each case unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCH$_2$F, OCHF$_2$, OCF$_3$, SH, SCF$_3$, a S—C$_{1-4}$ aliphatic residue, a S(=O)—C$_{1-4}$-aliphatic residue, a S(=O)$_2$—C$_{1-4}$-aliphatic residue, CH$_2$F, CHF$_2$, CF$_3$, CN, a C$_{1-4}$-aliphatic residue, C(=O)—OH, a C(=O)—O—C$_{1-4}$-aliphatic residue a C$_{3-6}$ cycloaliphatic residue, and a 3 to 6 membered heterocycloaliphatic residue,
  wherein the C$_{1-4}$-aliphatic residue in each case may be unsubstituted or mono- or polysubstituted with at least one substituent selected from the group consisting of F, Cl, Br, I, OH, OCH$_2$F, OCHF$_2$, OCF$_3$, CH$_2$F, CHF$_2$, CF$_3$ and an unsubstituted O—C$_{1-4}$-aliphatic residue, and
  wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCH$_2$F, OCHF$_2$, OCF$_3$, SH, SCF$_3$, a S—C$_{1-4}$ aliphatic residue, a S(=O)—C$_{1-4}$-aliphatic residue, a S(=O)$_2$—C$_{1-4}$-aliphatic residue, CH$_2$F, CHF$_2$, CF$_3$, CN, a C$_{1-4}$-aliphatic residue and C(=O)—OH,
  and wherein the C$_{3-10}$-cycloaliphatic residue or the 3 to 10 membered heterocycloaliphatic residue may in each case optionally bridged via a C$_{1-8}$ aliphatic group, preferably a C$_{1-4}$ aliphatic group, which in turn may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, a C(=O)—O—C$_{1-4}$-aliphatic residue, OCH$_2$F, OCHF$_2$, OCF$_3$, SH, SCF$_3$, a S—C$_{1-4}$ aliphatic residue, a S(=O)—C$_{1-4}$-aliphatic residue, a S(=O)$_2$—C$_{1-4}$-aliphatic residue, CH$_2$F, CHF$_2$, CF$_3$, CN, a C$_{1-4}$-aliphatic residue and C(=O)—OH, on the condition that if R$^{10}$ denotes a 3 to 10 membered heterocycloaliphatic residue, the binding is carried out via a carbon atom of the 3 to 10 membered heterocycloaliphatic residue, R$^{11}$ denotes H or a C$_{1-10}$-aliphatic residue, preferably a C$_{1-4}$-aliphatic residue, unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCH$_2$F, OCHF$_2$, OCF$_3$, SH, SCF$_3$, a S—C$_{1-4}$ aliphatic residue, CH$_2$F, CHF$_2$, CF$_3$, CN, a C$_{1-4}$-aliphatic residue and C(=O)—OH, preferably denotes a C$_{1-10}$-aliphatic residue, more preferably a C$_{1-4}$-aliphatic residue, unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCH$_2$F, OCHF$_2$, OCF$_3$, SH, SCF$_3$, a S—C$_{1-4}$ aliphatic residue, S(=O)—C$_{1-4}$-aliphatic residue, a S(=O)$_2$—C$_{1-4}$-aliphatic residue, CH$_2$F, CHF$_2$, CF$_3$, CN, a C$_{1-4}$-aliphatic residue and C(=O)—OH,
  wherein the C$_{1-4}$-aliphatic residue in each case may be unsubstituted or mono- or polysubstituted with at least one substituent selected from the group consisting of F, Cl, Br, I, OH, OCH$_2$F, OCHF$_2$, OCF$_3$, CH$_2$F, CHF$_2$, CF$_3$ and an unsubstituted O—C$_{1-4}$-aliphatic residue, or R$^{10}$ and R$^{11}$ form together with the nitrogen atom connecting them a 3 to 10 membered heterocycloaliphatic residue, preferably a 3 to 6 membered heterocycloaliphatic residue, unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCH$_2$F, OCHF$_2$, OCF$_3$, SH, SCF$_3$, a S—C$_{1-4}$ aliphatic residue, S(=O)—C$_{1-4}$-aliphatic residue, a S(=O)$_2$—C$_{1-4}$-aliphatic residue, CH$_2$F, CHF$_2$, CF$_3$, CN, a C$_{1-4}$-aliphatic residue, C(=O)—OH, a C$_{3-6}$ cycloaliphatic residue, and a 3 to 6 membered heterocycloaliphatic residue,
  wherein the C$_{1-4}$-aliphatic residue in each case may be unsubstituted or mono- or polysubstituted with at least one substituent selected from the group consisting of F, Cl, Br, I, OH, OCH$_2$F, OCHF$_2$, OCF$_3$, CH$_2$F, CHF$_2$, CF$_3$ and an unsubstituted O—C$_{1-4}$-aliphatic residue, and
  wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCH$_2$F, OCHF$_2$, OCF$_3$, SH, SCF$_3$, a S—C$_{1-4}$ aliphatic residue, S(=O)—C$_{1-4}$-aliphatic residue, a S(=O)$_2$—C$_{1-4}$-aliphatic residue, CH$_2$F, CHF$_2$, CF$_3$, CN, a C$_{1-4}$-aliphatic residue and C(=O)—OH,
  and wherein the 3 to 10 membered heterocycloaliphatic residue formed by R$^{10}$ and R$^{11}$ together with the nitrogen atom connecting them may optionally be condensed with aryl or heteroaryl, preferably with phenyl or pyridyl, wherein the aryl or heteroaryl residues condensed in this way can for their part be respectively unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, an O—C$_{1-4}$ aliphatic residue, OCH$_2$F, OCHF$_2$, OCF$_3$, SH, SCF$_3$, a S—C$_{1-4}$ aliphatic residue, S(=O)—C$_{1-4}$-aliphatic residue, a S(=O)$_2$—C$_{1-4}$-aliphatic residue, CH$_2$F, CHF$_2$, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, a C$_{3-6}$ cycloaliphatic residue, a 3 to 6 membered heterocycloaliphatic residue,

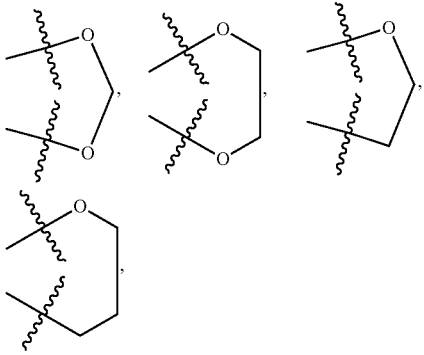

benzyl, phenyl, thienyl, pyridyl, furyl, thiazolyl and oxazolyl,
  wherein the C$_{1-4}$-aliphatic residue in each case may be unsubstituted or mono- or polysubstituted with at least one substituent selected from the group consisting of F, Cl, Br, I, OH, OCH$_2$F, OCHF$_2$, OCF$_3$, CH$_2$F, CHF$_2$, CF$_3$ and an unsubstituted O—C$_{1-4}$-aliphatic residue, and
  wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, an O—C$_{1-4}$ aliphatic residue, OCH$_2$F, OCHF$_2$, OCF$_3$, O—CH$_2$—OH, O—CH$_2$—O—CH$_3$, SH, SCF$_3$, a S—C$_{1-4}$ aliphatic residue, S(=O)—C$_{1-4}$-aliphatic residue, a S(=O)$_2$—C$_{1-4}$-aliphatic residue, CH$_2$F, CHF$_2$, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, and
  wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCH$_2$F, OCHF$_2$, OCF$_3$, SH, SCF$_3$, a S—C$_{1-4}$ aliphatic residue, S(=O)—C$_{1-4}$-aliphatic residue, a S(=O)$_2$—C$_{1-4}$-aliphatic residue, CH$_2$F, CHF$_2$, CF$_3$, CN, a C$_{1-4}$-aliphatic residue and C(=O)—OH.

Preferably,
R$^7$ denotes CF$_3$, CHF$_2$, CH$_2$F, CF$_2$Cl, CFCl$_2$, CH$_2$OH, CH$_2$OCH$_3$, a C$_{2-10}$-aliphatic residue, preferably a C$_{2-8}$-aliphatic residue, unsubstituted or mono- or polysubstituted with at least one substituent selected from the group consisting of F, Cl, Br, I, NO$_2$, OH, =O, an O—C$_{1-4}$- aliphatic residue, OCH$_2$F, OCHF$_2$, OCF$_3$, SH, SCF$_3$, a S—C$_{1-4}$-aliphatic residue, S(=O)—C$_{1-4}$-aliphatic residue, a S(=O)$_2$—C$_{1-4}$-aliphatic residue, a C(=O)—O—C$_{1-4}$-aliphatic residue, CH$_2$F, CHF$_2$, CF$_3$, CN, and a C$_{1-4}$-aliphatic residue
  wherein the C$_{1-4}$-aliphatic residue in each case may be unsubstituted or mono- or polysubstituted with at least one substituent selected from the group consisting of F, Cl, Br, I, OH, OCH$_2$F, OCHF$_2$, OCF$_3$, CH$_2$F, CHF$_2$, CF$_3$ and an unsubstituted O—C$_{1-4}$-aliphatic residue,
or denotes a C$_{3-10}$-cycloaliphatic residue or a 3 to 10 membered heterocycloaliphatic residue, in each case unsubstituted or mono- or polysubstituted with at least one substituent selected from the group consisting of F, Cl, Br, I, NO$_2$, OH, =O, an O—C$_{1-4}$ aliphatic residue, OCH$_2$F, OCHF$_2$, OCF$_3$, SH, SCF$_3$, a S—C$_{1-4}$ aliphatic residue, residue, a S(=O)—C$_{1-4}$-aliphatic residue, a S(=O)$_2$—C$_{1-4}$-aliphatic residue, a C(=O)—O—C$_{1-4}$-aliphatic residue, a C(=O)—O—C$_{1-4}$-aliphatic residue, CH$_2$F, CHF$_2$, CF$_3$, CN, a C$_{1-4}$-aliphatic residue,
  wherein the C$_{1-4}$-aliphatic residue in each case may be unsubstituted or mono- or polysubstituted with at least one substituent selected from the group consisting of F, Cl, Br, I, OH, OCH$_2$F, OCHF$_2$, OCF$_3$, CH$_2$F, CHF$_2$, CF$_3$ and an unsubstituted O—C$_{1-4}$-aliphatic residue, and
  and wherein the C$_{3-10}$-cycloaliphatic residue or the 3 to 10 membered heterocycloaliphatic residue may in each case optionally bridged via a C$_{1-8}$ aliphatic group, preferably a C$_{1-4}$ aliphatic group, which in turn may be unsubstituted or mono- or polysubstituted with at least one substituent selected from the group consisting of F, Cl, Br, I, NO$_2$, OH, =O, an O—C$_{1-4}$ aliphatic residue, a C(=O)—O—C$_{1-4}$-aliphatic residue, OCH$_2$F, OCHF$_2$, OCF$_3$, SH, SCF$_3$, a S—C$_{1-4}$ aliphatic residue, a S(=O)—C$_{1-4}$-aliphatic residue, a S(=O)$_2$—C$_{1-4}$-aliphatic residue, CH$_2$F, CHF$_2$, CF$_3$, CN, and a C$_{1-4}$-aliphatic residue.
on the condition that if R$^7$ denotes a 3 to 10 membered heterocycloaliphatic residue, the 3 to 10 membered heterocycloaliphatic residue is linked via a carbon atom,
or
R$^7$ denotes S—R$^{8a}$, S(=O)—R$^{8b}$, S(=O)$_2$—R$^{8c}$, O—R$^9$, wherein
  R$^{8a}$, R$^{8b}$, R$^{8c}$ and R$^9$ in each case represent a C$_{1-8}$-aliphatic residue, unsubstituted or mono- or polysubstituted with at least one substituent selected from the group consisting of F, Cl, Br, I, OH, =O, an O—C$_{1-4}$-aliphatic residue, OCH$_2$F, OCHF$_2$, OCF$_3$, SH, SCF$_3$, a S—C$_{1-4}$-aliphatic residue, a S(=O)—C$_{1-4}$-aliphatic residue, a S(=O)$_2$—C$_{1-4}$-aliphatic residue, an NH(C$_{1-4}$ aliphatic residue), an N(C$_{1-4}$ aliphatic residue)$_2$, a C(=O)—O—C$_{1-4}$-aliphatic residue, CH$_2$F, CHF$_2$, CF$_3$, and a C$_{1-4}$-aliphatic residue,
    wherein the C$_{1-4}$-aliphatic residue in each case may be unsubstituted or mono- or polysubstituted with at least one substituent selected from the group consisting of F, Cl, Br, I, OH, CH$_2$F, CHF$_2$, CF$_3$ and an unsubstituted O—C$_{1-4}$-aliphatic residue,
  or in each case denote a C$_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—C$_{1-4}$ aliphatic residue, OCH$_2$F, OCHF$_2$, OCF$_3$, SCF$_3$, a C(=O)—O—C$_{1-4}$- aliphatic residue, a S—C$_{1-4}$ aliphatic residue, a S(=O)—C$_{1-4}$-aliphatic residue, a S(=O)$_2$—C$_{1-4}$-aliphatic residue, CH$_2$F, CHF$_2$, CF$_3$, and a C$_{1-4}$-aliphatic residue,
    wherein the C$_{1-4}$-aliphatic residue in each case may be unsubstituted or mono- or polysubstituted with at least one substituent selected from the group consisting of F, Cl, Br, I, OH, $CH_2F$, $CHF_2$, $OCF_3$, $CH_2F$, $CHF_2$, $CF_3$ and an unsubstituted $O-C_{1-4}$-aliphatic residue, and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, OH, =O, an $O-C_{1-4}$ aliphatic residue, $OCH_2F$, $OCHF_2$, $OCF_3$, $SH$, $SCF_3$, a $S-C_{1-4}$ aliphatic residue, a $S(=O)-C_{1-4}$-aliphatic residue, a $S(=O)_2-C_{1-4}$-aliphatic residue, a $C(=O)-O-C_{1-4}$-aliphatic residue, $CH_2F$, $CHF_2$, $CF_3$, CN, and a $C_{1-4}$-aliphatic residue.

on the condition that if $R^{8a}$, $R^{8b}$, $R^{8c}$ or $R^9$ denotes a 3 to 10 membered heterocycloaliphatic residue, the 3 to 10 membered heterocycloaliphatic residue is linked via a carbon atom, or $R^7$ denotes $N(R^{10}R^{11})$, wherein $R^{10}$ denotes a $C_{1-8}$-aliphatic residue, unsubstituted or mono- or polysubstituted with at least one substituent selected from the group consisting of F, Cl, Br, I, OH, =O, an $O-C_{1-4}$-aliphatic residue, $OCH_2F$, $OCHF_2$, $OCF_3$, $SH$, $SCF_3$, a $S-C_{1-4}$-aliphatic residue, a $S(=O)-C_{1-4}$-aliphatic residue, a $S(=O)_2-C_{1-4}$-aliphatic residue, a $C(=O)-O-C_{1-4}$-aliphatic residue, $CH_2F$, $CHF_2$, $CF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $CH_2F$, $CHF_2$, $CF_3$ and an unsubstituted $O-C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an $O-C_{1-4}$ aliphatic residue, $OCH_2F$, $OCHF_2$, $OCF_3$, $SCF_3$, a $C(=O)-O-C_{1-4}$-aliphatic residue, a $S-C_{1-4}$ aliphatic residue, a $S(=O)-C_{1-4}$-aliphatic residue, a $S(=O)_2-C_{1-4}$-aliphatic residue, $CH_2F$, $CHF_2$, $CF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted $O-C_{1-4}$-aliphatic residue, and and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, OH, =O, an $O-C_{1-4}$ aliphatic residue, $OCH_2F$, $OCHF_2$, $OCF_3$, $SH$, $SCF_3$, a $S-C_{1-4}$ aliphatic residue, a $S(=O)-C_{1-4}$-aliphatic residue, a $S(=O)_2-C_{1-4}$-aliphatic residue, a $C(=O)-O-C_{1-4}$-aliphatic residue, $CH_2F$, $CHF_2$, $CF_3$, CN, and a $C_{1-4}$-aliphatic residue, on the condition that if $R^{10}$ denotes a 3 to 10 membered heterocycloaliphatic residue, the 3 to 10 membered heterocycloaliphatic residue is linked via a carbon atom, and wherein $R^{11}$ denotes H or a $C_{1-10}$-aliphatic residue, preferably a $C_{1-6}$-aliphatic residue, unsubstituted or mono- or polysubstituted with at least one substituent selected from the group consisting of F, Cl, Br, I, $NO_2$, OH, =O, an $O-C_{1-4}$ aliphatic residue, $OCH_2F$, $OCHF_2$, $OCF_3$, $SH$, $SCF_3$, a $S-C_{1-4}$ aliphatic residue, $CH_2F$, $CHF_2$, $CF_3$, CN, and a $C_{1-4}$-aliphatic residue, preferably denotes a $C_{1-10}$-aliphatic residue, more preferably a $C_{1-6}$-aliphatic residue, unsubstituted or mono- or polysubstituted with at least one substituent selected from the group consisting of F, Cl, Br, I, $NO_2$, OH, =O, an $O-C_{1-4}$ aliphatic residue, $OCH_2F$, $OCHF_2$, $OCF_3$, $SH$, $SCF_3$, a $S-C_{1-4}$ aliphatic residue, a $S(=O)-C_{1-4}$-aliphatic residue, a $S(=O)_2-C_{1-4}$-aliphatic residue, $CH_2F$, $CHF_2$, $CF_3$, CN, and a $C_{1-4}$-aliphatic residue wherein the $C_{1-4}$-aliphatic residue in each case may be unsubstituted or mono- or polysubstituted with at least one substituent selected from the group consisting of F, Cl, Br, I, OH, $CH_2F$, $CHF_2$, $CF_3$ and an unsubstituted $O-C_{1-4}$-aliphatic residue, or $R^{10}$ and $R^{11}$ form together with the nitrogen atom connecting them a 3 to 10 membered heterocycloaliphatic residue, preferably a 3 to 6 membered heterocycloaliphatic residue, more preferably selected from the group consisting of morpholinyl, piperidinyl, pyrrolidinyl, azetidinyl and piperazinyl, unsubstituted or mono- or polysubstituted with at least one substituent selected from the group consisting of F, Cl, Br, I, $NO_2$, OH, =O, an $O-C_{1-4}$ aliphatic residue, $OCH_2F$, $OCHF_2$, $OCF_3$, $SH$, $SCF_3$, a $S-C_{1-4}$ aliphatic residue, a $S(=O)-C_{1-4}$-aliphatic residue, a $S(=O)_2-C_{1-4}$-aliphatic residue, $CH_2F$, $CHF_2$, $CF_3$, CN, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $CH_2F$, $CHF_2CF_3$ and an unsubstituted $O-C_{1-4}$-aliphatic residue, and wherein the 3 to 10 membered heterocycloaliphatic residue formed by $R^{10}$ and $R^{11}$ together with the nitrogen atom connecting them may optionally be condensed with aryl or heteroaryl, preferably with phenyl or pyridyl, wherein the aryl or heteroaryl residues condensed in this way can for their part be respectively unsubstituted or mono- or polysubstituted with at least one substituent selected from the group consisting of F, Cl, Br, I, $NO_2$, OH, an $O-C_{1-4}$ aliphatic residue, $OCH_2F$, $OCHF_2$, $OCF_3$, $SH$, $SCF_3$, a $S-C_{1-4}$ aliphatic residue, a $S(=O)-C_{1-4}$-aliphatic residue, a $S(=O)_2-C_{1-4}$-aliphatic residue, $CH_2F$, $CHF_2$, $CF_3$, CN, a $C_{1-4}$-aliphatic residue, $C(=O)-OH$, a $C_{3-6}$ cycloaliphatic residue, a 3 to 6 membered heterocycloaliphatic residue,

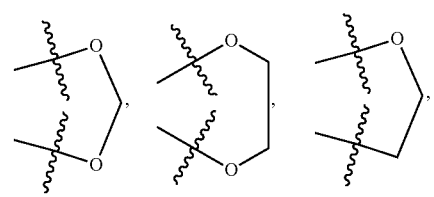

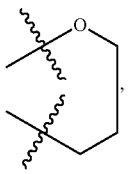

benzyl, phenyl, thienyl, and pyridyl,
wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted $O-C_{1-4}$-aliphatic residue, and wherein benzyl, phenyl, thienyl, and pyridyl, may in each case may be unsubstituted or mono- or polysubstituted with at least one substituent selected from the group consisting of F, Cl, Br, I, $NO_2$, OH, an $O-C_{1-4}$ aliphatic residue, $OCH_2F$, $OCHF_2$, $OCF_3$, $O-CH_2-OH$, $O-CH_2-O-CH_3$, SH, $SCF_3$, a $S-C_{1-4}$ aliphatic residue, a $S(=O)-C_{1-4}$-aliphatic residue, a $S(=O)_2-C_{1-4}$-aliphatic residue, $CH_2F$, $CHF_2$, $CF_3$, CN, a $C_{1-4}$-aliphatic residue, and $C(=O)-OH$, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, OH, =O, an $O-C_{1-4}$ aliphatic residue, $OCH_2F$, $OCHF_2$, $OCF_3$, SH, $SCF_3$, a $S-C_{1-4}$ aliphatic residue, a $S(=O)-C_{1-4}$-aliphatic residue, a $S(=O)_2-C_{1-4}$-aliphatic residue, $CH_2F$, $CHF_2$, $CF_3$, CN, a $C_{1-4}$-aliphatic residue and $C(=O)-OH$.

More preferably, $R^7$ denotes $CF_3$, $CHF_2$, $CH_2F$, $CF_2Cl$, $CFCl_2$, $CH_2OH$, $CH_2OCH_3$, or a $C_{2-8}$-aliphatic residue, unsubstituted or mono- or polysubstituted with at least one substituent selected from the group consisting of F, Cl, Br, I, OH, =O, an $O-C_{1-4}$-aliphatic residue, $OCH_2F$, $OCHF_2$, $OCF_3$, SH, $SCF_3$, a $S-C_{1-4}$-aliphatic residue, a $S(=O)-C_{1-4}$-aliphatic residue, a $S(=O)_2-C_{1-4}$-aliphatic residue, a $C(=O)-O-C_{1-4}$-aliphatic residue, $CH_2F$, $CHF_2$, $CF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $CH_2F$, $CHF_2$, $CF_3$ and an unsubstituted $O-C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an $O-C_{1-4}$ aliphatic residue, $OCH_2F$, $OCHF_2$, $OCF_3$, $SCF_3$, a $C(=O)-O-C_{1-4}$-aliphatic residue, a $S-C_{1-4}$ aliphatic residue, a $S(=O)-C_{1-4}$-aliphatic residue, a $S(=O)_2-C_{1-4}$-aliphatic residue, $CH_2F$, $CHF_2$, $CF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted $O-C_{1-4}$-aliphatic residue, and and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, OH, =O, an $O-C_{1-4}$ aliphatic residue, $OCH_2F$, $OCHF_2$, $OCF_3$, SH, $SCF_3$, a $S-C_{1-4}$ aliphatic residue, a $S(=O)-C_{1-4}$-aliphatic residue, a $S(=O)_2-C_{1-4}$-aliphatic residue, a $C(=O)-O-C_{1-4}$-aliphatic residue, $CH_2F$, $CHF_2$, $CF_3$, CN, and a $C_{1-4}$-aliphatic residue.

on the condition that if $R^7$ denotes a 3 to 10 membered heterocycloaliphatic residue, the 3 to 10 membered heterocycloaliphatic residue is linked via a carbon atom, or $R^7$ denotes $S-R^{8a}$, $S(=O)-R^{8b}$, $S(=O)_2-R^{8c}$, or $O-R^9$, wherein $R^{8a}$, $R^{8b}$, $R^{8c}$ and $R^9$ in each case denote a $C_{1-8}$-aliphatic residue, preferably a $C_{1-6}$-aliphatic residue, unsubstituted or mono- or polysubstituted with at least one substituent selected from the group consisting of F, Cl, Br, I, OH, =O, an $O-C_{1-4}$-aliphatic residue, $OCH_2F$, $OCHF_2$, $OCF_3$, SH, $SCF_3$, a $S-C_{1-4}$-aliphatic residue, a $S(=O)-C_{1-4}$-aliphatic residue, a $S(=O)_2-C_{1-4}$-aliphatic residue, an $NH(C_{1-4}$ aliphatic residue), an $N(C_{1-4}$ aliphatic residue)$_2$, $CH_2F$, $CHF_2$, $CF_3$, a $C(=O)-O-C_{1-4}$-aliphatic residue, and a $C_{1-4}$-aliphatic residue wherein the $C_{1-4}$-aliphatic residue in each case may be unsubstituted or mono- or polysubstituted with at least one substituent selected from the group consisting of F, Cl, Br, I, OH, $CH_2F$, $CHF_2$, $CF_3$ and an unsubstituted $O-C_{1-4}$-aliphatic residue, or in each case denote a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an $O-C_{1-4}$ aliphatic residue, $OCH_2F$, $OCHF_2$, $OCF_3$, $SCF_3$, a $S-C_{1-4}$ aliphatic residue, a $S(=O)-C_{1-4}$-aliphatic residue, a $S(=O)_2-C_{1-4}$-aliphatic residue, a $C(=O)-O-C_{1-4}$-aliphatic residue, $CH_2F$, $CHF_2$, $CF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted $O-C_{1-4}$-aliphatic residue, and wherein the $C_{3-10}$-cycloaliphatic residue or the 3 to 10 membered heterocycloaliphatic residue may be bridged, preferably is bridged, via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, OH, =O, an $O-C_{1-4}$ aliphatic residue, $OCH_2F$, $OCHF_2$, $OCF_3$, SH, $SCF_3$, a $S-C_{1-4}$ aliphatic residue, a $S(=O)-C_{1-4}$-aliphatic residue, a $S(=O)_2-C_{1-4}$-aliphatic residue, a $C(=O)-O-C_{1-4}$-aliphatic residue, $CH_2F$, $CHF_2$, $CF_3$, CN, and a $C_{1-4}$-aliphatic residue, on the condition that if $R^{8a}$, $R^{8b}$, $R^{8c}$ or $R^9$ denotes a 3 to 10 membered heterocycloaliphatic residue, the 3 to 10 membered heterocycloaliphatic residue is linked via a carbon atom, or $R^7$ denotes $N(R^{10}R^{11})$, wherein $R^{10}$ denotes a $C_{1-8}$-aliphatic residue, preferably a $C_{1-6}$-aliphatic residue, unsubstituted or mono- or polysubstituted with at least one substituent selected from the group consisting of F, Cl, Br, I, OH, =O, an $O-C_{1-4}$-aliphatic residue, $OCH_2F$, $OCHF_2$, $OCF_3$, SH, $SCF_3$, a S—$C_{1-4}$-aliphatic residue, a S(=O)—$C_{1-4}$-aliphatic residue, a S(=O)$_2$—$C_{1-4}$-aliphatic residue, $CH_2F$, $CHF_2$, $CF_3$, a C(=O)—O—$C_{1-4}$-aliphatic residue, and a $C_{1-4}$-aliphatic residue
  wherein the $C_{1-4}$-aliphatic residue in each case may be unsubstituted or mono- or polysubstituted with at least one substituent selected from the group consisting of F, Cl, Br, I, OH, $CH_2F$, $CHF_2$, $CF_3$ and an unsubstituted O—$C_{1-4}$-aliphatic residue,
or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, $OCH_2F$, $OCHF_2$, $OCF_3$, $SCF_3$, a S—$C_{1-4}$ aliphatic residue, a S(=O)—$C_{1-4}$-aliphatic residue, a S(=O)$_2$—$C_{1-4}$-aliphatic residue, a C(=O)—O—$C_{1-4}$-aliphatic residue, $CH_2F$, $CHF_2$, $CF_3$, and a $C_{1-4}$-aliphatic residue,
  wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue, and
wherein the $C_{3-10}$-cycloaliphatic residue or the 3 to 10 membered heterocycloaliphatic residue may in each case be bridged, preferably is bridged, via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a S(=O)$_2$—$C_{1-4}$-aliphatic residue, a C(=O)—O—$C_{1-4}$-aliphatic residue, $CH_2F$, $CHF_2$, $CF_3$, CN, and a $C_{1-4}$-aliphatic residue,
on the condition that if $R^{10}$ denotes a 3 to 10 membered heterocycloaliphatic residue, the 3 to 10 membered heterocycloaliphatic residue is linked via a carbon atom, and
$R^{11}$ denotes H or a $C_{1-6}$-aliphatic residue, preferably a $C_{1-4}$-aliphatic residue, unsubstituted or mono- or polysubstituted with at least one substituent selected from the group consisting of F, Cl, Br, I, $NO_2$, OH, =O, an O—$C_{1-4}$ aliphatic residue, $OCH_2F$, $OCHF_2$, $OCF_3$, SH, $SCF_3$, a S—$C_{1-4}$ aliphatic residue, $CH_2F$, $CHF_2$, $CF_3$, CN, and a $C_{1-4}$-aliphatic residue, preferably denotes a $C_{1-6}$-aliphatic residue, more preferably a $C_{1-4}$-aliphatic residue, unsubstituted or mono- or polysubstituted with at least one substituent selected from the group consisting of F, Cl, Br, I, $NO_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a S(=O)$_2$—$C_{1-4}$-aliphatic residue, $CH_2F$, $CHF_2$, $CF_3$, CN, and a $C_{1-4}$-aliphatic residue,
  wherein the $C_{1-4}$-aliphatic residue in each case may be unsubstituted or mono- or polysubstituted with at least one substituent selected from the group consisting of F, Cl, Br, I, OH, $CH_2F$, $CHF_2$, $CF_3$ and an unsubstituted O—$C_{1-4}$-aliphatic residue,
or
$R^{10}$ and $R^{11}$ form together with the nitrogen atom connecting them a 3 to 10 membered heterocycloaliphatic residue, preferably selected from the group consisting of morpholinyl, piperidinyl, pyrrolidinyl, azetidinyl and piperazinyl, unsubstituted or mono- or polysubstituted with at least one substituent selected from the group consisting of F, Cl, Br, I, $NO_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a S(=O)$_2$—$C_{1-4}$-aliphatic residue, $CH_2F$, $CHF_2$, $CF_3$, CN, and a $C_{1-4}$-aliphatic residue,
  wherein the $C_{1-4}$-aliphatic residue in each case may be unsubstituted or mono- or polysubstituted with at least one substituent selected from the group consisting of F, Cl, Br, I, OH, $CH_2F$, $CHF_2$, $CF_3$ and an unsubstituted O—$C_{1-4}$-aliphatic residue,
and wherein the 3 to 10 membered heterocycloaliphatic residue formed by $R^{10}$ and $R^{11}$ together with the nitrogen atom connecting them may optionally be condensed with aryl or heteroaryl, preferably with phenyl or pyridyl, wherein the aryl or heteroaryl residues condensed in this way can for their part be respectively unsubstituted or mono- or polysubstituted with at least one substituent selected from the group consisting of F, Cl, Br, I, $NO_2$, OH, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a S(=O)$_2$—$C_{1-4}$-aliphatic residue, $CH_2F$, $CHF_2$, $CF_3$, CN, a $C_{1-4}$-aliphatic residue, C(=O)—OH, residue,

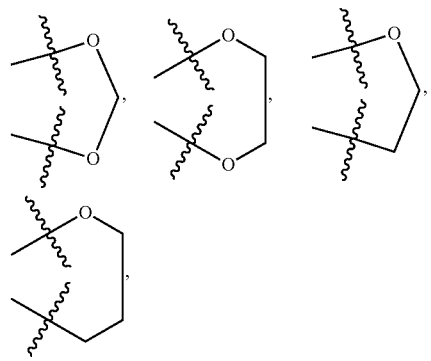

benzyl, phenyl, thienyl, and pyridyl,
  wherein the $C_{1-4}$-aliphatic residue in each case may be unsubstituted or mono- or polysubstituted with at least one substituent selected from the group consisting of F, Cl, Br, I, OH, $CH_2F$, $CHF_2$, $CF_3$ and an unsubstituted O—$C_{1-4}$-aliphatic residue, and
  wherein benzyl, phenyl, thienyl, and pyridyl, may in each case may be unsubstituted or mono- or polysubstituted with at least one substituent selected from the group consisting of F, Cl, Br, I, $NO_2$, OH, an O—$C_{1-4}$ aliphatic residue, $OCH_2F$, $OCHF_2$, $OCF_3$, O—$CH_2$—OH, O—$CH_2$—O—$CH_3$, SH, $SCF_3$, a S—$C_{1-4}$ aliphatic residue, a S(=O)—$C_{1-4}$-aliphatic residue, a S(=O)$_2$—$C_{1-4}$-aliphatic residue, $CH_2F$, $CHF_2$, $CF_3$, CN, a $C_{1-4}$-aliphatic residue, and C(=O)—OH.
Even more preferably,
$R^7$ denotes $CF_3$, $CHF_2$, $CH_2F$, $CH_2OH$, $CH_2OCH_3$, or a $C_{2-6}$-aliphatic residue, unsubstituted or mono- or polysubstituted with at least one substituent selected from the group consisting of F, Cl, Br, I, OH, =O, an O—$C_{1-4}$-aliphatic residue, a C(=O)—O—$C_{1-4}$-aliphatic residue, $OCH_2F$, $OCHF_2$, $OCF_3$, SH, $SCF_3$, a S—$C_{1-4}$-aliphatic residue, a S(=O)—$C_{1-4}$-aliphatic residue, a S(=O)$_2$—$C_{1-4}$-aliphatic residue, $CH_2F$, $CHF_2$, $CF_3$, and a $C_{1-4}$-aliphatic residue
  wherein the $C_{1-4}$-aliphatic residue in each case is unsubstituted, or denotes a $C_{3-10}$-cycloaliphatic residue, preferably a $C_{3-6}$-cycloaliphatic residue, or a 3 to 10 membered heterocycloaliphatic residue, preferably a 3 to 6 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, $OCH_2F$, $OCHF_2$, $OCF_3$, $SCF_3$, a S—$C_{1-4}$ aliphatic residue, a $S(=O)$—$C_{1-4}$-aliphatic residue, a $S(=O)_2$—$C_{1-4}$-aliphatic residue, a $C(=O)$—O—$C_{1-4}$-aliphatic residue, $CH_2F$, $CHF_2$, $CF_3$, and a $C_{1-4}$-aliphatic residue, wherein the $C_{1-4}$-aliphatic residue in each case may be unsubstituted or mono- or polysubstituted with OH or an unsubstituted O—$C_{1-4}$-aliphatic residue.

and wherein the $C_{3-10}$-cycloaliphatic residue or the 3 to 10 membered heterocycloaliphatic residue may in each case optionally bridged via a unsubstituted $C_{1-4}$ aliphatic group, on the condition that if $R^7$ denotes a 3 to 10 membered heterocycloaliphatic residue, the 3 to 10 membered heterocycloaliphatic residue is linked via a carbon atom, or $R^7$ denotes S—$R^{8a}$, $S(=O)$—$R^{8b}$, $S(=O)_2$—$R^{8c}$, or O—$R^9$, wherein $R^{8a}$, $R^{8b}$, $R^{8c}$ and $R^9$ in each case denote a $C_{1-8}$-aliphatic residue, preferably a $C_{1-6}$-aliphatic residue, unsubstituted or mono- or polysubstituted with at least one substituent selected from the group consisting of F, Cl, Br, I, OH, =O, an O—$C_{1-4}$-aliphatic residue, $OCH_2F$, $OCHF_2$, $OCF_3$, SH, $SCF_3$, a S—$C_{1-4}$-aliphatic residue, a $S(=O)$—$C_{1-4}$-aliphatic residue, a $S(=O)_2$—$C_{1-4}$-aliphatic residue, an NH($C_{1-4}$ aliphatic residue), an N($C_{1-4}$ aliphatic residue)$_2$, a $C(=O)$—O—$C_{1-4}$-aliphatic residue, $CH_2F$, $CHF_2$, $CF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $CH_2F$, $CHF_2$, $CF_3$ and an unsubstituted O—$C_{1-4}$-aliphatic residue, or in each case denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, $OCH_2F$, $OCHF_2$, $OCF_3$, $SCF_3$, a S—$C_{1-4}$ aliphatic residue, a $S(=O)$—$C_{1-4}$-aliphatic residue, a $S(=O)_2$—$C_{1-4}$-aliphatic residue, a $C(=O)$—O—$C_{1-4}$-aliphatic residue, $CH_2F$, $CHF_2$, $CF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue, and wherein the $C_{3-10}$-cycloaliphatic residue or the 3 to 10 membered heterocycloaliphatic residue in each case may be bridged, preferably is bridged, via an unsubstituted $C_{1-8}$ aliphatic group, preferably an unsubstituted $C_{1-4}$ aliphatic group, on the condition that if $R^{8a}$, $R^{8b}$, $R^{8c}$ or $R^9$ denotes a 3 to 10 membered heterocycloaliphatic residue, the 3 to 10 membered heterocycloaliphatic residue is linked via a carbon atom, or $R^7$ denotes N($R^{10}R^{11}$), wherein $R^{10}$ denotes a $C_{1-8}$-aliphatic residue, preferably a $C_{1-6}$-aliphatic residue, unsubstituted or mono- or polysubstituted with at least one substituent selected from the group consisting of F, Cl, Br, I, OH, =O, an O—$C_{1-4}$-aliphatic residue, $OCH_2F$, $OCHF_2$, $OCF_3$, SH, $SCF_3$, a S—$C_{1-4}$-aliphatic residue, a $S(=O)$—$C_{1-4}$-aliphatic residue, a $S(=O)_2$—$C_{1-4}$-aliphatic residue, a $C(=O)$—O—$C_{1-4}$-aliphatic residue, $CH_2F$, $CHF_2$, $CF_3$, and a $C_{1-4}$-aliphatic residue wherein the $C_{1-4}$-aliphatic residue in each case may be unsubstituted or mono- or polysubstituted with at least one substituent selected from the group consisting of F, Cl, Br, I, OH, $CH_2F$, $CHF_2$, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, $OCH_2F$, $OCHF_2$, $OCF_3$, $SCF_3$, a S—$C_{1-4}$ aliphatic residue, a $S(=O)$—$C_{1-4}$-aliphatic residue, a $S(=O)_2$—$C_{1-4}$-aliphatic residue, a $C(=O)$—O—$C_{1-4}$-aliphatic residue, $CH_2F$, $CHF_2$, $CF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue, and wherein the $C_{3-10}$-cycloaliphatic residue or the 3 to 10 membered heterocycloaliphatic residue is in each case bridged via a unsubstituted $C_{1-8}$ aliphatic group, preferably an unsubstituted $C_{1-4}$ aliphatic group, on the condition that if $R^{10}$ denotes a 3 to 10 membered heterocycloaliphatic residue, the 3 to 10 membered heterocycloaliphatic residue is linked via a carbon atom, and $R^{11}$ denotes H or an unsubstituted $C_{1-4}$-aliphatic residue, preferably selected from the group consisting of methyl, ethyl, n-propyl, 2-propyl, n-butyl, isobutyl, sec.-butyl and tert.-butyl, more preferably selected from the group consisting of methyl and ethyl, preferably denotes an unsubstituted $C_{1-4}$-aliphatic residue, preferably selected from the group consisting of methyl, ethyl, n-propyl, 2-propyl, n-butyl, isobutyl, sec.-butyl and tert.-butyl, more preferably selected from the group consisting of methyl and ethyl or $R^{10}$ and $R^{11}$ form together with the nitrogen atom connecting them a 3 to 6 membered heterocycloaliphatic residue, preferably selected from the group consisting of morpholinyl, piperidinyl, pyrrolidinyl, and azetidinyl, unsubstituted or mono- or polysubstituted with at least one substituent selected from the group consisting of F, Cl, Br, I, $NO_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a $S(=O)$—$C_{1-4}$-aliphatic residue, a $S(=O)_2$—$C_{1-4}$-aliphatic residue, $CH_2F$, $CHF_2$, $CF_3$, CN, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $CH_2F$, $CHF_2$, $CF_3$ and an unsubstituted O—$C_{1-4}$-aliphatic residue, and wherein the 3 to 6 membered heterocycloaliphatic residue formed by $R^{10}$ and $R^{11}$ together with the nitrogen atom connecting them may optionally be condensed with phenyl or pyridyl, wherein the phenyl or pyridyl residues condensed in this way can for their part be respectively unsubstituted or mono- or polysubstituted with at least one substituent selected from the group consisting of F, Cl, Br, I, OH, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a S(=O)$_2$—$C_{1-4}$-aliphatic residue, $CH_2F$, $CHF_2$, $CF_3$, CN, a $C_{1-4}$-aliphatic residue, C(=O)—OH, residue, benzyl, phenyl, and pyridyl, wherein the $C_{1-4}$-aliphatic residue in each case may be unsubstituted or mono- or polysubstituted with at least one substituent selected from the group consisting of F, Cl, OH, and an unsubstituted O—$C_{1-4}$-aliphatic residue, and wherein benzyl, phenyl, and pyridyl, may in each case may be unsubstituted or mono- or polysubstituted with at least one substituent selected from the group consisting of F, Cl, Br, I, $OCH_3$, $OCH_2F$, $OCHF_2$, $OCF_3$, O—$CH_2$—OH, O—$CH_2$—O—$CH_3$, SH, $SCF_3$, $CH_2F$, $CHF_2$, $CF_3$, and a $C_{1-4}$-aliphatic residue.

Still more preferably, $R^7$ denotes $CF_3$, $CHF_2$, $CH_2F$, $CH_2OH$, $CH_2OCH_3$, or a $C_{2-6}$-aliphatic residue, preferably selected from the group consisting of ethyl, n-propyl, 2-propyl, n-butyl, isobutyl, sec.-butyl, tert.-butyl, n-pentyl, isopentyl, neopentyl, n-hexyl, ethenyl and propenyl (—$CH_2CH$=$CH_2$, —CH=CH—$CH_3$, —C(=$CH_2$)—$CH_3$), unsubstituted or mono- or polysubstituted with at least one substituent selected from the group consisting of F, Cl, Br, I, OH, =O, an O—$C_{1-4}$-aliphatic residue, a C(=O)—O—$C_{1-4}$-aliphatic residue, $OCF_3$, SH, $SCF_3$, a S—$C_{1-4}$-aliphatic residue, a S(=O)—$C_{1-4}$-aliphatic residue, a S(=O)$_2$—$C_{1-4}$-aliphatic residue, $OCH_2F$, $OCHF_2$, $CH_2F$, $CHF_2$, $CF_3$, and a $C_{1-4}$-aliphatic residue, preferably in each case unsubstituted or mono- or polysubstituted with at least one substituent selected from the group consisting of F, Cl, OH, an O—$C_{1-4}$-aliphatic residue, $CF_3$, $CH_2F$, $CHF_2$, and a $C_{1-4}$-aliphatic residue, more preferably in each case unsubstituted or mono- or polysubstituted with at least one substituent selected from the group consisting of F, Cl, and an O—$C_{1-4}$-aliphatic residue, preferably O-methyl, even more preferably in each case unsubstituted, wherein the $C_{1-4}$-aliphatic residue in each case is unsubstituted, or denotes a $C_{3-6}$-cycloaliphatic residue, preferably selected from the group consisting of cyclopropyl, cyclobutyl, cyclopentyl and cyclohexyl, or a 3 to 6 membered heterocycloaliphatic residue, preferably selected from the group consisting of piperidinyl (preferably piperidin-4-yl or piperidin-3-yl), tetrahydrofuranyl, and tetrahydropyranyl, in each case unsubstituted or mono- or polysubstituted with at least one substituent selected from the group consisting of F, Cl, Br, I, OH, =O, an O—$C_{1-4}$-aliphatic residue, a C(=O)—O—$C_{1-4}$-aliphatic residue, $OCH_2F$, $OCHF_2$, $OCF_3$, SH, $SCF_3$, a S—$C_{1-4}$-aliphatic residue, a S(=O)—$C_{1-4}$-aliphatic residue, a S(=O)$_2$—$C_{1-4}$-aliphatic residue, $CH_2F$, $CHF_2$, $CF_3$, and a $C_{1-4}$-aliphatic residue, preferably in each case unsubstituted or mono- or polysubstituted with at least one substituent selected from the group consisting of F, Cl, OH, an O—$C_{1-4}$-aliphatic residue, $CH_2F$, $CHF_2$, $CF_3$, and a $C_{1-4}$-aliphatic residue, more preferably in each case unsubstituted or mono- or polysubstituted with at least one substituent selected from the group consisting of F, Cl, and an O—$C_{1-4}$-aliphatic residue, preferably O-methyl, even more preferably in each case unsubstituted, wherein the $C_{1-4}$-aliphatic residue in each case is unsubstituted, and wherein the $C_{3-6}$-cycloaliphatic residue or the 3 to 6 membered heterocycloaliphatic residue may in each case optionally bridged via an unsubstituted $C_{1-4}$ aliphatic group, preferably via an unsubstituted $C_{1-2}$ aliphatic group, on the condition that if $R^7$ a 3 to 6 membered heterocycloaliphatic residue, the 3 to 6 membered heterocycloaliphatic residue is linked via a carbon atom, or $R^7$ denotes S—$R^{8a}$, S(=O)—$R^{8b}$, S(=O)$_2$—$R^{8c}$, or O—$R^9$, wherein $R^{8a}$, $R^{8b}$, $R^{8c}$ and $R^9$ in each case denote a $C_{1-6}$-aliphatic residue, preferably selected from the group consisting of methyl, ethyl, n-propyl, 2-propyl, n-butyl, isobutyl, sec.-butyl, tert.-butyl, n-pentyl, isopentyl, neopentyl, n-hexyl, ethenyl and propenyl (—$CH_2CH$=$CH_2$, —CH=CH—$CH_3$, —C(=$CH_2$)—$CH_3$), unsubstituted or mono- or polysubstituted with at least one substituent selected from the group consisting of F, Cl, Br, I, OH, =O, an O—$C_{1-4}$-aliphatic residue, a C(=O)—O—$C_{1-4}$-aliphatic residue, $OCH_2F$, $OCHF_2$, $OCF_3$, SH, $SCF_3$, a S—$C_{1-4}$-aliphatic residue, S(=O)—$C_{1-4}$-aliphatic residue, a S(=O)$_2$—$C_{1-4}$-aliphatic residue, an NH($C_{1-4}$ aliphatic residue), an N($C_{1-4}$ aliphatic residue)$_2$, $CH_2F$, $CHF_2$, $CF_3$, and a $C_{1-4}$-aliphatic residue, more preferably in each case unsubstituted or mono- or polysubstituted with at least one substituent selected from the group consisting of F, Cl, OH, and an O—$C_{1-4}$-aliphatic residue, wherein the $C_{1-4}$-aliphatic residue in each case is unsubstituted, or denotes a $C_{3-6}$-cycloaliphatic residue, preferably cyclopropyl, or a 3 to 6 membered heterocycloaliphatic residue, preferably oxetanyl, in each case unsubstituted or mono- or polysubstituted with at least one substituent selected from the group consisting of F, Cl, Br, I, OH, =O, an O—$C_{1-4}$ aliphatic residue, $OCH_2F$, $OCHF_2$, $OCF_3$, $SCF_3$, a S—$C_{1-4}$ aliphatic residue, a S(=O)—$C_{1-4}$-aliphatic residue, a S(=O)$_2$—$C_{1-4}$-aliphatic residue, a C(=O)—O—$C_{1-4}$-aliphatic residue, $CH_2F$, $CHF_2$, $CF_3$, and a $C_{1-4}$-aliphatic residue, preferably in each case unsubstituted or mono- or polysubstituted with at least one substituent selected from the group consisting of F, Cl, OH, an O—$C_{1-4}$-aliphatic residue, $CH_2F$, $CHF_2$, $CF_3$, and a $C_{1-4}$-aliphatic residue, wherein the $C_{1-4}$-aliphatic residue in each case may be unsubstituted or mono- or polysubstituted with OH or an unsubstituted O—$C_{1-4}$-aliphatic residue, and wherein the $C_{3-10}$-cycloaliphatic residue or the 3 to 10 membered heterocycloaliphatic residue in each case may be bridged, preferably is bridged, via an unsubstituted $C_{1-4}$ aliphatic group, on the condition that if $R^{8a}$, $R^{8b}$, $R^{8c}$ or $R^9$ denotes a 3 to 10 membered heterocycloaliphatic residue, the 3 to 10 membered heterocycloaliphatic residue is linked via a carbon atom, or $R^7$ denotes N($R^{10}R^{11}$), wherein $R^{10}$ denotes a $C_{1-6}$-aliphatic residue, unsubstituted or mono- or polysubstituted with at least one substituent selected from the group consisting of F, Cl, Br, I, OH, =O, an O—$C_{1-4}$-aliphatic residue, a C(=O)—O—$C_{1-4}$-aliphatic residue, $OCH_2F$, $OCHF_2$, $OCF_3$, SH, $SCF_3$, a S—$C_{1-4}$-aliphatic residue, a S(=O)—$C_{1-4}$-aliphatic residue, a S(=O)$_2$—$C_{1-4}$-aliphatic residue, $CH_2F$, $CHF_2$, $CF_3$, and a $C_{1-4}$-aliphatic residue, preferably an unsubstituted $C_{1-6}$-aliphatic residue, more preferably selected from the group consisting of methyl, ethyl, n-propyl, 2-propyl, n-butyl, isobutyl, sec.-butyl, tert.-butyl, n-pentyl, isopentyl, neopentyl, and n-hexyl, wherein the $C_{1-4}$-aliphatic residue in each case is unsubstituted, or denotes a $C_{3-6}$-cycloaliphatic residue, preferably selected from the group consisting of cyclopropyl, cyclobutyl, cyclopentyl and cyclohexyl, or a 3 to 6 membered heterocycloaliphatic residue, preferably selected from the group consisting of piperidinyl (preferably piperidin-4-yl or piperidin-3-yl), tetrahydrofuranyl, and tetrahydropyranyl, in each case unsubstituted or mono- or polysubstituted with at least one substituent selected from the group consisting of F, Cl, a $C_{1-4}$-aliphatic residue and an O—$C_{1-4}$-aliphatic residue, even more preferably in each case unsubstituted, wherein the $C_{1-4}$-aliphatic residue in each case is unsubstituted, and wherein the $C_{3-6}$-cycloaliphatic residue or the 3 to 6 membered heterocycloaliphatic residue may in each case optionally bridged via an unsubstituted $C_{1-4}$ aliphatic group, on the condition that if $R^{10}$ denotes a 3 to 6 membered heterocycloaliphatic residue, the 3 to 6 membered heterocycloaliphatic residue is linked via a carbon atom, $R^{11}$ denotes H or an unsubstituted $C_{1-4}$-aliphatic residue, preferably represents an unsubstituted $C_{1-4}$-aliphatic residue, or denotes H, methyl, ethyl, n-propyl, 2-propyl, n-butyl, isobutyl, sec.-butyl or tert.-butyl, preferably denotes methyl, ethyl, n-propyl, 2-propyl, n-butyl, isobutyl, sec.-butyl or tert.-butyl, or $R^{10}$ and $R^{11}$ form together with the nitrogen atom connecting them a morpholinyl, piperidinyl, pyrrolidinyl, or azetidinyl, in each case unsubstituted or mono- or polysubstituted with at least one substituent selected from the group consisting of F, Cl, Br, I, OH, an O—$C_{1-4}$ aliphatic residue, and a $C_{1-4}$-aliphatic residue wherein the $C_{1-4}$-aliphatic residue in each case may be unsubstituted or mono- or polysubstituted with OH or an unsubstituted O—$C_{1-4}$-aliphatic residue.

Most preferred, $R^7$ denotes $CF_3$, $CHF_2$, $CH_2F$, $CH_2OH$, $CH_2OCH_3$, ethyl, n-propyl, 2-propyl, n-butyl, isobutyl, sec.-butyl, tert.-butyl, n-pentyl, isopentyl, neopentyl, n-hexyl, ethenyl or propenyl (—$CH_2CH$=$CH_2$, —$CH$=$CH$—$CH_3$, —$C$(=$CH_2$)—$CH_3$), in each case unsubstituted or mono- or polysubstituted with at least one substituent selected from the group consisting of F, Cl, OH, an O—$C_{1-4}$-aliphatic residue, $CH_2F$, $CHF_2$, $CF_3$, and a $C_{1-4}$-aliphatic residue, preferably in each case unsubstituted or mono- or polysubstituted with at least one substituent selected from the group consisting of F, Cl, and an O—$C_{1-4}$-aliphatic residue, preferably O-methyl, more preferably in each case unsubstituted, wherein the $C_{1-4}$-aliphatic residue in each case is unsubstituted, or denotes cyclopropyl, cyclobutyl, cyclopentyl and cyclohexyl, piperidinyl, tetrahydrofuranyl, or tetrahydropyranyl, preferably denotes cyclopropyl or tetrahydropyranyl, more preferably cyclopropyl, in each case unsubstituted or mono- or polysubstituted with at least one substituent selected from the group consisting of F, Cl, OH, an O—$C_{1-4}$-aliphatic residue, $CH_2F$, $CHF_2$, $CF_3$, and a $C_{1-4}$-aliphatic residue, preferably in each case unsubstituted or mono- or polysubstituted with at least one substituent selected from the group consisting of F, Cl, and an O—$C_{1-4}$-aliphatic residue, preferably O-methyl, more preferably in each case unsubstituted, wherein the $C_{1-4}$-aliphatic residue in each case is unsubstituted, and wherein cyclopropyl, cyclobutyl, cyclopentyl and cyclohexyl, piperidinyl, tetrahydrofuranyl, and tetrahydropyranyl may in each case be optionally bridged via an unsubstituted $C_{1-4}$ aliphatic group, preferably via an unsubstituted $C_{1-2}$ aliphatic group, on the condition that if $R^7$ denotes piperidinyl, tetrahydrofuranyl, or tetrahydropyranyl, piperidinyl, tetrahydrofuranyl, or tetrahydropyranyl is linked via a carbon atom, or $R^7$ denotes S—$R^{8a}$, S(=O)—$R^{8b}$, S(=O)$_2$—$R^{8c}$, or O—$R^9$, wherein $R^{8a}$, $R^{8b}$, $R^{8c}$ and $R^9$ in each case denote methyl, ethyl, n-propyl, 2-propyl, n-butyl, isobutyl, sec.-butyl, tert.-butyl, n-pentyl, isopentyl, neopentyl, n-hexyl, ethenyl and propenyl (—$CH_2CH$=$CH_2$, —$CH$=$CH$—$CH_3$, —$C$(=$CH_2$)—$CH_3$), in each case unsubstituted or mono- or polysubstituted with at least one substituent selected from the group consisting of F, Cl, OH, N($C_{1-4}$ aliphatic residue)$_2$ and an O—$C_{1-4}$-aliphatic residue, wherein the $C_{1-4}$-aliphatic residue in each case is unsubstituted, or in each case denote cyclopropyl, cyclobutyl, cyclopentyl cyclohexyl, oxetanyl, piperidinyl, tetrahydrofuranyl, or tetrahydropyranyl, preferably cyclopropyl or oxetanyl, in each case unsubstituted or mono- or polysubstituted with at least one substituent selected from the group consisting of F, Cl, OH, an O—$C_{1-4}$-aliphatic residue, $CH_2F$, $CHF_2$, $CF_3$, and a $C_{1-4}$-aliphatic residue, preferably in each case unsubstituted or mono- or polysubstituted with at least one substituent selected from the group consisting of F, Cl, and an O—$C_{1-4}$-aliphatic residue, more preferably in each case unsubstituted, wherein the $C_{1-4}$-aliphatic residue in each case is unsubstituted, and wherein cyclopropyl, cyclobutyl, cyclopentyl and cyclohexyl, oxetanyl, piperidinyl, tetrahydrofuranyl, and tetrahydropyranyl may in each case be optionally bridged via an unsubstituted $C_{1-4}$ aliphatic group, on the condition that if $R^{8a}$, $R^{8b}$, $R^{8c}$ or $R^9$ denotes piperidinyl, oxetanyl, tetrahydrofuranyl, or tetrahydropyranyl, each of these residues is linked via a carbon atom, or $R^7$ denotes N($R^{10}R^{11}$), wherein $R^{10}$ denotes a $C_{1-6}$-aliphatic residue, unsubstituted or mono- or polysubstituted with at least one substituent selected from the group consisting of F, Cl, =O, OH, and O-methyl, preferably unsubstituted or mono- or polysubstituted with at least one substituent selected from the group consisting of F, Cl, and O-methyl, more preferably unsubstituted or mono- or polysubstituted with at least one substituent selected from the group consisting of F and O-methyl, preferably denotes an unsubstituted $C_{1-6}$-aliphatic residue, more preferably selected from the group consisting of methyl, ethyl, n-propyl, 2-propyl, n-butyl, isobutyl, sec.-butyl, tert.-butyl, n-pentyl, isopentyl, neopentyl, and n-hexyl, $R^{11}$ denotes H, methyl, ethyl, n-propyl, 2-propyl, n-butyl, isobutyl, sec.-butyl or tert.-butyl, preferably methyl, ethyl, n-propyl, 2-propyl, n-butyl, isobutyl, sec.-butyl or tert.-butyl, more preferably methyl or ethyl, or
- $R^{10}$ and $R^{11}$ form together with the nitrogen atom connecting them a morpholinyl, piperidinyl, pyrrolidinyl, or azetidinyl, in each case unsubstituted or mono- or polysubstituted with at least one substituent selected from the group consisting of F, Cl, Br, I, OH, an $O$—$C_{1-4}$ aliphatic residue, and a $C_{1-4}$-aliphatic residue, more preferably unsubstituted or mono- or polysubstituted with at least one substituent selected from the group consisting of F, Cl and a $O$—$C_{1-4}$ aliphatic residue, preferably form together with the nitrogen atom connecting them a morpholinyl, piperidinyl, pyrrolidinyl, or azetidinyl, in each case unsubstituted.

In particular, $R^7$ denotes $CF_3$, $CHF_2$, $CH_2F$, $CH_2OH$, $CH_2OCH_3$, ethyl, n-propyl, 2-propyl, n-butyl, isobutyl, sec.-butyl, tert.-butyl, n-pentyl, isopentyl, neopentyl, n-hexyl, $CH_2$—CH$(CH_3)(C_2H_5)$, $C(CH_3)_2(C_2H_5)$, ethenyl or propenyl (—$CH_2CH=CH_2$, —$CH=CH$—$CH_3$, —$C(=CH_2)$—$CH_3$), $CH_2$—$OCH_3$, $C_2H_4$—$OCH_3$, $C_3H_6$—$OCH_3$, cyclopropyl, cyclobutyl, cyclopentyl, cyclobutyl, or tetrahydropyranyl, in each case unsubstituted, or $R^7$ denotes S—$R^{8a}$, $S(=O)$—$R^{8b}$, $S(=O)_2$—$R^{8c}$, or O—$R^9$,
wherein $R^{8a}$, $R^{8b}$, $R^{8c}$ and $R^9$ in each case denote methyl, ethyl, n-propyl, 2-propyl, n-butyl, isobutyl, sec.-butyl, tert.-butyl, n-pentyl, isopentyl, neopentyl, or n-hexyl, in each case unsubstituted or mono- or polysubstituted with at least one substituent selected from the group consisting of F, Cl, OH, a $N(C_{1-4}$ aliphatic residue$)_2$, and an O—$C_{1-4}$-aliphatic residue, preferably with at least one substituent selected from the group consisting of F, OH, $N(CH_3)_2$, O-methyl and O-ethyl, or in each case denote $CH_2$-cyclopropyl or oxetanyl, preferably, $R^{8a}$, $R^{8b}$, $R^{8c}$ and $R^9$ in each case denote methyl, ethyl, n-propyl, 2-propyl, n-butyl, isobutyl, sec.-butyl, tert.-butyl, n-pentyl, isopentyl, neopentyl, or n-hexyl, $CH_2$—$CH_2$—F, $CH_2CHF_2$, $CH_2$—$OCH_3$, $CH_2CH_2$—$OCH_3$, $CH_2CH_2$—$N(CH_3)_2$, $CH_2$-cyclopropyl or oxetanyl, wherein the $C_{1-4}$-aliphatic residue in each case is unsubstituted, or $R^7$ denotes $N(R^{10}R^{11})$,
wherein
- $R^{10}$ denotes methyl, ethyl, C(=O)—$CH_3$, n-propyl, 2-propyl, n-butyl, isobutyl, sec.-butyl, tert.-butyl, n-pentyl, isopentyl, neopentyl, or n-hexyl,
- $R^{11}$ denotes H, methyl or ethyl, preferably methyl or ethyl, or

- $R^{10}$ and $R^{11}$ form together with the nitrogen atom connecting them a morpholinyl, piperidinyl, pyrrolidinyl, or azetidinyl, in each case unsubstituted.

Particularly preferred is a compound according to general formula (I), wherein $R^1$ represents the partial structure (T1),

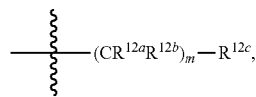
(T1)

wherein
m is 0, 1 or 2, preferably 0 or 2, more preferably 2, and
$R^{12a}$ and $R^{12b}$ each independently of one another represent H, F, OH, $CH_3$ or $OCH_3$ or together denote =O, more preferably H, F, OH or $CH_3$, even more preferably H,
$R^{12c}$ denotes a $C_{1-4}$ aliphatic residue, preferably methyl, ethyl, n-propyl, 2-propyl, n-butyl, isobutyl, sec.-butyl, or tert.-butyl, unsubstituted or mono- or polysubstituted with at least one substituent selected from the group consisting of F, Cl, Br, I, CN, OH, $S(=O)_2$—$CH_3$, an unsubstituted O—$C_{1-4}$ aliphatic residue, preferably O-methyl and O-tert.-butyl, and $CH_2F$, $CHF_2$, $CF_3$, preferably denotes a $C_{1-4}$ aliphatic residue, preferably methyl, ethyl, n-propyl, 2-propyl, n-butyl, isobutyl, sec.-butyl, or tert.-butyl, unsubstituted or mono- or polysubstituted with at least one substituent selected from the group consisting of F, Cl, Br, I, an unsubstituted O—$C_{1-4}$ aliphatic residue, preferably O-methyl and O-tert.-butyl, and $CH_2F$, $CHF_2$, and $CF_3$, or denotes a $C_{3-10}$-cycloaliphatic residue or a 3 to 10 membered heterocycloaliphatic residue, preferably cyclopropyl, cyclopentyl, cyclohexyl, morpholinyl, oxetanyl or tetrahydropyranyl, in each case unsubstituted or mono- or polysubstituted with at least one substituent selected from the group consisting of F, Cl, Br, I, an unsubstituted O—$C_{1-4}$ aliphatic residue, preferably O-methyl and O-ethyl, $CH_2F$, $CHF_2$, $CF_3$, and an unsubstituted $C_{1-4}$-aliphatic residue, preferably methyl or ethyl, or
wherein
m is 0, 1 or 2, more preferably 0, and
$R^{12a}$ and $R^{12b}$ each independently of one another represent H, F, $CH_3$ or $OCH_3$; and
$R^{12c}$ denotes an aryl or heteroaryl, preferably phenyl or pyridyl, in each case unsubstituted or mono- or polysubstituted with at least one substituent selected from the group consisting of F, Cl, Br, I, OH, an O—$C_{1-4}$ aliphatic residue, $OCF_3$, $OCH_2F$, $OCHF_2$, $CH_2$—OH, $CH_2$—$OCH_3$, $S(=O)_2$—$CH_3$, $SCF_3$, $NO_2$, $N(CH_3)_2$,

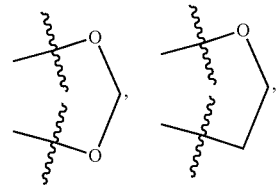 [SMILES: *OCO* ; *CCO*]

$CH_2F$, $CHF_2$, $CF_3$, CN, a $C_{1-4}$-aliphatic residue, C(=O)—$CH_3$, C(=O)—$C_2H_5$, C(=O)—O—$CH_3$, C(=O)—O—$C_2H_5$ and phenyl, preferably denotes an aryl or heteroaryl, preferably phenyl or pyridyl, in each case unsubstituted or mono- or polysubstituted with at least one substituent selected from the group consisting of F, Cl, Br, I, OH, an O—$C_{1-4}$ aliphatic residue, $OCH_2F$, $OCHF_2$, $OCF_3$, $CH_2F$, $CHF_2$, $CF_3$, CN, a $C_{1-4}$-aliphatic residue, C(=O)—$CH_3$, C(=O)—$C_2H_5$, C(=O)—O—$CH_3$, C(=O)—O—$C_2H_5$ and phenyl, wherein phenyl may be unsubstituted or mono- or polysubstituted, preferably unsubstituted or mono- or disubstituted with at least one substituent selected from the group consisting of F, Cl, Br, I, OH, an O—$C_{1-4}$ aliphatic residue, $OCH_2F$, $OCHF_2$, $OCF_3$, $CH_2F$, $CHF_2$, $CF_3$, CN, a $C_{1-4}$-aliphatic residue, C(=O)—$CH_3$, C(=O)—$C_2H_5$, C(=O)—O—$CH_3$ and C(=O)—O—$C_2H_5$, preferably with at least one substituent selected from the group consisting of F, Cl, $CH_3$, O—$CH_3$, $CH_2F$, $CHF_2$, $CF_3$ and $OCF_3$, $R^2$ represents F; Cl; Br; I; CN; $CF_3$; $CH_2F$, $CHF_2$, $NO_2$; $OCH_2F$, $OCHF_2$, $OCF_3$; $SCF_3$; methyl; ethyl; n-propyl; iso-propyl; n-butyl; sec.-butyl; tert.-butyl; $CH_2$—OH; $CH_2$—O—$CH_3$; $CH_2$—$CH_2$—OH; $CH_2$—$CH_2$—$OCH_3$; O-methyl; O-ethyl; O—$(CH_2)_2$—O—$CH_3$; O—$(CH_2)_2$—OH; S-Methyl; S-Ethyl; cyclopropyl, cyclobutyl, cyclopentyl, or cyclohexyl; preferably represents F; Cl; Br; I; CN; $CH_2F$, $CHF_2$, $CF_3$; $NO_2$; $OCH_2F$, $OCHF_2$, $OCF_3$; $SCF_3$; methyl; ethyl; n-propyl; iso-propyl; n-butyl; sec.-butyl; tert.-butyl; $CH_2$—OH; O-methyl; O-ethyl; O—$(CH_2)_2$—O—$CH_3$; O—$(CH_2)_2$—OH; S-Methyl; S-Ethyl; cyclopropyl, cyclobutyl, cyclopentyl, or cyclohexyl, $R^3$ represents H; F; Cl; Br; I; CN; $CH_2F$, $CHF_2$, $CF_3$; $SCF_3$; $NO_2$; $OCH_2F$, $OCHF_2$, $OCF_3$; methyl; ethyl; n-propyl; iso-propyl; n-butyl; sec.-butyl; tert.-butyl; O-methyl; O-ethyl; O—$(CH_2)_2$—O—$CH_3$; O—$(CH_2)_2$—OH; S-Methyl; or S-Ethyl, $R^4$ represents the partial structure (T2)

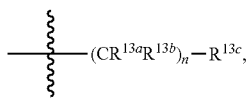
(T2)

wherein
n denotes 0, 1, 2 or 3, preferably denotes 1 or 2, more preferably denotes 1,
$R^{13a}$ and $R^{13b}$ each independently of one another represent H, F, $CH_3$ or $OCH_3$, or together denote =O, preferably each independently of one another represent H or $CH_3$, more preferably H,
$R^{13c}$ denotes a $C_{1-4}$ aliphatic residue, preferably methyl, ethyl, n-propyl, 2-propyl, n-butyl, isobutyl, sec.-butyl, or tert.-butyl, unsubstituted or mono- or polysubstituted with at least one substituent selected from the group consisting of F, Cl, Br, I, =O, an unsubstituted O—$C_{1-4}$ aliphatic residue, and $CH_2F$, $CHF_2$, $CF_3$,
or denotes cyclopropyl, cyclobutyl, cyclopentyl or cyclohexyl, pyrrolidinyl, morpholinyl, piperazinyl, piperidinyl and tetrahydropyranyl, more preferably tetrahydropyranyl or morpholinyl, in each case unsubstituted or mono- or polysubstituted with at least one substituent selected from the group consisting of F, Cl, Br, I, an unsubstituted O—$C_{1-4}$ aliphatic residue, $CH_2F$, $CHF_2$, $CF_3$, and an unsubstituted $C_{1-4}$-aliphatic residue,
or denotes an aryl or heteroaryl, preferably phenyl or pyridyl, more preferably phenyl, in each case unsubstituted or mono- or polysubstituted with at least one substituent selected from the group consisting of F, Cl, Br, I, OH, an O—$C_{1-4}$ aliphatic residue, $OCH_2F$, $OCHF_2$, $OCF_3$, $CH_2F$, $CHF_2$, $CF_3$, CN, and a $C_{1-4}$-aliphatic residue, $R^5$ denotes H, methyl or ethyl, $C_2H_4OCH_3$ or $C_3H_6OCH_3$, more preferably H or methyl, even more preferably methyl,
or
$R^4$ and $R^5$ form together with the nitrogen atom connecting them a morpholinyl, piperidinyl, pyrrolidinyl, azetidinyl, oxazepanyl, tetrahydroquinolinyl, tetrahydroisoquinolinyl, dihydroindolinyl, or dihydroisoindolyl, preferably a morpholinyl, piperidinyl, pyrrolidinyl, azetidinyl, oxazepanyl, tetrahydroquinolinyl, tetrahydroisoquinolinyl, thiomorpholinyl, azepanyl,

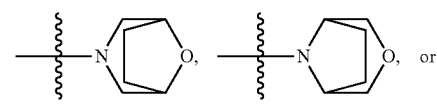

tetrahydroimidazo[1,2-a]pyrazinyl, octahydropyrrolo[1,2-a]pyrazinyl,

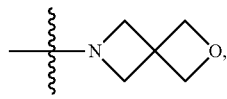 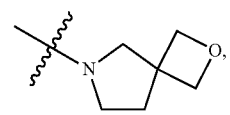

dihydroindolinyl, or dihydroisoindolyl, preferably a morpholinyl, piperidinyl, pyrrolidinyl, azetidinyl, oxazepanyl, tetrahydroquinolinyl, tetrahydroisoquinolinyl, dihydroindolinyl, or dihydroisoindolyl, more preferably a morpholinyl, piperidinyl, or pyrrolidinyl, in each case unsubstituted or mono- or polysubstituted with at least one substituent selected from the group consisting of F, Cl, OH, =O, C(=O)—OH, O-methyl, O-ethyl, $OCH_2F$, $OCHF_2$, $OCF_3$, $SCF_3$, $CH_2F$, $CHF_2$, $CF_3$, C(=O)—$CH_3$, C(=O)—$OCH_3$, $CH_2CF_3$, $CH_2OH$, $CH_2$—$OCH_3$, $CH_2CH_2$—$OCH_3$, methyl, ethyl, n-propyl, 2-propyl, cyclopropyl, and cyclobutyl, preferably selected from the group consisting of F, Cl, OH, =O, C(=O)—OH, O-methyl, O-ethyl, $OCH_2F$, $OCHF_2$, $OCF_3$, $SCF_3$, $CH_2F$, $CHF_2$, $CF_3$, methyl, ethyl, n-propyl, 2-propyl, cyclopropyl, and cyclobutyl, $R^6$ represents H; F; Cl; Br; I; CN; $CH_2F$, $CHF_2$, $CF_3$; $SCF_3$; $NO_2$; $OCH_2F$, $OCHF_2$, $OCF_3$; methyl; ethyl; n-propyl; iso-propyl; n-butyl; sec.-butyl; tert.-butyl; O-methyl; O-ethyl; O—$(CH_2)_2$—O—$CH_3$; O—$(CH_2)_2$—OH; S-Methyl; or S-Ethyl, $R^7$ denotes $CF_3$, $CHF_2$, $CH_2F$, $CH_2OH$, $CH_2OCH_3$, ethyl, n-propyl, 2-propyl, n-butyl, isobutyl, sec.-butyl, tert.-butyl, n-pentyl, isopentyl, neopentyl, n-hexyl, $CH_2$—CH($CH_3$)($C_2H_6$), C($CH_3$)$_2$($C_2H_5$), ethenyl or propenyl (—$CH_2CH$=$CH_2$, —CH=CH—$CH_3$, —C(=$CH_2$)—$CH_3$), $CH_2$—$OCH_3$, $C_2H_4$—$OCH_3$, $C_3H_6$—$OCH_3$, cyclopropyl, cyclobutyl, cyclopentyl or tetrahydropyranyl, in each case unsubstituted,
or
$R^7$ denotes S—$R^{8a}$, S(=O)—$R^{8b}$, S(=O)$_2$—$R_{8c}$ or O—$R^9$ wherein $R^{8a}$, $R^{8b}$, $R^{8c}$ and $R^9$ in each case denote methyl, ethyl, n-propyl, 2-propyl, n-butyl, isobutyl, sec.-butyl, tert.-butyl, n-pentyl, isopentyl, neopentyl, or n-hexyl, in each case unsubstituted or mono- or polysubstituted with at least one substituent selected from the group consisting of F, Cl, OH, a N($C_{1-4}$ aliphatic residue)$_2$, and an O—$C_{1-4}$-aliphatic residue, preferably with at least one substituent selected from the group consisting of F, OH, N($CH_3$)$_2$, O-methyl and O-ethyl, or in each case denote $CH_2$-cyclopropyl or oxetanyl, preferably, $R^{8a}$, $R^{8b}$, $R^{8c}$ and $R^9$ in each case denote methyl, ethyl, n-propyl, 2-propyl, n-butyl, isobutyl, sec.-butyl, tert.-butyl, n-pentyl, isopentyl, neopentyl, or n-hexyl, $CH_2$—$CH_2$—F, $CH_2CHF_2$, $CH_2$—$OCH_3$, $CH_2CH_2$—$OCH_3$, $CH_2CH_2$—N($CH_3$)$_2$, $CH_2$-cyclopropyl or oxetanyl, wherein the $C_{1-4}$-aliphatic residue in each case is unsubstituted,
or
$R^7$ denotes N($R^{10}R^{11}$),
wherein
$R^{10}$ denotes methyl, C(=O)—$CH_3$, ethyl, n-propyl, 2-propyl, n-butyl, isobutyl, sec.-butyl, tert.-butyl, n-pentyl, isopentyl, neopentyl, or n-hexyl,
$R^{11}$ denotes H, methyl or ethyl, preferably methyl or ethyl, or $R^{10}$ and $R^{11}$ form together with the nitrogen atom connecting them a morpholinyl, piperidinyl, pyrrolidinyl, or azetidinyl, in each case unsubstituted.

In another particularly preferred embodiment of the compound according to general formula (I), $R^1$ represents phenyl or pyridyl, preferably phenyl, in each case unsubstituted or mono- or disubstituted with at least one substituent selected from the group consisting of F, Cl, Br, OH, $OCH_3$, $OCH_2F$, $OCHF_2$, $OCF_3$, $CH_2F$, $CHF_2$, $CF_3$, and $CH_3$, or represents $CH_2CH_2$-tert.-butyl, $R^2$ represents $CH_2F$, $CHF_2$, $CF_3$; methyl; ethyl; iso-propyl; O-methyl; or cyclopropyl, preferably represents methyl;

$R^3$ represents H; F; Cl; Br; I; CN; $CH_2F$, $CHF_2$, $CF_3$; methyl; or O-methyl; preferably represents H, $R^4$ and $R^5$ form together with the nitrogen atom connecting them a morpholinyl, piperidinyl, pyrrolidinyl, azetidinyl, oxazepanyl, tetrahydroquinolinyl, tetrahydroisoquinolinyl, dihydroindolinyl, or dihydroisoindolyl, preferably a morpholinyl, piperidinyl, or pyrrolidinyl, in each case unsubstituted or monosubstituted with methyl;

$R^6$ represents H; F; Cl; Br; I; CN; $CH_2F$, $CHF_2$, $CF_3$; methyl; or O-methyl; preferably represents H, $R^7$ denotes $CF_3$, $CHF_2$, $CH_2F$, ethyl, n-propyl, 2-propyl (iso-propyl), tert.-butyl, ethenyl, propenyl, cyclopropyl, cyclobutyl or cyclopentyl or tetrahydropyranyl, or $R^7$ denotes S—$R^{8a}$, S(=O)—$R^{8b}$, S(=O)$_2$—$R_{8c}$ or O—$R^9$ wherein $R^{8a}$, $R^{8b}$, $R^{8c}$ and $R^9$ in each case denote methyl, ethyl, 2-propyl, or tert.-butyl, or $R^6$ denotes $N(R^{10}R^{11})$, wherein $R^{10}$ denotes methyl, ethyl, n-propyl, 2-propyl, or tert.-butyl, $R^{11}$ denotes H, methyl or ethyl, preferably methyl or ethyl, or $R^9$ and $R^{10}$ form together with the nitrogen atom connecting them a morpholinyl, piperidinyl, pyrrolidinyl, or azetidinyl.

Especially particularly preferred are compounds according to general formula (I) selected from the group comprising:

1  2-Ethylsulfanyl-N-[(3-fluorophenyl)-methyl]-6-methyl-4-morpholin-4-yl-benzamide;
2  N-[(4-Chlorophenyl)-methyl]-2-ethylsulfanyl-6-methyl-4-morpholin-4-yl-benzamide;
3  N-(4,4-Dimethyl-pentyl)-2-ethylsulfanyl-6-methyl-4-morpholin-4-yl-benzamide;
4  N-[(4-Chlorophenyl)-methyl]-2-ethylsulfanyl-6-methyl-4-[(3R)-3-methyl-morpholin-4-yl]-benzamide;
5  N-(4,4-Dimethyl-pentyl)-2-ethylsulfanyl-6-methyl-4-[(3R)-3-methyl-morpholin-4-yl]-benzamide;
6  N-[(4-Chlorophenyl)-methyl]-2-(ethylsulfinyl)-6-methyl-4-morpholin-4-yl-benzamide;
7  N-(4,4-Dimethyl-pentyl)-2-(ethylsulfinyl)-6-methyl-4-morpholin-4-yl-benzamide;
8  N-[(4-Chlorophenyl)-methyl]-2-(ethylsulfonyl)-6-methyl-4-morpholin-4-yl-benzamide;
9  N-(4,4-Dimethyl-pentyl)-2-(ethylsulfonyl)-6-methyl-4-morpholin-4-yl-benzamide;
10  N-[(4-Chlorophenyl)-methyl]-2-methoxy-6-methyl-4-morpholin-4-yl-benzamide;
11  N-[(4-Chlorophenyl)-methyl]-2-ethoxy-6-methyl-4-morpholin-4-yl-benzamide;
12  N-[(4-Chlorophenyl)-methyl]-2-ethyl-6-methyl-4-morpholin-4-yl-benzamide;
13  N-[(4-Chlorophenyl)-methyl]-2-methyl-4-morpholin-4-yl-6-propyl-benzamide;
14  N-[(4-Chlorophenyl)-methyl]-2-isopropyl-6-methyl-4-morpholin-4-yl-benzamide;
15  N-[(4-Chlorophenyl)-methyl]-2-cyclopropyl-6-methyl-4-morpholin-4-yl-benzamide;
16  N-[(4-Chlorophenyl)-methyl]-2-cyclopentyl-6-methyl-4-morpholin-4-yl-benzamide;
17  N-[(4-Fluorophenyl)-methyl]-2-isopropyl-6-methyl-4-morpholin-4-yl-benzamide;
18  2-Cyclopropyl-N-[(4-fluorophenyl)-methyl]-6-methyl-4-morpholin-4-yl-benzamide;
19  N-[(4-Chlorophenyl)-methyl]-2-methyl-4-morpholin-4-yl-6-(trifluoromethyl)-benzamide;
20  N-[(4-Chlorophenyl)-methyl]-2-(difluoro-methyl)-6-methyl-4-morpholin-4-yl-benzamide,
21  2-Isopropenyl-6-methyl-4-morpholin-4-yl-N-[[4-(trifluoromethyl)-phenyl]-methyl]-benzamide;
22  2-Isopropyl-6-methyl-4-morpholin-4-yl-N-[[4-(trifluoromethyl)-phenyl]-methyl]-benzamide;
23  2-Isopropyl-6-methyl-4-morpholin-4-yl-N-[[4-(trifluoromethyloxy)-phenyl]-methyl]-benzamide;
24  2-Cyclopropyl-6-methyl-4-morpholin-4-yl-N-[[4-(trifluoromethyl)-phenyl]-methyl]-benzamide;
25  2-Cyclopropyl-6-methyl-4-morpholin-4-yl-N-[[4-(trifluoromethyloxy)-phenyl]-methyl]-benzamide;
26  N-[(3-Fluorophenyl)-methyl]-2-methyl-4-pyrrolidin-1-yl-6-(trifluoromethyl)-benzamide;
27  N-[(3-Fluorophenyl)-methyl]-2-methyl-4-piperidin-1-yl-6-(trifluoromethyl)-benzamide,
28  2-Cyclopropyl-N-[(3R)-3-hydroxy-4,4-dimethyl-pentyl]-6-methyl-4-morpholin-4-yl-benzamide;
29  2-Cyclopropyl-N-[(3S)-3-hydroxy-4,4-dimethyl-pentyl]-6-methyl-4-morpholin-4-yl-benzamide;
30  N-[(3R)-3-Hydroxy-4,4-dimethyl-pentyl]-2-isopropyl-6-methyl-4-morpholin-4-yl-benzamide;
31  N-[(3S)-3-Hydroxy-4,4-dimethyl-pentyl]-2-isopropyl-6-methyl-4-morpholin-4-yl-benzamide;
32  2-Cyclopropyl-N-(2-hydroxy-4,4-dimethyl-pentyl)-6-methyl-4-morpholin-4-yl-benzamide;
33  N-(2-Hydroxy-4,4-dimethyl-pentyl)-2-isopropyl-6-methyl-4-morpholin-4-yl-benzamide;
34  N-[(5-Chloro-pyridin-2-yl)-methyl]-2-isopropyl-6-methyl-4-morpholin-4-yl-benzamide;
35  2-Isopropyl-6-methyl-4-morpholin-4-yl-N-[[5-(trifluoromethyl)-pyridin-2-yl]-methyl]-benzamide;
36  2-Cyclopropyl-6-methyl-4-morpholin-4-yl-N-[[5-(trifluoromethyl)-pyridin-2-yl]-methyl]-benzamide;
37  N-[(4-Chlorophenyl)-methyl]-2-methyl-4-morpholin-4-yl-6-tetrahydro-furan-3-yl-benzamide;
38  N-[(4-Chlorophenyl)-methyl]-2-[(3R)-3-fluoro-pyrrolidin-1-yl]-6-methyl-4-morpholin-4-yl-benzamide;
39  N-[(4-Chlorophenyl)-methyl]-2-fluoro-6-isopropyl-4-morpholin-4-yl-benzamide;
40  N-[(4-Chlorophenyl)-methyl]-2-isopropyl-6-methoxy-4-morpholin-4-yl-benzamide; and
41  N-[(4-Chlorophenyl)-methyl]-2,6-diethyl-4-morpholin-4-yl-benzamide, optionally in the form of a single stereoisomer or a mixture of stereoisomers, in the form of the free compound and/or a physiologically acceptable salt thereof.

The substituted compounds according to the invention of the aforementioned general formula (I) and corresponding stereoisomers and also the respective corresponding salts and solvates are toxicologically safe and are therefore suitable as pharmaceutical active ingredients in pharmaceutical compositions.

The present invention therefore further relates to a pharmaceutical composition containing at least one compound according to general formula (I), in each case optionally in the form of a single stereoisomer or a mixture of stereoisomers, in the form of the free compound and/or a physiologically acceptable salt and/or a solvate, in particular hydrate, thereof, and also optionally one or more pharmaceutically acceptable auxiliaries.

These pharmaceutical compositions according to the invention are suitable in particular for the modulation of KCNQ2/3 K$^+$ channels, preferably for KCNQ2/3 K$^+$ channel inhibition and/or KCNQ2/3 K$^+$ channel stimulation, i.e. they exert an agonistic or antagonistic effect.

Likewise, the pharmaceutical compositions according to the invention are preferably suitable for the prophylaxis and/or treatment of disorders and/or diseases which are mediated, at least in part, by KCNQ2/3 K$^+$ channels.

The pharmaceutical composition according to the invention is suitable for administration to adults and children, including toddlers and babies.

The pharmaceutical composition according to the invention may be prepared as a liquid, semisolid or solid pharmaceutical form, for example in the form of injection solutions, drops, juices, syrups, sprays, suspensions, tablets, patches, capsules, plasters, suppositories, ointments, creams, lotions, gels, emulsions, aerosols or in multiparticulate form, for example in the form of pellets or granules, if appropriate pressed into tablets, decanted in capsules or suspended in a liquid, and also be administered as much.

In addition to at least one substituted compound of general formula (I), optionally in the form of a single stereoisomer or a mixture of stereoisomers, in the form of the free compound and/or a physiologically acceptable salt and/or a solvate, in particular hydrate, thereof, the pharmaceutical composition according to the invention conventionally may contain further physiologically acceptable pharmaceutical auxiliaries which, for example, can be selected from the group consisting of excipients, fillers, solvents, diluents, surface-active substances, dyes, preservatives, blasting agents, slip additives, lubricants, aromas and binders.

The selection of the physiologically acceptable auxiliaries and also the amounts thereof to be used depend on whether the pharmaceutical composition is to be applied orally, subcutaneously, parenterally, intravenously, intraperitoneally, intradermally, intramuscularly, intranasally, buccally, rectally or locally, for example to infections of the skin, the mucous membranes and of the eyes. Preparations in the form of tablets, dragées, capsules, granules, pellets, drops, juices and syrups are preferably suitable for oral application; solutions, suspensions, easily reconstitutable dry preparations and also sprays are preferably suitable for parenteral, topical and inhalative application. The substituted compounds according to the invention used in the pharmaceutical composition according to the invention in a repository, in a dissolved form or in a plaster, and further agents promoting skin penetration being added if appropriate, are suitable percutaneous application preparations. Orally or percutaneously applicable preparation forms can release the respective substituted compound according to the invention also in a delayed manner.

The pharmaceutical compositions according to the invention can be prepared with the aid of conventional means, devices, methods and process known in the art, such as are described for example in "Remington's Pharmaceutical Sciences", A. R. Gennaro (Editor), 17$^{th}$ edition, Mack Publishing Company, Easton, Pa., 1985, in particular in Part 8, Chapters 76 to 93. The corresponding description is introduced herewith by way of reference and forms part of the disclosure. The amount to be administered to the patient of the respective substituted compounds according to the invention of the above-indicated general formula (I) may vary and is for example dependent on the patient's weight or age and also on the type of application, the indication and the severity of the disorder. Conventionally, 0.001 to 100 mg/kg, preferably 0.05 to 75 mg/kg, particularly preferably 0.05 to 50 mg of at least one compound according to the invention are applied per kg of the patient's body weight.

The pharmaceutical composition according to the invention is preferably suitable for the prophylaxis and/or treatment of disorders and/or diseases which are mediated, at least in part, by KCNQ2/3 K$^+$ channels. The pharmaceutical composition according to the invention is more preferably suitable for the treatment and/or prophylaxis of one or more diseases and/or disorders selected from the group consisting of pain, in particular pain selected from the group consisting of acute pain, chronic pain, neuropathic pain, muscular pain, visceral pain and inflammatory pain, epilepsy, urinary incontinence, anxiety, dependency, mania, bipolar disorders, migraine, cognitive diseases and dystonia-associated dyskinesias.

The pharmaceutical composition according to the invention is suitable particularly preferably for the treatment of pain, more particularly preferably of acute pain, chronic pain, neuropathic pain, visceral pain, inflammatory pain and muscular pain, and most particularly for the treatment of neuropathic pain.

The pharmaceutical composition according to the invention is also preferably suitable for the treatment and/or prophylaxis of epilepsy.

The present invention further relates to at least one compound according to general formula (I), optionally in the form of a single stereoisomer or a mixture of stereoisomers, in the form of the free compound and/or a physiologically acceptable salt and/or a solvate, in particular hydrate, thereof, and also optionally of one or more pharmaceutically acceptable auxiliaries for use in the modulation of KCNQ2/3 K$^+$ channels, preferably for use in KCNQ2/3 K$^+$ channel inhibition and/or stimulation.

The present invention therefore further relates to at least one compound according to general formula (I), optionally in the form of a single stereoisomer or a mixture of stereoisomers, in the form of the free compound and/or a physiologically acceptable salt and/or a solvate, in particular hydrate, thereof, and also optionally of one or more pharmaceutically acceptable auxiliaries for use in the prophylaxis and/or treatment of disorders and/or diseases which are mediated, at least in part, by KCNQ2/3 K$^+$ channels.

Preference is given to at least one compound according to general formula (I), optionally in the form of a single stereoisomer or a mixture of stereoisomers, in the form of the free compound and/or a physiologically acceptable salt and/or a solvate, in particular hydrate, thereof, and optionally one or more pharmaceutically acceptable auxiliaries for use in the prophylaxis and/or treatment of disorders and/or diseases selected from the group consisting of pain, in particular pain selected from the group consisting of acute pain, chronic pain, neuropathic pain, muscular pain, visceral pain and inflammatory pain, epilepsy, urinary incontinence, anxiety, dependency, mania, bipolar disorders, migraine, cognitive diseases and dystonia-associated dyskinesias.

Particular preference is given to at least one compound according to general formula (I) and optionally one or more pharmaceutically acceptable auxiliaries for use in the prophylaxis and/or treatment of disorders and/or diseases selected from the group consisting of pain, in particular pain selected from the group consisting of acute pain, chronic pain, neuropathic pain, muscular pain, visceral pain and inflammatory pain, most particularly neuropathic pain.

Particular preference is also given to at least one compound according to general formula (I) and optionally one or more pharmaceutically acceptable auxiliaries for use in the prophylaxis and/or treatment of epilepsy.

The present invention further relates to at least one compound according to general formula (I) and also optionally one or more pharmaceutically acceptable auxiliaries for the modulation of KCNQ2/3 K$^+$ channels, preferably for KCNQ2/3 K$^+$ channel inhibition and/or stimulation.

The present invention therefore further relates to at least one compound according to general formula (I) and also optionally of one or more pharmaceutically acceptable auxiliaries for the prophylaxis and/or treatment of disorders and/or diseases which are mediated, at least in part, by KCNQ2/3 K$^+$ channels.

Preference is given to at least one compound according to general formula (I) and optionally one or more pharmaceutically acceptable auxiliaries for the prophylaxis and/or treatment of disorders and/or diseases selected from the group consisting of pain, especially pain selected from the group consisting of acute pain, chronic pain, neuropathic pain, muscular pain, visceral pain and inflammatory pain, epilepsy, urinary incontinence, anxiety, dependency, mania, bipolar disorders, migraine, cognitive diseases and dystonia-associated dyskinesias.

Particular preference is given to at least one compound according to general formula (I) and optionally one or more pharmaceutically acceptable auxiliaries for the prophylaxis and/or treatment of disorders and/or diseases selected from the group consisting of pain, in particular pain selected from the group consisting of acute pain, chronic pain, neuropathic pain, muscular pain, visceral pain and inflammatory pain, most particularly neuropathic pain.

Particular preference is also given to at least one compound according to general formula (I) and optionally one or more pharmaceutically acceptable auxiliaries for the prophylaxis and/or treatment of epilepsy.

The present invention further relates to at least one compound according to general formula (I) and also optionally one or more pharmaceutically acceptable auxiliaries for use in the preparation of a medicament for prophylaxis and/or treatment of disorders and/or diseases which are mediated, at least in part, by KCNQ2/3 K$^+$ channels.

Preference is given to at least one compound according to general formula (I) and optionally one or more pharmaceutically acceptable auxiliaries for use in the preparation of a medicament for the prophylaxis and/or treatment of disorders and/or diseases selected from the group consisting of pain, in particular pain selected from the group consisting of acute pain, chronic pain, neuropathic pain, muscular pain, visceral pain and inflammatory pain, epilepsy, urinary incontinence, anxiety, dependency, mania, bipolar disorders, migraine, cognitive diseases and dystonia-associated dyskinesias.

Particular preference is given to at least one compound according to general formula (I) and optionally one or more pharmaceutically acceptable auxiliaries for use in the preparation of a medicament for the prophylaxis and/or treatment of disorders and/or diseases selected from the group consisting of pain, in particular pain selected from the group consisting of acute pain, chronic pain, neuropathic pain, muscular pain, visceral pain and inflammatory pain, most particularly neuropathic pain.

Particular preference is also given to at least one compound according to general formula (I) and optionally one or more pharmaceutically acceptable auxiliaries for use in the preparation of a medicament for the prophylaxis and/or treatment of epilepsy.

Another aspect of the present invention is a method of treatment and/or prophylaxis of disorders and/or diseases, which are mediated, at least in part, by KCNQ2/3 K$^+$ channels, in a mammal, preferably of disorders and/or diseases selected from the group consisting of pain, preferably pain selected from the group consisting of acute pain, chronic pain, neuropathic pain, muscular pain, visceral pain and inflammatory pain, epilepsy, urinary incontinence, anxiety, dependency, mania, bipolar disorders, migraine, cognitive diseases and dystonia-associated dyskinesias, which comprises administering an effective amount of at least one compound of general formula (I) to the mammal.

The effectiveness against pain can be shown, for example, in the Bennett or Chung model (Bennett, G. J. and Xie, Y. K., A peripheral mononeuropathy in rat that produces disorders of pain sensation like those seen in man, Pain 1988, 33(1), 87-107; Kim, S. H. and Chung, J. M., An experimental model for peripheral neuropathy produced by segmental spinal nerve ligation in the rat, Pain 1992, 50(3), 355-363), by tail flick experiments (e.g. according to D'Amour and Smith (J. Pharm. Exp. Ther. 72, 74 79 (1941)) or by the formalin test (e.g. according to D. Dubuisson et al., Pain 1977, 4, 161-174). The effectiveness against epilepsy can be demonstrated, for example, in the DBA/2 mouse model (De Sarro et al., Naunyn-Schmiedeberg's Arch. Pharmacol. 2001, 363, 330-336).

The compounds according to the invention preferably have a $EC_{50}$ value of not more than 10000 nM or not more than 8000 nM, more preferably not more than 7000 nM or not more than 6000 nM, yet more preferably not more than 5000 nM or not more than 3000 nM, even more preferably not more than 2000 nM or not more than 1000 nM, yet even more preferably not more than 800 nM or not more than 700 nM, still more preferably not more than 600 nM or not more than 500 nM, yet still more preferably not more than 400 nM or not more than 300 nM, most preferably not more than 200 nM or not more than 150 nM and especially not more than 120 nM or not more than 100 nM. Methods for determining the $EC_K$ value are known to the person skilled in the art. The $EC_{50}$ value is preferably determined by fluorimetry, particularly preferably as described below under "pharmacological experiments".

The invention further provides processes for the preparation of the substituted compounds according to the invention.

The chemicals and reaction components used in the reactions and schemes described below are available commercially or in each case can be prepared by conventional methods known to the person skilled in the art.

The reactions described can each be carried out under the conventional conditions with which the person skilled in the art is familiar, for example with regard to pressure or the order in which the components are added. If appropriate, the person skilled in the art can determine the optimum procedure under the respective conditions by carrying out simple preliminary tests. The intermediate and end products obtained using the reactions described hereinbefore can each be purified and/or isolated, if desired and/or required, using conventional methods known to the person skilled in the art. Suitable purifying processes are for example extraction processes and chromatographic processes such as column chromatography or preparative chromatography. All of the process steps described below, as well as the respective purification and/or isolation of intermediate or end products, can be carried out partly or completely under an inert gas atmosphere, preferably under a nitrogen atmosphere.

If the substituted compounds according to the invention of the aforementioned general formula (I) are obtained, after preparation thereof, in the form of a mixture of their stereoisomers, preferably in the form of their racemates or other mixtures of their various enantiomers and/or diastereomers, they can be separated and if appropriate isolated using conventional processes known to the person skilled in the art. Examples include chromatographic separating processes, in particular liquid chromatography processes under normal pressure or under elevated pressure, preferably MPLC and HPLC processes, and also fractional crystallisation processes. These processes allow individual enantiomers, for example diastereomeric salts formed by means of chiral stationary phase HPLC or by means of crystallisation with chiral acids, for example (+)-tartaric acid, (−)-tartaric acid or (+)-10-camphorsulphonic acid, to be separated from one another.

General reaction scheme I (synthesis of precursors SM01-SM06):

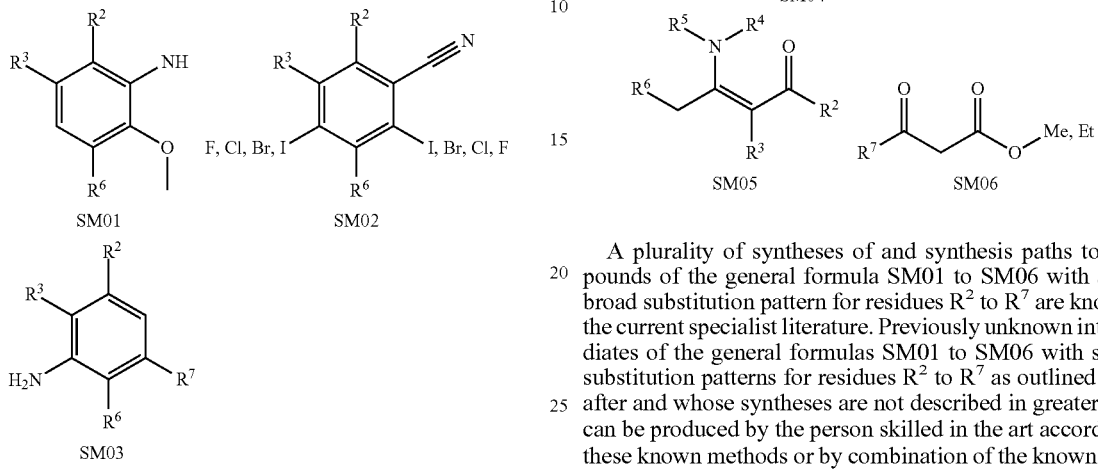

A plurality of syntheses of and synthesis paths to compounds of the general formula SM01 to SM06 with a very broad substitution pattern for residues $R^2$ to $R^7$ are known in the current specialist literature. Previously unknown intermediates of the general formulas SM01 to SM06 with similar substitution patterns for residues $R^2$ to $R^7$ as outlined thereafter and whose syntheses are not described in greater detail can be produced by the person skilled in the art according to these known methods or by combination of the known methods.

General reaction scheme II:

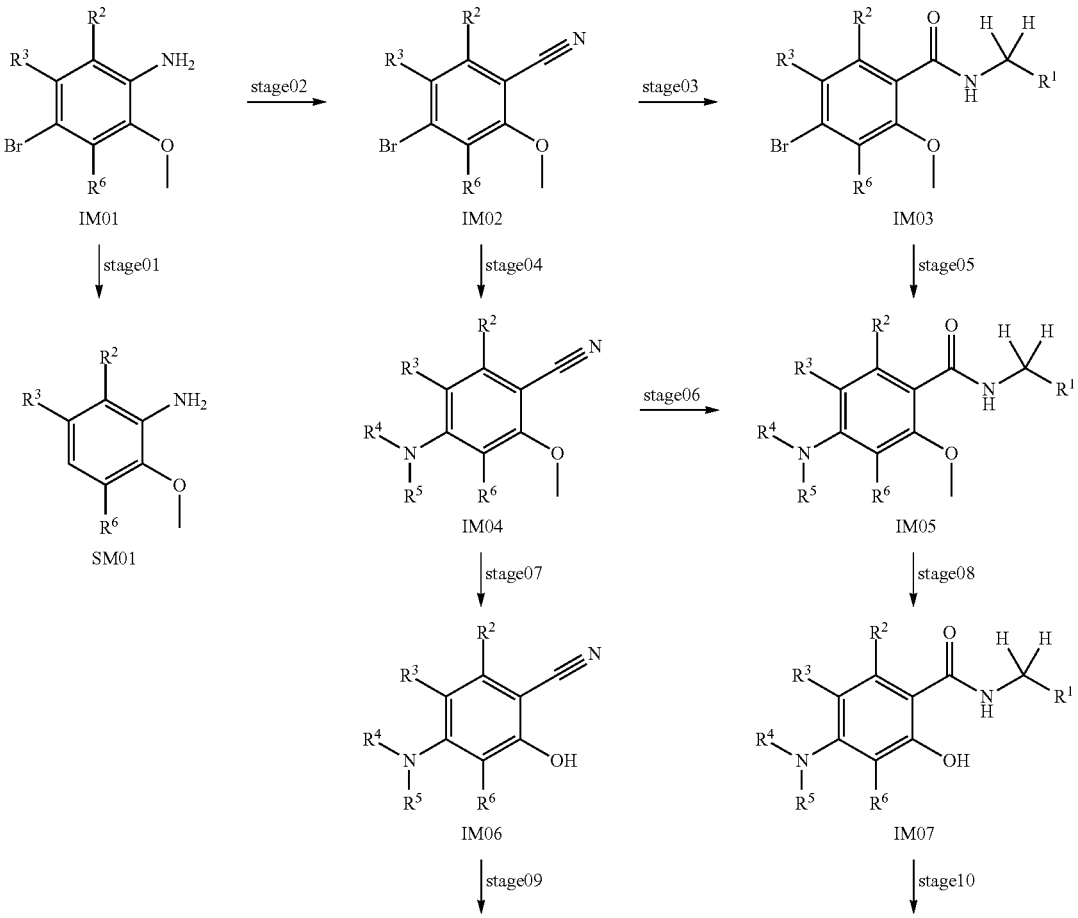

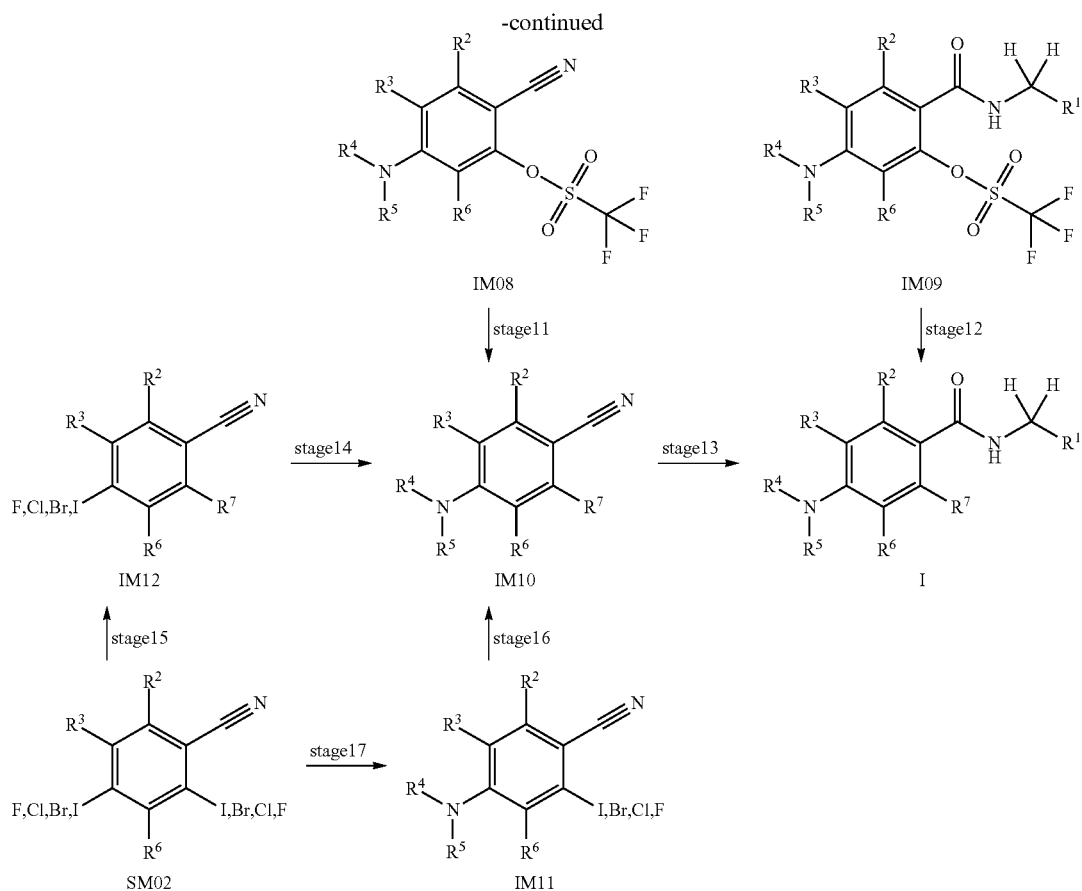

In stage 01 anilines of the general formula SM01 can be transformed into 4-bromo-anilines of the general formula IM01 according to methods known to the person skilled in the art, for example using a suitable bromination reagent, for example bromine or N-bromosuccinimide.

In stage02 4-bromo-anilines of the general formula IM01 can be transformed into 4-bromo-benzonitriles of the general formula IM02 according to methods known to the person skilled in the art, for example by treatment of the corresponding diazonium solution, prepared from IM01 by using a suitable diazotation reagent, for example sodium nitrite and mineral acid or organic nitrites, with a solution of copper(I) cyanide in aqueous sodium cyanide.

In stage03, stage06, and stage13 benzonitriles of the general formulae IM02, IM04, and IM10 can be transformed into N-substituted benzamides of the general formulae IM03, IM05, and I respectively according to methods known to the person skilled in the art, for example by hydrolysis of the nitriles to afford the corresponding carboxamides followed by treatment with alkylating reagents of the general formula $R^1$—$CH_2$—X where X denotes halogen or a sulfonic acid ester, for example mesylate, according to methods known to the person skilled in the art, or alternatively by hydrolysis of the nitriles to afford the corresponding carboxylic acids, followed by treatment with amines of the general formula $R^1$—$CH_2$—$NH_2$ according to methods known to the person skilled in the art, for example using a suitable coupling reagent, for example O-(7-azabenzotriazol-1-yl)-N,N,N',N'-tetramethyluronium hexafluorophosphate, or alternatively by reduction of the nitriles to afford the corresponding aldehydes, for example by using diisobutylaluminium hydride, followed by oxidation to afford the corresponding carboxylic acids, for example by using sodium chlorite, followed by treatment with amines of the general formula $R^1$—$CH_2$—$NH_2$ according to methods known to the person skilled in the art.

In stage04, stage05, stage14, and stage17 4-halogeno-benzonitriles of the general formulae IM02, IM12 and SM02, or 4-halogeno-benzamides of the general formula IM03 respectively, can be transformed into 4-amino-benzenonitriles of the general formulae IM04, IM10 and IM11 or 4-halogeno-benzamides of the general formula IM05 respectively, with amines of the general formula $HNR^4R^5$ according to methods known to the person skilled in the art, for example by conventional or microwave heating, neat or in solution, for example in acetonitrile, dimethylformamide, dioxane, N-methyl-2-pyrrolidone or tetrahydrofuran, optionally in the presence of a suitable base, for example triethylamine, N,N-diisopropylethylamine, potassium carbonate, caesium carbonate, sodium tert-butoxide or potassium tert-butoxide, optionally by addition of a suitable coupling reagent, for example tetrakis(triphenylphosphin)-palladium, bis(dibenzylideneacetone)-palladium(0), or tris(dibenzylideneacetone)-dipalladium(0), optionally in presence of an additional ligand, for example (2-biphenyl)di-tert-butylphosphine or 2'-bis(diphenylphosphino)-1,1'-binaphthyl.

In stage07 and stage08 4-amino-2-methoxy-benzonitriles of the general formula IM04 or N-substituted 4-amino-2-methoxy-benzamides of the general formula IM05 can be transformed into 4-amino-2-hydroxy-benzonitriles of the general formula IM06 or N-substituted 4-amino-2-hydroxy-benzamides of the general formula IM07 according to methods known to the person skilled in the art, for example, using a suitable O-demethylation reagent, for example borontribromide.

In stage09 and stage10 4-amino-2-hydroxy-benzonitriles of the general formula IM06 or N-substituted 4-amino-2-hydroxy-benzamides of the general formula IM07 can be transformed into the corresponding trifluoro-methanesulfonic acid esters IM08 and IM09 according to methods known to the person skilled in the art, for example, using N-phenyl bis(rifluoromethane sulfonamide) or trifluoromethanesulfonic anhydride, optionally in the presence of a suitable base, for example triethylamine or caesium carbonate.

In stage11, stage12, stage15, and stage16 trifluoro-methanesulfonic acid 2-carbamoylphenyl esters of the general formulae IM08 and SM09 or 2-halogeno-benzonitriles of the general formulae, IM11 and SM02, can be transformed into the intermediates of the general formula IM12, IM10, or the benzamide of the general formula I (stage12) according to methods known to the person skilled in the art with compounds of the general formula Y—$R^7$, where Y denotes hydrogen, a metal or organometallic residue, for example sodium, magnesium bromide, magnesium chloride, tributyltin or boronic acid, or a residue to form an organometallic reagent, according to methods known to the person skilled in the art, for example by conventional or microwave heating, neat or in solution, for example in acetonitrile, dimethylformamide, dioxane, N-methyl-2-pyrrolidone, tetrahydrofuran, methanol or ethanol, optionally in the presence of a suitable base, for example triethylamine, N,N-diisopropylethylamine, potassium carbonate, caesium carbonate, sodium tert-butoxide or potassium tert-butoxide, optionally by addition of a suitable coupling reagent, for example tetrakis(triphenylphosphin)-palladium, bis(dibenzylideneacetone)-palladium(0), tris(dibenzylideneacetone)-dipalladium(0), [1,3-bis (diphenylphosphino)propane]-dichloronickel(II) or iron(III) acetylacetonate, optionally in presence of an additional ligand, for example (2-biphenyl)di-tert-butylphosphine or 2'-bis(diphenylphosphino)-1,1'-binaphthyl.

General reaction scheme III:

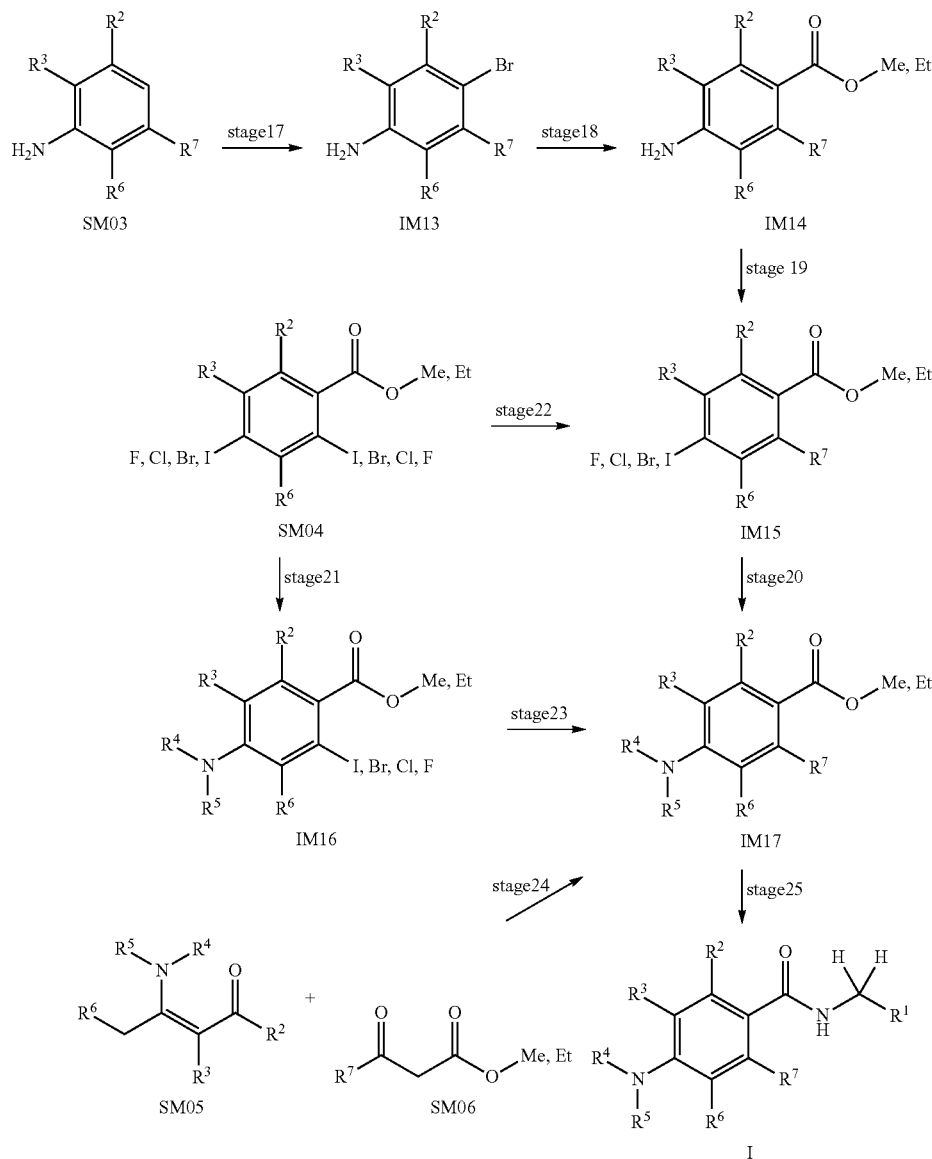

In stage17 anilines of the general formula SM03 can be transformed into 4-bromo-anilines of the general formula IM13 according to methods known to the person skilled in the art, for example using a suitable bromination reagent, for example bromine or N-bromosuccinimide.

In stage18, 4-bromo-anilines of the general formula IM13 can be transformed into 4-amino-benzoic acid esters of the general formula IM14 according to methods known to the person skilled in the art, for example using carbon monoxide by addition of a suitable coupling reagent, for example tetrakis(triphenylphosphin)-palladium or palladium(II) acetate, optionally in presence of an additional ligand, for example 4,5-bis(diphenylphosphino)-9,9-dimethylxanthene, optionally in the presence of a suitable base, for example triethylamine, N,N-diisopropylethylamine.

In stage19, 4-amino-benzoic acid esters of the general formula IM14 can be transformed into 4-halogeno-benzoic acid esters of the general formula IM15 according to methods known to the person skilled in the art, for example by treatment of the corresponding diazonium solution, prepared from IM14 by using a suitable diazotation reagent, for example sodium nitrite and mineral acid or organic nitrites, with a copper(I) halide.

In stage20 and stage21 4-halogeno-benzoic acid esters of the general formulae SM04 and IM15 can be transformed into 4-amino-benzoic acid esters of the general formulae IM16 and IM17 respectively, with amines of the general formula $HNR^4R^5$ according to methods known to the person skilled in the art, for example by conventional or microwave heating, neat or in solution, for example in acetonitrile, dimethylformamide, dioxane, N-methyl-2-pyrrolidone or tetrahydrofuran, optionally in the presence of a suitable base, for example triethylamine, N,N-diisopropylethylamine, potassium carbonate, caesium carbonate, sodium tert-butoxide or potassium tert-butoxide, optionally by addition of a suitable coupling reagent, for example tetrakis(triphenylphosphin)-palladium, bis(dibenzylideneacetone)-palladium(0), or tris(dibenzylideneacetone)-dipalladium(0), optionally in presence of an additional ligand, for example (2-biphenyl)di-tert-butylphosphine or 2'-bis(diphenylphosphino)-1,1'-binaphthyl.

In stage22 and stage23 2-halogeno-benzoic acid esters of the general formulae SM04 and IM16 can be transformed into the intermediates of the general formula IM15 and IM17 respectively according to methods known to the person skilled in the art with compounds of the general formula $Y—R^7$, where Y denotes hydrogen, a metal or organometallic residue, for example sodium, magnesium bromide, magnesium chloride, tributyltin or boronic acid, or a residue to form an organometallic reagent, according to methods known to the person skilled in the art, for example by conventional or microwave heating, neat or in solution, for example in acetonitrile, dimethylformamide, dioxane, N-methyl-2-pyrrolidone, tetrahydrofuran, methanol or ethanol, optionally in the presence of a suitable base, for example triethylamine, N,N-diisopropylethylamine, potassium carbonate, caesium carbonate, sodium tert-butoxide or potassium tert-butoxide, optionally by addition of a suitable coupling reagent, for example tetrakis(triphenylphosphin)-palladium, bis(dibenzylideneacetone)-palladium(0), tris(di-benzylideneacetone)-dipalladium(0), [1,3-bis(diphenylphosphino)propane]-dichloronickel(II) or iron(III) acetylacetonate, optionally in presence of an additional ligand, for example (2-biphenyl)di-tert-butylphosphine or 2'-bis(diphenylphosphino)-1,1'-binaphthyl.

In stage24 4-aminopent-3-en-2-ones of the general formula SM05 can react with 3-oxocarboxylic acid esters of the general formula SM06 to yield 4-amino-benzoic acid esters of the general formula IM17, for example by heating in a suitable solvent, for example acetic acid.

In stage25 benzoic acid esters of the general formula IM17 can be converted to yield amides of the general formula I with amines of the general formula $R^1—CH_2—NH_2$ according to methods known to the person skilled in the art, for example by the addition of trimethyl aluminium, or by ester hydrolysis to yield the corresponding carboxylic acid followed by reaction with amines of the general formula $R^1—CH_2—NH_2$ according to methods known to the person skilled in the art, for example using a suitable coupling reagent, for example O-(7-azabenzotriazol-1-yl)-N,N,N',N'-tetramethyluronium hexafluorophosphate.

Thus obtained compounds of the general formula I can be further transformed to introduce and/or exchange one or more of the substituents $R^1$, $R^2$, $R^3$, $R^4$, $R^5$, $R^6$ and $R^7$ by simple derivatization reactions known to the person skilled in the art, for example esterification, ester formation, amide formation, etherification, ether cleavage, oxidation, reduction, hydrogenation, substitution or cross-coupling reactions.

The invention will be described hereinafter with the aid of a number of examples. This description is intended merely by way of example and does not limit the general idea of the invention.

EXAMPLES

The indication "M" are indications of concentration in mol/l, "d" means days, "brine" means saturated aqueous sodium chloride solution, "h" means hour(s), "MS" means mass spectrometry, "RT" means room temperature (23±7° C.), "TLC" means thin layer chromatography, "v/v" means volume to volume.

The yields of the compounds prepared were not optimized. All temperatures are uncorrected.

The stationary phase used for the column chromatography was silica gel 60 (0.04-0.063 mm) from E. Merck, Darmstadt.

All starting materials which are not explicitly described were either commercially available (the details of suppliers such as for example Acros, Avocado, Aldrich, Bachem, Fluka, Lancaster, Maybridge, Merck, Sigma, TCI, Oakwood, etc. can be found in the Symyx® Available Chemicals Database of MDL, San Ramon, US or the SciFinder® Database of the ACS, Washington D.C., US, respectively, for example) or the synthesis thereof has already been described precisely in the specialist literature (experimental guidelines can be found in the Reaxys® Database of Elsevier, Amsterdam, NL or the SciFinder® Database of the ACS, Washington DC, US, respectively, for example) or can be prepared using the conventional methods known to the person skilled in the art.

The mixing ratios of solvents or eluents for chromatography are specified in v/v.

All the intermediate products and exemplary compounds were analytically characterised by means of $^1$H-NMR spectroscopy. In addition, mass spectrometry tests (MS, m/z for $[M+H]^+$) were carried out for all the exemplary compounds and selected intermediate products.

Synthesis of Exemplary Compounds

Synthesis of Example 1

2-Ethylsulfanyl-N-[(3-fluorophenyl)-methyl]-6-methyl-4-morpholin-4-yl-benzamide

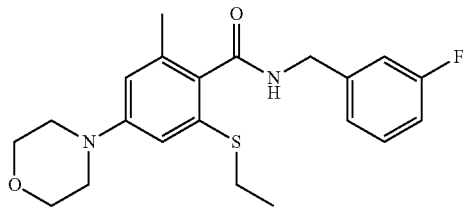 [SMILES: CCSc1cc(N2CCOCC2)cc(C)c1C(=O)NCc1cccc(F)c1]

a) Synthesis of 4-chloro-2-ethylsulfanyl-6-methyl-benzonitrile

To a solution of 2,4-dichloro-6-methyl-benzonitrile (5.0 g, 26.9 mmol) in DMF (50 ml) in a sealed tube are added tripotassium phosphate (5.7 g, 26.9 mmol) and L-proline (0.62 g, 5.37 mmol) at RT. The reaction mixture is degassed and flushed with argon for 30 min and then are added CuI (0.51 g, 2.68 mmol) and ethanethiol (6.0 ml, 80.6 mmol) at RT. The reaction mixture is stirred at 80° C. for 16 h. After completion of the reaction (monitored by TLC), the reaction mixture is diluted with water (50 ml) and extracted with ethyl acetate (50×3 ml). The organic layer is washed with water (50 ml), brine (15 ml) dried over anhydrous sodium sulfate and evaporated to get the crude which is purified by column chromatography (silica gel, 5% acetone/hexane) to yield 4-chloro-2-ethylsulfanyl-6-methyl-benzonitrile (1.3 g, 6.14 mmol, 23%).

b) Synthesis of 2-ethylsulfanyl-6-methyl-4-morpholin-4-yl-benzonitrile

To a solution of 4-chloro-2-ethylsulfanyl-6-methyl-benzonitrile (0.9 g, 4.26 mmol) in dioxane (90 ml) are added morpholine (0.56 g, 6.39 mmol) and sodium tert-butoxide (1.2 g, 12.8 mmol). The reaction mixture is degassed and flushed with Argon for 30 min and then (2-biphenyl)di-tert-butylphosphine (0.25 g, 0.85 mmol) and bis(dibenzylideneacetone)-palladium(0) (0.5 g, 0.85 mmol) are added. The reaction mixture is stirred at 100° C. for 16 h. After completion of the reaction (monitored by TLC), the reaction mixture is filtered through a pad of celite pad. The filtrate is concentrated to get the crude product, which is purified by column chromatography (silica gel, 5% acetone/hexane) to yield 2-ethylsulfanyl-6-methyl-4-morpholin-4-yl-benzonitrile (0.30 g, 1.14 mmol, 27%).

c) Synthesis of 2-ethylsulfanyl-6-methyl-4-morpholin-4-yl-benzamide

A solution of 2-ethylsulfanyl-6-methyl-4-morpholin-4-yl-benzonitrile (0.30 g, 1.14 mmol) in concentrated sulfuric acid (15 ml) is stirred at 100° C. for 4 h. After completion of the reaction (monitored by TLC), the reaction mixture is diluted with water (30 ml), basified with aqueous ammonia, and extracted with ethyl acetate (3×15 ml). The organic layer is washed with water (20 ml), brine (15 ml), dried over anhydrous sodium sulfate and evaporated to get 2-ethylsulfanyl-6-methyl-4-morpholin-4-yl-benzamide, which is used in the next step without further purification (0.26 g, 0.92 mmol, 81%).

d) Synthesis of 2-ethylsulfanyl-N-[(3-fluorophenyl)-methyl]-6-methyl-4-morpholin-4-yl-benzamide To a solution of 2-ethylsulfanyl-6-methyl-4-morpholin-4-yl-benzamide (0.26 g, 0.92 mmol) in benzene-tetrahydrofuran (1:1) (20 ml) are added tetrabutylammonium hydrogensulfate (0.031 g, 0.091 mmol) and 50% sodium hydroxide solution (8 ml) at RT. The reaction mixture is heated to 80° C. and 3-fluorobenzyl bromide (0.14 ml of a 2M solution in benzene, 0.28 mmol) is added. The reaction mixture is stirred at 80° C. for 15 min. After completion of the reaction (monitored by TLC), the reaction mixture is diluted with water (15 ml) and extracted with ethyl acetate (15×3 ml). The organic layer is washed with water (20 ml), brine (15 ml), dried over anhydrous sodium sulfate and evaporated to get the crude product, which is purified by column chromatography (silica gel, 25% ethyl acetate/hexane) to yield 2-ethylsulfanyl-N-[(3-fluorophenyl)-methyl]-6-methyl-4-morpholin-4-yl-benzamide (example 1) (0.06 g, 0.15 mmol, 16%). [M+H]$^+$ 389.1.

Synthesis of Example 2

N-[(4-Chlorophenyl)-methyl]-2-ethylsulfanyl-6-methyl-4-morpholin-4-yl-benzamide

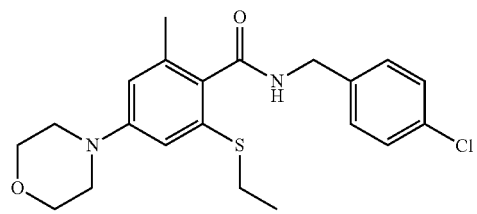

a) Synthesis of 4-chloro-2-ethylsulfanyl-6-methyl-benzonitrile

To a suspension of sodium hydride (60% suspension in mineral oil, 0.54 g, 13.6 mmol) in dry tetrahydrofuran (15 ml) is added ethanethiol (0.36 ml, 4.84 mmol) at 0° C. After effervescence has ceased, a solution of 2,4-dichloro-6-methyl-benzonitrile (1.00 g, 5.37 mmol) in THF (5 ml) is added drop wise at 0° C. The reaction mixture is stirred at RT for 16 h. After completion of the reaction (monitored by TLC), the reaction is quenched with ice water and extracted with ethyl acetate (3×30 ml). The organic layer is washed with saturated sodium hydrogen carbonate solution (20 ml), water (20 ml), brine (20 ml), dried over anhydrous sodium sulfate and evaporated to get the crude product, which is purified by column chromatography (silica gel, 5% dichloromethane/hexane) to yield 4-chloro-2-ethylsulfanyl-6-methyl-benzonitrile (0.50 g, 2.37 mmol, 44%).

b) Synthesis of N-[(4-chlorophenyl)-methyl]-2-ethylsulfanyl-6-methyl-4-morpholin-4-yl-benzamide To a solution of 2-ethylsulfanyl-6-methyl-4-morpholin-4-yl-benzamide (synthesized according to the methods described in sections b) and c) of example 1) (0.20 g, 0.71 mmol) in benzene-tetrahydrofuran (1:1) (16 ml) are added tetrabutylammonium hydrogensulfate (0.024 g, 0.071 mmol) and 50% sodium hydroxide solution (6 ml) at RT. The reaction mixture is heated to 70° C. and 4-chlorobenzyl bromide (0.15 g, 0.71 mmol) is added. The reaction mixture is stirred at 70° C. for 20 min. After completion of the reaction (monitored by TLC), the organic layer is separated and the aqueous layer is extracted with ethyl acetate (2×20 ml). The organic layer is washed with water (20 ml), brine (20 ml), dried over anhydrous sodium sulfate and evaporated to get the crude product, which is purified by column chromatography (silica gel, 28% ethyl acetate/hexane) to yield N-[(4-chlorophenyl)-methyl]-2-ethylsulfanyl-6-methyl-4-morpholin-4-yl-benzamide (example 2) (0.095 g, 0.24 mmol, 50%). [M+H]$^+$ 405.1.

Synthesis of Example 3

N-(4,4-Dimethyl-pentyl)-2-ethylsulfanyl-6-methyl-4-morpholin-4-yl-benzamide

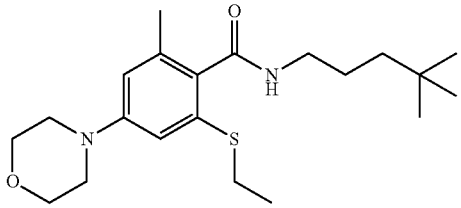 [SMILES: CCSc1cc(N2CCOCC2)cc(C)c1C(=O)NCCCC(C)(C)C]

a) Synthesis of 4,4-dimethyl-pent-2-yn-1-ol

To a solution of 3,3-dimethyl-but-1-yne (5.0 g, 60.9 mmol) in diethylether (50 ml) is added n-butyllithium (2.47 M in hexane) (23.4 ml, 57.9 mmol) at −78° C. and stirred for 15 min at that temperature. The temperature of the reaction mixture is slowly raised to −40° C. over 1 h and again cooled to −78° C. followed by the addition of paraformaldehyde (2.2 g, 73.2 mmol). The temperature is then slowly raised to RT over a period of 3 h. The reaction is quenched with saturated ammonium chloride solution and the product is extracted with ethyl acetate (3×100 ml). The combined organic extracts are washed with brine (50 ml) and dried over Na$_2$SO$_4$. Evaporation under vacuum afforded 4,4-dimethyl-pent-2-yn-1-ol (6.1 g, 54.5 mmol, 90%).

b) Synthesis of 4,4-dimethyl-pentan-1-ol

To a stirred solution of 4,4-dimethyl-pent-2-yn-1-ol (3.1 g, 27.6 mmol) in ethanol (30 ml) is added 10% palladium on carbon (0.3 g). The mixture is stirred under an atmosphere of hydrogen for 16 h. The reaction mixture is filtered through a pad of celite and the celite bed is washed with methanol (10 ml). The filtrate thus obtained is concentrated and the crude product is purified by column chromatography (5-10% ethyl acetate/hexane) to afford 4,4-dimethyl-pentan-1-ol and 4,4-dimethyl-pentan-1-al. To a stirred solution of 4,4-dimethyl-pentan-1-al (0.85 g, 7.45 mmol) in methanol (12 ml) is added sodium borohydride (0.56 g, 14.9 mmol) at 0° C. The reaction mixture is stirred at RT for 1.5 h. On completion, the solvent is evaporated and then diluted with ethyl acetate (30 ml). The organic layer is washed with water (2×20 ml), brine (20 ml), dried over sodium sulfate and concentrated affording 4,4-dimethyl-pentan-1-ol (1.52 g, 13.1 mmol, 48%).

c) Synthesis of methanesulfonic acid 4,4-dimethyl-pentan-1-ol ester

To a stirred solution of 4,4-dimethyl-pentan-1-ol (0.7 g, 6.03 mmol) in dichloromethane (20 ml) are added methanesulfonyl chloride (0.93 ml, 12.1 mmol) and triethylamine (4.2 ml, 30.2 mmol) at 0° C. The reaction mixture is stirred at RT for 1.5 h. On completion, the reaction mixture is diluted with water (20 ml) and extracted with dichloromethane (2×30 ml). The organic layer is washed with saturated citric acid solution (20 ml), water (20 ml), brine (20 ml), dried over sodium sulfate and concentrated to dryness affording methanesulfonic acid 4,4-dimethyl-pentan-1-ol ester (0.9 g, 4.63 mmol, 77%).

d) Synthesis of N-(4,4-dimethyl-pentyl)-2-ethylsulfanyl-6-methyl-4-morpholin-4-yl-benzamide To a solution of 2-ethylsulfanyl-6-methyl-4-morpholin-4-yl-benzamide (synthesized according to the methods described in sections b) and c) of example 1) (0.12 g, 0.43 mmol) in benzene-tetrahydrofuran (1:1) (5 ml) are added tetrabutylammonium hydrogensulfate (0.014 g, 0.043 mmol) and 50% sodium hydroxide solution (3.5 ml) at RT. The reaction mixture is heated to 70° C. and methanesulfonic acid 4,4-dimethyl-pentan-1-ol ester (0.08 g, 0.43 mmol) is added. The reaction mixture is stirred at 70° C. for 20 min. After completion of the reaction (monitored by TLC), the organic layer is separated and the aqueous layer is extracted with ethyl acetate (2×20 ml). The organic layer is washed with water (20 ml), brine (20 ml), dried over anhydrous sodium sulfate and evaporated to get the crude product, which is purified by column chromatography (silica gel, 10% acetone/hexane) to yield N-(4,4-dimethyl-pentyl)-2-ethylsulfanyl-6-methyl-4-morpholin-4-yl-benzamide (example 3) (0.04 g, 0.106 mmol, 33%). [M+H]$^+$ 379.2.

Synthesis of Example 4

N-[(4-Chlorophenyl)-methyl]-2-ethylsulfanyl-6-methyl-4-[(3R)-3-methyl-morpholin-4-yl]-benzamide

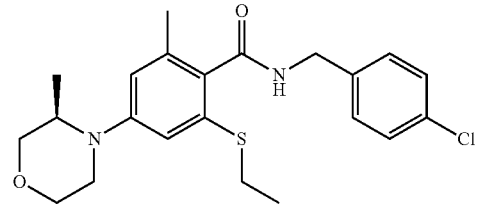 [SMILES: CCSc1cc(N2CCOC[C@H]2C)cc(C)c1C(=O)NCc1ccc(Cl)cc1]

a) Synthesis of 2-ethylsulfanyl-6-methyl-4-[(3R)-3-methyl-morpholin-4-yl]-benzonitrile 4-Chloro-2-ethylsulfanyl-6-methyl-benzonitrile (synthesized according to the method described in section a) of example 2) (0.20 g, 0.95 mmol), (R)-3-methylmorpholine (0.14 g, 1.42 mmol) and sodium tert-butoxide (0.27 g, 2.85 mmol) are mixed together with dioxane (1 ml) in a microwave vial. The resulting mixture is degassed and flushed with argon for 20 min followed by the addition of (2-biphenyl)di-tert-butylphosphine (0.056 g, 0.19 mmol) and bis(dibenzylidene-acetone)-palladium(0) (0.11 g, 0.19 mmol). The reaction mixture is heated at 100° C. in a microwave oven for 1 h. After completion of the reaction (monitored by TLC), the mixture is filtered through a pad of celite and the filtrate is concentrated to get the crude product, which is purified by column chromatography (silica gel, 8% acetone/hexane) to yield 2-ethylsulfanyl-6-methyl-4-[(3R)-3-methyl-morpholin-4-yl]-benzonitrile (0.06 g, 0.217 mmol, 22%).

b) Synthesis of 2-ethylsulfanyl-6-methyl-4-[(3R)-3-methyl-morpholin-4-yl]-benzamide Concentrated sulfuric acid (5 ml) is added to 2-ethylsulfanyl-6-methyl-4-[(3R)-3-methyl-morpholin-4-yl]-benzonitrile (0.11 g, 0.40 mmol) at RT and the resulting mixture is heated at 100° C. for 4 h. Upon completion (monitored by TLC), the reaction is slowly quenched with ice at 0° C. The mixture is basified with aqueous ammonia (pH=10). The aqueous part is extracted with ethyl acetate (3×10 ml). The combined organic layers are washed with water (10 ml), brine (10 ml), dried over anhydrous sodium sulfate and evaporated to get 2-ethylsulfanyl-6-methyl-4-[(3R)-3-methyl-morpholin-4-yl]-benzamide which is used in the next step without further purification (0.075 g, 0.26 mmol, 55%).

c) Synthesis of N-[(4-chlorophenyl)-methyl]-2-ethylsulfanyl-6-methyl-4-[(3R)-3-methyl-morpholin-4-yl]-benzamide To a solution of 2-ethylsulfanyl-6-methyl-4-[(3R)-3-methyl-morpholin-4-yl]-benzamide (0.05 g, 0.17 mmol) in benzene-tetrahydrofuran (1:1) (2 ml) are added tetrabutylammonium hydrogensulfate (0.006 g, 0.017 mmol) and 50% sodium hydroxide solution (1.5 ml) at RT. 4-Chlorobenzyl bromide (0.038 g, 0.19 mmol) is added and the reaction mixture is slowly heated to 70° C. The reaction mixture is stirred at 70° C. for additional 45 min. After completion of the reaction (monitored by TLC), the organic layer is separated and the aqueous layer is extracted with ethyl acetate (2×20 ml). The organic layer is washed with water (20 ml), brine (20 ml), dried over anhydrous sodium sulfate and evaporated to get the crude product, which is purified by column chromatography (silica gel, 8% acetone/hexane) to yield N-[(4-chlorophenyl)-methyl]-2-ethylsulfanyl-6-methyl-4-[(3R)-3-methyl-morpholin-4-yl]-benzamide (example 4) (0.023 g, 0.055 mmol, 32%). [M+H]⁺ 419.2.

Synthesis of Example 5

N-(4,4-Dimethyl-pentyl)-2-ethylsulfanyl-6-methyl-4-[(3R)-3-methyl-morpholin-4-yl]-benzamide

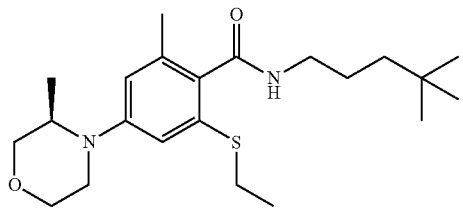 [SMILES: CCSc1cc(N2CCOC[C@H]2C)cc(C)c1C(=O)NCCCC(C)(C)C]

To a solution of 2-ethylsulfanyl-6-methyl-4-[(3R)-3-methyl-morpholin-4-yl]-benzamide (synthesized according to the methods described in sections a) and b) of example 4) (0.09 g, 0.31 mmol) in benzene-tetrahydrofuran (1:1) (4 ml) are added tetrabutylammonium hydrogensulfate (0.01 g, 0.031 mmol) and 50% sodium hydroxide solution (2.7 ml) at RT. Methanesulfonic acid 4,4-dimethyl-pentan-1-ol ester (synthesized according to the methods described in sections a), b) and c) of example 3) (0.06 g, 0.31 mmol) is added and the reaction mixture is heated to 70° C. The reaction mixture is stirred at 70° C. for additional 45 min. After completion of the reaction (monitored by TLC), the organic layer is separated and the aqueous layer is extracted with ethyl acetate (2×20 ml). The organic layer is washed with water (20 ml), brine (20 ml), dried over anhydrous sodium sulfate and evaporated to get the crude product, which is purified by column chromatography (silica gel, 5% acetone/hexane) to yield N-(4,4-dimethyl-pentyl)-2-ethylsulfanyl-6-methyl-4-[(3R)-3-methyl-morpholin-4-yl]-benzamide (example 5) (0.022 g, 0.056 mmol, 60%). [M+H]⁺ 393.3.

Synthesis of Example 6

N-[(4-Chlorophenyl)-methyl]-2-(ethylsulfinyl)-6-methyl-4-morpholin-4-yl-benzamide

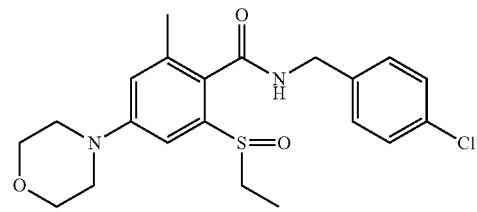 [SMILES: CCS(=O)c1cc(N2CCOCC2)cc(C)c1C(=O)NCc1ccc(Cl)cc1]

a) Synthesis of 4-chloro-2-(ethylsulfinyl)-6-methyl-benzonitrile

To a stirred solution of 4-chloro-2-ethylsulfanyl-6-methyl-benzonitrile (synthesized according to the method described in section a) of example 2) (1.00 g, 4.73 mmol) in dichloromethane (20 ml) is added meta-chloroperoxybenzoic acid (0.58 g, 2.36 mmol, 70% suspension) portion wise at 0° C. The resulting mixture is stirred at 0° C. for 15 min. The white suspension is dissolved in ethyl acetate (25 ml) and the solvent is distilled off. The residue is again diluted with ethyl acetate (15 ml) and washed with 10% sodium sulphite solution (3×15 ml), saturated sodium hydrogen sulfate solution (3×15 ml), brine (15 ml), dried over anhydrous sodium sulfate and evaporated to get the crude product, which is purified by column chromatography (silica gel, 8% ethyl acetate/hexane) to yield 4-chloro-2-(ethylsulfinyl)-6-methyl-benzonitrile (0.4 g, 1.76 mmol, 37%).

b) Synthesis of 2-(ethylsulfinyl)-6-methyl-4-morpholin-4-yl-benzonitrile

4-Chloro-2-(ethylsulfinyl)-6-methyl-benzonitrile (0.31 g, 1.36 mmol), morpholine (0.36 ml, 4.09 mmol) and potassium carbonate (0.24 g, 1.77 mmol) are taken up in N-methyl-2-pyrrolidone (3 ml) in a sealed tube and the resulting mixture is heated at 100° C. for 16 h. The mixture is then diluted with water (6 ml) and extracted with ethyl acetate (3×10 ml). The organic layer is washed with water (2×10 ml), brine (20 ml), dried over anhydrous sodium sulfate and evaporated to get the crude product, which is purified by column chromatography (silica gel, 50% ethyl acetate/hexane) to yield 2-(ethylsulfinyl)-6-methyl-4-morpholin-4-yl-benzonitrile (0.22 g, 0.79 mmol, 58%).

c) Synthesis of 2-(ethylsulfinyl)-6-methyl-4-morpholin-4-yl-benzamide

To a stirred solution of 2-(ethylsulfinyl)-6-methyl-4-morpholin-4-yl-benzonitrile (0.78 g, 2.81 mmol) in ethanol (8.5 ml) is added a 5M solution of sodium hydroxide (8.5 ml) and the mixture is heated at 80° C. for 16 h. After completion of the reaction (monitored by TLC) the reaction mixture is concentrated to get a residue, which is diluted with water (10 ml) and extracted with ethyl acetate (3×30 ml). The combined organic layers are washed with water (10 ml), brine (10 ml), dried over anhydrous sodium sulfate and evaporated to get the crude product which is purified by column chromatography (alumina, 5% methanol/dichloromethane) to yield 2-(ethylsulfinyl)-6-methyl-4-morpholin-4-yl-benzamide (0.30 g, 1.01 mmol, 36%).

d) Synthesis of N-[(4-chlorophenyl)-methyl]-2-(ethylsulfinyl)-6-methyl-4-morpholin-4-yl-benzamide To a solution of 2-(ethylsulfinyl)-6-methyl-4-morpholin-4-yl-benzamide (0.17 g, 0.57 mmol) in benzene-tetrahydrofuran (1:1) (8 ml) are added tetrabutylammonium hydrogensulfate (0.02 g, 0.057 mmol) and 15% sodium hydroxide solution (5 ml) at RT. 4-Chlorobenzyl bromide (0.083 g, 0.40 mmol) in tetrahydrofuran (0.5 ml) is added and the reaction mixture is slowly heated to 70° C. The reaction mixture is stirred at 70° C. for additional 25 min. After completion of the reaction (monitored by TLC), the organic layer is separated and the aqueous layer is extracted with ethyl acetate (2×20 ml). The organic layer is washed with water (20 ml), brine (20 ml), dried over anhydrous sodium sulfate and evaporated to get the crude product, which is purified by column chromatography (silica gel, 20% acetone/hexane) to yield N-[(4-chlorophenyl)-methyl]-2-(ethylsulfinyl)-6-methyl-4-morpholin-4-yl-benzamide (example 6) (0.12 g, 0.28 mmol, 50%). [M+H]$^+$ 421.1.

Synthesis of Example 7

N-(4,4-Dimethyl-pentyl)-2-(ethylsulfinyl)-6-methyl-4-morpholin-4-yl-benzamide

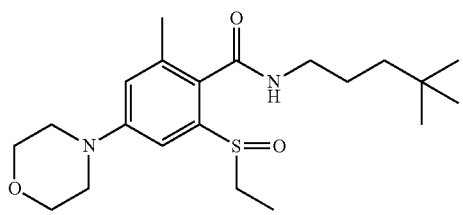 [SMILES: CCS(=O)c1cc(N2CCOCC2)cc(C)c1C(=O)NCCCC(C)(C)C]

To a stirred suspension of sodium hydride (60% suspension in mineral oil, 0.08 g, 1.92 mmol) in dry dimethylformamide (3 ml) is added a solution of 2-(ethylsulfinyl)-6-methyl-4-morpholin-4-yl-benzamide (synthesized according to the methods described in sections a), b) and c) of example 6) (0.38 g, 1.18 mmol) in dimethylformamide (5.5 ml) at 0° C. The resulting mixture is stirred at 0° C. and slowly raised to RT over a period of 30 min followed by the addition of a solution of methanesulfonic acid 4,4-dimethyl-pentan-1-ol ester (synthesized according to the methods described in sections a), b) and c) of example 3) (0.25 g, 1.28 mmol) in dimethylformamide (0.5 ml). The resulting mixture is stirred at RT for 16 h. The reaction is quenched with ice and extracted with ethyl acetate (3×15 ml). The combined organic layers are washed with water (20 ml), brine (20 ml), dried over anhydrous sodium sulfate and evaporated to get the crude product, which is purified by column chromatography (silica gel, 18% acetone/hexane) followed by preparative TLC (silica gel, 40% acetone/hexane) to yield N-(4,4-dimethyl-pentyl)-2-(ethylsulfinyl)-6-methyl-4-morpholin-4-yl-benzamide (example 7) (0.06 g, 0.15 mmol, 16%). [M+H]$^+$ 395.2.

Synthesis of Example 8

N-[(4-Chlorophenyl)-methyl]-2-(ethylsulfonyl)-6-methyl-4-morpholin-4-yl-benzamide

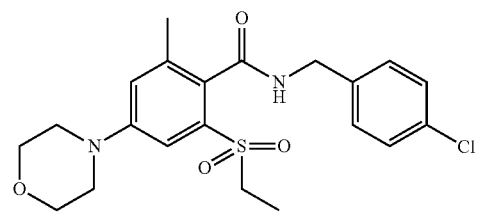 [SMILES: CCS(=O)(=O)c1cc(N2CCOCC2)cc(C)c1C(=O)NCc1ccc(Cl)cc1]

a) Synthesis of 4-chloro-2-(ethylsulfonyl)-6-methyl-benzonitrile

To a stirred solution of 4-chloro-2-ethylsulfanyl-6-methyl-benzonitrile (synthesized according to the method described in section a) of example 2) (1.50 g, 7.11 mmol) in dichloromethane (35 ml) is added added meta-chloroperoxybenzoic acid (5.26 g, 21.3 mmol, 70% suspension) portion wise at 0° C. The resulting mixture is stirred at RT for 1.5 h. After completion of the reaction (monitored by TLC), the white suspension is dissolved in ethyl acetate (25 ml) and the dichloromethane is distilled off. The residue is again diluted with ethyl acetate (15 ml) and washed with 10% sodium sulphite solution (3×15 ml), saturated sodium hydrogen carbonate solution (3×15 ml), brine (15 ml), dried over anhydrous sodium sulfate and evaporated to get the crude product, which is purified by column chromatography (silica gel, 10% ethyl acetate/hexane) to yield 4-chloro-2-(ethylsulfonyl)-6-methyl-benzonitrile (1.20 g, 4.94 mmol, 69%).

b) Synthesis of 2-(ethylsulfonyl)-6-methyl-4-morpholin-4-yl-benzonitrile

4-Chloro-2-(ethylsulfonyl)-6-methyl-benzonitrile (0.43 g, 1.77 mmol), morpholine (0.46 ml, 5.31 mmol) and potassium carbonate (0.32 g, 2.30 mmol) are taken up in N-methyl-2-pyrrolidone (3 ml) in a sealed tube and the resulting mixture is heated at 150° C. for 2 d. The mixture is then diluted with water (6 ml) and extracted with ethyl acetate (3×10 ml). The organic layer is washed with water (2×10 ml), brine (20 ml), dried over anhydrous sodium sulfate and evaporated to get the crude product, which is purified by column chromatography (silica gel, 25% ethyl acetate/hexane) to yield 2-(ethylsulfonyl)-6-methyl-4-morpholin-4-yl-benzonitrile (0.50 g, 1.70 mmol, 96%).

c) Synthesis of 2-(ethylsulfonyl)-6-methyl-4-morpholin-4-yl-benzamide

A solution of 2-(ethylsulfonyl)-6-methyl-4-morpholin-4-yl-benzonitrile (0.50 g, 1.70 mmol) in concentrated sulfuric acid (4 ml) is stirred at 100° C. for 1.5 h. After completion of reaction (monitored by TLC), the reaction mixture is diluted with water (30 ml), basified with aqueous ammonia, and extracted with ethyl acetate (3×15 ml). The organic layer is washed with water (20 ml), brine (15 ml), dried over anhydrous sodium sulfate and evaporated to get 2-(ethylsulfonyl)-6-methyl-4-morpholin-4-yl-benzamide which is used in the next step without further purification (0.50 g, 1.60 mmol, 94%).

d) Synthesis of N-[(4-chlorophenyl)-methyl]-2-(ethylsulfonyl)-6-methyl-4-morpholin-4-yl-benzamide To a solution 2-(ethylsulfonyl)-6-methyl-4-morpholin-4-yl-benzamide (0.27 g, 0.88 mmol) in benzene-tetrahydrofuran (1:1) (10 ml) are added tetrabutylammonium hydrogensulfate (0.03 g, 0.09 mmol) and 15% sodium hydroxide solution (8 ml) at RT. 4-Chlorobenzyl bromide (0.083 g, 0.40 mmol) in tetrahydrofuran (1.5 ml) is added and the reaction mixture is slowly heated to 70° C. The reaction mixture is stirred at 70° C. for additional 25 min. After completion of the reaction (monitored by TLC), the organic layer is separated and the aqueous layer is extracted with ethyl acetate (2×20 ml). The organic layer is washed with water (20 ml), brine (20 ml), dried over anhydrous sodium sulfate and evaporated to get the crude product, which is purified by column chromatography (silica gel, 15% acetone/hexane) to yield N-[(4-chlorophenyl)-methyl]-2-(ethylsulfonyl)-6-methyl-4-morpholin-4-yl-benzamide (example 8) (0.20 g, 0.46 mmol, 74%). [M+H]$^+$ 437.1.

Synthesis of Example 9

N-(4,4-Dimethyl-pentyl)-2-(ethylsulfonyl)-6-methyl-4-morpholin-4-yl-benzamide

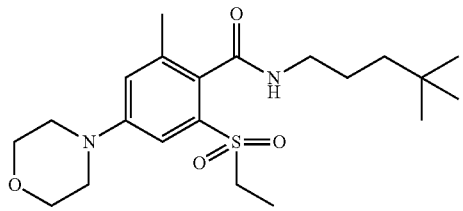 [SMILES: CCS(=O)(=O)c1cc(N2CCOCC2)cc(C)c1C(=O)NCCCC(C)(C)C]

To a stirred suspension of sodium hydride (60% suspension in mineral oil, 0.07 g, 1.68 mmol) in dry dimethylformamide (5 ml) is added a solution of 2-(ethylsulfonyl)-6-methyl-4-morpholin-4-yl-benzamide (synthesized according to the methods described in sections a), b) and c) of example 8) (0.35 g, 1.12 mmol) in dimethylformamide (2 ml) at 0° C. The resulting mixture is stirred at 0° C. and slowly raised to RT over a period of 30 min followed by the addition of a solution of methanesulfonic acid 4,4-dimethyl-pentan-1-ol ester (synthesized according to the methods described in sections a), b) and c) of example 3) (0.22 g, 1.12 mmol) in dimethylformamide (1 ml). The resulting mixture is stirred at RT for 16 h. The reaction is quenched with ice and extracted with ethyl acetate (3×10 ml). The combined organic layers are washed with water (10 ml), brine (10 ml), dried over anhydrous sodium sulfate and evaporated to get the crude product, which is purified by column chromatography (silica gel, 10% acetone/hexane) to yield N-(4,4-dimethyl-pentyl)-2-(ethylsulfonyl)-6-methyl-4-morpholin-4-yl-benzamide (example 9) (0.06 g, 0.15 mmol, 23%). [M+H]$^+$ 411.2.

Synthesis of Example 10

N-[(4-Chlorophenyl)-methyl]-2-methoxy-6-methyl-4-morpholin-4-yl-benzamide

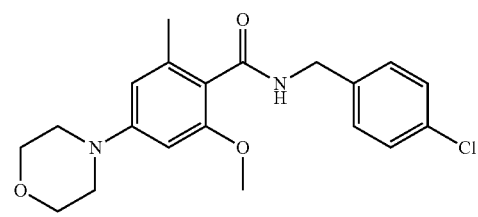 [SMILES: COc1cc(N2CCOCC2)cc(C)c1C(=O)NCc1ccc(Cl)cc1]

a) Synthesis of (4-bromo-2-methoxy-6-methyl-phenyl)-amine

To solution of (2-methoxy-6-methyl-phenyl)-amine (14.5 g, 0.11 mol) in methanol (45.6 ml) and acetic acid (14.5 ml) is added dropwise a solution of bromine (5.45 ml) in acetic acid (45.6 ml) via an addition funnel at 0° C. The reaction mixture is allowed to warm to RT and stirred for 2 h at RT. Ethyl acetate (90 ml) is added and the solid is collected by filtration. The solid thus obtained is washed with ethyl acetate to obtain (4-bromo-2-methoxy-6-methyl-phenyl)-amine as hydrobromide.

b) Synthesis of 4-bromo-2-methoxy-6-methyl-benzonitrile (4-Bromo-2-methoxy-6-methyl-phenyl)-amine hydrobromide (5.0 g, 23.2 mmol) is suspended in concentrated hydrochloric acid (5.5 ml) and ice (20 g) followed by the drop wise addition of a solution of sodium nitrite (1.63 g, 23.6 mmol) in water (5.5 ml) at 0° C. The resulting mixture is stirred at 0° C. for 30 min and neutralized with aqueous sodium carbonate. This mixture is then added with vigorous stirring at 0° C. to a suspension prepared by mixing copper(I) cyanide (2.6 g, 28.9 mmol) in water (11 ml) with a solution of sodium cyanide (3.6 g, 73.6 mmol) in water (5.5 ml) at 0° C. To the mixture is added toluene (45 ml) and stirred at 0° C. for 1 h, at RT for 2 h and at 50° C. for 1 h. The reaction mixture is cooled and the toluene layer is separated. The organic layer is washed with water (2×40 ml), dried over sodium sulfate and evaporated to get the crude product which is purified by column chromatography (silica gel, 10% ethyl acetate/hexane) to obtain 4-bromo-2-methoxy-6-methyl-benzonitrile (2.8 g, 12.4 mmol, 53%).

c) Synthesis of 4-bromo-2-methoxy-6-methyl-benzaldehyde

To a solution of 4-bromo-2-methoxy-6-methyl-benzonitrile (2.8 g, 12.38 mmol) in tetrahydrofuran (24.8 ml) is added diisobutylaluminium hydride (1.2 M in toluene) (24.8 ml, 29.7 mmol) at −78° C. The reaction mixture is slowly warmed to RT and stirred at RT for 18 h. The reaction is quenched with 1 M hydrochloric acid at 0° C. The resulting mixture is stirred at RT for 1 h and extracted with ethyl acetate (3×50 ml). The combined organic layers are washed with water (40 ml), dried over sodium sulfate and evaporated. The crude product is purified by column chromatography (silica gel, 1.5% ethyl acetate/hexane) yielding 4-bromo-2-methoxy-6-methyl-benzaldehyde (1.25 g, 5.45 mmol, 44%).

d) Synthesis of 4-bromo-2-methoxy-6-methyl-benzoic acid

To a suspension of 4-bromo-2-methoxy-6-methyl-benzaldehyde (1.25 g, 5.45 mmol) in tert-butanol (21.7 ml) is added a solution of sodium chlorite (0.98 g, 10.9 mmol) and monosodium phosphate (4.25 g, 27.3 mmol) in water (11 ml). To the solution is added 2-methyl-2-butene (4.63 ml, 43.7 mmol). The resulting homogeneous solution is stirred at RT for 30 min. After completion of the reaction, the solvent is evaporated and the residue is diluted with water and acidified with 1 M hydrochloric acid to pH=1 and extracted with methyl tert-butyl ether (3×40 ml). The combined organic layers are extracted with 1 M sodium hydroxide solution which is further acidified with 6 M hydrochloric acid and extracted with ethyl acetate (3×50 ml). The organic layer is washed with brine (40 ml), dried over sodium sulfate and concentrated to yield 4-bromo-2-methoxy-6-methyl-benzoic acid (1.2 g, 4.89 mmol, 90%).

e) Synthesis of 4-bromo-N-[(4-chlorophenyl)-methyl]-2-methoxy-6-methyl-benzamide To a stirred solution of 4-bromo-2-methoxy-6-methyl-benzoic acid (1.2 g, 4.89 mmol) in dichloromethane (10 ml) are added oxalyl chloride (0.52 ml, 5.86 mmol) and dimethylformamide (catalytic amount) at 0° C. The reaction mixture is stirred for 30 min at RT. Excess oxalyl chloride is distilled off under nitrogen. The residue is dissolved in dichloromethane (10 ml), cooled to 0° C. followed by the addition of triethylamine (1.7 ml, 12.2 mmol) and 4-chlorobenzylamine (0.71 ml, 5.86 mmol). The reaction mixture is stirred for 1 h at RT. After completion of the reaction (monitored by TLC) the mixture is diluted with water (50 ml) and extracted with dichloromethane (3×50 ml). The organic layer is washed with water (50 ml), brine (50 ml), dried over anhydrous sodium sulfate and evaporated to get the crude product, which is purified by column chromatography (silica gel, 15% ethyl acetate/hexane) to yield 4-bromo-N-[(4-chlorophenyl)-methyl]-2-methoxy-6-methyl-benzamide (1.67 g, 4.53 mmol, 92%).

f) Synthesis of N-[(4-chlorophenyl)-methyl]-2-methoxy-6-methyl-4-morpholin-4-yl-benzamide To a stirred solution of 4-bromo-N-[(4-chlorophenyl)-methyl]-2-methoxy-6-methyl-benzamide (0.37 g, 1.02 mmol) in N-methyl-2-pyrrolidone (1 ml) is added morpholine (0.10 ml, 1.20 mmol) at RT. The reaction mixture is degassed and flushed with argon for 30 min followed by addition of caesium carbonate (0.49 g, 1.52 mmol). The reaction mixture is heated to 40° C. At this temperature are added tris(dibenzylideneacetone)dipalladium(0) (0.009 g, 0.01 mmol) and 2,2'-bis(diphenylphosphino)-1,1'-binaphthyl (0.019 g, 0.030 mmol) and stirred at 110° C. for 16 h. After completion of the reaction (monitored by TLC), the mixture is diluted with water (20 ml) and extracted with ethyl acetate (3×20 ml). The organic layer is washed with water (20 ml), brine (20 ml), dried over anhydrous sodium sulfate and evaporated to get the crude product, which is purified by column chromatography (silica gel, 20% acetone/hexane) to yield N-[(4-chlorophenyl)-methyl]-2-methoxy-6-methyl-4-morpholin-4-yl-benzamide (example 10) (0.11 g, 0.29 mmol, 29%). [M+H]$^+$ 375.2.

Synthesis of Example 11

N-[(4-Chlorophenyl)-methyl]-2-ethoxy-6-methyl-4-morpholin-4-yl-benzamide

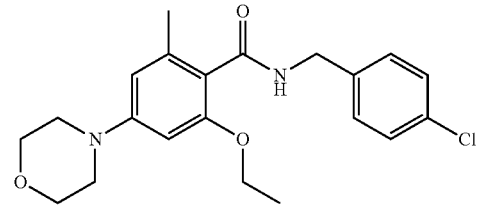 [SMILES: CCOc1cc(N2CCOCC2)cc(C)c1C(=O)NCc1ccc(Cl)cc1]

a) Synthesis of N-[(4-chlorophenyl)-methyl]-2-hydroxy-6-methyl-4-morpholin-4-yl-benzamide To a solution of N-[(4-chlorophenyl)-methyl]-2-methoxy-6-methyl-4-morpholin-4-yl-benzamide (synthesized according to the methods described in sections a) to f) of example 10) (0.25 g, 0.67 mmol) in dichloromethane (10 ml) is added neat boron tribromide (0.095 ml, 1.0 mmol) at −78° C. The temperature is slowly raised to RT over a period of 30 min and stirred for 1 h at RT. The reaction mixture is poured onto cold water and extracted with dichloromethane (3×30 ml). The combined organic layers are washed with brine (30 ml), dried over sodium sulfate and evaporated to dryness. The crude material is purified by column chromatography (silica gel, 40% ethyl acetate/hexane) affording N-[(4-chlorophenyl)-methyl]-2-hydroxy-6-methyl-4-morpholin-4-yl-benzamide (0.11 g, 0.30 mmol, 45%).

b) Synthesis of N-[(4-chlorophenyl)-methyl]-2-ethoxy-6-methyl-4-morpholin-4-yl-benzamide To a solution of N-[(4-chlorophenyl)-methyl]-2-hydroxy-6-methyl-4-morpholin-4-yl-benzamide (0.2 g, 0.56 mmol) in acetone (5 ml) are added potassium carbonate (0.092 g, 0.66 mmol) and ethyl iodide (0.066 ml, 0.83 mmol). The reaction mixture is stirred at 50° C. for 1 h. Additional ethyl iodide (0.22 ml, 2.77 mmol) is added and heating is continued for another 2 h. Additional ethyl iodide (0.22 ml, 2.77 mmol) is then added and the reaction mixture is stirred for 15 h. After completion of reaction, the solution is filtered through a pad of celite and concentrated to obtain the crude product, which is purified by column chromatography (silica gel, 15% ethyl acetate/hexan) yielding N-[(4-chlorophenyl)-methyl]-2-ethoxy-6-methyl-4-morpholin-4-yl-benzamide (example 11) (0.12 g, 0.3 mmol, 56%). [M+H]$^+$ 389.2.

Synthesis of Example 12

N-[(4-Chlorophenyl)-methyl]-2-ethyl-6-methyl-4-morpholin-4-yl-benzamide

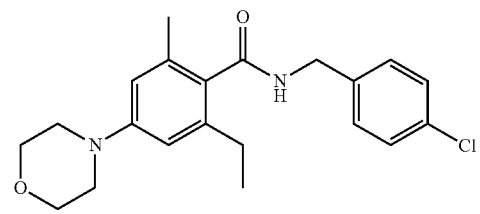 [SMILES: CCc1cc(N2CCOCC2)cc(C)c1C(=O)NCc1ccc(Cl)cc1]

a) Synthesis of trifluoro-methanesulfonic acid [2-[(4-chlorophenyl)-methyl-carbamoyl]-3-methyl-5-morpholin-4-yl-phenyl]ester To a solution of N-[(4-chlorophenyl)-methyl]-2-hydroxy-6-methyl-4-morpholin-4-yl-benzamide (synthesized according to the method described in section a) of example 11) (0.90 g, 2.5 mmol) in dichloromethane-acetonitrile (1:1) (30 ml) are added caesium carbonate (1.22 g, 3.75 mmol) and N-phenyl bis(rifluoromethane sulfonamide) (1.34 g, 3.75 mmol). The mixture is stirred at RT for 16 h. After completion of the reaction, the mixture is diluted with dichloromethane (30 ml), washed with saturated ammonium chloride solution (20 ml), water (20 ml) and brine (20 ml). The organic layer is dried over sodium sulfate and concentrated to get the crude product, which is purified by column chromatography (silica gel, 30% ethyl acetate/hexane) affording trifluoro-methanesulfonic acid [2-[(4-chlorophenyl)-methyl-carbamoyl]-3-methyl-5-morpholin-4-yl-phenyl]ester (0.9 g, 1.83 mmol, 73%).

b) Synthesis of N-[(4-chlorophenyl)-methyl]-2-methyl-4-morpholin-4-yl-6-vinyl-benzamide To a solution of trifluoro-methanesulfonic acid [2-[(4-chlorophenyl)-methyl-carbamoyl]-3-methyl-5-morpholin-4-yl-phenyl]ester (0.20 g, 0.4 mmol) in dioxane (10 ml) are added 2,6-di-tert-butyl-4-methylphenol (few crystals), lithium chloride (0.052 g, 1.22 mmol) and tributylvinyl tin (0.13 ml, 0.45 mmol). The mixture is degassed and flushed with argon for 30 min followed by the addition of tetrakis(triphenylphosphin)palladium(0) (0.01 g, 0.008 mmol). The resulting mixture is heated at 110° C. for 16 h. The reaction mixture is concentrated, diluted with water (10 ml) and extracted with ethyl acetate (3×30 ml). The organic layer is washed with water (20 ml), saturated potassium fluoride solution (2×20 ml), brine (20 ml) and dried over anhydrous sodium sulfate. Evaporation under vacuum afforded the crude product, which is purified by column chromatography (silica gel-10% KF, 30% ethyl acetate/hexane) to yield N-[(4-chlorophenyl)-methyl]-2-methyl-4-morpholin-4-yl-6-vinyl-benzamide (0.12 g, 0.32 mmol, 79%).

c) Synthesis of N-[(4-chlorophenyl)-methyl]-2-ethyl-6-methyl-4-morpholin-4-yl-benzamide A solution of N-[(4-chlorophenyl)-methyl]-2-methyl-4-morpholin-4-yl-6-vinyl-benzamide (0.18 g, 0.48 mmol) in ethyl acetate is degassed and flushed with argon for 10 min followed by the addition of Pearlman's catalyst (20% Pd(OH)$_2$/C, 0.08 g). The resulting mixture is stirred under an atmosphere of hydrogen for 2 h. After completion of reaction (monitored by NMR), the reaction mixture is filtered through a pad of celite. The filtrate is concentrated and the residue is purified by preparative HPLC affording N-[(4-chlorophenyl)-methyl]-2-ethyl-6-methyl-4-morpholin-4-yl-benzamide (example 12) (0.105 g, 0.28 mmol, 59%). [M+H]$^+$ 373.2.

Synthesis of Example 13
N-[(4-Chlorophenyl)-methyl]-2-methyl-4-morpholin-4-yl-6-propyl-benzamide

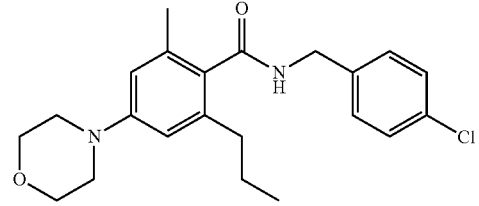 [SMILES: CCCc1cc(N2CCOCC2)cc(C)c1C(=O)NCc1ccc(Cl)cc1]

a) Synthesis of 2-allyl-N-[(4-chlorophenyl)-methyl]-6-methyl-4-morpholin-4-yl-benzamide A solution of trifluoro-methanesulfonic acid [2-[(4-chlorophenyl)-methyl-carbamoyl]-3-methyl-5-morpholin-4-yl-phenyl]ester (synthesized according to the method described in section a) of example 12) (0.35 g, 0.71 mmol), lithium chloride (0.09 g, 2.13 mmol) and allyl tributyl tin (0.44 ml, 1.43 mmol) in dimethylformamide (3 ml) is degassed and flushed with argon for 30 min. Tetrakis(triphenylphosphin)palladium(0) (0.016 g, 0.014 mmol) is added and the mixture is heated at 110° C. for 16 h. The reaction mixture is diluted with ice water (10 ml) and extracted with ethyl acetate (3×30 ml). The organic layer is washed with water (20 ml), brine (20 ml), and dried over anhydrous sodium sulfate. Evaporation under vacuum afforded the crude product, which is purified by column chromatography (silica gel-10% KF, 10% ethyl acetate/hexane) affording 2-allyl-N-[(4-chlorophenyl)-methyl]-6-methyl-4-morpholin-4-yl-benzamide (0.25 g, 0.65 mmol, 91%).

b) Synthesis of N-[(4-chlorophenyl)-methyl]-2-methyl-4-morpholin-4-yl-6-propyl-benzamide A mixture of 2-allyl-N-[(4-chlorophenyl)-methyl]-6-methyl-4-morpholin-4-yl-benzamide (0.25 g, 0.65 mmol) and Platinum(IV) oxide (Adams' catalyst (PtO$_2$), 0.014 g) in ethyl acetate (10 ml) is stirred under an atmosphere of hydrogen for 2 h at RT. The reaction mixture is filtered through a pad of celite and the filtrate is evaporated to get the crude product, which is purified by column chromatography (silica gel, 10% acetone/hexane) affording N-[(4-chlorophenyl)-methyl]-2-methyl-4-morpholin-4-yl-6-propyl-benzamide (example 13) (0.165 g, 0.43 mmol, 66%). [M+H]$^+$ 387.2.

Synthesis of Example 14
N-[(4-Chlorophenyl)-methyl]-2-isopropyl-6-methyl-4-morpholin-4-yl-benzamide

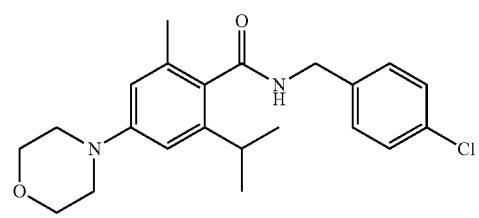

a) Synthesis of N-[(4-chlorophenyl)-methyl]-2-isopropenyl-6-methyl-4-morpholin-4-yl-benzamide To a solution of trifluoro-methanesulfonic acid [2-[(4-chlorophenyl)-methyl-carbamoyl]-3-methyl-5-morpholin- 4-yl-phenyl]ester (synthesized according to the method described in section a) of example 12) (0.30 g, 0.61 mmol) in N-methyl-2-pyrrolidone (3 ml) are added lithium chloride (0.078 g, 1.83 mmol) and triphenylarsine (0.015 g, 0.05 mmol). The reaction mixture is degassed and flushed with argon for 30 min before the addition of copper(I) iodide (0.006 g, 0.03 mmol) and tris(dibenzylideneacetone)dipalladium(0) (0.011 g, 0.012 mmol). The mixture is stirred for 10 min followed by the addition of tributyl-isopropenyl stannane (0.32 g, 1.04 mmol). The reaction mixture is heated at 120° C. for 4 h. After completion of the reaction, the reaction mixture is poured onto water, extracted with ethyl acetate (3×30 ml). The combined organic layers are washed with saturated potassium fluoride solution (2×20 ml), brine (20 ml), dried over sodium sulfate and concentrated to get the crude product, which is purified by column chromatography (silica gel-10% KF, 30% ethyl acetate/hexane) affording N-[(4-chlorophenyl)-methyl]-2-isopropenyl-6-methyl-4-morpholin-4-yl-benzamide (0.19 g, 0.49 mmol, 81%).

b) Synthesis of N-[(4-chlorophenyl)-methyl]-2-isopropyl-6-methyl-4-morpholin-4-yl-benzamide A solution of N-[(4-chlorophenyl)-methyl]-2-isopropenyl-6-methyl-4-morpholin-4-yl-benzamide (0.19 g, 0.49 mmol) in ethyl acetate is degassed and flushed with argon for 10 min followed by the addition of Pearlman's catalyst (20% Pd(OH)$_2$/C, 0.08 g). The resulting mixture is stirred under an atmosphere of hydrogen for 2 h. After completion of reaction (monitored by NMR), the reaction mixture is filtered through a pad of celite. The filtrate is concentrated and the residue is purified by preparative HPLC affording N-[(4-chlorophenyl)-methyl]-2-isopropyl-6-methyl-4-morpholin-4-yl-benzamide (example 14) (0.075 g, 0.28 mmol, 57%). [M+H]$^+$ 387.2.

Synthesis of Example 15

N-[(4-Chlorophenyl)-methyl]-2-cyclopropyl-6-methyl-4-morpholin-4-yl-benzamide

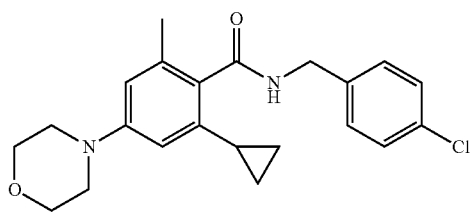 [SMILES: Cc1cc(N2CCOCC2)cc(C2CC2)c1C(=O)NCc1ccc(Cl)cc1]

A mixture of trifluoro-methanesulfonic acid [2-[(4-chlorophenyl)-methyl-carbamoyl]-3-methyl-5-morpholin-4-yl-phenyl]ester (synthesized according to the method described in section a) of example 12) (0.20 g, 0.41 mmol), potassium fluoride (0.10 g, 1.71 mmol), potassium bromide (0.06 g, 0.49 mmol) and cyclopropylboronic acid (0.07 g, 0.81 mmol) in dry toluene (4 ml) is degassed and flushed with argon for 20 min. To the reaction mixture is added tetrakis(triphenylphosphin)palladium(0) (0.047 g, 0.046 mmol) and subjected to microwave irradiation at 100° C. for 1 h. The reaction mixture is poured onto ice and extracted with ethyl acetate (3×30 ml). The combined organic layers are washed with water (20 ml), brine (20 ml) and dried over sodium sulfate. The solvent is evaporated to get the crude product. The reaction is repeated once and the combined fractions are purified by column chromatography (silica gel, 20% ethyl acetate/hexane) followed by preparative HPLC to afford N-[(4-chlorophenyl)-methyl]-2-cyclopropyl-6-methyl-4-morpholin-4-yl-benzamide (example 15) (0.085 g, 0.22 mmol, 27%). [M+H]$^+$ 385.2.

Synthesis of Example 16

N-[(4-Chlorophenyl)-methyl]-2-cyclopentyl-6-methyl-4-morpholin-4-yl-benzamide

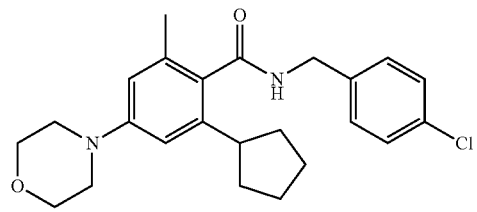 [SMILES: Cc1cc(N2CCOCC2)cc(C2CCCC2)c1C(=O)NCc1ccc(Cl)cc1]

a) Synthesis of tributyl-1-cyclopenten-1-yl-stannane

To a solution of diisopropylamine (2.97 ml, 21.2 mmol) in dry tetrahydrofuran (140 ml) is added n-butyllithium (1.4 M in hexane) (15.3 ml, 21.4 mmol) drop wise at 0° C. and the resulting mixture stirred for 30 min. To the reaction mixture is then added tributylstannane (6.2 ml, 23.1 mmol) and stirring is continued for 30 min at 0° C. before cooling to −78° C. Cyclopentanone (2.1 ml, 23.8 mmol) in tetrahydrofuran (10 ml) is added and stirring is continued for 1 h at −78° C. Methanesulfonyl chloride (7.4 ml, 96.0 mmol) and triethylamine (24.9 ml, 179 mmol) are added successively to the reaction mixture at −78° C. The temperature of the reaction mixture is slowly raised to room temperature over a period of 1 h. Hexane (300 ml) is added and partitioned with acetonitrile (100 ml). The combined hexane layers are washed with acetonitrile (2×100 ml) and evaporated to get the crude product. Column chromatography (silica gel, hexane) afforded tributyl-1-cyclopenten-1-yl-stannane (6.1 g, 17.1 mmol, 72%).

b) Synthesis of N-[(4-chlorophenyl)-methyl]-2-cyclopenten-1-yl-6-methyl-4-morpholin-4-yl-benzamide To a mixture of trifluoro-methanesulfonic acid [2-[(4-chlorophenyl)-methyl-carbamoyl]-3-methyl-5-morpholin-4-yl-phenyl]ester (synthesized according to the method described in section a) of example 12) (1.0 g, 2.03 mmol) in dioxane (50 ml) are added 2,6-di-tert-butyl-4-methylphenol (0.044 g, 0.20 mmol), lithium chloride (0.688 g, 16.3 mmol) and tributyl-1-cyclopenten-1-yl-stannane (1.46 g, 4.06 mmol). The mixture is degassed and flushed with argon for 30 min followed by the addition bis(triphenylphosphine)palladium-chloride (0.17 g, 0.24 mmol). The resulting mixture is heated at 120° C. for 16 h. The reaction mixture is diluted with water (30 ml) and extracted with ethyl acetate (3×50 ml). The organic layer is washed with water (20 ml), saturated potassium fluoride solution (2×20 ml), brine (20 ml) and dried over anhydrous sodium sulfate. Evaporation under vacuum afforded the crude product, which is purified by column chromatography (silica gel-10% KF, 20% ethyl acetate/hexane) to yield N-[(4-chlorophenyl)-methyl]-2-cyclopenten-1-yl-6-methyl-4-morpholin-4-yl-benzamide (0.50 g, 1.22 mmol, 60%).

c) Synthesis of N-[(4-chlorophenyl)-methyl]-2-cyclopentyl-6-methyl-4-morpholin-4-yl-benzamide A mixture of N-[(4-chlorophenyl)-methyl]-2-cyclopenten-1-yl-6-methyl-4-morpholin-4-yl-benzamide (0.50 g, 1.22 mmol) and Platinum(IV) oxide (Adams' catalyst (PtO$_2$), 0.027 g, 0.12 mmol) in toluene (30 ml) is stirred under an atmosphere of hydrogen for 16 h at RT. The reaction mixture is filtered through a pad of celite and the filtrate is evaporated to get the crude product, which is purified by column chromatography (silica gel, 25% ethyl acetate/hexane) followed by preparative HPLC affording N-[(4-chlorophenyl)-methyl]-2-cyclopentyl-6-methyl-4-morpholin-4-yl-benzamide (example 16) (0.20 g, 0.49 mmol, 40%). [M+H]$^+$ 413.2.

Synthesis of Example 17

N-[(4-Fluorophenyl)methyl]-2-isopropyl-6-methyl-4-morpholin-4-yl-benzamide

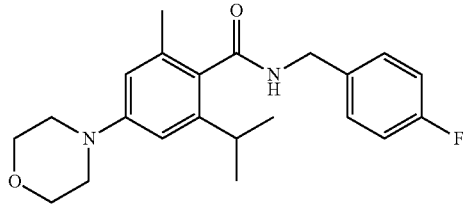 [SMILES: Cc1cc(N2CCOCC2)cc(C(C)C)c1C(=O)NCc1ccc(F)cc1]

a) Synthesis of 4-bromo-N-[(4-fluorophenyl)-methyl]-2-methoxy-6-methyl-benzamide To a stirred solution of 4-bromo-2-methoxy-6-methyl-benzoic acid (synthesized according to the methods described in sections a) to d) of example 10) (2.0 g, 8.16 mmol) in dichloromethane (50 ml) are added oxalyl chloride (0.84 ml, 9.79 mmol) and dimethylformamide (catalytic amount) at 0° C. The reaction mixture is stirred for 30 min at RT. Excess oxalyl chloride is distilled off under nitrogen. The residue is dissolved in dichloromethane (20 ml), cooled to 0° C. followed by the addition of triethylamine (2.8 ml, 20.4 mmol) and 4-fluorobenzylamine (1.12 ml, 9.79 mmol). The reaction mixture is stirred for 1 h at RT. After completion of the reaction (monitored by TLC) the mixture is diluted with water (50 ml) and extracted with dichloromethane (3×50 ml). The organic layer is washed with water (50 ml), brine (50 ml), dried over anhydrous sodium sulfate and evaporated to get the crude product, which is purified by column chromatography (silica gel, 15% ethyl acetate/hexane) to yield 4-bromo-N-[(4-fluorophenyl)-methyl]-2-methoxy-6-methyl-benzamide (2.70 g, 7.67 mmol, 94%).

b) Synthesis of N-[(4-fluorophenyl)-methyl]-2-methoxy-6-methyl-4-morpholin-4-yl-benzamide To a stirred solution of 4-bromo-N-[(4-fluorophenyl)-methyl]-2-methoxy-6-methyl-benzamide (2.7 g, 7.67 mmol) in N-methyl-2-pyrrolidone (10 ml) is added morpholine (0.93 g, 10.7 mmol) at RT. The reaction mixture is degassed and flushed with argon for 30 min followed by addition of sodium tert-butoxide (0.95 g, 9.9 mmol). The reaction mixture is heated to 40° C. At this temperature are added tris(dibenzylideneacetone)dipalladium(0) (0.31 g, 0.34 mmol) and 2,2'-bis(diphenylphosphino)-1,1'-binaphthyl (0.47 g, 0.76 mmol) and stirred at 100° C. for 12 h. After completion of the reaction (monitored by TLC), the mixture is diluted with water (50 ml) and extracted with ethyl acetate (3×75 ml). The organic layer is washed with water (50 ml), brine (50 ml), dried over anhydrous sodium sulfate and evaporated to get the crude product, which is purified by column chromatography (silica gel, 40% acetone/hexane) to yield N-[(4-fluorophenyl)-methyl]-2-methoxy-6-methyl-4-morpholin-4-yl-benzamide (2.50 g, 6.90 mmol, 91%).

c) Synthesis of N-[(4-fluorophenyl)-methyl]-2-hydroxy-6-methyl-4-morpholin-4-yl-benzamide To a solution of N-[(4-fluorophenyl)-methyl]-2-methoxy-6-methyl-4-morpholin-4-yl-benzamide (2.50 g, 6.98 mmol) in dichloromethane (70 ml) is added neat boron tribromide (0.99 ml, 10.3 mmol) at −78° C. The temperature is slowly raised to RT over a period of 30 min and stirred for 1 h at RT. The reaction mixture is poured onto cold water and extracted with dichloromethane (3×50 ml). The combined organic layers are washed with brine (30 ml), dried over sodium sulfate and evaporated to dryness. The crude material is purified by column chromatography (silica gel, 25% ethyl acetate/hexane) affording N-[(4-fluorophenyl)-methyl]-2-hydroxy-6-methyl-4-morpholin-4-yl-benzamide (0.90 g, 2.58 mmol, 37%).

d) Synthesis of trifluoro-methanesulfonic acid [2-[(4-fluorophenyl)-methyl-carbamoyl]-3-methyl-5-morpholin-4-yl-phenyl]ester To a solution of N-[(4-fluorophenyl)-methyl]-2-hydroxy-6-methyl-4-morpholin-4-yl-benzamide (0.90 g, 2.60 mmol) in dichloromethane-acetonitrile (1:1) (30 ml) are added caesium carbonate (1.30 g, 3.90 mmol) and N-phenyl bis(rifluoromethane sulfonamide) (1.40 g, 3.90 mmol). The mixture is stirred at RT for 16 h. After completion of the reaction, the mixture is diluted with dichloromethane (30 ml), washed with saturated ammonium chloride solution (20 ml), water (20 ml) and brine (20 ml). The organic layer is dried over sodium sulfate and concentrated to get the crude product, which is purified by column chromatography (silica gel, 30% ethyl acetate/hexane) affording trifluoro-methanesulfonic acid [2-[(4-fluorophenyl)-methyl-carbamoyl]-3-methyl-5-morpholin-4-yl-phenyl]ester (0.9 g, 1.89 mmol, 75%).

e) Synthesis of N-[(4-fluorophenyl)-methyl]-2-isopropenyl-6-methyl-4-morpholin-4-yl-benzamide To a solution of trifluoro-methanesulfonic acid [2-[(4-fluorophenyl)-methyl-carbamoyl]-3-methyl-5-morpholin-4-yl-phenyl]ester (0.60 g, 1.26 mmol) in N-methyl-2-pyrrolidone (5 ml) are added lithium chloride (0.67 g, 1.89 mmol) and triphenylarsine (0.03 g, 0.10 mmol). The reaction mixture is degassed and flushed with argon for 30 min before the addition of copper(I) iodide (0.011 g, 0.03 mmol) and tris(dibenzylideneacetone)dipalladium(0) (0.026 g, 0.02 mmol). The mixture is stirred for 10 min followed by the addition of tributyl-isopropenyl stannane (0.67 g, 1.89 mmol). The reaction mixture is heated at 120° C. for 14 h. After completion of the reaction, the reaction mixture is poured onto saturated potassium fluoride solution and extracted with ethyl acetate (3×75 ml). The combined organic layers are washed with water (50 ml), brine (50 ml), dried over sodium sulfate and concentrated to get the crude product, which is purified by column chromatography (silica gel, 35% ethyl acetate/hexane) affording N-[(4-fluorophenyl)-methyl]-2-isopropenyl-6-methyl-4-morpholin-4-yl-benzamide (0.23 g, 0.63 mmol, 50%).

f) Synthesis of N-[(4-fluorophenyl)-methyl]-2-isopropyl-6-methyl-4-morpholin-4-yl-benzamide To a stirred solution of N-[(4-fluorophenyl)-methyl]-2-isopropenyl-6-methyl-4-morpholin-4-yl-benzamide (0.23 g, 0.63 mmol) in ethanol (10 ml) is added 10% palladium on carbon (0.06 g). The reaction mixture is stirred under an atmosphere of hydrogen at RT for 2 h. After completion of reaction (monitored by TLC), the reaction mixture is filtered through a pad of celite, washed with ethanol and concentrated to get the crude product, which is purified by column chromatography (silica gel, 25% ethyl acetate/hexane) to afford N-[(4-fluorophenyl)-methyl]-2-isopropyl-6-methyl-4-morpholin-4-yl-benzamide (example 17) (0.16 g, 0.43 mmol, 69%). [M+H]$^+$ 371.2.

Synthesis of Example 18

2-Cyclopropyl-N-[(4-fluorophenyl)-methyl]-6-methyl-4-morpholin-4-yl-benzamide

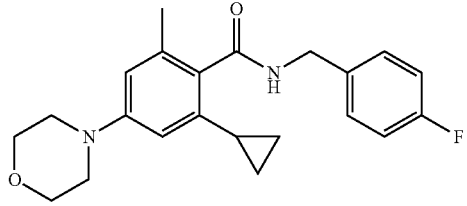 [SMILES: Cc1cc(N2CCOCC2)cc(C2CC2)c1C(=O)NCc1ccc(F)cc1]

A solution of trifluoro-methanesulfonic acid [2-[(4-fluorophenyl)-methyl-carbamoyl]-3-methyl-5-morpholin-4-yl-phenyl]ester (synthesized according to the methods described in sections a) to d) of example 17) (0.16 g, 0.34 mmol), potassium fluoride (0.08 g, 1.41 mmol), potassium bromide (0.05 g, 0.40 mmol) and cyclopropylboronic acid (0.06 g, 0.67 mmol) in dry toluene (3 ml) is degassed and flushed with argon for 20 min. To the reaction mixture is added tetrakis(triphenylphosphin)palladium(0) (0.039 g, 0.033 mmol) and subjected to microwave irradiation at 120° C. for 1 h. The reaction mixture is poured onto ice and extracted with ethyl acetate (3×30 ml). The combined organic layers are washed with water (20 ml), brine (20 ml) and dried over sodium sulfate. The solvent is evaporated to get the crude product. The reaction is repeated once and the combined fractions are purified by column chromatography (silica gel, 20% ethyl acetate/hexane) followed by preparative HPLC to afford N-[(4-fluorophenyl)-methyl]-2-cyclopropyl-6-methyl-4-morpholin-4-yl-benzamide (example 18) (0.12 g, 0.32 mmol, 28%). [M+H]$^+$ 369.2.

Synthesis of Example 19

N-[(4-Chlorophenyl)-methyl]-2-methyl-4-morpholin-4-yl-6-(trifluoromethyl)-benzamide

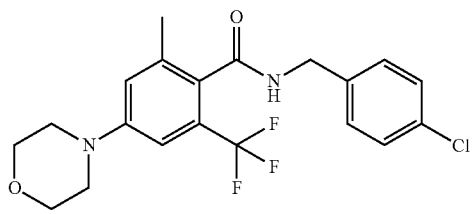 [SMILES: Cc1cc(N2CCOCC2)cc(C(F)(F)F)c1C(=O)NCc1ccc(Cl)cc1]

a) Synthesis of 2-methyl-4-morpholin-4-yl-6-(trifluoromethyl)-benzoic acid ethyl ester A mixture of 4-morpholin-4-yl-pent-3-en-2-one (2.50 g, 14.8 mmol) and ethyl 4,4,4-trifluoro-3-oxobutanoate (3.0 g, 16.3 mmol) in acetic acid (40 ml) is heated at 120° C. for 3 h. After completion of the reaction (monitored by TLC), the solvent is distilled off, the residue is taken up in water (20 ml) and the pH of the mixture was adjusted to pH=8 with 25% aqueous ammonia. The aqueous layer is extracted with ethyl acetate (2×20 ml) and the combined organic layers are dried over sodium sulfate, evaporated and the crude product is purified by column chromatography (silica gel, 10% ethyl acetate/cyclohexane) to afford 2-methyl-4-morpholin-4-yl-6-(trifluoromethyl)-benzoic acid ethyl ester (1.55 g, 4.89 mmol, 33%).

a) Synthesis of N-[(4-chlorophenyl)-methyl]-2-methyl-4-morpholin-4-yl-6-(trifluoromethyl)-benzamide A mixture of 2-methyl-4-morpholin-4-yl-6-(trifluoromethyl)-benzoic acid ethyl ester (0.27 g, 0.85 mmol), 4-chlorobenzylamine (1.21 g, 8.51 mmol) and trimethylaluminium (2M in toluene) (2.98 ml, 5.96 mmol) in toluene (9 ml) is heated at 110° C. for 4 d. After completion of the reaction (monitored by TLC), a 2M aqueous solution of sodium hydroxide is carefully added and the mixture is extracted with ethyl acetate (2×15 ml). The combined organic layers are washed with 2M aqueous solution of sodium hydroxide (10 ml), brine (10 ml) and dried over sodium sulfate. The solvent is evaporated to get the crude product, which is purified by column chromatography (silica gel, 30% ethyl acetate/cyclohexane) to afford N-[(4-chlorophenyl)-methyl]-2-methyl-4-morpholin-4-yl-6-(trifluoromethyl)-benzamide (example 19) (0.28 g, 0.68 mmol, 80%). [M+H]$^+$ 413.1.

Synthesis of Example 20

N-[(4-Chlorophenyl)-methyl]-2-(difluoro-methyl)-6-methyl-4-morpholin-4-yl-benzamide

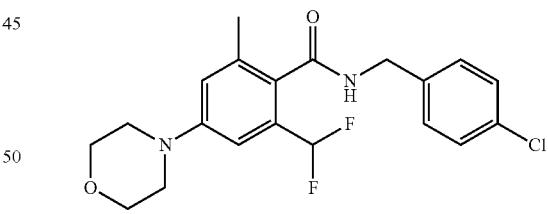

a) Synthesis of 2-(difluoro-methyl)-6-methyl-4-morpholin-4-yl-benzoic acid ethyl ester A mixture of 4-morpholin-4-yl-pent-3-en-2-one (1.50 g, 8.87 mmol) and ethyl ethyl 4,4-difluoro-3-oxobutanoate (1.62 g, 9.75 mmol) in acetic acid (25 ml) is heated at 120° C. for 3 h. After completion of the reaction (monitored by TLC), the solvent is distilled off, the residue is taken up in water (20 ml) and the pH of the mixture was adjusted to pH=8 with 25% aqueous ammonia. The aqueous layer is extracted with ethyl acetate (2×20 ml) and the combined organic layers are dried over sodium sulfate, evaporated and the crude product is purified by column chromatography (silica gel, 30% ethyl acetate/cyclohexane) to afford 2-(difluoro-methyl)-6-methyl-4-morpholin-4-yl-benzoic acid ethyl ester (0.55 g, 1.84 mmol, 21%).

b) Synthesis of N-[(4-chlorophenyl)-methyl]-2-(difluoro-methyl)-6-methyl-4-morpholin-4-yl-benzamide A mixture of 2-(difluoro-methyl)-6-methyl-4-morpholin-4-yl-benzoic acid ethyl ester (0.30 g, 1.00 mmol), 4-chlorobenzylamine (1.42 g, 10.0 mmol) and trimethylaluminium (2M in toluene) (3.50 ml, 7.00 mmol) in toluene (10 ml) is heated at 110° C. for 18 h. After completion of the reaction (monitored by TLC), a 2M aqueous solution of sodium hydroxide is carefully added and the mixture is extracted with ethyl acetate (2×15 ml). The combined organic layers are washed with 2M aqueous solution of sodium hydroxide (10 ml), brine (10 ml) and dried over sodium sulfate. The solvent is evaporated to get the crude product, which is purified by column chromatography (silica gel, 30% ethyl acetate/cyclohexane) to afford N-[(4-chlorophenyl)-methyl]-2-(difluoro-methyl)-6-methyl-4-morpholin-4-yl-benzamide (example 20) (0.05 g, 0.13 mmol, 13%). [M+H]$^+$ 395.1.

Synthesis of Example 28

2-Cyclopropyl-N-[(3R)-3-hydroxy-4,4-dimethyl-pentyl]-6-methyl-4-morpholin-4-yl-benzamide

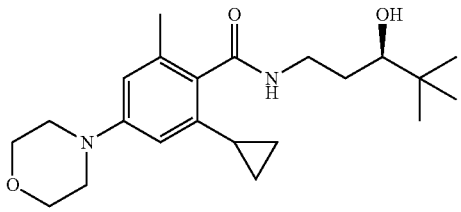 [SMILES: Cc1cc(N2CCOCC2)cc(C2CC2)c1C(=O)NCC[C@@H](O)C(C)(C)C]

a) Synthesis of 4-bromo-2-methoxy-6-methyl-benzoic acid ethyl ester

To a stirred solution of 4-bromo-2-methoxy-6-methyl-benzoic acid (synthesized according to the methods described in sections a) to d) of example 10) (10.7 g, 43.7 mmol) in DMF (90 ml) are added potassium carbonate (12.1 g, 87.3 mmol) and ethyl iodide (17.5 ml, 218 mmol) and the resulting mixture is stirred at room temperature for 2 h. After completion of reaction the reaction mixture is diluted with water (200 ml) and extracted with ethyl acetate (3×50 ml). The combined organic layers are washed with water (2×30 ml), brine (2×30 ml), dried over sodium sulfate and concentrated in vacuo yielding 4-bromo-2-methoxy-6-methyl-benzoic acid ethyl ester (10.5 g, 39 mmol, 89%).

b) Synthesis of 2-methoxy-6-methyl-4-morpholin-4-yl-benzoic acid ethyl ester

To a stirred solution of 4-bromo-2-methoxy-6-methyl-benzoic acid ethyl ester (7.3 g, 26.7 mmol) in toluene (190 ml) are added morpholine (0.14 ml, 1.6 mmol) and caesium carbonate (11.9 g, 36.4 mmol) and the mixture is degassed and flushed with argon for 30 min followed by the addition of tris(dibenzylideneacetone)-dipalladium(0) (1.10 g, 1.2 mmol) and 2'-bis(diphenylphosphino)-1,1'-binaphthyl (1.65 g, 2.67 mmol). The resulting mixture is stirred at 120° C. for 16 h. After completion of reaction (monitored by TLC) the mixture is diluted with water (50 ml) and extracted with ethyl acetate (3×70 ml). The organic layer is washed water (50 ml), brine (50 ml), dried over anhydrous sodium sulfate and evaporated to get the crude product, which is purified by column chromatography (silica gel, 20% ethyl acetate/hexane) to yield compound 2-methoxy-6-methyl-4-morpholin-4-yl-benzoic acid ethyl ester (4.5 g, 16.1 mmol, 60%).

c) Synthesis of 2-hydroxy-6-methyl-4-morpholin-4-yl-benzoic acid ethyl ester

To a solution of 2-methoxy-6-methyl-4-morpholin-4-yl-benzoic acid ethyl ester (7.0 g, 25.1 mmol) in dichloromethane (370 ml) is added neat boron tribromide (5.94 ml, 62.7 mmol) at −78° C. The temperature is slowly raised to room temperature over a period of 30 min and stirred for 1 h at room temperature. The reaction mixture is poured onto cold water, extracted with dichloromethane (3×30 ml). Combined organic layers are washed with brine (30 ml), dried over sodium sulfate and evaporated to dryness. The crude material is used in the next step without further purification.

d) Synthesis of 2-methyl-4-morpholin-4-yl-6-(trifluoromethylsulfonyl)oxy-benzoic acid ethyl ester To a solution of compound 2-hydroxy-6-methyl-4-morpholin-4-yl-benzoic acid ethyl ester (6.7 g, 25.3 mmol) in dichloromethane/acetonitrile (1:1) (190 ml) are added caesium carbonate (12.4 g, 37.9 mmol) and N-phenyl bis(trifluoromethane sulfonamide) (13.5 g, 37.9 mmol). The mixture is stirred at room temperature for 2 h. After completion of reaction, the mixture is diluted with dichloromethane (30 ml), washed with water (50 ml) and brine (50 ml). The organic layer is dried over sodium sulfate and concentrated in vacuo to get the crude product, which is purified column chromatography (silica gel, 3% acetone/hexane) affording compound 2-methyl-4-morpholin-4-yl-6-(trifluoromethylsulfonyl)oxy-benzoic acid ethyl ester (7.0 g, 17.6 mmol, 70%).

e) Synthesis of 2-cyclopropyl-6-methyl-4-morpholin-4-yl-benzoic acid ethyl ester A solution of 2-methyl-4-morpholin-4-yl-6-(trifluoromethylsulfonyl)oxy-benzoic acid ethyl ester (0.7 g, 1.76 mmol), potassium fluoride (0.43 g, 7.41 mmol), potassium bromide (0.25 g, 2.12 mmol) and cyclopropylboronic acid (0.30 g, 3.53 mmol) in dry toluene (16 ml) is degassed and flushed with argon for 20 min. To the reaction mixture is added tetrakis(triphenylphosphin)palladium(0) (0.20 g, 0.18 mmol) and subjected to microwave irradiation at 120° C. for 1 h. The reaction mixture is poured onto ice and extracted with ethyl acetate (3×30 ml). The combined organic layers are washed with water (20 ml), brine (20 ml) and dried over sodium sulfate. The solvent is evaporated to get the crude product, which is purified by column chromatography (silica gel, 8% acetone/hexane) to afford 2-cyclopropyl-6-methyl-4-morpholin-4-yl-benzoic acid ethyl ester (0.46 g, 1.59 mmol, 85%).

f) Synthesis of 2-cyclopropyl-6-methyl-4-morpholin-4-yl-benzoic acid

To a stirred solution of 2-cyclopropyl-6-methyl-4-morpholin-4-yl-benzoic acid ethyl ester (0.54 g, 1.86 mmol) in ethylene glycol (10 ml) is added solid potassium hydroxide (0.42 g, 7.47 mmol) and the mixture is stirred at 150-160° C. for 16 h. After completion of the reaction, the mixture is diluted with water (30 ml) and extracted with ethyl acetate (2×10 ml). The aqueous layer is acidified with 2M HCl to pH 3 and extracted with ethyl acetate (3×30 ml). The combined organic layers are washed with water (3×40 ml), dried over sodium sulfate and concentrated in vacuo yielding 2-cyclopropyl-6-methyl-4-morpholin-4-yl-benzoic acid (0.34 g, 1.3 mmol, 70%).

g) Synthesis of (2S)-3,3-dimethyl-butane-1,2-diol

To a suspension of lithium aluminiumhydride (2.28 g, 60.5 mmol) in tetrahydrofuran (50 ml) is slowly added a solution of (2S)-2-Hydroxy-3,3-dimethyl-butyric acid (4.0 g, 30.2 mmol) in tetrahydrofuran (20 ml) at 0° C. After addition, the mixture allowed to warm to room temperature and stirring is continued for 2 h. After completion of the reaction, the mixture is cooled to 0° C. and a 10% aqueous solution of sodium hydroxide is added carefully. The resulting mixture is stirred at 0° C. for 30 min and the solid is filtered off. The filtrate is dried over sodium sulfate and concentrated in vacuo affording (2S)-3,3-dimethyl-butane-1,2-diol (3.1 g, 26.3 mmol, 87%).

h) Synthesis of 4-methyl-benzenesulfonic acid [(2S)-2-hydroxy-3,3-dimethyl-butyl]ester To a solution of (2S)-3,3-dimethyl-butane-1,2-diol (3.1 g, 26.3 mmol) in dichloromethane (25 ml) is added pyridine (4.3 ml, 52.6 mmol). To the mixture is then added dropwise a solution of 4-toluenesulfonyl chloride (5.0 g, 26.3 mmol) in dichloromethane (25 ml) at 0° C. The reaction mixture is warmed to room temperature and stirred for additional 16 h. The reaction mixture is diluted with dichloromethane (50 ml) and washed with 10% copper(II) sulfate solution (2×30 ml). The organic layer is dried over sodium sulfate and evaporated to get the crude product, which is purified by column chromatography (silica gel, 5% ethyl acetate/hexane) affording 4-methyl-benzenesulfonic acid [(2S)-2-hydroxy-3,3-dimethyl-butyl]ester (4.2 g, 14.4 mmol, 54%).

i) Synthesis of (3R)-3-hydroxy-4,4-dimethyl-pentanenitrile

To a stirred solution of 4-methyl-benzenesulfonic acid [(2S)-2-hydroxy-3,3-dimethyl-butyl]ester (4.2 g, 14.4 mmol) in dimethylsulfoxide (30 ml) is added sodium cyanide (3.6 g, 71.9 mmol) and the reaction mixture is heated at 60° C. for 16 h. The reaction mixture is poured onto water (100 ml) and extracted with ethyl acetate (3×30 ml). The combined organic layers are washed with water (3×50 ml), dried over sodium sulfate and evaporated to dryness affording (3R)-3-hydroxy-4,4-dimethyl-pentanenitrile, which is used in next step without further purification (1.3 g, 10.2 mmol, 71%).

j) Synthesis of N-[(3R)-3-hydroxy-4,4-dimethyl-pentyl]-carbamic acid tert-butyl ester To a stirred solution of (3R)-3-hydroxy-4,4-dimethyl-pentanenitrile (0.8 g, 6.3 mmol) in methanol (10 ml) are added nickel(II) chloride hexahydrate (0.15 g, 0.63 mmol) and di-tert-butyl dicarbonate (2.8 ml, 12.6 mmol) at 0° C. To the solution is added sodium borohydride (1.68 g, 44.1 mmol) portion wise at 0° C. and the mixture is subsequently stirred at room temperature for 3 h. The reaction mixture is concentrated in vacuo and the resulting solid is taken up in 25% aqueous ammonia. The suspension is stirred for 30 min followed by extraction with dichloromethane (3×50 ml). The combined organic layers are dried over sodium sulfate and concentrated yielding N-[(3R)-3-hydroxy-4,4-dimethyl-pentyl]-carbamic acid tert-butyl ester, which is used in next step without further purification (1.2 g, 5.19 mmol, 82%).

k) Synthesis of (3R)-1-amino-4,4-dimethyl-pentan-3-ol

To a stirred solution of N-[(3R)-3-hydroxy-4,4-dimethyl-pentyl]-carbamic acid tert-butyl ester (1.2 g, 5.19 mmol) in dioxane (5 ml) is added 4N hydrochloric acid in dioxane (12 ml) at 0° C. and the mixture is stirred for 1 h at room temperature. The reaction mixture is concentrated in vacuo and solid is triturated with pentane yielding (3R)-1-amino-4,4-dimethyl-pentan-3-ol (0.5 g, 2.98 mmol, 57%).

l) Synthesis of 2-cyclopropyl-N-[(3R)-3-hydroxy-4,4-dimethyl-pentyl]-6-methyl-4-morpholin-4-yl-benzamide To a stirred solution of 2-cyclopropyl-6-methyl-4-morpholin-4-yl-benzoic acid (synthesized according to the methods described in sections a) to f)) (0.34 g, 1.3 mmol) in dichloromethane (10 ml) are added 1-ethyl-3-(3-dimethylaminopropyl)carbodiimide (0.30 g, 1.56 mmol), hydroxybenzotriazole (0.21 g, 1.56 mmol) and diisopropylethylamine (0.65 ml, 3.9 mmol) at 0° C. and stirred for 15 min before the addition of (3R)-1-amino-4,4-dimethyl-pentan-3-ol (synthesized according to the methods described in sections g) to k)) (0.28 g, 1.69 mmol). The resulting mixture is stirred at room temperature for 16 h. Water (20 ml) is added to the mixture and extracted with dichloromethane (3×20 ml). The combined organic layers are washed with 10% sodium hydrogen carbonate solution (30 ml), brine (30 ml), dried over sodium sulfate and concentrated in vacuo. The crude product is purified by column chromatography (silica gel, 55% ethyl acetate/dichloromethane) yielding 2-cyclopropyl-N-[(3R)-3-hydroxy-4,4-dimethyl-pentyl]-6-methyl-4-morpholin-4-yl-benzamide (example 28) (0.19 g, 0.51 mmol, 39%). [M+H]+ 375.3. $[\alpha]_D^{25}$=+30.0° (c 1.0, methanol).

Synthesis of Example 38

N-[(4-Chlorophenyl)-methyl]-2-[(3R)-3-fluoro-pyrrolidin-1-yl]-6-methyl-4-morpholin-4-yl-benzamide

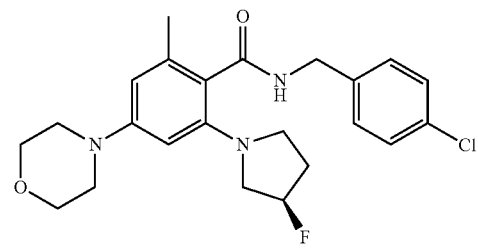 [SMILES: Cc1cc(N2CCOCC2)cc(N2CC[C@@H](F)C2)c1C(=O)NCc1ccc(Cl)cc1]

a) Synthesis of 2-methoxy-6-methyl-4-morpholin-4-yl-benzonitrile

A solution of 4-bromo-2-methoxy-6-methyl-benzonitrile (synthesized according to the methods described in sections a) and b) of example 10) (2.0 g, 8.85 mmol), morpholine (1.2 ml, 12.8 mmol) and caesium carbonate (3.9 g, 12.0 mmol) in toluene (75 ml) is degassed and flushed with argon for 30 min and the mixture is heated to 40° C. followed by the addition of tris(dibenzylideneacetone)-dipalladium(0) (0.37 g, 0.39 mmol) and 2,2'-bis(diphenylphosphino)-1,1'-binaphthyl (0.55 g, 0.88 mmol). The resulting mixture is stirred at 110° C. for 16 h. After completion of the reaction (monitored by TLC), the mixture is poured into water (60 ml) and extracted with ethyl acetate (3×50 ml).The combined organic layers are washed with water (2×50 ml), brine (2×30 ml), dried over sodium sulfate and concentrated in vacuo. The crude product is purified by flash column chromatography (silica gel, 25% ethyl acetate/hexane) affording 2-methoxy-6-methyl-4-morpholin-4-yl-benzonitrile (0.6 g, 2.58 mmol, 29%).

b) Synthesis of 2-hydroxy-6-methyl-4-morpholin-4-yl-benzonitrile

To a solution of 2-methoxy-6-methyl-4-morpholin-4-yl-benzonitrile (0.9 g, 3.88 mmol) in dimethylformamide (15 ml) are added potassium carbonate (2.1 g, 15.5 mmol) and ethanethiol (2.3 ml, 31.0 mmol) and the resulting mixture is heated at 90° C. for 16 h. The reaction mixture is poured onto cold water (50 ml), acidified with 2M hydrochloric acid to pH 3 and extracted with ethyl acetate (3×30 ml). The combined organic layers are washed with brine (30 ml), dried over sodium sulfate and evaporated to dryness. The crude product is purified by flash column chromatography (silica gel, 30% ethyl acetate/hexane) affording 2-hydroxy-6-methyl-4-morpholin-4-yl-benzonitrile (0.41 g, 1.88 mmol, 48%).

c) Synthesis of trifluoro-methanesulfonic acid (2-cyano-3-methyl-5-morpholin-4-yl-phenyl)ester To a solution of 2-hydroxy-6-methyl-4-morpholin-4-yl-benzonitrile (0.41 g, 1.88 mmol) in dichloromethane/acetonitrile (1:1) (20 ml) are added caesium carbonate (1.5 g, 4.7 mmol) and N-phenyl bis(trifluoromethane sulfonamide) (1.6 g, 4.7 mmol). The mixture is stirred at room temperature for 1 h. After completion of the reaction, the mixture is diluted with dichloromethane (30 ml), washed with saturated ammonium chloride solution (20 ml), water (20 ml) and brine (20 ml). The organic layer is dried over sodium sulfate and concentrated to get the crude product, which is purified by flash chromatography (silica gel, 10% ethyl acetate/hexane) affording trifluoro-methanesulfonic acid (2-cyano-3-methyl-5-morpholin-4-yl-phenyl)ester (0.43 g, 1.22 mmol, 65%).

d) Synthesis of 2-[(3R)-3-fluoro-pyrrolidin-1-yl]-6-methyl-4-morpholin-4-yl-benzonitrile A solution of affording trifluoro-methanesulfonic acid (2-cyano-3-methyl-5-morpholin-4-yl-phenyl)ester (0.43 g, 1.22 mmol), (3R)-3-fluoro-pyrrolidin (0.19 g, 1.47 mmol) and caesium carbonate (1.6 g, 4.92 mmol) in tetrahydrofuran (25 ml) is degassed and flushed with Argon for 30 min followed by the addition of palladium(II) acetate (6.0 mg, 0.03 mmol) and 2,2'-bis(diphenylphosphino)-1,1'-binaphthyl (23 mg, 0.04 mmol). The resulting mixture is stirred at 90° C. for 16 h. After completion of the reaction (monitored by TLC), the mixture is poured onto water (30 ml) and extracted with ethyl acetate (3×50 ml).The combined organic layers are washed with water (2×20 ml), brine (2×20 ml), dried over sodium sulfate and concentrated in vacuo. The crude product is purified by flash column chromatography (silica gel, 15% ethyl acetate/hexane) affording 2-[(3R)-3-fluoro-pyrrolidin-1-yl]-6-methyl-4-morpholin-4-yl-benzonitrile (0.18 g, 0.62 mmol, 50%).

e) Synthesis of 2-[(3R)-3-fluoro-pyrrolidin-1-yl]-6-methyl-4-morpholin-4-yl-benzamide A solution of 2-[(3R)-3-fluoro-pyrrolidin-1-yl]-6-methyl-4-morpholin-4-yl-benzonitrile (0.18 g, 0.62 mmol) in sulphuric acid (8 ml) is heated at 100° C. for 1 h. After completion of the reaction (monitored by TLC), the mixture is poured onto ice water. The aqueous layer is basified with aqueous ammonia to pH 10 and extracted with ethyl acetate (3×20 ml). The combined organic layers are washed with water (10 ml), dried over sodium sulfate and concentrated in vacuo yielding 2-[(3R)-3-fluoro-pyrrolidin-1-yl]-6-methyl-4-morpholin-4-yl-benzamide (0.13 g, 0.423 mmol, 68%).

f) Synthesis of N-[(4-chlorophenyl)-methyl]-2-[(3R)-3-fluoro-pyrrolidin-1-yl]-6-methyl-4-morpholin-4-yl-benzamide To a stirred solution of 2-[(3R)-3-fluoro-pyrrolidin-1-yl]-6-methyl-4-morpholin-4-yl-benzamide (0.13 g, 0.42 mmol) in tetrahydrofuran/benzene (1:1) (6 ml) is added tetrabutylammonium hydrogen sulfate (15.0 mg, 0.04 mmol) followed by the addition of 15% aqueous sodium hydroxide (3.7 ml) at room temperature. A solution of 4-chloro-benzyl bromide (0.087 g, 0.42 mmol) in tetrahydrofuran (1 ml) is slowly added to the solution and the resulting mixture is heated to 80° C. for 45 min. The mixture is cooled to room temperature and extracted with ethyl acetate (3×10 ml). The combined organic layers are washed with water (10 ml), brine (10 ml), dried over anhydrous sodium sulfate and concentrated in vacuo to get crude product, which is purified by flash column chromatography (silica gel, 10% acetone/hexane) to yield N-[(4-chlorophenyl)-methyl]-2-[(3R)-3-fluoro-pyrrolidin-1-yl]-6-methyl-4-morpholin-4-yl-benzamide (example 38) (0.04 g, 0.09 mmol, 22%). [M+H]$^+$ 432.2.

Synthesis of Example 39

N-[(4-Chlorophenyl)-methyl]-2-fluoro-6-isopropyl-4-morpholin-4-yl-benzamide

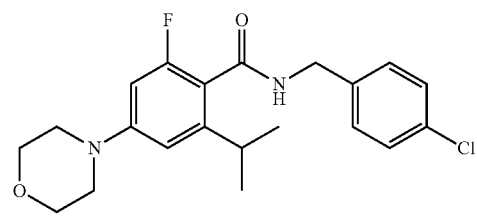

a) Synthesis of 4-bromo-2-fluoro-6-methoxy-benzonitrile

To a solution of 4-bromo-2,6-difluoro-benzonitrile (15.0 g, 68.8 mmol) in tetrahydrofuran (150 ml) is added sodium methoxide (4.5 g, 82.6 mmol) at room temperature and the mixture is stirred for 16 h. The reaction mixture is concentrated under reduced pressure and the resulting solid is purified by column chromatography (silica gel, 5% ethyl acetate/hexane) to obtain 4-bromo-2-fluoro-6-methoxy-benzonitrile (8.5 g, 36.9 mmol, 53%).

b) Synthesis of 4-bromo-2-fluoro-6-methoxy-benzaldehyde

To a solution of 4-bromo-2-fluoro-6-methoxy-benzonitrile (8.5 g, 36.9 mmol) in dichloromethane (400 ml) diisobutylaluminium hydride (25% in toluene, 50.4 ml, 88.7 mmol) is added drop wise at 0° C. and the mixture is stirred at same temperature for 2 h. After completion of the reaction, the mixture is quenched with 2N hydrochloric acid (50 ml) and stirred for another 30 minutes at 0° C. The mixture is extracted with dichloromethane (3×100 ml). The combined organic layers are washed with brine (50 ml) and dried over sodium sulfate and evaporated to dryness. The resulting residue is purified by column chromatography (silica gel, 2% ethyl acetate/hexane) obtain 4-bromo-2-fluoro-6-methoxy-benzaldehyde (3.4 g, 14.6 mmol, 39%).

c) Synthesis of 4-bromo-2-fluoro-6-methoxy-benzoic acid

To a solution of 4-bromo-2-fluoro-6-methoxy-benzaldehyde (3.4 g, 14.6 mmol) in tert-butanol (70 ml) and water (35 ml), sodium chlorite (2.64 g, 29.2 mmol), monosodium phosphate dihydrate (11.4 g, 72.9 mmol) and 2-methyl-2-butene (12.4 ml, 116.7 mmol) are added successively at room temperature and the mixture is stirred for 2 h. After completion of the reaction (monitored by TLC), the mixture is concentrated under reduced pressure and the residue is diluted with ice water (50 ml) and acidified to pH 5 by adding 2N hydrochloric acid. The mixture is extracted with methyl tert-butyl ether (2×100 ml). The methyl tert-butyl ether layer is extracted again with 10% aqueous sodium hydroxide (100 ml). The aqueous layer is acidified to pH 2 with 5N hydrochloric acid and extracted with dichloromethane (2×50 ml). The organic layer is washed with brine (50 ml), dried over sodium sulfate and evaporated to dryness to obtain 4-bromo-2-fluoro-6-methoxy-benzoic acid (2.5 g, 10.0 mmol, 68%).

d) Synthesis of 4-bromo-N-[(4-chlorophenyl)-methyl]-2-fluoro-6-methoxy-benzamide To a solution 4-bromo-2-fluoro-6-methoxy-benzoic acid (2.5 g, 10.0 mmol) in dichloromethane (30 ml) is added oxalyl chloride (1.04 ml, 12.0 mmol) added drop wise at 0° C. followed by addition of a catalytic amount of dimethylformamide. The mixture is stirred at the same temperature for 2 h. The solution is added via a cannula to a mixture of 4-chloro benzyl amine (1.7 g, 12.0 mmol) and triethyl amine (4.2 ml, 30.0 mmol) in dry tetrahydrofuran (50 ml) at 0° C. After stirring at room temperature for 16 h the mixture is diluted with dichloromethane (50 ml) and washed with water (50 ml), brine (50 ml), dried over sodium sulfate and evaporated in vacuo. The crude product is purified by column chromatography (silica gel, 5% ethyl acetate/dichloromethane) to obtain 4-bromo-N-[(4-chlorophenyl)-methyl]-2-fluoro-6-methoxy-benzamide (2.8 g, 7.52 mmol, 74%).

e) Synthesis of N-[(4-chlorophenyl)-methyl]-2-fluoro-6-methoxy-4-morpholin-4-yl-benzamide 2,2'-Bis(diphenylphosphino)-1,1'-binaphthyl (468 mg, 0.75 mmol) is added to a stirred solution of 4-bromo-N-[(4-chlorophenyl)-methyl]-2-fluoro-6-methoxy-benzamide (2.8 g, 7.52 mmol), morpholine (0.92 g, 10.5 mmol) and sodium tert-butoxide (0.94 g, 9.78 mmol) in toluene (90 ml) and the mixture is degassed and flushed with argon for 45 min. Tris (dibenzylideneacetone)-dipalladium(0) (344 mg, 0.38 mmol) is added and the mixture is heated at 120° C. for 16 h. The mixture is cooled to room temperature and diluted with water (50 ml). The mixture is extracted with ethyl acetate (2×30 ml). The combined organic layers are washed with water (30 ml), brine (40 ml), dried over anhydrous sodium sulfate and evaporated to get the crude which is purified by column chromatography (silica gel, 5% ethyl acetate/dichloromethane) to yield N-[(4-chlorophenyl)-methyl]-2-fluoro-6-methoxy-4-morpholin-4-yl-benzamide (1.3 g, 3.2 mmol, 33%).

f) Synthesis of N-[(4-chlorophenyl)-methyl]-2-fluoro-6-hydroxy-4-morpholin-4-yl-benzamide To a solution of N-[(4-chlorophenyl)-methyl]-2-fluoro-6-methoxy-4-morpholin-4-yl-benzamide (1.3 g, 3.44 mmol) in dichloromethane (40 ml) is added neat boron tribromide (0.82 ml, 8.6 mmol) at −78° C. The temperature is raised to room temperature over a period of 2 h. The reaction mixture is poured onto cold water, extracted with dichloromethane (3×50 ml). The combined organic layers are washed with brine (30 ml), dried over sodium sulfate and evaporated to dryness. The crude product is purified by column chromatography (silica gel, 5% ethyl acetate/dichloromethane) to yield N-[(4-chlorophenyl)-methyl]-2-fluoro-6-hydroxy-4-morpholin-4-yl-benzamide (0.5 g, 1.3 mmol, 39%).

g) Synthesis of trifluoro-methanesulfonic acid [2-[(4-chlorophenyl)-methyl-carbamoyl]-3-fluoro-5-morpholin-4-yl-phenyl]ester To a solution of N-[(4-chlorophenyl)-methyl]-2-fluoro-6-hydroxy-4-morpholin-4-yl-benzamide (0.5 g, 1.37 mmol) in dichloromethane/acetonitrile (1:1) (40 ml) are added caesium carbonate (0.67 g, 2.05 mmol) and N-phenyl bis(trifluoromethane sulfonamide) (0.73 g, 2.05 mmol). The mixture is stirred at room temperature for 4 h. After completion of the reaction, the mixture is diluted with dichloromethane (30 ml), washed with saturated ammonium chloride solution (10 ml), water (10 ml) and brine (10 ml). The organic layer is dried over sodium sulfate and concentrated to get the crude product, which is purified by column chromatography (silica gel, 5% acetone/hexane) affording trifluoro-methanesulfonic acid [2-[(4-chlorophenyl)-methyl-carbamoyl]-3-fluoro-5-morpholin-4-yl-phenyl]ester (0.5 g, 1.0 mmol, 73%).

h) Synthesis of N-[(4-chlorophenyl)-methyl]-2-fluoro-6-isopropenyl-4-morpholin-4-yl-benzamide To a solution of trifluoro-methanesulfonic acid [2-[(4-chlorophenyl)-methyl-carbamoyl]-3-fluoro-5-morpholin-4-yl-phenyl]ester (0.50 g, 1.0 mmol) in dimethylformamide (20 ml) are added potassium phosphate (637 mg, 3.0 mmol) and 2-isopropenyl-4,4,5,5-tetramethyl-[1,3,2]dioxaborolane (218 mg, 1.3 mmol). The mixture is degassed and flushed with argon for min followed by the addition of 1,1'-bis(diphenylphosphino)ferrocene-palladium(II)dichloride (73 mg, 0.1 mmol) and the resulting mixture is heated at 120° C. for 16 h. After completion of reaction, the mixture is cooled to room temperature and diluted with methyl tert-butyl ether (75 ml), washed with water (3×20 ml) and brine (20 ml). The organic layer is dried over sodium sulfate and concentrated in vacuo to get the crude product, which is purified by column chromatography (silica gel, 10% acetone/hexane) affording N-[(4-chlorophenyl)-methyl]-2-fluoro-6-isopropenyl-4-morpholin-4-yl-benzamide (0.12 g, 0.31 mmol, 30%).

i) Synthesis of N-[(4-chlorophenyl)-methyl]-2-fluoro-6-isopropyl-4-morpholin-4-yl-benzamide A stirred solution of N-[(4-chlorophenyl)-methyl]-2-fluoro-6-isopropenyl-4-morpholin-4-yl-benzamide (0.12 g, 0.31 mmol) in methanol (10 ml) is degassed and flushed with nitrogen before 10% palladium on carbon (25 mg) is added and the mixture is hydrogenated under hydrogen for 45 min at room temperature. After completion of the reaction (monitored by TLC), the mixture is filtered through a pad of celite and concentrated in vacuo. The resulting crude product is purified by preparative HPLC to obtain N-[(4-chlorophenyl)-methyl]-2-fluoro-6-isopropyl-4-morpholin-4-yl-benzamide (example 39) (0.04 g, 0.10 mmol, 33%). [M+H]+ 391.2.

Synthesis of Example 40

N-[(4-Chlorophenyl)-methyl]-2-isopropyl-6-methoxy-4-morpholin-4-yl-benzamide

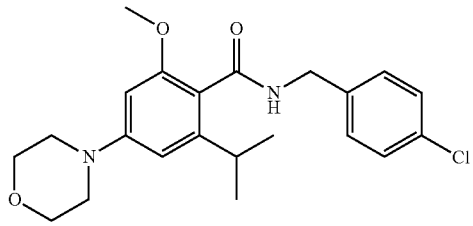 [SMILES: COc1cc(N2CCOCC2)cc(C(C)C)c1C(=O)NCc1ccc(Cl)cc1]

a) Synthesis of 5-fluoro-3-methoxy-2-nitro-phenol

To a solution of 1,5-difluoro-3-methoxy-2-nitro-benzene (20 g, 105 mmol) in dimethylsulfoxide (50 ml) is added a 10N aqueous solution of sodium hydroxide (31.5 ml) and the mixture is stirred at room temperature for 18 h and at 60° C. for 3 h. After completion of reaction (monitored by TLC), the mixture is diluted with water (50 ml), acidified with 2N hydrochloric acid to pH 3 and extracted with ethyl acetate (3×100 ml). The combined organic layers are washed with water (50 ml), brine (50 ml), dried over sodium sulfate and concentrated in vacuo. The crude product is purified by flash column chromatography (15% ethyl acetate/hexane) to yield 5-fluoro-3-methoxy-2-nitro-phenol (12.0 g, 63.5 mmol, 60%).

b) Synthesis of 3-methoxy-5-morpholin-4-yl-2-nitro-phenol

To a stirred solution of 5-fluoro-3-methoxy-2-nitro-phenol (2.0 g, 10.6 mmol) in dimethylsulfoxide (25 ml) is added morpholine (9.2 ml, 106 mmol) at room temperature. The resulting mixture is heated at 100° C. for 2 h. After completion of reaction (monitored by TLC), the mixture is diluted with water (40 ml) and the aqueous layer is extracted with ethyl acetate (3×30 ml). The combined organic layers are washed with water (30 ml), brine (20 ml), dried over sodium sulfate and concentrated in vacuo. The crude product is purified by flash column chromatography (45% ethyl acetate/hexane) to yield 3-methoxy-5-morpholin-4-yl-2-nitro-phenol (0.71 g, 2.78 mmol, 26%).

c) Synthesis of trifluoro-methanesulfonic acid (3-methoxy-5-morpholin-4-yl-2-nitro-phenyl)ester To a solution of 3-methoxy-5-morpholin-4-yl-2-nitro-phenol (0.7 g, 2.7 mmol) in dichloromethane/acetonitrile (1:1) (20 ml) are added caesium carbonate (1.5 g, 4.1 mmol) and N-phenyl bis(trifluoromethane sulfonamide) (1.3 g, 4.1 mmol). The mixture is stirred at room temperature for 2 h. After completion of reaction, the mixture is diluted with dichloromethane (30 ml), washed with water (50 ml) and brine (50 ml). The organic layer is dried over sodium sulfate and concentrated in vacuo to get the crude product, which is purified by flach column chromatography (silica gel, 10% ethyl acetate/dichloromethane) affording trifluoro-methanesulfonic acid (3-methoxy-5-morpholin-4-yl-2-nitro-phenyl) ester (1.0 g, 2.58 mmol, 94%).

d) Synthesis of 4-(3-isopropenyl-5-methoxy-4-nitro-phenyl)-morpholine

A solution of trifluoro-methanesulfonic acid (3-methoxy-5-morpholin-4-yl-2-nitro-phenyl)ester (15.0 g, 38.7 mmol), potassium phosphate (24.6 g, 116 mmol) and 2-isopropenyl-4,4,5,5-tetramethyl-[1,3,2]dioxaborolane (8.4 g, 50.3 mmol) in dimethylformamide (80 ml) is degassed and flushed with argon for 20 min. To the reaction mixture is added 1,1'-bis (diphenylphosphino)ferrocene-palladium(II)dichloride (2.9 g, 3.9 mmol) and the resulting mixture is stirred at 120° C. for 16 h. After completion of the reaction (monitored by TLC), the mixture is diluted with water (50 ml) and extracted with ethyl acetate (3×70 ml). The combined organic layers are washed water (50 ml), brine (50 ml), dried over anhydrous sodium sulfate and evaporated in vacuo to get the crude product, which is purified by flash column chromatography (silica gel, 5% acetone/hexane) to yield 4-(3-isopropenyl-5-methoxy-4-nitro-phenyl)-morpholine (5.6 g, 20.0 mmol, 52%).

e) Synthesis of (2-isopropyl-6-methoxy-4-morpholin-4-yl-phenyl)amine

A solution of 4-(3-isopropenyl-5-methoxy-4-nitro-phenyl)-morpholine (3.0 g, 10.7 mmol) in methanol (170 ml) is degassed and flushed with argon for 20 min. To the reaction mixture is added 10% palladium on carbon (1.1 g) and the resulting mixture is hydrogenated in a par shaker (50 psi) for 16 h. After completion of reaction (monitored by TLC), the mixture is filtered through a pad of celite. The filtrate is concentrated in vacuo yielding (2-isopropyl-6-methoxy-4-morpholin-4-yl-phenyl)-amine. The crude material is used in the next step without further purification (2.3 g, 9.2 mmol, 86%).

f) Synthesis of 2-isopropyl-6-methoxy-4-morpholin-4-yl-benzonitrile

Copper(I) cyanide (1.07 g, 11.9 mmol) is added to dimethylsulfoxide (15 ml) at 50° C. followed by the addition of tert-Butyl nitrite (3.8 ml, 27.6 mmol) at once. A solution of (2-isopropyl-6-methoxy-4-morpholin-4-yl-phenyl)-amine (2.3 g, 9.2 mmol) in dimethylsulfoxide (15 ml) is added drop wise via an addition funnel to the above mixture. After completion of the addition, the reaction mixture is allowed to stir for 1 h at 50° C. After being cooled to 45° C., the reaction mixture is slowly treated with 5N hydrochloric acid and cooled to ambient temperature. The resulting mixture is extracted with ethyl acetate (3×50 ml). The combined organic layers are washed with water (30 ml), brine (30 ml), dried over sodium sulfate and evaporated to dryness. The crude product is purified by flash column chromatography (silica gel, 20% ethyl acetate/hexane) to afford 2-isopropyl-6-methoxy-4-morpholin-4-yl-benzonitrile (0.4 g, 1.54 mmol, 17%).

g) Synthesis of 2-isopropyl-6-methoxy-4-morpholin-4-yl-benzamide

A solution of 2-isopropyl-6-methoxy-4-morpholin-4-yl-benzonitrile (0.37 g, 1.42 mmol) in sulfuric acid (20 ml) is heated at 100° C. for 3 h. After completion of the reaction (monitored by TLC), the mixture is poured onto ice water. The aqueous layer is basified with aqueous ammonia to pH 10 and extracted with ethyl acetate (3×20 ml). The combined organic layers are washed with water (10 ml), dried over sodium sulfate and concentrated in vacuo yielding 2-isopropyl-6-methoxy-4-morpholin-4-yl-benzamide (0.34 g, 1.22 mmol, 86%).

h) Synthesis of N-[(4-chlorophenyl)-methyl]-2-isopropyl-6-methoxy-4-morpholin-4-yl-benzamide To a stirred solution of 2-isopropyl-6-methoxy-4-morpholin-4-yl-benzamide (0.31 g, 1.1 mmol) in tetrahydrofuran/benzene (1:2) (10 ml) is added tetrabutylammonium hydrogen sulfate (38.0 mg, 0.10 mmol) followed by the addition of 30% aqueous sodium hydroxide (10 ml) at room temperature. A solution of 4-chloro-benzyl bromide (0.23 g, 1.1 mmol) in tetrahydrofuran (4 ml) is slowly added to the solution and the resulting mixture is heated to 90° C. for 45 min. The mixture is cooled to room temperature and extracted with ethyl acetate (3×10 ml). The combined organic layers are washed with water (10 ml), brine (10 ml), dried over anhydrous sodium sulfate and concentrated in vacuo to get crude product, which is purified by flash column chromatography (silica gel, 10% acetone/hexane) to yield N-[(4-chlorophenyl)-methyl]-2-isopropyl-6-methoxy-4-morpholin-4-yl-benzamide (example 40) (0.115 g, 0.45 mmol, 28%). [M+H]$^+$ 403.2.

Synthesis of Example 41

N-[(4-Chlorophenyl)-methyl]-2,6-diethyl-4-morpholin-4-yl-benzamide

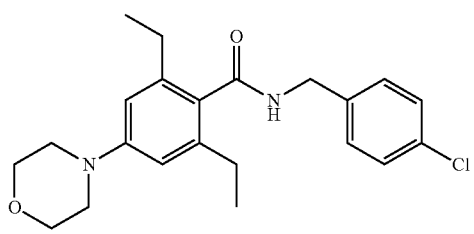 [SMILES: CCc1cc(N2CCOCC2)cc(CC)c1C(=O)NCc1ccc(Cl)cc1]

a) Synthesis of 4-bromo-N-quinolin-8-yl-benzamide

To a solution of compound quinolin-8-yl-amine (3.0 g, 20.8 mmol) in dichloromethane (40 ml) and triethylamine (3.1 ml, 21.9 mmol), 4-bromo-benzoyl chloride (4.8 g, 21.9 mmol) in dichloromethane (20 ml) is added drop wise at room temperature and the resulting mixture is stirred for 16 h. After completion of the reaction (monitored by TLC) the mixture is diluted with dichloromethane (100 ml) and washed with water and saturated sodium hydrogen carbonate solution. The organic layer is dried over sodium sulfate and concentrated in vacuo. The resulting crude product is purified by column chromatography (silica gel, 10% ethyl acetate/hexane) to obtain 4-bromo-N-quinolin-8-yl-benzamide (5.2 g, 15.9 mmol, 76%).

b) Synthesis of 4-bromo-2,6-diethyl-N-quinolin-8-yl-benzamide

To a solution of 4-bromo-N-quinolin-8-yl-benzamide (3.2 g, 9.79 mmol) in tert-amyl alcohol (10 ml) are added pivalic acid (0.2 g, 1.96 mmol), potassium carbonate (3.37 g, 24.5 mmol) and ethyl iodide (6.36 ml, 78.3 mmol) in a sealed tube. After degassing with argon for 30 min palladium(II) acetate (0.11 g, 0.49 mmol) is added and the mixture is heated at 100° C. for 48 h. After completion of the reaction (monitored by TLC) the mixture is diluted with ethyl acetate (50 ml), washed with water (2×30 ml), and the organic layer is dried over sodium sulfate and concentrated in vacuo. The resulting crude product is purified by column chromatography (silica gel, 10% ethyl acetate/hexane) to yield 4-bromo-2,6-diethyl-N-quinolin-8-yl-benzamide (2.9 g, 7.57 mmol, 77%).

c) Synthesis of 4-bromo-2,6-diethyl-benzoic acid

A mixture of 4-bromo-2,6-diethyl-N-quinolin-8-yl-benzamide (2.9 g, 7.6 mmol) in 40% sulphuric acid (15 ml) is heated at 120° C. for 16 h. After completion, the reaction mixture is extracted with ether (2×100 ml) and the combined organic layers are dried over sodium sulfate and concentrated to obtain 4-bromo-2,6-diethyl-benzoic acid (1.1 g, 4.28 mmol, 56%).

d) Synthesis of 4-bromo-N-[(4-chlorophenyl)-methyl]-2,6-diethyl-benzamide

To a solution of 4-bromo-2,6-diethyl-benzoic acid (0.30 g, 1.20 mmol) in dichloromethane (3.6 ml) are added diisopropylethylamine (0.58 ml, 3.56 mmol) and O-(7-azabenzotriazol-1-yl)-N,N,N',N'-tetramethyluronium hexafluorophosphate (0.54 g, 1.42 mmol) at 0° C. and the mixture is stirred for 20 min followed by the addition of 4-chloro-benzyl amine (0.17 ml, 1.42 mmol). The resulting mixture is stirred at room temperature for 16 h. After completion of the reaction (monitored by TLC) the reaction mixture is diluted with dichloromethane (20 ml) and washed with water (30 ml). The organic layer is dried over sodium sulfate and concentrated in vacuo. The resulting crude product is purified column chromatography (silica gel, 25% ethyl acetate/hexane) to obtain 4-bromo-N-[(4-chlorophenyl)-methyl]-2,6-diethyl-benzamide (0.34 g, 0.90 mmol, 75%).

e) Synthesis of N-[(4-chlorophenyl)-methyl]-2,6-diethyl-4-morpholin-4-yl-benzamide To a solution of 4-bromo-N-[(4-chlorophenyl)-methyl]-2,6-diethyl-benzamide (0.34 g, 0.90 mmol) in toluene (3 ml), morpholine (0.11 g, 1.29 mmol), caesium carbonate (0.40 g, 1.22 mmol) and 2,2'-bis(diphenylphosphino)-1,1'-binaphthyl (0.06 g, 0.09 mmol) are added. After degassing with argon for 30 min tris(dibenzylideneacetone)-dipalladium(0) (0.04 g, 0.04 mmol) are added and the mixture is heated at 120° C. for 16 h. After completion of the reaction (monitored by TLC) the mixture is filtered through a pad of celite and diluted with ethyl acetate (30 ml), the organic layer is washed with water and dried over sodium sulfate and concentrated in vacuo. The resulting crude product is purified by preparative HPLC to obtain the N-[(4-chlorophenyl)-methyl]-2,6-diethyl-4-morpholin-4-yl-benzamide (example 41) (0.18 g, 0.47 mmol, 26%). [M+H]$^+$ 387.2.

Synthesis of Further Examples

The synthesis of further examples was carried out according to the methods already described. Table 1 shows which compound were produced according to which method. It is evident to the person skilled in the art which educts and reagents were used in each case.

effect, which can be achieved by applying a saturated concentration of a reference compound, e.g. Retigabine (50 μM), in independent wells of the same experimental plate or series.

TABLE 1

| Example | Chemical name | Preparation according to example | MS m/z $[M + H]^+$ |
|---|---|---|---|
| 21 | 2-Isopropenyl-6-methyl-4-morpholin-4-yl-N-[[4-(trifluoromethyl)-phenyl]-methyl]-benzamide | 14 | 419.2 |
| 22 | 2-Isopropyl-6-methyl-4-morpholin-4-yl-N-[[4-(trifluoromethyl)-phenyl]-methyl]-benzamide | 14 | 421.2 |
| 23 | 2-Isopropyl-6-methyl-4-morpholin-4-yl-N-[[4-(trifluoromethyloxy)-phenyl]-methyl]-benzamide | 14 | 437.2 |
| 24 | 2-Cyclopropyl-6-methyl-4-morpholin-4-yl-N-[[4-(trifluoromethyl)-phenyl]-methyl]-benzamide | 15 | 419.2 |
| 25 | 2-Cyclopropyl-6-methyl-4-morpholin-4-yl-N-[[4-(trifluoromethyloxy)-phenyl]-methyl]-benzamide | 15 | 435.2 |
| 26 | N-[(3-Fluorophenyl)-methyl]-2-methyl-4-pyrrolidin-1-yl-6-(trifluoromethyl)-benzamide | 19 | 381.1 |
| 27 | N-[(3-Fluorophenyl)-methyl]-2-methyl-4-piperidin-1-yl-6-(trifluoromethyl)-benzamide | 19 | 395.2 |
| 29 | 2-Cyclopropyl-N-[(3S)-3-hydroxy-4,4-dimethyl-pentyl]-6-methyl-4-morpholin-4-yl-benzamide | 28 | 375.3 |
| 30 | N-[(3R)-3-Hydroxy-4,4-dimethyl-pentyl]-2-isopropyl-6-methyl-4-morpholin-4-yl-benzamide | 28 | 377.3 |
| 31 | N-[(3S)-3-Hydroxy-4,4-dimethyl-pentyl]-2-isopropyl-6-methyl-4-morpholin-4-yl-benzamide | 28 | 377.3 |
| 32 | 2-Cyclopropyl-N-(2-hydroxy-4,4-dimethyl-pentyl)-6-methyl-4-morpholin-4-yl-benzamide | 28 | 375.3 |
| 33 | N-(2-Hydroxy-4,4-dimethyl-pentyl)-2-isopropyl-6-methyl-4-morpholin-4-yl-benzamide | 28 | 377.3 |
| 34 | N-[(5-Chloro-pyridin-2-yl)-methyl]-2-isopropyl-6-methyl-4-morpholin-4-yl-benzamide | 28 | 388.2 |
| 35 | 2-Isopropyl-6-methyl-4-morpholin-4-yl-N-[[5-(trifluoromethyl)-pyridin-2-yl]-methyl]-benzamide | 28 | 422.2 |
| 36 | 2-Cyclopropyl-6-methyl-4-morpholin-4-yl-N-[[5-(trifluoromethyl)-pyridin-2-yl]-methyl]-benzamide | 28 | 420.2 |
| 37 | N-[(4-Chlorophenyl)-methyl]-2-methyl-4-morpholin-4-yl-6-tetrahydro-furan-3-yl-benzamide | 16 | 415.2 |

Pharmacological Experiments

Method I. Fluorescence Assay Using a Voltage Sensitive Dye (Fluorimetry)

The modulation of the KCNQ opening state (and consequently the voltage potential of a cell) by test compounds such as compounds according to the present invention results in an increased or reduced amount of a voltage-sensitive dye in the cytoplasm of the cells tested. These voltage-sensitive dyes are fluorescent dyes and, therefore, are forming the link between cell potential influenced by KCNQ modulation and fluorescence intensity. A KCNQ agonist leads to an opening of the channel, potassium and dye efflux, a following hyperpolarization and a reduction of the inner fluorescence intensity in a kinetic protocol. If applying an ion jump by KCl depolarization, KCNQ agonists increase the ΔF/F value. An antagonist performs vice versa, respectively.

The 'fluorimetry $EC_{50}$' is the half maximum effective concentration ($EC_{50}$), where the concentration of a drug/compound induces a response halfway between the baseline and maximum plateau effect. In other words, said value represents the concentration of a compound, where 50% of its maximal effect in the fluorimetric assay is observed if the substance concentration is graphed against the corresponding ΔF/F values (for which the calculation method is described below). Therefore, 'fluorimetry $EC_{50}$' is a measure for the compound potency. The compound efficacy is mirrored by 'fluorimetry % efficacy' ('% Efficacy') and refers to the maximum response achievable by the test compound, i.e. the plateau effect. This drug's plateau effect is related to the plateau A compound showing 100% efficacy is as efficacious as the reference compound (Retigabine) with a saturated concentration. This calculation '% Efficacy' method was introduced in order to normalize the ΔF/F values of different experiments to a common comparator compound, and make the test drug effects comparable.

Human CHO-K1 cells expressing KCNQ2/3 channels are cultivated adherently at 37° C., 5% $CO_2$ and 95% humidity in cell culture bottles (e.g. 80 $cm^2$ TC flasks, Nunc) with DMEM-high glucose (Sigma Aldrich, D7777) including 10% FCS (PAN Biotech, e.g. 3302-P270521) or alternatively MEM Alpha Medium (1×, liquid, Invitrogen, #22571), 10% fetal calf serum (FCS) (Invitrogen, #10270-106, heat-inactivated) and the necessary selection antibiotics.

Before being sown out for the measurements, the cells are washed with 1× DPBS buffer $Ca^{2+}/Mg^{2+}$-free (e.g. Invitrogen, #14190-094) and detached from the bottom of the culture vessel by using Accutase (PAA Laboratories, #L11-007) (incubation with Accutase for 15 min at 37° C.). The cell number is determined using a CASY™ cell counter (TCC, Schärfe System). Depending on the optimal density for each individual cell line, 20,000-30,000 cells/well/100 μl are seeded onto 96-well Corning™ CellBIND™ assay plates (Flat Clear Bottom Black Polystyrene Microplates, #3340). Freshly seeded cells are then left to settle for one hour at room temperature, followed by incubation for 24 hours at 37° C., 5% $CO_2$ and 95% humidity.

The voltage-sensitive fluorescent dye from the Membrane Potential Assay Kit (Red™ Bulk format part R8123 for FLIPR, MDS Analytical Technologies™) is prepared by dissolving the contents of one vessel Membrane Potential Assay Kit Red Component A in 200 ml of extracellular buffer (ES buffer, 120 mM NaCl, 1 mM KCl, 10 mM HEPES, 2 mM CaCl$_2$, 2 mM MgCl$_2$, 10 mM glucose; pH 7.4). After removal of the nutrient medium, the cells are washed once with 200 µl of ES buffer, then loaded for 45 min at room temperature in 100 µl of dye solution in the dark.

Fluorescence measurements are carried out in a BMG Labtech FLUOstar™, BMG Labtech NOVOstar™ or BMG Labtech POLARstar™ instrument (525 nm excitation, 560 nm emission, Bottom Read mode). After incubation with the dye, 50 µl of the test substances in the desired concentrations, or 50 µl of ES buffer for control purposes, are applied to the wells of the assay plate and incubated for 30 min at room temperature while being shielded from light. The fluorescence intensity of the dye is then measured for 5 min and the fluorescence value $F_1$ of each well is thus determined at a given, constant time. 15 µl of a KCl solution are then added to each well (final concentration of potassium ions 92 mM). The change in fluorescence intensity is subsequently monitored until all the relevant values have been obtained (mainly 5-30 min). At a given time post KCl application, a fluorescence value $F_2$ is determined, in this case at the time of the fluorescence peak.

For calculation, the fluorescence intensity $F_2$ is corrected for the fluorescence intensity $F_1$, and the activity (ΔF/F) of the target compound on the potassium channel is determined as follows:

$$\left(\frac{F_2 - F_1}{F_1}\right) \times 100 = \frac{\Delta F}{F}(\%)$$

In order to determine whether a substance has agonistic activity, $$\frac{\Delta F}{F}$$

can be related to $$\left(\frac{\Delta F}{F}\right)_K$$

of control wells.

$$\left(\frac{\Delta F}{F}\right)_K$$

is determined by adding to the well only the buffer solution instead of the test substance, determining the value $F_{1K}$ of the fluorescence intensity, adding the potassium ions as described above, and measuring a value $F_{2K}$ of the fluorescence intensity. $F_{2K}$ and $F_{1K}$ are then calculated as follows:

$$\left(\frac{F_{2K} - F_{1K}}{F_{1K}}\right) \times 100 = \left(\frac{\Delta F}{F}\right)_K (\%)$$

A substance has an agonistic activity on the potassium channel if $$\frac{\Delta F}{F}$$

is greater than $$\left(\frac{\Delta F}{F}\right)_K:$$

$$\frac{\Delta F}{F} \rangle \left(\frac{\Delta F}{F}\right)_K$$

Independently of the comparison of $$\frac{\Delta F}{F} \text{ with } \left(\frac{\Delta F}{F}\right)_K$$

it is possible to conclude that a target compound has agonistic activity if $$\frac{\Delta F}{F}$$

increases dose dependently.

Calculations of EC$_{50}$ and IC$_{50}$ values are carried out with the aid of 'Prism v4.0' software (GraphPad Software™)

Method II. Low-Intensity Tail Flick Test (Rat)

In the low-intensity tail flick test, the determination of the antinociceptive effect of the compounds according to the invention towards an acute noxious thermal stimulus is carried out by measuring the withdrawal reflex of the rat tail (tail flick) in response to a radiant heat beam (analgesia meter; model 2011 of the company Rhema Labortechnik, Hofheim, Germany) according to the method described by D'Amour and Smith (J. Pharm. Exp. Ther. 72, 74 79 (1941). To this end, the rats were placed in a plexiglas restrainer, and a low-intensity radiant heat beam (48° C.) was focused onto the dorsal surface of the tail root. The stimulus intensity was adjusted to result in a mean pre-drug control withdrawal latency of about 7 s, thus also allowing a supraspinal modulation of the spinally mediated acute nociceptive reflex. A cutoff time of 30 s was applied to avoid tissue damage. Male Sprague-Dawley rats (Janvier, Le Genest St. Isle, Frankreich) with weights of 200-250 g were used. 10 rats were used per group. Before administration of a compound according to the invention, the animals were pre-tested twice in the course of five minutes and the mean of these measurements was calculated as the pre-test mean. The antinociceptive effect was determined at 20, 40 and 60 min after peroral compound administration. The antinociceptive effect was calculated based on the increase in the tail withdrawal latency according to the following formula and is expressed as percentage of the maximum possible effect (MPE [%]):

MPE=[($T_1$-$T_0$)/($T_2$-$T_0$)]*100

In this, $T_0$ is the control latency time before and $T_1$ the latency time after administration of the compound, $T_2$ is the cutoff time and MPE is the maximum possible effect. Employing variant analysis (repeated measures ANOVA) allowed testing of statistically significant differences between the compounds according to the invention and the vehicle group. The significance level was set to p≤0.05. To determine the dose dependency, the particular compound according to the invention was administered in 3-5 logarithmically increasing doses, including a threshold dose and a maximum effective dose, and the ED$_{50}$ values were determined with the aid of regression analysis. The ED$_{50}$ calculation was performed at the time of maximum efficacy (usually 20 min after administration of the compounds).

Pharmacological Data

The pharmacological effects of the compounds according to the invention were determined as described hereinbefore (pharmacological experiments, methods I and II respectively).

The corresponding pharmacological data are summarized in Table 2.

TABLE 2

| Example | Fluorimetry % efficacy (retigabine = 100%) | Fluorimetry $EC_{50}/IC_{50}$ [nM] | Low intensity tail flick, rat, peroral, $ED_{50}$ and/or MPE (dose) [mg/kg] |
|---|---|---|---|
| 1 | 163 | 1481 | |
| 2 | 152 | 483 | |
| 3 | 220 | 335 | |
| 4 | 200 | 260 | |
| 5 | 246 | 108 | |
| 7 | 66 | 8799 | |
| 8 | 88 | 5558 | |
| 9 | 65 | 9300 | |
| 10 | 147 | 1643 | |
| 11 | 141 | 1354 | |
| 12 | 169 | 369 | |
| 13 | 183 | 217 | |
| 14 | 175 | 136 | 3.6; 92 (10) |
| 15 | 170 | 552 | |
| 16 | 194 | 33 | |
| 17 | 179 | 663 | 2.5; 100 (14.7) |
| 18 | 169 | 982 | |
| 19 | 185 | 400 | |
| 20 | 144 | 708 | |
| 21 | 118 | 626 | |
| 22 | 148 | 184 | |
| 23 | 161 | 139 | |
| 24 | 134 | 693 | |
| 25 | 144 | 355 | |
| 26 | 156 | 453 | |
| 27 | 197 | 673 | |
| 28 | 155 | 4663 | |
| 29 | 195 | 1812 | |
| 30 | 212 | 3099 | |
| 31 | 230 | 416 | |
| 32 | 159 | 3811 | |
| 33 | 216 | 1366 | |
| 34 | 156 | 3608 | |
| 35 | 134 | 3074 | |
| 36 | 89 | 5264 | |
| 37 | 166 | 1690 | |
| 38 | 167 | 748 | |
| 39 | 196 | 217 | |
| 40 | 196 | 165 | |
| 41 | 181 | 506 | |

The invention claimed is:

1. A substituted compound of formula (I):

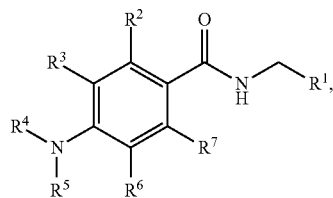

wherein $R^1$ represents a $C_{1-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted; aryl or heteroaryl, in each case unsubstituted or mono- or polysubstituted and in each case optionally bridged via a $C_{1-8}$ aliphatic group, which in turn may be unsubstituted or mono-or polysubstituted;

$R^2$ represents F; Cl; Br; I; CN; $CH_2F$; $CHF_2$; $CF_3$; C(=O)H; $NO_2$; $OCH_2F$; $OCHF_2$; $OCF_3$; $SCF_3$; a $C_{1-4}$-aliphatic residue, a C(=O)—$C_{1-4}$ aliphatic residue, a C(=O)—O—$C_{1-4}$ aliphatic residue, a C(=O)—NH—$C_{1-4}$ aliphatic residue, a C(=O)—N($C_{1-4}$ aliphatic residue)$_2$, wherein the $C_{1-4}$ aliphatic residue may in each case be unsubstituted or mono- or polysubstituted; a O—$C_{1-4}$-aliphatic residue, a O—C(=O)—$C_{1-4}$-aliphatic residue, a S—$C_{1-4}$-aliphatic residue, a S(=O)—$C_{1-4}$-aliphatic residue, a S(=O)$_2$—$C_{1-4}$-aliphatic residue, a S(=O)$_2$—O—$C_{1-4}$-aliphatic residue, a S(=O)$_2$—NH($C_{1-4}$-aliphatic residue) or a S(=O)$_2$—N($C_{1-4}$-aliphatic residue)$_2$, wherein the $C_{1-4}$ aliphatic residue may in each case be unsubstituted or mono- or polysubstituted; a $C_{3-6}$-cycloaliphatic residue or a 3 to 6 membered heterocycloaliphatic residue, in each case unsubstituted or mono- or polysubstituted and in each case optionally bridged via a $C_{1-4}$ aliphatic group, which in turn may be unsubstituted or mono- or polysubstituted;

$R^3$ represents H; F; Cl; Br; I; CN; $CH_2F$; $CHF_2$; $CF_3$; $SCF_3$; $NO_2$; $OCH_2F$; $OCHF_2$; $OCF_3$; a $C_{1-4}$-aliphatic residue, a O—$C_{1-4}$-aliphatic residue, a S—$C_{1-4}$-aliphatic residue, a S(=O)—$C_{1-4}$-aliphatic residue, or a S(=O)$_2$—$C_{1-4}$-aliphatic residue, wherein the $C_{1-4}$ aliphatic residue may in each case be unsubstituted or mono- or polysubstituted; a $C_{3-6}$-cycloaliphatic residue or a 3 to 6 membered heterocycloaliphatic residue, in each case unsubstituted or mono- or polysubstituted and in each case optionally bridged via a $C_{1-4}$ aliphatic group, which in turn may be unsubstituted or mono- or polysubstituted;

$R^4$ and $R^5$ form together with the nitrogen atom connecting them a ring selected from the group consisting of morpholinyl, piperidinyl, pyrrolidinyl, azetidinyl, oxazepanyl, tetrahydroquinolinyl and tetrahydroquinolinyl, each of which is unsubstituted or mono -or polysubstituted by one or more substituents independently selected from the group consisting of F, Cl, OH, =O, C(=O)—OH, O-methyl, O-ethyl, $OCF_3$, $OCH_2F$, $OCHF_2$, $SCF_3$, $CH_2F$, $CHF_2$, $CF_3$, methyl, ethyl, n-propyl, 2-propyl, cyclopropyl and cyclobutyl;

$R^6$ represents H; F; Cl; Br; I; CN; $CH_2F$; $CHF_2$; $CF_3$; $SCF_3$; $NO_2$; $OCH_2F$; $OCHF_2$; $OCF_3$; a $C_{1-4}$-aliphatic residue, a O—$C_{1-4}$-aliphatic residue, a S—$C_{1-4}$-aliphatic residue, a S(=O)—$C_{1-4}$-aliphatic residue, or a S(=O)$_2$—$C_{1-4}$-aliphatic residue, wherein the $C_{1-4}$ aliphatic residue may be in each case be unsubstituted or mono- or polysubstituted; a $C_{3-6}$-cycloaliphatic residue or a 3 to 6 membered heterocycloaliphatic residue, in each case unsubstituted or mono- or polysubstituted and in each case optionally bridged via a $C_{1-4}$ aliphatic group, which in turn may be unsubstituted or mono- or polysubstituted;

$R^7$ represents a $C_1$-aliphatic residue, mono- or polysubstituted; a $C_{2-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted;

provided that if $R^7$ denotes a 3 to 10 membered heterocycloaliphatic residue, the 3 to 10 membered heterocycloaliphatic residue is linked via a carbon atom,
or
denotes S—$R^{8a}$, S(=O)—$R^{8b}$, S(=O)$_2$—$R^{8c}$, O—$R^9$ or N($R^{10}R^{11}$),
wherein
$R^{8a}$, $R^{8b}$, $R^{8c}$ and $R^9$ in each case represent a $C_{1-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted;
provided that if $R^{8a}$, $R^{8b}$, $R^{8c}$ or $R^9$ denotes a 3 to 10 membered heterocycloaliphatic residue, the 3 to 10 membered heterocycloaliphatic residue is linked via a carbon atom,
$R^{10}$ represents a $C_{1-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted;
provided that if $R^{10}$ denotes a 3 to 10 membered heterocycloaliphatic residue, the 3 to 10 membered heterocycloaliphatic residue is linked via a carbon atom;
$R^{11}$ denotes H or a $C_{1-10}$-aliphatic residue, unsubstituted or mono- or polysubstituted;
or
$R^{10}$ and $R^{11}$ form together with the nitrogen atom connecting them a 3 to 10 membered heterocycloaliphatic residue, unsubstituted or mono- or polysubstituted; which may optionally be condensed with aryl or heteroaryl, wherein the aryl or heteroaryl residues condensed in this way can for their part be respectively unsubstituted or mono- or polysubstituted;
in which an "aliphatic group" and an "aliphatic residue" can in each case be branched or unbranched, saturated or unsaturated,
in which a "cycloaliphatic residue" and a "heterocycloaliphatic residue" can in each case be saturated or unsaturated,
in which "mono- or polysubstituted" with respect to an "aliphatic group" and an "aliphatic residue" relates, with respect to the corresponding residues or groups, to the substitution of one or more hydrogen atoms each independently of one another by at least one substituent selected from the group consisting of F, Cl, Br, I, NO$_2$, NH$_2$, an NH(C$_{1-4}$ aliphatic residue), an N(C$_{1-4}$ aliphatic residue)$_2$, a NH—C(=O)—C$_{1-4}$ aliphatic residue, a N(C$_{1-4}$-aliphatic residue)-C(=O)—C$_{1-4}$ aliphatic residue, a NH—S(=O)$_2$—C$_{1-4}$ aliphatic residue, a N(C$_{1-4}$-aliphatic residue)-S(=O)$_2$—C$_{1-4}$ aliphatic residue, =O, OH, OCH$_2$F, OCHF$_2$, OCF$_3$, a O—C$_{1-4}$-aliphatic residue, a O—C(=O)—C$_{1-4}$-aliphatic residue, SH, SCF$_3$, a S—C$_{1-4}$-aliphatic residue, S(=O)$_2$OH, a S(=O)—C$_{1-4}$-aliphatic residue, a S(=O)$_2$—C$_{1-4}$-aliphatic residue, a S(=O)$_2$—O—C$_{1-4}$-aliphatic residue, a S(=O)$_2$—NH—C$_{1-4}$-aliphatic residue, a S(=O)$_2$—N(C$_{1-4}$-aliphatic residue)$_2$, CN, CH$_2$F, CHF$_2$, CF$_3$, CHO, COOH, a C$_{1-4}$-aliphatic residue, CH$_2$OH, CH$_2$—OCH$_3$, C$_2$H$_4$—OH, C$_2$H$_4$—OCH$_3$CH$_2$—CF$_3$, a C(=O)—C$_{1-4}$-aliphatic residue, a C(=O)—O—C$_{1-4}$-aliphatic residue, a C$_{3-6}$-cycloaliphatic residue, a 3 to 6 membered heterocycloaliphatic residue, C(=O)—NH$_2$, a C(=O)—NH(C$_{1-4}$ aliphatic residue), and a C(=O)—N(C$_{1-4}$ aliphatic residue)$_2$;
in which "mono- or polysubstituted" with respect to a "cycloaliphatic residue" and a "heterocycloaliphatic residue" relates, with respect to the corresponding residues, to the substitution of one or more hydrogen atoms each independently of one another by at least one substituent selected from the group consisting of F, Cl, Br, I, NO$_2$, NH$_2$, an NH(C$_{1-4}$ aliphatic residue), an N(C$_{1-4}$ aliphatic residue)$_2$, a NH—C(=O)—C$_{1-4}$ aliphatic residue, a N(C$_{1-4}$-aliphatic residue)-C(=O)—C$_{1-4}$ aliphatic residue, a NH—S(=O)$_2$—C$_{1-4}$ aliphatic residue, a N(C$_{1-4}$-aliphatic residue)-S(=O)$_2$—C$_{1-4}$ aliphatic residue, =O, OH, OCH$_2$F, OCHF$_2$, OCF$_3$, a O—C$_{1-4}$-aliphatic residue, a O—C(=O)—C$_{1-4}$-aliphatic residue, SH, SCF$_3$, a S—C$_{1-4}$-aliphatic residue, S(=O)$_2$OH, a S(=O)—C$_{1-4}$-aliphatic residue, a S(=O)$_2$—C$_{1-4}$-aliphatic residue, a S(=O)$_2$—O—C$_{1-4}$-aliphatic residue, a S(=O)$_2$—NH—C$_{1-4}$—C$_{1-4}$-aliphatic residue, a S(=O)$_2$—N(C$_{1-4}$-aliphatic residue)$_2$, CN, CH$_2$F, CHF$_2$, CF$_3$, CHO, COOH, a C$_{1-4}$-aliphatic residue, CH$_2$OH, CH$_2$—OCH$_3$, C$_2$H$_4$—OH, C$_2$H$_4$—OCH$_3$CH$_2$—CF$_3$, a C(=O)—C$_{1-4}$-aliphatic residue, a C(=O)—O—C$_{1-4}$-aliphatic residue, a C$_{3-6}$-cycloaliphatic residue, a 3 to 6 membered heterocycloaliphatic residue, C(=O)—NH$_2$, a C(=O)—NH(C$_{1-4}$ aliphatic residue), and a C(=O)—N(C$_{1-4}$ aliphatic residue)$_2$;
in which "mono- or polysubstituted" with respect to "aryl" and a "heteroaryl" relates, with respect to the corresponding residues, to the substitution of one or more hydrogen atoms each independently of one another by at least one substituent selected from the group consisting of F, Cl, Br, I, NO$_2$, NH$_2$,

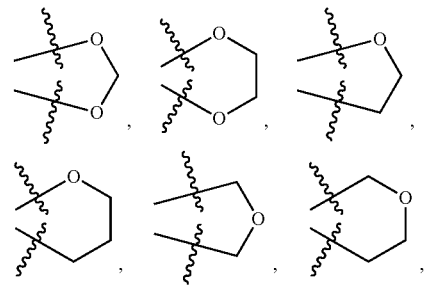

an NH(C$_{1-4}$ aliphatic residue), an N(C$_{1-4}$ aliphatic residue)$_2$, an NH—C(=O)—C$_{1-4}$ aliphatic residue, a N(C$_{1-4}$-aliphatic residue)-C(=O)—C$_{1-4}$ aliphatic residue, an NH—S(=O)$_2$—C$_{1-4}$ aliphatic residue, a N(C$_{1-4}$-aliphatic residue)-S(=O)$_2$—C$_{1-4}$ aliphatic residue, OH, OCF$_3$, OCFH$_2$, OCF$_2$H, a O—C$_{1-4}$-aliphatic residue, a O—C(=O)—C$_{1-4}$-aliphatic residue, SH, SCF$_3$, a S—C$_{1-4}$-aliphatic residue, S(=O)$_2$OH, a S(=O)—C$_{1-4}$-aliphatic residue, a S(=O)$_2$—C$_{1-4}$-aliphatic residue, a S(=O)$_2$—O—C$_{1-4}$-aliphatic residue, a S(=O)$_2$—NH—C$_{1-4}$-aliphatic residue, a S(=O)$_2$—N(C$_{1-4}$-aliphatic residue)$_2$, CN, CF$_3$, CF$_2$H, CHF$_2$, C(=O)H, C(=O)OH, a C$_{1-4}$-aliphatic residue, CH$_2$OH, CH$_2$—OCH$_3$, C$_2$H$_4$—OH, C$_2$H$_4$—OCH$_3$, a C(=O)—C$_{1-4}$-aliphatic residue, a C(=O)—O—C$_{1-4}$-aliphatic residue, a C$_{3-6}$-cycloaliphatic residue, a 3 to 6 membered heterocycloaliphatic residue, benzyl, aryl, heteroaryl, C(=O)—NH$_2$, a C(=O)—NH(C$_{1-4}$ aliphatic residue), and a C(=O)—N(C$_{1-4}$ aliphatic residue)$_2$;

optionally in the form of a single stereoisomer or a mixture of stereoisomers, in the form of the free compound and/or a physiologically acceptable salt thereof.

2. The compound according to claim 1, wherein

R$^1$ denotes a C$_{1-10}$-aliphatic residue, unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$-aliphatic residue, OCH$_2$F, OCHF$_2$, OCF$_3$, SH, SCF$_3$, a S—C$_{1-4}$-aliphatic residue, a S(=O)—C$_{1-4}$-aliphatic a S(=O)$_2$—C$_{1-4}$-aliphatic residue, CH$_2$F, CHF$_2$, CF$_3$, CN, a C$_{1-4}$-aliphatic residue and C(=O)—OH, wherein the C$_{1-4}$-aliphatic residue in each case may be unsubstituted or mono- or polysubstituted with at least one substituent selected from the group consisting of F, Cl, Br, I, OH, OCH$_2$F, OCHF$_2$, OCF$_3$, CH$_2$F, CHF$_2$, CF$_3$ and an unsubstituted O—C$_{1-4}$-aliphatic residue, or denotes a C$_{3-10}$-cycloaliphatic residue or a 3 to 10 membered heterocycloaliphatic residue, in each case unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCH$_2$F, OCHF$_2$, OCF$_3$, SH, SCF$_3$, a S—C$_{1-4}$ aliphatic residue, a S(=O)—C$_{1-4}$-aliphatic residue, a S(=O)$_2$—C$_{1-4}$-aliphatic residue, CH$_2$F, CHF$_2$, CF$_3$, CN, a C$_{1-4}$-aliphatic residue, C(=O)—OH, a C$_{3-6}$-cycloaliphatic residue, and a 3 to 6 membered heterocycloaliphatic residue, wherein the C$_{1-4}$-aliphatic residue in each case may be unsubstituted or mono- or polysubstituted with at least one substituent selected from the group consisting of F, Cl, Br, I, OH, OCH$_2$F, OCHF$_2$, OCF$_3$, CH$_2$F, CHF$_2$, CF$_3$ and an unsubstituted O—C$_{1-4}$-aliphatic residue, and wherein the C$_{3-6}$ cycloaliphatic residue and the 3 to 6 membered heterocycloaliphatic residue may in each case be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCH$_2$F, OCHF$_2$, OCF$_3$, SH, SCF$_3$, a S—C$_{1-4}$ aliphatic residue, a S(=O)—C$_{1-4}$-aliphatic residue, a S(=O)$_2$—C$_{1-4}$-aliphatic residue, CH$_2$F, CHF$_2$, CF$_3$, CN, a C$_{1-4}$-aliphatic residue and C(=O)—OH, and wherein the C$_{3-10}$-cycloaliphatic residue or the 3 to 10 membered heterocycloaliphatic residue may in each case be optionally bridged via a C$_{1-8}$ aliphatic group, which in turn may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCH$_2$F, OCHF$_2$, OCF$_3$, SH, SCF$_3$, a S—C$_{1-4}$ aliphatic residue, a S(=O)—C$_{1-4}$-aliphatic residue, a S(=O)$_2$—C$_{1-4}$-aliphatic residue, CH$_2$F, CHF$_2$, CF$_3$, CN, a C$_{1-4}$-aliphatic residue and C(=O)—OH, or denotes an aryl or heteroaryl, in each case unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, an O—C$_{1-4}$ aliphatic residue, OCH$_2$F, OCHF$_2$, OCF$_3$, SH, SCF$_3$, a S—C$_{1-4}$ aliphatic residue, a S(=O)—C$_{1-4}$-aliphatic residue, a S(=O)$_2$—C$_{1-4}$-aliphatic residue, CH$_2$F, CHF$_2$, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, a C$_{3-6}$ cycloaliphatic residue, a 3 to 6 membered heterocycloaliphatic residue,

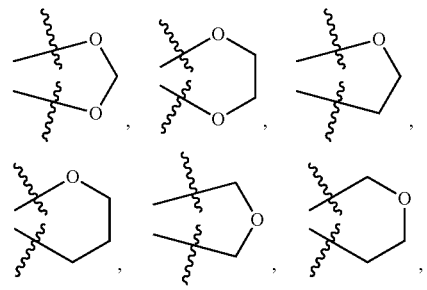

benzyl, phenyl, thienyl, pyridyl, furyl, thiazolyl and oxazolyl, wherein the C$_{1-4}$-aliphatic residue in each case may be unsubstituted or mono- or polysubstituted with at least one substituent selected from the group consisting of F, Cl, Br, I, OH, OCH$_2$F, OCHF$_2$, OCF$_3$, CH$_2$F, CHF$_2$, CF$_3$ and an unsubstituted O—C$_{1-4}$-aliphatic residue, and wherein benzyl, phenyl, thienyl, pyridyl, furyl, thiazolyl and oxazolyl may in each case be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, an O—C$_{1-4}$ aliphatic residue, OCH$_2$F, OCHF$_2$, OCF$_3$, O—CH$_2$—OH, O—CH$_2$—O—CH$_3$, SH, SCF$_3$, a S—C$_{1-4}$ aliphatic residue, a S(=O)—C$_{1-4}$-aliphatic residue, a S(=O)$_2$—C$_{1-4}$-aliphatic residue, CH$_2$F, CHF$_2$, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, and wherein the C$_{3-6}$ cycloaliphatic residue and the 3 to 6 membered heterocycloaliphatic residue may in each case be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCH$_2$F, OCHF$_2$, OCF$_3$, SH, SCF$_3$, a S—C$_{1-4}$ aliphatic residue, a S(=O)—C$_{1-4}$-aliphatic residue, a S(=O)$_2$—C$_{1-4}$-aliphatic residue, CH$_2$F, CHF$_2$, CF$_3$, CN, a C$_{1-4}$-aliphatic residue and C(=O)—OH, and wherein the aryl or the heteroaryl residue may in each case be optionally bridged via a C$_{1-8}$ aliphatic group, which in turn may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCH$_2$F, OCHF$_2$, OCF$_3$, SH, SCF$_3$, a S—C$_{1-4}$ aliphatic residue, a S(=O)—C$_{1-4}$-aliphatic residue, a S(=O)$_2$—C$_{1-4}$-aliphatic residue, CH$_2$F, CHF$_2$, CF$_3$, CN and C(=O)—OH, $R^2$ represents F; Cl; Br; I; CN; $CH_2F$, $CHF_2$, $CF_3$; $NO_2$; $OCH_2F$, $OCHF_2$, $OCF_3$; $SCF_3$; a $C_{1-4}$-aliphatic residue, a S—$C_{1-4}$-aliphatic residue, a S(=O)—$C_{1-4}$-aliphatic residue, a S(=O)$_2$—$C_{1-4}$-aliphatic residue, or a O—$C_{1-4}$-aliphatic residue, wherein the $C_{1-4}$-aliphatic residue in each case may be unsubstituted or mono- or polysubstituted with at least one substituent selected from the group consisting of F, Cl, Br, I, =O, OH, and an unsubstituted O—$C_{1-4}$-aliphatic residue; a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a $C_{1-4}$-aliphatic residue and an O—$C_{1-4}$-aliphatic residue, wherein the $C_{1-4}$-aliphatic residue in each case may be unsubstituted or mono- or polysubstituted with at least one substituent selected from the group consisting of F, Cl, Br, I, =O, OH, and an unsubstituted O—$C_{1-4}$-aliphatic residue, and wherein the $C_{3-6}$-cycloaliphatic residue or the 3 to 6 membered heterocycloaliphatic residue may in each case be optionally bridged via a $C_{1-4}$ aliphatic group, which in turn may be unsubstituted or mono- or polysubstituted with at least one substituent selected from the group consisting of F, Cl, Br, I, =O, OH, an unsubstituted $C_{1-4}$-aliphatic residue and an unsubstituted O—$C_{1-4}$-aliphatic residue, $R^3$ represents H; F; Cl; Br; I; CN; $CH_2F$, $CHF_2$, $CF_3$; $SCF_3$; $NO_2$; $OCH_2F$, $OCHF_2$, $OCF_3$; a $C_{1-4}$-aliphatic residue, a O—$C_{1-4}$-aliphatic residue, a S—$C_{1-4}$-aliphatic residue, a S(=O)—$C_{1-4}$-aliphatic residue, a S(=O)$_2$—$C_{1-4}$-aliphatic residue,
  wherein the $C_{1-4}$ aliphatic residue may in each case be unsubstituted or mono- or polysubstituted with at least one substituent selected from the group consisting of F, Cl, Br, I, =O, OH, and an unsubstituted O—$C_{1-4}$-aliphatic residue;
a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a $C_{1-4}$-aliphatic residue and a O—$C_{1-4}$-aliphatic residue,
  wherein the $C_{1-4}$-aliphatic residue in each case may be unsubstituted or mono- or polysubstituted with at least one substituent selected from the group consisting of F, Cl, Br, I, =O, OH, and an unsubstituted O—$C_{1-4}$-aliphatic residue,
and wherein the $C_{3-6}$-cycloaliphatic residue or the 3 to 6 membered heterocycloaliphatic residue may in each case be optionally bridged via a $C_{1-4}$ aliphatic group, which in turn may be unsubstituted or mono- or polysubstituted with at least one substituent selected from the group consisting of F, Cl, Br, I, =O, OH, an unsubstituted $C_{1-4}$-aliphatic residue and an unsubstituted O—$C_{1-4}$-aliphatic residue, $R^4$ and $R^5$ form together with the nitrogen atom connecting them a ring selected from the group consisting of morpholinyl, piperidinyl, pyrrolidinyl, azetidinyl, oxazepanyl, tetrahydroquinolinyl and tetrahydroquinolinyl, each of which is unsubstituted or mono -or polysubstituted by one or more substituents independently selected from the group consisting of F, Cl, OH, =O, C(=O)—OH, O-methyl, O-ethyl, $OCF_3$, $OCH_2F$, $OCHF_2$, $SCF_3$, $CH_2F$, $CHF_2$, $CF_3$, methyl, ethyl, n-propyl, 2-propyl, cyclopropyl and cyclobutyl;

$R^6$ represents H; F; Cl; Br; I; CN; $CH_2F$; $CHF_2$; $CF_3$; $SCF_3$; $NO_2$; $OCH_2F$; $OCHF_2$; $OCF_3$; a $C_{1-4}$-aliphatic residue, a O—$C_{1-4}$-aliphatic residue, a S—$C_{1-4}$-aliphatic residue, a S(=O)—$C_{1-4}$-aliphatic residue, or a S(=O)$_2$—$C_{1-4}$-aliphatic residue,
  wherein the $C_{1-4}$-aliphatic residue in each case may be unsubstituted or mono- or polysubstituted with at least one substituent selected from the group consisting of F, Cl, Br, I, =O, OH, and an unsubstitutend O—$C_{1-4}$-aliphatic residue;
a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a ($C_{1-4}$-aliphatic residue), and a O—$C_{1-4}$-aliphatic residue,
  wherein the $C_{1-4}$-aliphatic residue in each case may be unsubstituted or mono- or polysubstituted with at least one substituent selected from the group consisting of F, Cl, Br, I, =O, OH, and an unsubstituted O—$C_{1-4}$-aliphatic residue,
and wherein the $C_{3-6}$ cycloaliphatic residue or the 3 to 6 membered heterocycloaliphatic residue may in each case be optionally bridged via a $C_{1-4}$ aliphatic group, which in turn may be unsubstituted or mono- or polysubstituted with at least one substituent selected from the group consisting of F, Cl, Br, I, =O, OH, an unsubstituted $C_{1-4}$ -aliphatic residue and an unsubstituted O—$C_{1-4}$-aliphatic residue, $R^7$ denotes $CF_3$, $CHF_2$ $CH_2F$, $CF_2Cl$, $CFCl_2$, $CH_2OH$, $CH_2OCH_3$, a $C_{2-10}$-aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCH_2F$, $OCHF_2$, $OCF_3$, SH, $SCF_3$, a S—$C_{1-4}$ -aliphatic residue, a S(=O)—$C_{1-4}$-aliphatic residue, a S(=O)$_2$—$C_{1-4}$-aliphatic residue, CN, a $C_{1-4}$-aliphatic residue and C(=O)—OH,
  wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an Unsubstituted O—$C_{1-4}$-aliphatic residue,
or denotes a $C_{3-10}$-cycloaliphatic residue or a 3 to 10 membered heterocycloaliphatic residue in each case be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a S(=O)$_2$—$C_{1-4}$-aliphatic residue, $CH_2F$, $CHF_2$, $CF_3$, CN, a $C_{1-4}$-aliphatic residue, and C(=O)—OH,
  wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue, and
wherein the $C_{3-10}$-cycloaliphatic residue or the 3 to 10 membered heterocycloaliphatic Residue may in each case be optionally bridged via a $C_{1-8}$ aliphatic group, which in turn may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a $S(=O)_2$—$C_{1-4}$-aliphatic residue, $CH_2F$, $CHF_2$, $CF_3$, CN, a $C_{1-4}$-aliphatic residue and C(=O)—OH, prvided that if $R^7$ denotes a 3 to 10 membered heterocycloaliphatic residue, the binding is carried out via a carbon atom of the 3 to 10 membered heterocycloaliphatic residue, or $R^7$ denotes S—$R^{8a}$, S(=O)—$R^{8b}$, $S(=O)_2$—$R^{8c}$, O—$R^9$ or $N(R^{10}R^{11})$, wherein $R^{8a}$, $R^{8b}$, $R^{8c}$ and $R^9$ in each case represent a $C_{1-10}$-aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$-aliphatic residue, $OCH_2F$, $OCHF_2$, $OCF_3$, SH, $SCF_3$, a S—$C_{1-4}$-aliphatic residue, a S(=O)—$C_{1-4}$-aliphatic residue, a $S(=O)_2$—$C_{1-4}$-aliphatic residue, $CH_2F$, $CHF_2$, $CF_3$, CN, a $C_{1-4}$-aliphatic residue and C(=O)—OH, wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue, or in each case represent a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a $S(=O)_2$—$C_{1-4}$-aliphatic residue, $CH_2F$, $CHF_2$, $CF_3$, CN, a $C_{1-4}$-aliphatic residue, C(=O)—OH, a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue, and wherein the $C_{3-6}$ cycloaliphatic residue and the 3 to 6 membered heterocycloaliphatic residue may in each case be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a $S(=O)_2$—$C_{1-4}$-aliphatic residue, $CH_2F$, $CHF_2$, $CF_3$, CN, a $C_{1-4}$-aliphatic residue and C(=O)—OH, and wherein the $C_{3-10}$-cycloaliphatic residue or the 3 to 10 membered heterocycloaliphatic residue may in each case be optionally bridged via a $C_{1-8}$ aliphatic group, which in turn may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a $S(=O)_2$—$C_{1-4}$-aliphatic residue, $CH_2F$, $CHF_2$, $CF_3$, CN, a $C_{1-4}$-aliphatic residue and C(=O)—OH, provided that if $R^{8a}$, $R^{8b}$, $R^{8c}$ or $R^9$ denotes a 3 to 10 membered heterocycloaliphatic residue, the binding is carried out via a carbon atom of the 3 to 10 membered heterocycloaliphatic residue, $R^{10}$ denotes a $C_{1-10}$-aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$-aliphatic residue, $OCH_2F$, $OCHF_2$, $OCF_3$, SH, $SCF_3$, a S—$C_{1-4}$-aliphatic residue, a S(=O)—$C_{1-4}$-aliphatic residue, a $S(=O)_2$—$C_{1-4}$-aliphatic residue, $CH_2F$, $CHF_2$, $CF_3$, CN, a $C_{1-4}$-aliphatic residue, a C(=O)—O—$C_{1-4}$-aliphatic residue, and C(=O)—OH, wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a $S(=O)_2$—$C_{1-4}$-aliphatic residue, $CH_2F$, $CHF_2$, $CF_3$, CN, a $C_{1-4}$-aliphatic residue, C(=O)—OH, a C(=O)—O—$C_{1-4}$-aliphatic residue a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue, and wherein the $C_{3-6}$ cycloaliphatic residue and the 3 to 6 membered heterocycloaliphatic residue may in each case be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a $S(=O)_2$—$C_{1-4}$-aliphatic residue, $CH_2F$, $CHF_2$, $CF_3$, CN, a $C_{1-4}$-aliphatic residue and C(=O)—OH, and wherein the $C_{3-10}$-cycloaliphatic residue or the 3 to 10 membered heterocycloaliphatic residue may in each case be optionally bridged via a $C_{1-8}$ aliphatic group, which in turn may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$ aliphatic residue, a C(=O)—O—$C_{1-4}$-aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a $S(=O)_2$—$C_{1-4}$-aliphatic residue, $CH_2F$, $CHF_2$, $CF_3$, CN, a $C_{1-4}$-aliphatic residue and C(=O)—OH, provided that if $R^{10}$ denotes a 3 to 10 membered heterocycloaliphatic residue, the binding is carried out via a carbon atom of the 3 to 10 membered heterocycloaliphatic residue, $R^{11}$ denotes H or a $C_{1-10}$-aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a $S(=O)_2$—$C_{1-4}$-aliphatic residue, $CH_2F$, $CHF_2$, $CF_3$, CN, a $C_{1-4}$-aliphatic residue and C(=O)—OH, wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue, or $R^{10}$ and $R^{11}$ form together with the nitrogen atom connecting them a 3 to 10 membered heterocycloaliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a $S(=O)_2$—$C_{1-4}$-aliphatic residue, $CH_2F$, $CHF_2$, $CF_3$, CN, a $C_{1-4}$-aliphatic residue, C(=O)—OH, a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-6}$ cycloaliphatic residue and the 3 to 6 membered heterocycloaliphatic residue may in each case be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a $S(=O)_2$—$C_{1-4}$-aliphatic residue, $CH_2F$, $CHF_2$, $CF_3$, CN, a $C_{1-4}$-aliphatic residue and C(=O)—OH, and wherein the 3 to 10 membered heterocycloaliphatic residue formed by $R^{10}$ and $R^{11}$ together with the nitrogen atom connecting them may optionally be condensed with aryl or heteroaryl, wherein the aryl or heteroaryl residues condensed in this way can for their part be respectively unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a $S(=O)_2$—$C_{1-4}$-aliphatic residue, $CH_2F$, $CHF_2$, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, a $C_{3-6}$ cycloaliphatic residue, a 3 to 6 membered heterocycloaliphatic residue,

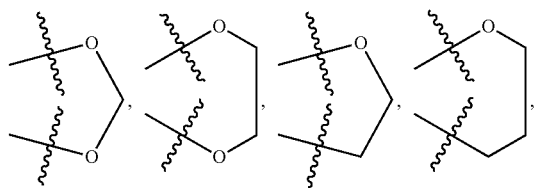 [SMILES: *OCO* ; *OCCO* ; *CCO* ; *CCCO*]

benzyl, phenyl, thienyl, pyridyl, furyl, thiazolyl and oxazolyl, wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue, and wherein benzyl, phenyl, thienyl, pyridyl, furyl, thiazolyl and oxazolyl may in each case be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, an O—$C_{1-4}$ aliphatic residue, $OCH_2F$, $OCHF_2$, $OCF_3$, O—$CH_2$—OH, O—$CH_2$—O—$CH_3$, SH, $SCF_3$, a S—$C_{1-4}$ aliphatic residue, a S(=O)—$C_{1-4}$-aliphatic residue, a $S(=O)_2$—$C_{1-4}$-aliphatic residue, $CH_2F$, $CHF_2$, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, and wherein the $C_{3-6}$ cycloaliphatic residue and the 3 to 6 membered heterocycloaliphatic residue may in each case be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, a $S(=O)_2$—$C_{1-4}$-aliphatic residue, $CH_2F$, $CHF_2$, $CF_3$, CN, a $C_{1-4}$-aliphatic residue and C(=O)—OH.

3. The compound according to claim 1, wherein $R^1$ represents the partial structure (T1)

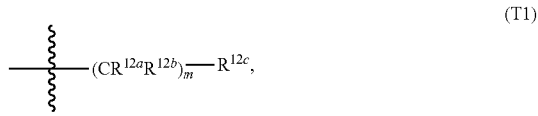

wherein m denotes 0, 1, 2, 3 or 4, $R^{12a}$ and $R^{12b}$ each independently of one another represent H, F, Cl, Br, I, $NO_2$, $NH_2$, a $NH(C_{1-4}$ aliphatic residue), an $N(C_{1-4}$ aliphatic residue)$_2$, OH, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, or a $S(=O)_2$—$C_{1-4}$-aliphatic residue, $CH_2F$, $CHF_2$, $CF_3$, CN, a $C_{1-4}$ aliphatic residue or C(=O)—OH, or together denote =O, and $R^{12c}$ denotes a $C_{1-4}$ aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—C$_{1-4}$ aliphatic residue, OCH$_2$F, OCHF$_2$, OCF$_3$, SH, SCF$_3$, a S—C$_{1-4}$ aliphatic residue, a S(=O)—C$_{1-4}$-aliphatic residue, or a S(=O)$_2$—C$_{1-4}$-aliphatic residue, CH$_2$F, CHF$_2$, CF$_3$, CN, a C$_{1-4}$-aliphatic residue and C(=O)—OH, or denotes a C$_{3-10}$-cycloaliphatic residue or a 3 to 10 membered heterocycloaliphatic residue, in each case unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCH$_2$F, OCHF$_2$, OCF$_3$, SH, SCF$_3$, a S—C$_{1-4}$ aliphatic residue, a S(=O)—C$_{1-4}$-aliphatic residue, or a S(=O)$_2$—C$_{1-4}$-aliphatic residue, CH$_2$F, CHF$_2$, CF$_3$, CN, a C$_{1-4}$-aliphatic residue, C(=O)—OH, a C$_{3-6}$ cycloaliphatic residue and a 3 to 6 membered heterocycloaliphatic residue, wherein the C$_{1-4}$-aliphatic residue in each case may be unsubstituted or mono- or polysubstituted with at least one substituent selected from the group consisting of F, Cl, Br, I, OH, OCH$_2$F, OCHF$_2$, OCF$_3$, CH$_2$F, CHF$_2$, CF$_3$ and an unsubstituted O—C$_{1-4}$-aliphatic residue, and wherein the C$_{3-6}$ cycloaliphatic residue and the 3 to 6 membered heterocycloaliphatic residue may in each case be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCH$_2$F, OCHF$_2$, OCF$_3$, SH, SCF$_3$, a S—C$_{1-4}$ aliphatic residue, a S(=O)—C$_{1-4}$-aliphatic residue, or a S(=O)$_2$—C$_{1-4}$-aliphatic residue, CH$_2$F, CHF$_2$, CF$_3$, CN, a C$_{1-4}$-aliphatic residue and C(=O)—OH, or denotes an aryl or heteroaryl, in each case unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, an O—C$_{1-4}$ aliphatic residue, OCH$_2$F, OCHF$_2$, OCF$_3$, SH, SCF$_3$, a S—C$_{1-4}$ aliphatic residue, a S(=O)—C$_{1-4}$-aliphatic residue, or a S(=O)$_2$—C$_{1-4}$-aliphatic residue, CH$_2$F, CHF$_2$, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, a C$_{3-6}$ cycloaliphatic residue, a 3 to 6 membered heterocycloaliphatic residue,

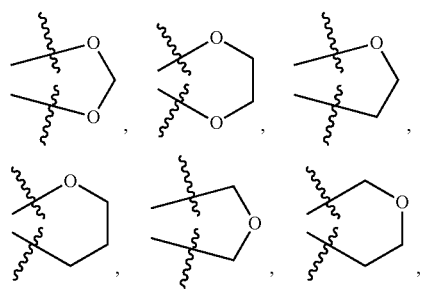

benzyl, phenyl, thienyl, pyridyl, furyl, thiazolyl and oxazolyl, wherein the C$_{1-4}$-aliphatic residue in each case may be unsubstituted or mono- or polysubstituted with at least one substituent selected from the group consisting of F, Cl, Br, I, OH, OCH$_2$F, OCHF$_2$, OCF$_3$, CH$_2$F, CHF$_2$, CF$_3$ and an unsubstituted O—C$_{1-4}$-aliphatic residue, and wherein benzyl, phenyl, thienyl, pyridyl, furyl, thiazolyl and oxazolyl may in each case be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, an O—C$_{1-4}$ aliphatic residue, OCH$_2$F, OCHF$_2$, OCF$_3$, SH, SCF$_3$, a S—C$_{1-4}$ aliphatic residue, a S(=O)—C$_{1-4}$-aliphatic residue, or a S(=O)$_2$—C$_{1-4}$-aliphatic residue, CH$_2$F, CHF$_2$, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, and wherein the C$_{3-6}$ cycloaliphatic residue and the 3 to 6 membered heterocycloaliphatic residue may in each case be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCH$_2$F, OCHF$_2$, OCF$_3$, SH, SCF$_3$, a S—C$_{1-4}$ aliphatic residue, a S(=O)—C$_{1-4}$-aliphatic residue, or a S(=O)$_2$—C$_{1-4}$-aliphatic residue, CH$_2$F, CHF$_2$, CF$_3$, CN, a C$_{1-4}$-aliphatic residue and C(=O)—OH.

4. The compound according to claim 1, wherein R$^1$ represents the partial structure (T1),

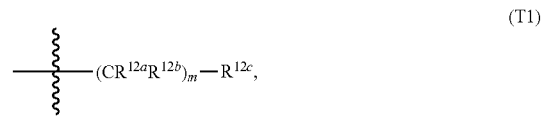

(T1)

wherein m denotes 0, 1, or 2 or 3,

R$^{12a}$ and R$^{12b}$ each independently of one another represent H, F, Cl, Br, I, OH, an O—C$_{1-4}$ aliphatic residue or a C$_{1-4}$ aliphatic residue or together denote =O, and R$^{12c}$ denotes a C$_{1-4}$ aliphatic residue, unsubstituted or mono- or polysubstituted with at least one substituent selected from the group consisting of F, Cl, Br, I, OH, an O—C$_{1-4}$ aliphatic residue, CN, a S(=O)—C$_{1-4}$-aliphatic residue, or a S(=O)$_2$—C$_{1-4}$-aliphatic residue, CH$_2$F, CHF$_2$, CF$_3$, and a C$_{1-4}$-aliphatic residue, wherein the C$_{1-4}$-aliphatic residue in each case may be unsubstituted or mono- or polysubstituted with at least one substituent selected from the group consisting of F, Cl, CH$_2$F, CHF$_2$, CF$_3$ and an unsubstituted O—C$_{1-4}$-aliphatic residue, or denotes a C$_{3-10}$-cycloaliphatic residue or a 3 to 10 membered heterocycloaliphatic residue, in each case unsubstituted or mono- or polysubstituted with at least one substituent selected from the group consisting of F, Cl, Br, I, an O—C$_{1-4}$ aliphatic residue, CH$_2$F, CHF$_2$, CF$_3$, and a C$_{1-4}$-aliphatic residue, wherein the C$_{1-4}$-aliphatic residue in each case may be unsubstituted or mono- or polysubstituted with at least one substituent selected from the group consisting of F, Cl, CH$_2$F, CHF$_2$, CF$_3$ and an unsubstituted O—C$_{1-4}$-aliphatic residue, or an aryl or heteroaryl, in each case unsubstituted or mono- or polysubstituted with at least one substituent selected from the group consisting of F, Cl, Br, I, OH, an O—C$_{1-4}$ aliphatic residue, OCF$_3$, OCH$_2$F, OCHF$_2$, $CH_2F$, $CHF_2$, $CF_3$, CN, a $C_{1-4}$-aliphatic residue, $CH_2$—OH, $CH_2$—$OCH_3$, $S(=O)_2$—$CH_3$, $SCF_3$, $NO_2$, $N(C_{1-4}$ aliphatic residue$)_2$,

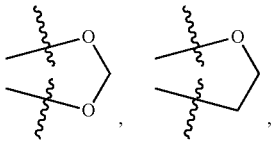 [SMILES: *OCO* ; *CCO*]

$C(=O)$—$CH_3$, $C(=O)$—$C_2H_5$, $C(=O)$—O—O—$CH_3$ and $C(=O)$—O—$C_2H_5$, a $C_{3-6}$ cycloaliphatic residue, a 3 to 6 membered heterocycloaliphatic residue, benzyl, phenyl, thienyl or pyridyl, wherein benzyl, phenyl, thienyl and pyridyl, may in each case be unsubstituted or mono- or polysubstituted with at least one substituent selected from the group consisting of F, Cl, Br, I, OH, an O—$C_{1-4}$ aliphatic residue, $OCH_2F$, $OCHF_2$, $OCF_3$, $CH_2F$, $CHF_2$, $CF_3$, CN, a $C_{1-4}$-aliphatic residue, $C(=O)$—$CH_3$, $C(=O)$—$C_2H_5$, $C(=O)$—O—$CH_3$ and $C(=O)$—O—$C_2H_5$, and wherein the $C_{3-6}$ cycloaliphatic residue and the 3 to 6 membered heterocycloaliphatic residue may in each case be unsubstituted or mono- or polysubstituted with at least one substituent selected from the group consisting of F, Cl, Br, I, OH, =O, an O—$C_{1-4}$ aliphatic residue, $OCH_2F$, $OCHF_2$, $OCF_3$, $CH_2F$, $CHF_2$, $CF_3$ a $C_{1-4}$-aliphatic residue and $C(=O)$—OH.

5. The compound according to claim 1, wherein
$R^2$ represents F; Cl; Br; I; CN; $CH_2F$, $CHF_2$, $CF_3$; $NO_2$; $OCH_2F$, $OCHF_2$, $OCF_3$; $SCF_3$; a $C_{1-4}$-aliphatic residue, a S—$C_{1-4}$-aliphatic residue, a $S(=O)$—$C_{1-4}$-aliphatic residue, or a $S(=O)_2$—$C_{1-4}$-aliphatic residue, or a O—$C_{1-4}$-aliphatic residue, wherein the $C_{1-4}$-aliphatic residue in each case may be unsubstituted or mono- or polysubstituted with at least one substituent selected from the group consisting of F, Cl, Br, I, =O, OH, and an unsubstituted O—$C_{1-4}$-aliphatic residue, or denotes cyclopropyl, cyclobutyl, cyclopentyl, cyclohexyl, pyrrolidinyl, piperazinyl, 4-methylpiperazinyl, morpholinyl, or piperidinyl, in each case unsubstituted or mono- or polysubstituted with at least one substituent selected from the group consisting of F, Cl, Br, I, =O, OH, an unsubstituted $C_{1-4}$-aliphatic residue and an unsubstituted O—$C_{1-4}$-aliphatic residue, and wherein cyclopropyl, cyclobutyl, cyclopentyl, cyclohexyl, pyrrolidinyl, piperazinyl, 4-methylpiperazinyl, morpholinyl or piperidinyl may in each case be optionally bridged via an $C_{1-4}$ aliphatic group, which in turn may be unsubstituted or mono- or polysubstituted with at least one substituent selected from the group consisting of F, Cl, OH, an unsubstituted $C_{1-4}$-aliphatic residue and an unsubstituted O—$C_{1-4}$-aliphatic residue.

6. The compound according to claim 1, wherein
$R^3$ and $R^6$ independently of one another represent H; F; Cl; Br; I; CN; $CH_2F$, $CHF_2$, $CF_3$; $SCF_3$; $NO_2$; $OCH_2F$, $OCHF_2$, $OCF_3$; a $C_{1-4}$-aliphatic residue, a O—$C_{1-4}$-aliphatic residue, a $S(=O)$—$C_{1-4}$-aliphatic residue, or a $S(=O)_2$—$C_{1-4}$-aliphatic residue, or a S—$C_{1-4}$-aliphatic residue, wherein the $C_{1-4}$ aliphatic residue may be in each case be unsubstituted or mono- or polysubstituted with at least one substituent selected from the group consisting of F, Cl, Br, I, =O, OH, and an unsubstituted O—$C_{1-4}$-aliphatic residue.

7. The compound according to claim 1, wherein
$R^7$ denotes $CF_3$, $CHF_2$, $CH_2F$, $CF_2Cl$, $CFCl_2$, $CH_2OH$, $CH_2OCH_3$, a $C_{2-8}$-aliphatic residue, unsubstituted or mono- or polysubstituted with at least one substituent selected from the group consisting of F, Cl, Br, I, OH, =O, an O—$C_{1-4}$-aliphatic residue, $OCH_2F$, $OCHF_2$, $OCF_3$, SH, $SCF_3$, a S—$C_{1-4}$-aliphatic residue, a $S(=O)$—$C_{1-4}$-aliphatic residue, or a $S(=O)_2$—$C_{1-4}$-aliphatic residue, a $C(=O)$—O—$C_{1-4}$-aliphatic residue, $CF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $CH_2F$, $CHF_2$, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, $OCH_2F$, $OCHF_2$, $OCF_3$, $SCF_3$, a $C(=O)$—O—$C_{1-4}$-aliphatic residue, a S—$C_{1-4}$ aliphatic residue, a $S(=O)$—$C_{1-4}$-aliphatic residue, or a $S(=O)_2$—$C_{1-4}$-aliphatic residue, $CH_2F$, $CHF_2$, $CF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue, and and wherein the $C_{3-10}$-cycloaliphatic residue or the 3 to 10 membered heterocycloaliphatic residue may in each case be optionally bridged via a $C_{1-8}$ aliphatic group, which in turn may be unsubstituted or mono- or polysubstituted with at least one substituent selected from the group consisting of F, Cl, Br, I, OH, =O, an O—$C_{1-4}$ aliphatic residue, $OCH_2F$, $OCHF_2$, $OCF_3$, SH, $SCF_3$, a S—$C_{1-4}$ aliphatic residue, a $S(=O)$—$C_{1-4}$-aliphatic residue, or a $S(=O)_2$—$C_{1-4}$-aliphatic residue, a $C(=O)$—O—$C_{1-4}$-aliphatic residue, $CH_2F$, $CHF_2$, $CF_3$, CN, and a $C_{1-4}$-aliphatic residue, provided that if $R^7$ denotes a 3 to 10 membered heterocycloaliphatic residue, the 3 to 10 membered heterocycloaliphatic residue is linked via a carbon atom, or
$R^7$ denotes S—$R^{8a}$, $S(=O)$—$R^{8b}$, $S(=O)_2$—$R^{8c}$ or O—$R^9$, wherein
$R^{8a}$, $R^{8b}$, $R^{8c}$ and $R^9$ in each case denote a $C_{1-8}$-aliphatic residue, unsubstituted or mono- or polysubstituted with at least one substituent selected from the group consisting of F, Cl, Br, I, OH, =O, an O—$C_{1-4}$-aliphatic residue, $OCH_2F$, $OCHF_2$, $OCF_3$, SH, $SCF_3$, a S—$C_{1-4}$-aliphatic residue, a $S(=O)$—$C_{1-4}$-aliphatic residue, or a $S(=O)_2$—$C_{1-4}$-aliphatic residue, an $NH(C_{1-4}$ aliphatic residue), an $N(C_{1-4}$ aliphatic residue$)_2$, $CH_2F$, $CHF_2$, $CF_3$, a $C(=O)$—O—$C_{1-4}$-aliphatic residue, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $CH_2F$, $CHF_2$, $CF_3$ and an unsubstituted O—$C_{1-4}$-aliphatic residue, or in each case denote a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, $OCH_2F$, $OCHF_2$, $OCF_3$, $SCF_3$, a S—$C_{1-4}$ aliphatic residue, a S(=O)—$C_{1-4}$-aliphatic residue, or a $S(=O)_2$—$C_{1-4}$-aliphatic residue, a C(=O)—O—$C_{1-4}$-aliphatic residue, $CH_2F$, $CHF_2$, $CF_3$, and a $C_{1-4}$-aliphatic residue,
wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue, and
wherein the $C_{3-10}$-cycloaliphatic residue or the 3 to 10 membered heterocycloaliphatic residue may be bridged via a $C_{1-8}$ aliphatic group, which in turn may be unsubstituted or mono- or polysubstituted with at least one substituent selected from the group consisting of F, Cl, Br, I, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, or a $S(=O)_2$—$C_{1-4}$-aliphatic residue, a C(=O)—O—$C_{1-4}$-aliphatic residue, $CH_2F$, $CHF_2$, $CF_3$, CN, and a $C_{1-4}$-aliphatic residue, provided that if $R^{8a}$, $R^{8b}$, $R^{8c}$ and $R^9$ denotes a 3 to 10 membered heterocycloaliphatic residue, the 3 to 10 membered heterocycloaliphatic residue is linked via a carbon atom,
or
$R^7$ denotes N ($R^{10}R^{11}$),
wherein
$R^{10}$ denotes a $C_{1-8}$-aliphatic residue, unsubstituted or mono- or polysubstituted with at least one substituent selected from the group consisting of F, Cl, Br, I, OH, =O, an O—$C_{1-4}$-aliphatic residue, $OCH_2F$, $OCHF_2$, $OCF_3$, SH, $SCF_3$, a S—$C_{1-4}$-aliphatic residue, a S(=O)—$C_{1-4}$-aliphatic residue, or a $S(=O)_2$—$C_{1-4}$-aliphatic residue, $CH_2F$, $CHF_2$, $CF_3$, a C(=O)—O—$C_{1-4}$-aliphatic residue, and a $C_{1-4}$-aliphatic residue,
wherein the $C_{1-4}$-aliphatic residue in each case may be unsubstituted or mono- or polysubstituted with at least one substituent selected from the group consisting of F, Cl, Br, I, OH, $CH_2F$, $CHF_2$, $CF_3$ and an unsubstituted O—$C_{1-4}$-aliphatic residue,
or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, $OCH_2F$, $OCHF_2$, $OCF_3$, $SCF_3$, a S—$C_{1-4}$ aliphatic residue, a S(=O)—$C_{1-4}$-aliphatic residue, or a $S(=O)_2$—$C_{1-4}$-aliphatic residue, a C(=O)—O—$C_{1-4}$-aliphatic residue, $CH_2F$, $CHF_2$, $CF_3$, and a $C_{1-4}$-aliphatic residue,
wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue, and
wherein the $C_{3-10}$-cycloaliphatic residue or the 3 to 10 membered heterocycloaliphatic residue may in each case be bridged via a $C_{1-8}$ aliphatic group, which in turn may be unsubstituted or mono- or polysubstituted with at least one substituent selected from the group consisting of F, Cl, Br, I, OH, =O, an O—$C_{1-4}$ aliphatic residue, $OCH_2F$, $OCHF_2$, $OCF_3$, SH, $SCF_3$, a S—$C_{1-4}$ aliphatic residue, a C(=O)—O—$C_{1-4}$-aliphatic residue, $CH_2F$, $CHF_2$, $CF_3$, CN, and a $C_{1-4}$-aliphatic residue,
provided that if $R^9$ denotes a 3 to 10 membered heterocycloaliphatic residue, the 3 to 10 membered heterocycloaliphatic residue is linked via a carbon atom,
and
$R^{11}$ denotes H or a $C_{1-6}$-aliphatic residue, unsubstituted or mono- or polysubstituted with at least one substituent selected from the group consisting of F, Cl, Br, I, $NO_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, or a $S(=O)_2$—$C_{1-4}$-aliphatic residue, $CH_2F$, $CHF_2$, $CF_3$, CN, and a $C_{1-4}$-aliphatic residue,
wherein the $C_{1-4}$-aliphatic residue in each case may be unsubstituted or mono- or polysubstituted with at least one substituent selected from the group consisting of F, Cl, Br, I, OH, $CH_2F$, $CHF_2$, $CF_3$ and an unsubstituted O—$C_{1-4}$-aliphatic residue,
or
$R^{10}$ and $R^{11}$ form together with the nitrogen atom connecting them a 3 to 10 membered heterocycloaliphatic residue, unsubstituted or mono- or polysubstituted with at least one substituent selected from the group consisting of F, Cl, Br, I, $NO_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, or a $S(=O)_2$—$C_{1-4}$-aliphatic residue, $CH_2F$, $CHF_2$, $CF_3$, CN, and a $C_{1-4}$-aliphatic residue,
wherein the $C_{1-4}$-aliphatic residue in each case may be unsubstituted or mono- or polysubstituted with at least one substituent selected from the group consisting of F, Cl, Br, I, OH, $CH_2F$, $CHF_2$, $CF_3$ and an unsubstituted O—$C_{1-4}$-aliphatic residue,
and wherein the 3 to 10 membered heterocycloaliphatic residue formed by $R^{10}$ and $R^{11}$ together with the nitrogen atom connecting them may optionally be condensed with aryl or heteroaryl, wherein the aryl or heteroaryl residues condensed in this way can for their part be respectively unsubstituted or mono- or polysubstituted with at least one substituent selected from the group consisting of F, Cl, Br, I, $NO_2$, OH, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, or a $S(=O)_2$—$C_{1-4}$-aliphatic residue, $CH_2F$, $CHF_2$, $CF_3$, CN, a $C_{1-4}$-aliphatic residue, C(=O)—OH, residue,

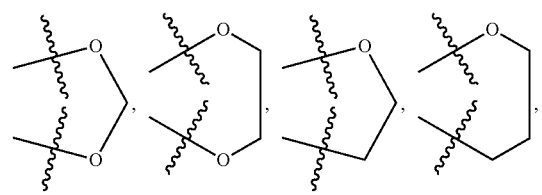 [SMILES: *OCO* ; *OCCO* ; *CCO* ; *CCCO*]

benzyl, phenyl, thienyl, and pyridyl,
wherein the $C_{1-4}$-aliphatic residue in each case may be unsubstituted or mono- or polysubstituted with at least one substituent selected from the group consisting of F, Cl, Br, I, OH, $CH_2F$, $CHF_2$, $CF_3$ and an unsubstituted O—$C_{1-4}$-aliphatic residue, and
wherein benzyl, phenyl, thienyl, and pyridyl, may in each case be unsubstituted or mono- or polysubstituted with at least one substituent selected from the group consisting of F, Cl, Br, I, $NO_2$, OH, an O—$C_{1-4}$ aliphatic residue, $OCH_2F$, $OCHF_2$, $OCF_3$, O—$CH_2$—OH, O—$CH_2$—O—$CH_3$, SH, $SCF_3$, a S—$C_{1-4}$ aliphatic residue, a S(=O)—$C_{1-4}$-aliphatic residue, or a $S(=O)_2$—$C_{1-4}$-aliphatic residue, $CH_2F$, $CHF_2$, $CF_3$, CN, a $C_{1-4}$-aliphatic residue, and C(=O)—OH.

8. The compound according to claim 1, wherein $R^7$ denotes $CF_3$, $CHF_2$, $CH_2F$, $CH_2OH$, $CH_2OCH_3$, or a $C_{2-6}$-aliphatic residue, unsubstituted or mono- or polysubstituted with at least one substituent selected from the group consisting of F, Cl, Br, I, OH, =O, an O—$C_{1-4}$-aliphatic residue, a C(=O)—O—$C_{1-4}$-aliphatic residue, $OCF_3$, $OCH_2F$, $OCHF_2$, SH, $SCF_3$, a S—$C_{1-4}$-aliphatic residue, a S(=O)—$C_{1-4}$-aliphatic residue, or a $S(=O)_2$—$C_{1-4}$-aliphatic residue, $CH_2F$, $CHF_2$, $CF_3$, and a $C_{1-4}$-aliphatic residue,
wherein the $C_{1-4}$-aliphatic residue in each case is unsubstituted,
or denotes a $C_{3-10}$-cycloaliphatic residue, or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, $OCH_2F$, $OCHF_2$, $OCF_3$, $SCF_3$, a S—$C_{1-4}$ aliphatic residue, a S(=O)—$C_{1-4}$-aliphatic residue, or a $S(=O)_2$—$C_{1-4}$-aliphatic residue, a C(=O)—O—$C_{1-4}$-aliphatic residue, $CH_2F$, $CHF_2$, $CF_3$, and a $C_{1-4}$-aliphatic residue,
wherein the $C_{1-4}$-aliphatic residue in each case may be unsubstituted or mono- or polysubstituted with OH or an unsubstituted O—$C_{1-4}$-aliphatic residue,
and wherein the $C_{3-10}$-cycloaliphatic residue or the 3 to 10 membered heterocycloaliphatic residue may in each case be optionally bridged via a unsubstituted $C_{1-4}$ aliphatic group,
provided that if $R^7$ denotes a 3 to 10 membered heterocycloaliphatic residue, the 3 to 10 membered heterocycloaliphatic residue is linked via a carbon atom, or $R^7$ denotes S—$R^{8a}$, S(=O)—$R^{8b}$, $S(=O)_2$—$R^{8c}$ or O—$R^9$,
wherein
$R^{8a}$, $R^{8b}$, $R^{8c}$ and $R^9$ in each case denote a $C_{1-8}$-aliphatic residue, unsubstituted or mono- or polysubstituted with at least one substituent selected from the group consisting of F, Cl, Br, I, OH, =O, an O—$C_{1-4}$-aliphatic residue, $OCH_2F$, $OCHF_2$, $OCF_3$, SH, $SCF_3$, a S—$C_{1-4}$-aliphatic residue, a S(=O)—$C_{1-4}$-aliphatic residue, or a $S(=O)_2$—$C_{1-4}$-aliphatic residue, an NH($C_{1-4}$ aliphatic residue), an N($C_{1-4}$ aliphatic residue)$_2$, a C(=O)—O—$C_{1-4}$-aliphatic residue, $CH_2F$, $CHF_2$, $CF_3$, and a $C_{1-4}$-aliphatic residue,
wherein the $C_{1-4}$-aliphatic residue in each case may be unsubstituted or mono- or polysubstituted with at least one substituent selected from the group consisting of F, Cl, Br, I, OH, $CH_2F$, $CHF_2$, $CF_3$ and an unsubstituted O—$C_{1-4}$-aliphatic residue,
or in each case denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, $OCH_2F$, $OCHF_2$, $OCF_3$, $SCF_3$, a S—$C_{1-4}$ aliphatic residue, a S(=O)—$C_{1-4}$-aliphatic residue, or a $S(=O)_2$—$C_{1-4}$-aliphatic residue, a C(=O)—O—$C_{1-4}$-aliphatic residue, $CH_2F$, $CHF_2$, $CF_3$, and a $C_{1-4}$-aliphatic residue,
wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue, and
wherein the $C_{3-10}$-cycloaliphatic residue or the 3 to 10 membered heterocycloaliphatic residue in each case may be bridged via an unsubstituted $C_{1-8}$ aliphatic group,
provided that if $R^{8a}$, $R^{8b}$, $R^{8c}$ or $R^9$ denotes a 3 to 10 membered heterocycloaliphatic residue, the 3 to 10 membered heterocycloaliphatic residue is linked via a carbon atom, or $R^7$ denotes $N(R^{10}R^{11})$,
wherein
$R^{10}$ denotes a $C_{1-8}$-aliphatic residue, unsubstituted or mono- or polysubstituted with at least one substituent selected from the group consisting of F, Cl, Br, I, OH, =O, an O—$C_{1-4}$-aliphatic residue, $OCH_2F$, $OCHF_2$, $OCF_3$, SH, $SCF_3$, a S—$C_{1-4}$-aliphatic residue, a S(=O)—$C_{1-4}$-aliphatic residue, or a $S(=O)_2$—$C_{1-4}$-aliphatic residue, a C(=O)—O—$C_{1-4}$-aliphatic residue, $CH_2F$, $CHF_2$, $CF_3$, and a $C_{1-4}$-aliphatic residue,
wherein the $C_{1-4}$-aliphatic residue in each case may be unsubstituted or mono- or polysubstituted with at least one substituent selected from the group consisting of F, Cl, Br, I, OH, $CH_2F$, $CHF_2$, $CF_3$ and an unsubstituted O—$C_{1-4}$-aliphatic residue,
or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, $OCH_2F$, $OCHF_2$, $OCF_3$, $SCF_3$, a S—$C_{1-4}$ aliphatic residue, a S(=O)—$C_{1-4}$-aliphatic residue, or a $S(=O)_2$—$C_{1-4}$-aliphatic residue, a C(=O)—O—$C_{1-4}$-aliphatic residue, $CH_2F$, $CHF_2$, $CF_3$, and a $C_{1-4}$-aliphatic residue,
wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue, and
wherein the $C_{3-10}$-cycloaliphatic residue or the 3 to 10 membered heterocycloaliphatic residue is in each case bridged via a unsubstituted $C_{1-8}$ aliphatic group,
provided that if $R^{10}$ denotes a 3 to 10 membered heterocycloaliphatic residue, the 3 to 10 membered heterocycloaliphatic residue is linked via a carbon atom,
and
$R^{11}$ denotes H or an unsubstituted $C_{1-4}$-aliphatic residue, or $R^{10}$ and $R^{11}$ form together with the nitrogen atom connecting them a 3 to 6 membered heterocycloaliphatic residue, unsubstituted or mono- or polysubstituted with at least one substituent selected from the group consisting of F, Cl, Br, I, $NO_2$, OH, =O, an O—$C_{1-4}$ aliphatic residue, $OCH_2F$, $OCHF_2$, $OCF_3$, SH, $SCF_3$, a S—$C_{1-4}$ aliphatic residue, a S(=O)—$C_{1-4}$-aliphatic residue, or a $S(=O)_2$—$C_{1-4}$-aliphatic residue, $CH_2F$, $CHF_2$, $CF_3$, CN, and a $C_{1-4}$-aliphatic residue,
wherein the $C_{1-4}$-aliphatic residue in each case may be unsubstituted or mono- or polysubstituted with at least one substituent selected from the group consisting of F, Cl, Br, I, OH, $CH_2F$, $CHF_2$, $CF_3$ and an unsubstituted $O$—$C_{1-4}$-aliphatic residue, and wherein the 3 to 6 membered heterocycloaliphatic residue formed by $R^9$ and $R^{10}$ together with the nitrogen atom connecting them may optionally be condensed with phenyl or pyridyl, wherein the phenyl or pyridyl residues condensed in this way can for their part be respectively unsubstituted or mono- or polysubstituted with at least one substituent selected from the group consisting of F, Cl, Br, I, OH, an $O$—$C_{1-4}$ aliphatic residue, $OCH_2F$, $OCHF_2$, $OCF_3$, SH, $SCF_3$, a S—$C_{1-4}$ aliphatic residue, a $S(=O)$—$C_{1-4}$-aliphatic residue, or a $S(=O)_2$—$C_{1-4}$-aliphatic residue, $CH_2F$, $CHF_2$, $CF_3$, CN, a $C_{1-4}$-aliphatic residue, $C(=O)$—OH, residue, benzyl, phenyl, and pyridyl, wherein the $C_{1-4}$-aliphatic residue in each case may be unsubstituted or mono- or polysubstituted with at least one substituent selected from the group consisting of F, Cl, OH, and an unsubstituted $O$—$C_{1-4}$-aliphatic residue, and wherein benzyl, phenyl, and pyridyl, may in each case be unsubstituted or mono- or polysubstituted with at least one substituent selected from the group consisting of F, Cl, Br, I, $OCH_3$, $OCH_2F$, $OCHF_2$, $OCF_3$, $O$—$CH_2$—OH, $O$—$CH_2$—$O$—$CH_3$, SH, $SCF_3$, $CH_2F$, $CHF_2$, $CF_3$, and a $C_{1-4}$-aliphatic residue.

9. The compound according to claim 1, wherein $R^1$ represents the partial structure (T1),

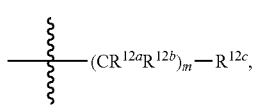

(T1)

wherein
m is 0, 1 or 2, and
$R^{12a}$ and $R^{12b}$ each independently of one another represent H, F, OH, $CH_3$ or together denote =O,
$R^{12c}$ denotes a $C_{1-4}$ aliphatic residue, unsubstituted or mono- or polysubstituted with at least one substituent selected from the group consisting of F, Cl, Br, I, CN, OH, $S(=O)_2$—$CH_3$, an unsubstituted $O$—$C_{1-4}$ aliphatic residue, and $CH_2F$, $CHF_2$, and $CF_3$,
or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, an unsubstituted $O$—$C_{1-4}$ aliphatic residue, $CH_2F$, $CHF_2$, $CF_3$, and an unsubstituted $C_{1-4}$-aliphatic residue,
or
wherein
m is 0, 1 or 2, and
$R^{12a}$ and $R^{12b}$ each independently of one another represent H, F, OH, $CH_3$ or $OCH_3$; and
$R^{12c}$ denotes an aryl or heteroaryl, in each case unsubstituted or mono- or polysubstituted with at least one substituent selected from the group consisting of F, Cl, Br, I, OH, an $O$—$C_{1-4}$ aliphatic residue, $OCH_2F$, $OCHF_2$, $OCF_3$, $OCF_2H$, $CH_2$—OH, $CH_2$—$OCH_3$, $S(=O)_2$—$CH_3$, $SCF_3$, $NO_2$, $N(CH_3)_2$,

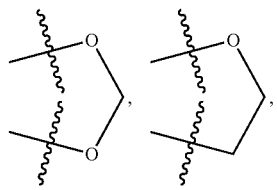 [SMILES: *OCO* ; *CCO*]

$CH_2F$, $CHF_2$, $CF_3$, CN, a $C_{1-4}$-aliphatic residue, $C(=O)$—$CH_3$, $C(=O)$—$C_2H_5$, $C(=O)$—$O$—$CH_3$, $C(=O)$—$O$—$C_2H_5$ and phenyl, wherein phenyl may be unsubstituted or mono- or polysubstituted with at least one substituent selected from the group consisting of F, Cl, Br, I, OH, an $O$—$C_{1-4}$ aliphatic residue, $OCF_3$, $OCH_2F$, $OCHF_2$, $CH_2F$, $CHF_2$, $CF_3$, CN, a $C_{1-4}$-aliphatic residue, $C(=O)$—$CH_3$, $C(=O)$—$C_2H_5$, $C(=O)$—$O$—$CH_3$ and $C(=O)$—$O$—$C_2H_5$, $R^2$ represents F; Cl; Br; I; CN; $CF_3$; $NO_2$; $OCH_2F$, $OCHF_2$, $OCF_3$; $CH_2F$, $CHF_2$, $SCF_3$; methyl; ethyl; n-propyl; iso-propyl; n-butyl; sec.-butyl; tert.-butyl; $CH_2$—OH; $CH_2$—$O$—$CH_3$; $CH_2$—$CH_2$—OH; $CH_2$—$CH_2$—$OCH_3$; O-methyl; O-ethyl; $O$—$(CH_2)_2$—$O$—$CH_3$; $O$—$(CH_2)_2$—OH; S-Methyl; S-Ethyl; cyclopropyl, cyclobutyl, cyclopentyl, or cyclohexyl, $R^3$ represents H; F; Cl; Br; I; CN; $CH_2F$, $CHF_2$, $CF_3$; $SCF_3$; $NO_2$; $OCH_2F$, $OCHF_2$, $OCF_3$; methyl; ethyl; n-propyl; iso-propyl; n-butyl; sec.-butyl; tert.-butyl; O-methyl; O-ethyl; $O$—$(CH_2)_2$—$O$—$CH_3$; $O$—$(CH_2)_2$—OH; S-Methyl; or S-Ethyl, $R^4$ and $R^5$ form together with the nitrogen atom connecting them a ring selected from the group consisting of morpholinyl, piperidinyl, pyrrolidinyl, azetidinyl, oxazepanyl, tetrahydroquinolinyl and tetrahydroisoquinolinyl, each of which is unsubstituted or mono-or polysubstituted by one or more substituents independently selected from the group consisting of F, Cl, OH, =O, $C(=O)$—OH, O-methyl, O-ethyl, $OCF_3$, $OCH_2F$, $OCHF_2$, $SCF_3$, $CH_2F$, $CHF_2$, $CF_3$, methyl, ethyl, n-propyl, 2-propyl, cyclopropyl, and cyclobutyl;

$R^6$ represents H; F; Cl; Br; I; CN; $CH_2F$, $CHF_2$, $CF_3$; $SCF_3$; $NO_2$; $OCH_2F$, $OCHF_2$, $OCF_3$; methyl; ethyl; n-propyl; iso-propyl; n-butyl; sec.-butyl; tert.-butyl; O-methyl; O-ethyl; $O$—$(CH_2)_2$—$O$—$CH_3$; $O$—$(CH_2)_2$—OH; S-Methyl; or S-Ethyl, $R^7$ denotes $CF_3$, $CHF_2$, $CH_2F$, $CH_2OH$, $CH_2OCH_3$, ethyl, n-propyl, 2-propyl, n-butyl, isobutyl, sec.-butyl, tert.-butyl, n-pentyl, isopentyl, neopentyl, n-hexyl, $CH_2$—$CH(CH_3)(C_2H_5)$, $C(CH_3)_2(C_2H_5)$, $CH_2$—$OCH_3$, $C_2H_4$—$OCH_3$, $C_3H_6$—$OCH_3$, cyclopropyl, cyclobutyl, cyclopentyl or tetrahydropyranyl, ethenyl or propenyl (—$CH_2CH=CH_2$, —CH=CH—$CH_3$, —$C(=CH_2)$—$CH_3$), in each case unsubstituted, or $R^7$ denotes S—$R^{8a}$, $S(=O)$—$R^{8b}$, $S(=O)_2$—$R^{8c}$ or O—$R^9$, wherein $R^{8a}$, $R^{8b}$, $R^{8c}$ and $R^9$ in each case denote methyl, ethyl, n-propyl, 2-propyl, n-butyl, isobutyl, sec.-butyl, tert.-butyl, n-pentyl, isopentyl, neopentyl, or n-hexyl, in each case unsubstituted or mono- or polysubstituted with at least one substituent selected from the group consisting of F, Cl, OH, $N(C_{1-4}$ aliphatic residue) and an $O$—$C_{1-4}$-aliphatic residue, or in each case denote $CH_2$-cyclopropyl or oxetanyl, wherein the $C_{1-4}$-aliphatic residue in each case is unsubstituted,
or
$R^7$ denotes $N(R^{10}R^{11})$, wherein
$R^{10}$ denotes methyl, $C(=O)$—$CH_3$, ethyl, n-propyl, 2-propyl, n-butyl, isobutyl, sec.-butyl, tert.-butyl, n-pentyl, isopentyl, neopentyl, or n-hexyl,
$R^{11}$ denotes H, methyl or ethyl,
or
$R^{10}$ and $R^{11}$ form together with the nitrogen atom connecting them a morpholinyl, piperidinyl, pyrrolidinyl, or azetidinyl, in each case unsubstituted.

10. The compound according to claim 1, which is selected from the group consisting of:
1 2-Ethylsulfanyl-N-[(3-fluorophenyl)-methyl]-6-methyl-4-morpholin-4-yl-benzamide;
2 N-[(4-Chlorophenyl)-methyl]-2-ethylsulfanyl-6-methyl-4-morpholin-4-yl-benzamide;
3 N-(4,4-Dimethyl-pentyl)-2-ethylsulfanyl-6-methyl-4-morpholin-4-yl-benzamide;
4 N-[(4-Chlorophenyl)-methyl]-2-ethylsulfanyl-6-methyl-4-[(3R)-3-methyl-morpholin-4-yl]-benzamide;
5 N-(4,4-Dimethyl-pentyl)-2-ethylsulfanyl-6-methyl-4-[(3R)-3-methyl-morpholin-4-yl]-benzamide;
6 N-[(4-Chlorophenyl)-methyl]-2-(ethylsulfinyl)-6-methyl-4-morpholin-4-yl-benzamide;
7 N-(4,4-Dimethyl-pentyl)-2-(ethylsulfinyl)-6-methyl-4-morpholin-4-yl-benzamide;
8 N-[(4-Chlorophenyl)-methyl]-2-(ethylsulfonyl)-6-methyl-4-morpholin-4-yl-benzamide;
9 N-(4,4-Dimethyl-pentyl)-2-(ethylsulfonyl)-6-methyl-4-morpholin-4-yl-benzamide;
10 N-[(4-Chlorophenyl)-methyl]-2-methoxy-6-methyl-4-morpholin-4-yl-benzamide;
11 N-[(4-Chlorophenyl)-methyl]-2-ethoxy-6-methyl-4-morpholin-4-yl-benzamide;
12 N-[(4-Chlorophenyl)-methyl]-2-ethyl-6-methyl-4-morpholin-4-yl-benzamide;
13 N-[(4-Chlorophenyl)-methyl]-2-methyl-4-morpholin-4-yl-6-propyl-benzamide;
14 N-[(4-Chlorophenyl)-methyl]-2-isopropyl-6-methyl-4-morpholin-4-yl-benzamide;
15 N-[(4-Chlorophenyl)-methyl]-2-cyclopropyl-6-methyl-4-morpholin-4-yl-benzamide;
16 N-[(4-Chlorophenyl)-methyl]-2-cyclopentyl-6-methyl-4-morpholin-4-yl-benzamide;
17 N-[(4-Fluorophenyl)-methyl]-2-isopropyl-6-methyl-4-morpholin-4-yl-benzamide;
18 2-Cyclopropyl-N-[(4-fluorophenyl)-methyl]-6-methyl-4-morpholin-4-yl-benzamide;
19 N-[(4-Chlorophenyl)-methyl]-2-methyl-4-morpholin-4-yl-6-(trifluoromethyl)-benzamide;
20 N-[(4-Chlorophenyl)-methyl]-2-(difluoro-methyl)-6-methyl-4-morpholin-4-yl-benzamide;
21 2-Isopropenyl-6-methyl-4-morpholin-4-yl-N-[[4-(trifluoromethyl)-phenyl]-methyl]-benzamide;
22 2-Isopropyl-6-methyl-4-morpholin-4-yl-N-[[4-(trifluoromethyl)-phenyl]-methyl]-benzamide;
23 2-Isopropyl-6-methyl-4-morpholin-4-yl-N-[[4-(trifluoromethyloxy)-phenyl]-methyl]-benzamide;
24 2-Cyclopropyl-6-methyl-4-morpholin-4-yl-N-[[4-(trifluoromethyl)-phenyl]-methyl]-benzamide;
25 2-Cyclopropyl-6-methyl-4-morpholin-4-yl-N-[[4-(trifluoromethyloxy)-phenyl]-methyl]-benzamide;
26 N-[(3-Fluorophenyl)-methyl]-2-methyl-4-pyrrolidin-1-yl-6-(trifluoromethyl)-benzamide;
27 N-[(3-Fluorophenyl)-methyl]-2-methyl-4-piperidin-1-yl-6-(trifluoromethyl)-benzamide;
28 2-Cyclopropyl-N-[(3R)-3-hydroxy-4,4-dimethyl-pentyl]-6-methyl-4-morpholin-4-yl-benzamide;
29 2-Cyclopropyl-N-[(3S)-3-hydroxy-4,4-dimethyl-pentyl]-6-methyl-4-morpholin-4-yl-benzamide;
30 N-[(3R)-3-Hydroxy-4,4-dimethyl-pentyl]-2-isopropyl-6-methyl-4-morpholin-4-yl-benzamide;
31 N-[(3S)-3-Hydroxy-4,4-dimethyl-pentyl]-2-isopropyl-6-methyl-4-morpholin-4-yl-benzamide;
32 2-Cyclopropyl-N-(2-hydroxy-4,4-dimethyl-pentyl)-6-methyl-4-morpholin-4-yl-benzamide;
33 N-(2-Hydroxy-4,4-dimethyl-pentyl)-2-isopropyl-6-methyl-4-morpholin-4-yl-benzamide;
34 N-[(5-Chloro-pyridin-2-yl)-methyl]-2-isopropyl-6-methyl-4-morpholin-4-yl-benzamide;
35 2-Isopropyl-6-methyl-4-morpholin-4-yl-N-[[5-(trifluoromethyl)-pyridin-2-yl]-methyl]-benzamide;
36 2-Cyclopropyl-6-methyl-4-morpholin-4-yl-N-[[5-(trifluoromethyl)-pyridin-2-yl]-methyl]-benzamide;
37 N-[(4-Chlorophenyl)-methyl]-2-methyl-4-morpholin-4-yl-6-tetrahydro-furan-3-yl-benzamide;
38 N-[(4-Chlorophenyl)-methyl]-2-[(3R)-3-fluoro-pyrrolidin-1-yl]-6-methyl-4-morpholin-4-yl-benzamide;
39 N-[(4-Chlorophenyl)-methyl]-2-fluoro-6-isopropyl-4-morpholin-4-yl-benzamide;
40 N-[(4-Chlorophenyl)-methyl]-2-isopropyl-6-methoxy-4-morpholin-4-yl-benzamide; and
41 N-[(4-Chlorophenyl)-methyl]-2,6-diethyl-4-morpholin-4-yl-benzamide,
optionally in the form of a single stereoisomer or a mixture of stereoisomers, in the form of the free compound and/or a physiologically acceptable salt thereof.

11. A pharmaceutical composition comprising at least one compound according to claim 1, optionally in the form of a single stereoisomer or a mixture of stereoisomers, in the form of the free compound and/or a physiologically acceptable salt thereof, and optionally at least one pharmaceutically acceptable auxiliary.

12. A pharmaceutical composition comprising at least one compound according to claim 10, optionally in the form of a single stereoisomer or a mixture of stereoisomers, in the form of the free compound and/or a physiologically acceptable salt thereof, and optionally at least one pharmaceutically acceptable auxiliary.

13. A method for the treatment in a mammal in need thereof of a disease and/or disorder that is mediated, at least in part, by KCNQ2/3 K$^+$channels, wherein the disorder and/or disease is selected from the group consisting of pain, epilepsy, urinary incontinence, anxiety, dependency, mania, bipolar disorders, migraine and dystonia-associated dyskinesias, said method comprising administering to the mammal an effective amount therefor of at least one compound according to claim 1.

14. A method for the treatment in a mammal in need thereof of a disease and/or disorder that is mediated, at least in part, by KCNQ2/3 K$^+$channels, wherein the disorder and/or disease is selected from the group consisting of pain, epilepsy, urinary incontinence, anxiety, dependency, mania, bipolar disorders, migraine and dystonia-associated dyskinesias, said method comprising administering to the mammal an effective amount therefor of at least one compound according to claim 10.

* * * * *